US012565660B2

(12) United States Patent
Raab et al.

(10) Patent No.: US 12,565,660 B2
(45) Date of Patent: Mar. 3, 2026

(54) IMMUNOMODULATING TRANSGENIC PLANTS AND RELATED METHODS

(71) Applicant: AGRIVIDA, INC., Woburn, MA (US)

(72) Inventors: R. Michael Raab, Arlington, MA (US); Oleg Bougri, Winchester, MA (US); Matthew Parker, Cambridge, MA (US); Philip A. Lessard, Framingham, MA (US)

(73) Assignee: AGRIVIDA, INC., Woburn, MA (US)

( * ) Notice: Subject to any disclaimer, the term of this patent is extended or adjusted under 35 U.S.C. 154(b) by 94 days.

(21) Appl. No.: 18/421,496

(22) Filed: Jan. 24, 2024

(65) Prior Publication Data

US 2024/0200089 A1 Jun. 20, 2024
US 2024/0384286 A2 Nov. 21, 2024

Related U.S. Application Data

(63) Continuation of application No. 17/748,507, filed on May 19, 2022, now Pat. No. 11,932,864, which is a continuation of application No. 16/609,633, filed as application No. PCT/US2018/034856 on May 29, 2018, now Pat. No. 11,390,879.

(60) Provisional application No. 62/512,444, filed on May 30, 2017.

(51) Int. Cl.

*C07K 14/54* (2006.01)
*A61P 33/00* (2006.01)
*C07K 16/24* (2006.01)
*C12N 15/82* (2006.01)
*A61K 39/00* (2006.01)

(52) U.S. Cl.

CPC .......... *C12N 15/8258* (2013.01); *A61P 33/00* (2018.01); *C07K 14/5428* (2013.01); *C07K 16/244* (2013.01); *A61K 2039/505* (2013.01); *A61K 2039/542* (2013.01); *C07K 2317/13* (2013.01); *C07K 2317/22* (2013.01); *C07K 2317/23* (2013.01); *C07K 2317/569* (2013.01); *C07K 2317/76* (2013.01); *C07K 2317/92* (2013.01); *C07K 2317/94* (2013.01)

(58) Field of Classification Search

None
See application file for complete search history.

(56) References Cited

U.S. PATENT DOCUMENTS

| | | | |
|---|---|---|---|
| 8,652,457 B2 | 2/2014 | Sand | |
| 8,802,825 B2 | 8/2014 | Mugica | |
| 2014/0017248 A1 | 1/2014 | Sand et al. | |
| 2015/0208693 A1 | 7/2015 | Gilbert | |
| 2016/0280778 A1 | 9/2016 | Cook | |

FOREIGN PATENT DOCUMENTS

| | | |
|---|---|---|
| CN | 10353843 | 1/2014 |
| CN | 103571796 B | 4/2015 |
| WO | 2017059397 A1 | 4/2017 |

OTHER PUBLICATIONS

Lessard et al, 2020, Nature Food, 1:199-126.*
Walter, 2014, Curr Top Microbial Immunol, 380: 191-212.*
Sand et al, 2016, Poultry Science, 95:439-446.*
Tschofen et al, 2016, Annu. Rev. Anal. Chem., 9:271-294.*
Rothwell et al 2004, Journal of Immunology, 173:2675-2682.*
Arbabi Ghahroudi et al., 1997, Selection and identification of single domain antibody fragments from camel heavy-chain antibodies. FEBS Letters, 414(3), pp. 521-526.
Asadullah, Sterry and Volk, 2003, Interleukin-10 Theraphy—Review of a New Approach, Pharmacological Reviews, 55(2), pp. 241-269.
Bartlett, Snape and Harwood, 2009, Intron-mediated enhancement as a method for increasing transgene expression levels in barley, Plant Biotechnology Journal, 7, pp. 856-866.
Bombarely, Rosli, Vrebalov, Moffett, Mueller, and Martin, 2012, A draft genome sequence of Nicotiana benthamiana to enhance molecular plant-microbe biology research. Molecular Plant-Microbe Interactions 25, pp. 1523-1530.
Callis, Fromm, and Walbot, 1987, Introns increase gene expression in cultured maize cells, Genes Dev., 1, pp. 1183-1200 ; doi:10.1101/gad.1.10.1183.
Cervantes, 2002, Incidence of pathological conditions in clinically normal broilers from different regions of the USA. 51st Western Poultry Disease Conference, May 1-4, Casa Magna Marriott Resort, Puerto Vallart, Jalisco, Mexico, 220-223.
Cervantes, 2006, Incidence of subclinical diseases and pathological conditions in clinically normal broilers from 3 production complexes sorted by sex and age. 143rd Annual Convention of the American Veterinary Medical Association and 50th Annual Meeting of the American Association of Avian Pathologists, Jul. 15-19, Hawaii Convention Center, Honolulu, Hawaii.

(Continued)

*Primary Examiner* — Jason Deveau Rosen
(74) *Attorney, Agent, or Firm* — Volpe Koenig

(57) ABSTRACT

The transgenic plants expressing one or more antagonist IL-10R peptides and anti-IL-10 single domain antibodies that stimulate or modulate the immune system and improve gastrointestinal physiology of an animal fed the transgenic plants or tissues thereof and the genes encoding the antagonist IL-10R peptides and anti-IL-10 single domain antibodies are described. The animal feed additives and animal feed incorporating the transgenic plants or tissues thereof are also described. Methods of stimulating or modulating an animal's immune system, improving an animal's gastrointestinal physiology, improving animal performance by using the transgenic plants or tissues thereof, and treating animals infected with a gastrointestinal pathogen are provided.

20 Claims, 23 Drawing Sheets

Specification includes a Sequence Listing.

(56) References Cited

OTHER PUBLICATIONS

Conley et al., 2009, Induction of protein body formation in plant leaves by elastin-like polypeptide fusions, BMC Biology, 7:48 doi: 10.1186/1741-7007-7-48.
Couper, Blount, and Riley, 2008, IL-10: The master regulator of immunity to infection, The Journal of Immunology, 180, pp. 5771-5777.
Diaz-Valdes, Manterola, Belsue, Riezu-Boj, Larrea, Echeverria, LLopiz, Lopez-Sagaseta, Lerat, Pawlotsky, Prieto, Lasarte, Borras-Cuesta, and Sarobe, 2011, Improved dendritic cell-based immunization against hepatitis C virus using peptide inhibitors of Interleukin 10, Hepatology, 53, pp. 23-31.
Goldman et al., 2006, Facile generation of heat stable antiviral and antitoxin aingle domain antibodies from a semi-synthetic llama library, 78(24), pp. 8245-8255.
Jacquet et al., 2014, Hydrophobin fusion of an influenza virus Hemagglutinin allows high transient expression in Nicotiana benthamiana, easy purification and immune response with neutralizing activity, PLOS ONE, DOI: 10.1371/journal.pone. 0115944.
Johnson and Reid, 1970, Anticoccidial drugs: lesion scoring techniques in battery and floor-pen experiments with chickens, Experimental Parasitology, 28, pp. 30-36.
Josephson, Logsdon, and Walter, 2001, Crystal structure of the IL-10/IL-10R1 complex reveals a shared receptor binding site, Immunity 14, pp. 35-46.
Joensuu et al., 2010, Hydrophobin fusions for high-level transient protein expression and purification in Nicotiana benthamiana, Plant Physiology, vol. 152, pp. 622-633.
Lin et al., 2006, Functional expression of a biologically active fragment of soluble gp130 as an ELP-fusion protein in transgenic plants: purification via inverse transition cycling, Biochem. J., 398, pp. 577-583.
Liu et al., 2013, Selection and evaluation of single domain antibodies toward MS2 phage and coat protein. Molecular Immunology, 53(1-2), pp. 118-125.
Llop-Tous et al., 2011, The expression of a xylanase targeted to ER-protein bodies provides a simple strategy to produce active insoluble enzyme polymers in tobacco plants, PLoS ONE 6(4): e19474. doi:10.1371/journal.pone.0019474.
Mainieri et al., 2004, Zeolin. A New Recombinant Storage Protein Constructed Using Maize g-Zein and Bean Phaseolin, Plant Physiology, , vol. 136, pp. 3447-3456.
Nakasugi, Crowhurst, Bally, Wood, Hellens, Waterhouse, 2013, De Novo transcriptome sequence assembly and analysis of RNA silencing genes of Nicotiana benthamiana. PLoS ONE 8(3): e59534. https://doi.org/10.1371/journal.pone.0059534.
Naiyer, Saha, Hemke, Roy, Singh, Musti, and Saha, 2013, Identification and characterization of a human IL-10 receptor antagonist, Human Immunology, 74, pp. 28-31.
Ni, Chen, Yang, Cummins, Zhan, Li, Zhu, Mounsey, Walton, Wei, Wang, Zhou, Wang, and Liu, 2016, Investigation the possibility of using peptides with a helical repeating pattern of hydrophobic and hydrophilic residues to inhibit IL-10, PLS ONE, 11(4): e0153939. doi:10.1371/journal.pone.0153939.
Patel et al., 2007, Elastin-like polypeptide fusions enhance the accumulation of recombinant protein in tobacco leaves, Transgenic Res, 16, pp. 239-249.
Reina et al. 1990, DNA sequence of the gene encoding the Zcl protein from *Zea mays* W64 A, Nucleic Acids Research, vol. 18, No. 21., p. 6425.
Reineke, Sabat, Volk, and Schneider-Mergener, 1998, Mapping of the interleukin-10/interleukin-10 receptor combining site, Protein Sci. 7, pp. 951-960.
Rothwell, Young, Zoorob, Whittaker, Hesketh, Archer, Smith, and Kaiser, 2004, Cloning and characterization of chicken IL-10 and its role in the immune response to Eimeria maxima, J. Immunol. 173, pp. 2675-2682.
Smith, and Waterman, 1981, Identification of Common Molecular Subsequences, J Mol Biol 147, pp. 195-197.
Urry et al. , 1992, Hydrophobicity-induced pK shifts in elastin protein-based polymers, Biopolymers, vol. 32, pp. 373-379.
Vasil, Clancy, Ferl, Vasil, and Hannah, 1989, Increased Gene Expression by the First Intron of Maize Shrunken-1 Locus in Grass Species, Plant Physiol. 9, pp. 1575-1579.
Wu, Hu, Rothwell, Vervelde, Kaiser, Boulton, Nolan, Tomley, Blake, and Hume, 2016, Analysis of the function of IL-10 in chickens using specific neutralizing antibodies and a sensitive capture ELISA, Devel. Comp. Immunol. 63, pp. 206-212.
Yoon, Jones, Logsdon, and Walter, 2005, Same structure, different function: crystal structure of the Epstein-Barr virus IL-10 bound to the soluble IL-10R1 chain, Structure 13, pp. 551-564.
Zdanov, Schalk-Hihi, and Wlodawer, 1996, Crystal structure of human interleukin-10 at 1.6 A resolution and a model of a complex with its soluble receptor, Protein Sci. 5, pp. 1955-1962.
Arendt et al., 2016 "Interleukin-10 neutralizing antibody for detection of intestinal luminal levels and as a dietary additive in Eimeria challenged broiler chicks," Poult Sci, vol. 95, No. 2 pp. 430-438.
De Meyer et al., 2015, "Comparison of VHH-Fc antbody production in Arabidopsis thaliana, Nicotiana benthamiana, and Pichia pastoris," Plant Biotechnol J., vol. 13, No. 7, pp. 938-947.
Lizuka et al., 2014, "Prophylactic effect of the oral administration of transgenic rice seeds containing altered peptide ligands of type II collagen on rheumatoid arthritis," Biosci Biotechnol Biochem, vol. 87, No. 10, pp. 1662-1668.
Piazzon et al., 2016, "A tale of an evolutionary conserved cytokine across vertebrates," Crit Rev Immunol, vol. 36, No. 2, pp. 99-129.
International Search Report and Written Opinion issued in corresponding International Patent Appln. No. PCT/US2018/34856 on Oct. 30, 2018.
Sand et al., 2016, Oral antibody to interleukin-10 reduces growth rate depression due to Eimeria spp. infection in broiler chickens, Poultry Science, vol. 95(2), pp. 439-446.
Lessard et al., 2020, Improved performance of Eimeria-infected chickens fed corn expressing a single-domain antibody against interleukin-10, Nature Food , pp. 119-126.
Office Action issued for European. Patent Application No. 8808980.9 on Feb. 5, 2021.
Anonymous: "IL-10-Interleukin-10 precursor-Gallu gallus (chicken) -IL10 gene & protein," Jul. 27, 2007, Retrieved from Internet: URL:https://uniprot.org (UniProtKQ6A2H4(IL10_Chick).
Office Action issued for European. Patent Application No. 8808980.9 on May 31, 2021.
Walter, 2014, The Molecular Basis of IL-10 Function: From Receptor Structure to the Onset of Signaling, Curr Top Microbiol Immunology, 380: 191-212.
Rothwell et al., 2004, Cloning and Characterization of Chicken IL-10 and Its Role in the Immune Response to Eimeria maxima Journal of Immunology, 173: 2675-2682.
Tschofen et al., 2016, Plant Molecular Farming: Much More than Medicines, Annu. Rev. Anal Chem, 9: 271-94.
Otvos Jr. et al. 2014, Current Challenges in peptide-based drug discovery, Frontiers in Chemistry, 2:1-4.
Office Action issued for Chinese Patent Application No. 201880036216.X on Mar. 1, 2022.
Pan Hong et al. 2011, Role and Application of Cytokines against Chicken Coccidiosis, China Animal Husbandry & Veterinary Medicine, vol. 38 >> Issue (7): 176-179. Abstract in English.
Gao Jun-Feng et al. Dec. 22, 2016, Development and Identification of monoclonal antibodies against chIL-10, Chinese Journal of Veterinary Medicine, No. 10. Abstract in English.
Yang Cheng-huai et al. May 20, 2003, Reserach progress of edible vaccine from transgenic plants, Advances in Animal Medicine, No. 3. Abstract in English.
Tschofen et al. 2016, Annu. Rev. Anal. Chem., 9:271-94.

* cited by examiner

IMMUNOMODULATING TRANSGENIC PLANTS AND RELATED METHODS

CROSS REFERENCE TO RELATED APPLICATION

This application is a continuation of U.S. patent application Ser. No. 17/748,507 filed on May 19, 2022. The U.S. patent application Ser. No. 17/748,507 is a continuation of U.S. patent application Ser. No. 16/609,633 filed on Oct. 30, 2019 as U.S. National Stage of International Patent Application No. PCT/US2018/034856, which was filed on May 29, 2018, and issued as U.S. Pat. No. 11,390,879 on Jul. 19, 2022. The International Patent Application No. PCT/US2018/034856 claimed the benefit of U.S. Provisional Application No. 62/512,444 filed May 30, 2017. All of these applications are incorporated herein by reference as if fully set forth.

The sequence listing electronically filed with this application titled "Sequence Listing," which was created on Jan. 24, 2024 and had a size of 594,991 bytes is incorporated by reference herein as if fully set forth.

FIELD OF INVENTION

This disclosure relates to antagonist IL-10 receptor (IL-10R) peptides and anti-IL-10 antibodies, including anti-IL-10 single domain antibodies. This disclosure relates to transgenic plants that express and accumulate antagonist IL-10R peptides and anti-IL-10 single domain antibodies that stimulate or modulate the immune system and improve gastrointestinal physiology of an animal fed the transgenic plants or tissues thereof. This disclosure also relates to the genes encoding these peptides and antibodies.

This disclosure relates to animal feed additives and animal feed that incorporates the transgenic plants or tissues thereof including the peptides and antibodies. This disclosure also relates to animal feed additives and animal feed that incorporates the peptides and antibodies.

This disclosure relates to methods of treating animals infected with a gastrointestinal pathogen by administering to them antagonist IL-10R peptides and anti-IL-10 single domain antibodies, transgenic plants expressing the peptides and antibodies disclosed herein, or feeding animals with animal feed that includes these transgenic plants, peptides or antibodies. The disclosure also relates to methods of stimulating or modulating an animal's immune system, methods of improving an animal's gastrointestinal physiology, methods of improving animal performance by using the disclosed transgenic plants or tissues thereof, antagonist IL-10R peptides, or anti-IL-10 single domain antibodies.

This disclosure relates to methods of making antagonist IL-10R peptides and anti-IL-10 single domain antibodies, and methods of making transgenic plants expressing the peptides and antibodies disclosed herein.

The sequence listing electronically filed with this application titled "Sequence Listing," created on May 30, 2017, and having a file size of 210,215 bytes is incorporated herein by reference as if fully set forth.

BACKGROUND

Coccidiosis is a common poultry disease caused by protozoan parasites that infect the gastrointestinal tract (Cervantes, H., 2002; Cervantes, H., 2006).

The disease spreads from one animal to another by contact with infected feces or ingestion of infected tissue.

Coccidiosis in chickens is caused by infection of the intestinal lining cells by parasitic protozoa of the genus *Eimeria*, and commonly by *Eimeria tenella*. The most common medications used to treat coccidial infections are anti-Coccidial drugs, antibiotics, and vaccines.

Anti-Coccidial drugs and Coccidiostats are used in poultry production to control Coccidiosis and maintain animal productivity, which generally decreases when animals are infected by *Eimeria*, and develop subclinical or clinical Coccidiosis. Clinical Coccidiosis results in disruption of the digestive tract, and symptoms include weight loss, growth suppression, diarrhea, bloody droppings and increased mortality. Subclinical Coccidiosis is common in poultry production, even when employing current Coccidiostats or vaccines, and does not present many of the same symptoms as clinical Coccidiosis, but still decreases animal productivity. The reduced animal productivity from Coccidiosis results in significant losses for the poultry industry, estimated at over one billion US dollars per year.

Anti-Coccidial drugs, antibiotics, and vaccines are important for efficient poultry production, but are being phased out in many countries due to consumer concerns over their use and safety. Vaccine use is challenged by incomplete immunity within the flock, and anti-Coccidial drugs are costly, need to be administered at the right time and dose, and can lead to the development of resistant *Eimeria* strains. Industry has witnessed a rise in the number of drug-resistant strains, which lowers the value of these products and necessitates the development of other methods for controlling Coccidiosis.

*Eimeria* stimulates production of an anti-inflammatory cytokine interleukin 10 (IL-10). IL-10 interacts with its receptor IL-10R in the intestinal lining to suppress the immune response. In turn, this allows *Eimeria* infection to proceed without interference from the immune system. IL-10 is a potent anti-inflammatory cytokine that helps animals control inflammation responses. IL-10 also controls the immune system to prevent hyper immune responses. Blocking IL-10 to prevent its interaction with IL-10R would prevent immune suppression, and thus, helps the animal's normal immune response to reduce and clear *Eimeria* infection. In contrast to other prophylactic or therapeutic approaches to controlling Coccidiosis, blocking IL-10 suppression of the immune system should not lead to the development of resistant *Eimeria* strains because such intervention focuses on stimulating the host's immune response and not on attenuating or killing the infectious agent itself.

As previously described, this approach currently suffers from significant limitations that have prevented widespread commercial adoption and industrial use. First, the antibodies used thus far have been generated by inoculating either a maternal hen, or eggs, with the target peptide. In the case of the former, only chicks from the inoculated hen may be used, requiring the inoculation of many hens for chick production, and full protection is not guaranteed due to inadequate immunity, an ineffective peptide (stimulating antigen), or an unprolonged response. Peptide effectiveness may also be challenged since it is well known that small peptides often do not mobilize an effective immune response, and because IL-10 (or IL-10 homologs) is produced by the host, it may be difficult to generate adequate antibodies without the use of adjuvants or conjugates, which further increases the cost and complexity of this approach. Furthermore, because IL-10 is known to dimerize in vivo, selected peptides may generate antibodies to epitopes that are not normally exposed by the IL-10 dimer and therefore may be ineffective in binding IL-10 in the host animal. Likewise, inoculating eggs (or collecting eggs from inoculated hens) is cumbersome and increases costs, suffers from many of the same issues that challenge hen inoculation, and adds additional costs when the antibodies must be harvested from the yolks. In the case where the antibodies are harvested from the eggs, the material must be dried, stabilized, and then mixed into feed to deliver to chicks. While the added processing steps (including harvesting the eggs, drying, formulating and packaging for feed addition), add extra cost, it is unclear how consistent this production method will be, how susceptible it is to contamination by other infectious agents, or whether the antibodies generated in this manner will be thermally stable enough to survive the pelleting processes used in preparing animal feed. Many full-length antibodies do not possess the thermal stability required to maintain their solubility, structure, and affinity for IL-10, when combined with animal feed and processed through a pellet mill. Antibodies delivered in pelleted feed will be exposed to pelleting temperatures that may be 65° C., 70° C., 75° C., 80° C., 82° C., 85° C., 90° C., 95° C., or even greater. For these reasons, using eggs to produce antibodies for animal feed is a very challenging, high-cost practice, and because the antibodies are never fully sequenced or characterized, this production method precludes the use of biotechnology to improve antibody properties and the cost, efficiency, and efficacy of production. Therefore, new technologies are greatly needed if modulation of the IL-10 signaling pathway is to achieve any market relevance in the animal production industry. To address these shortcomings, there exists a need for a novel, low-cost feed additive that ideally is delivered in existing diet ingredients, that has increased thermal stability to endure the feed pelleting process, and that can more effectively inhibit the IL-10 signaling process.

SUMMARY

In an aspect, the invention relates to a transgenic plant or tissues thereof comprising a synthetic polynucleotide encoding at least one antagonist IL-10R peptide, or an anti-IL-10 single domain antibody.

In an aspect, the invention relates to at least one antagonist IL-10R peptide. The at least one antagonist IL-10R peptide is one peptide comprising an amino acid sequence with at least 90% identity to a reference sequence selected from the group consisting of: SEQ ID NOS: 1-13. The at least one antagonist IL-10R peptide comprises concatenated peptides comprising an amino acid sequence with at least 90% identity to a reference sequence selected from the group consisting of: SEQ ID NOS: 32-40.

In an aspect, the invention relates to a synthetic polynucleotide encoding the at least one IL-10R antagonist peptide described herein.

In an aspect, the invention relates to an anti-IL-10 single domain antibody that binds to a polypeptide comprising an amino acid sequence of SEQ ID NO: 80.

In an aspect, the invention relates to a synthetic polynucleotide encoding any one of the anti-IL-10 single domain antibodies described herein.

In an aspect, the invention relates to an animal feed comprising any one of the transgenic plants or tissues thereof described herein.

In an aspect, the invention relates to an animal feed comprising any of the antagonist IL-10R peptides, or anti-IL-10 single domain antibodies described herein.

In an aspect, the invention relates to a method of treating or preventing a gastrointestinal infection in an animal comprising feeding the animal any one of the transgenic plants or tissues thereof, antagonist IL-10R peptides, anti-IL-10 single domain antibodies, or animal feed described herein.

In an aspect, the invention relates to a method of stimulating or modulating the immune system and improving gastrointestinal physiology of an animal comprising feeding the animal any one of the transgenic plants or tissues thereof, antagonist IL-10R peptides, anti-IL-10 single domain antibodies or the animal feed described herein.

In an aspect, the invention relates to a method of improving animal performance comprising feeding an animal any one of the transgenic plants or tissues thereof, antagonist IL-10R peptides, anti-IL-10 single domain antibodies or animal feed described herein.

In an aspect, the invention relates to a method of preparing an animal feed comprising mixing any one of the transgenic plants or tissues thereof described herein with plant material to form a mixture.

In an aspect, the invention relates to a method of preparing an animal feed comprising mixing any one of the antagonist IL-10R peptides or anti-IL-10 single domain antibodies described herein with plant material to form a mixture.

In an aspect, the invention relates to a method of preparing a transgenic plant or tissues thereof comprising any of the antagonist IL-10R peptides or anti-IL-10 single domain antibodies described herein.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown. In the drawings.

DETAILED DESCRIPTION OF THE PREFERRED EMBODIMENTS

Figure 1A:
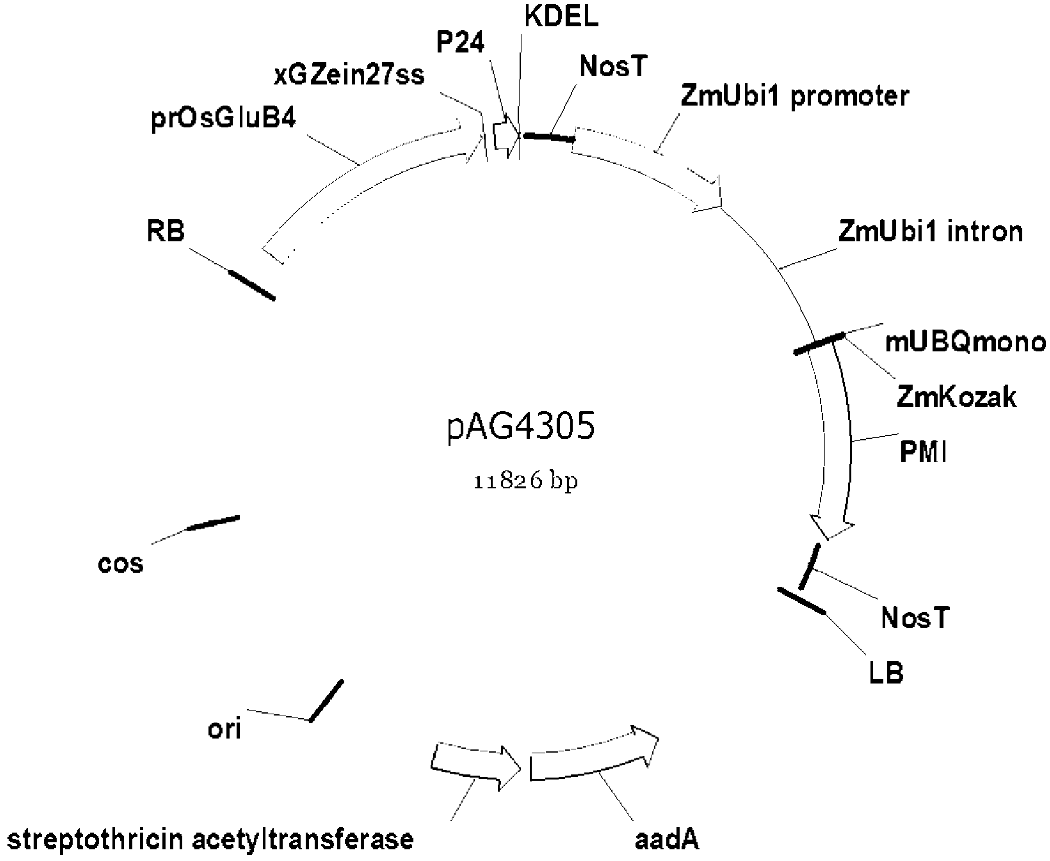
FIGS. 1A-1G are schematic drawings of the vectors pAG4305 (FIG. 1A), pAG4306 (FIG. 1B), pAG4308 (FIG. 1C), pAG4310 (FIG. 1D), pAG4311 (FIG. 1E), pAG4312 (FIG. 1F), and pAG4313 (FIG. 1G).
Figure 1B:
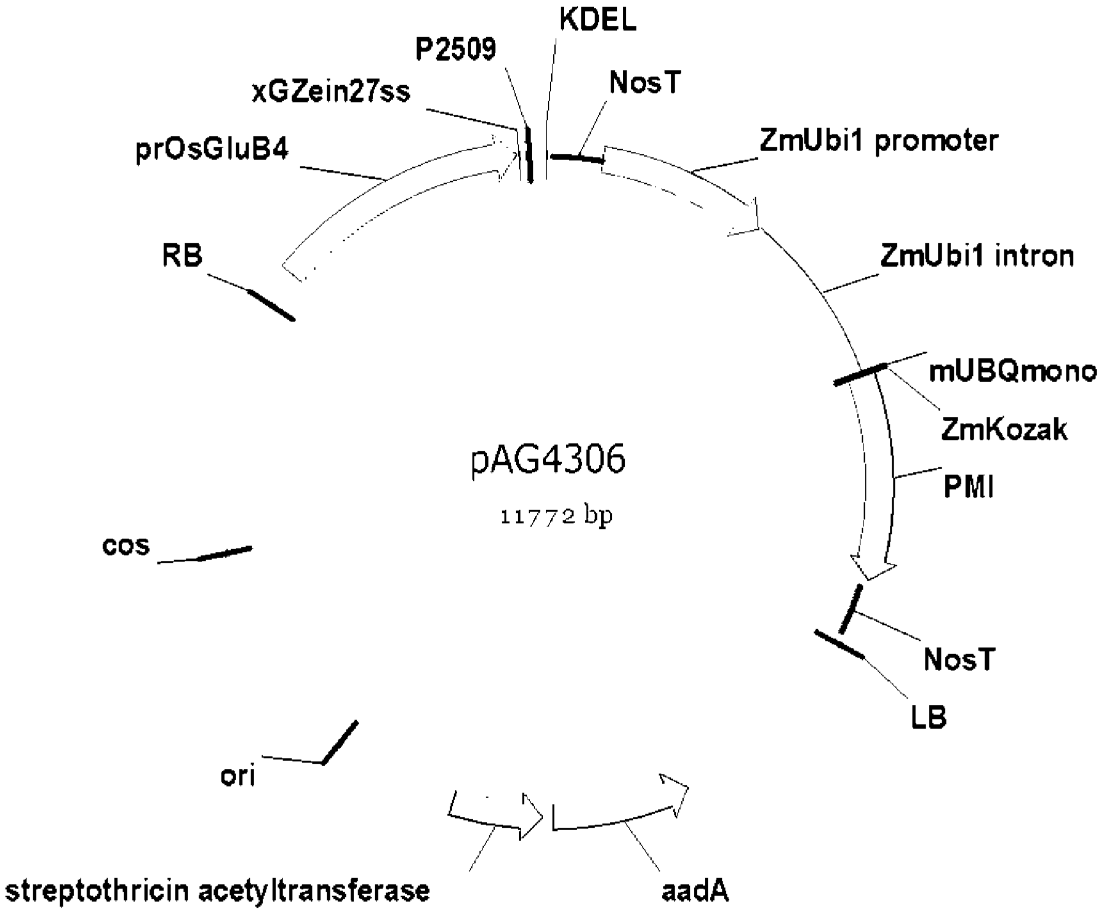
Figure 1C:
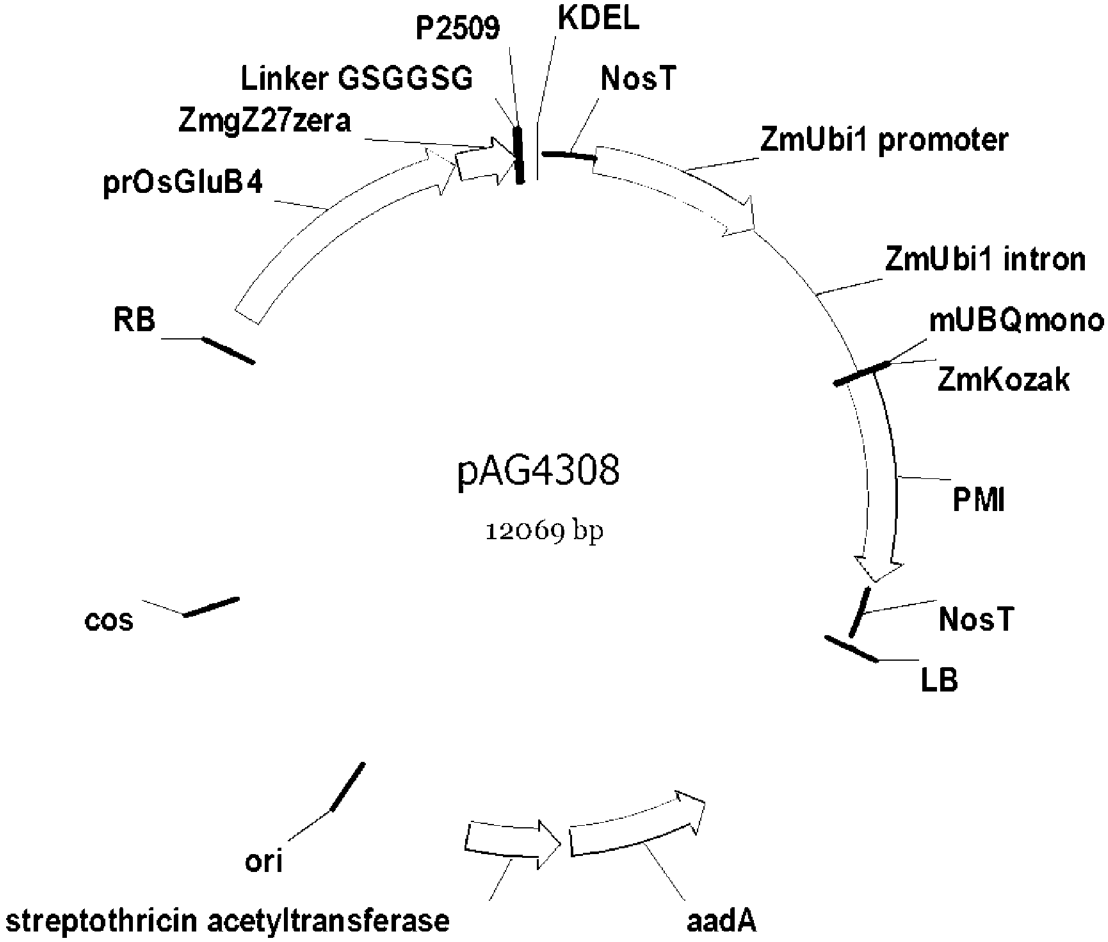
Figure 1D:
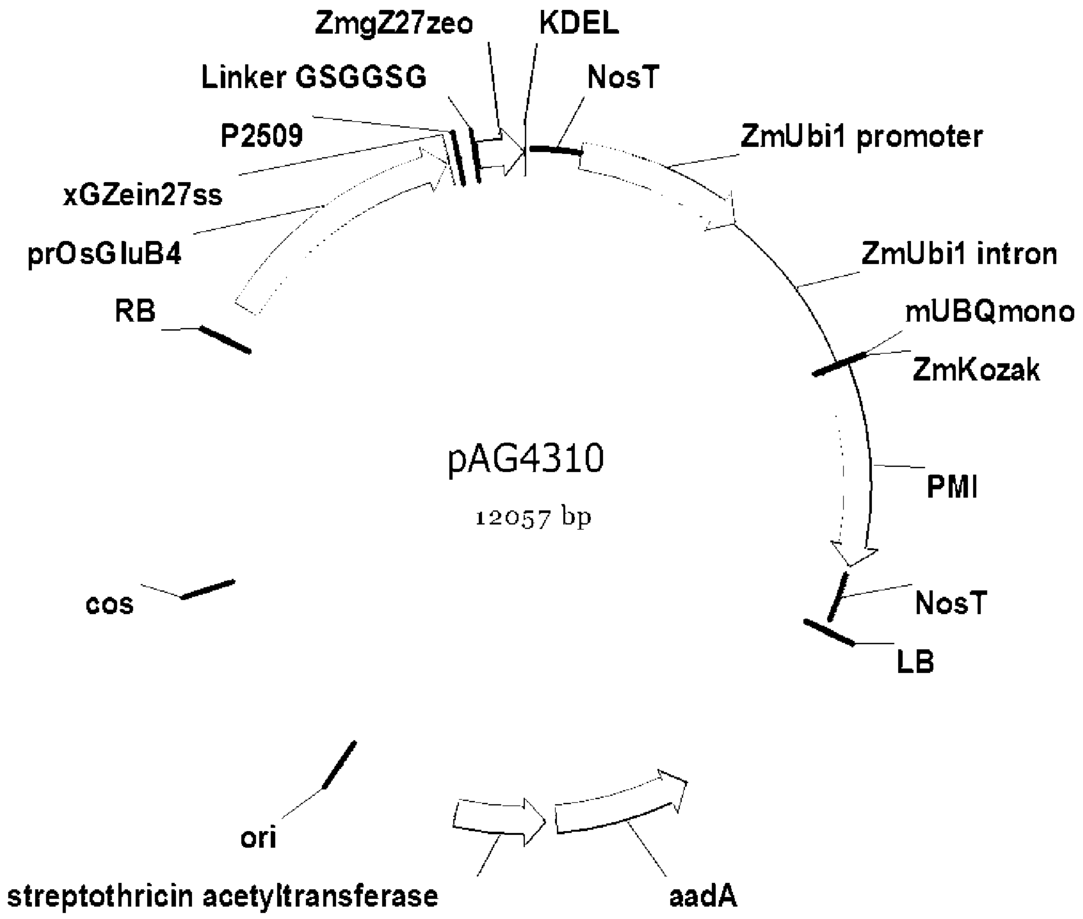
Figure 1E:
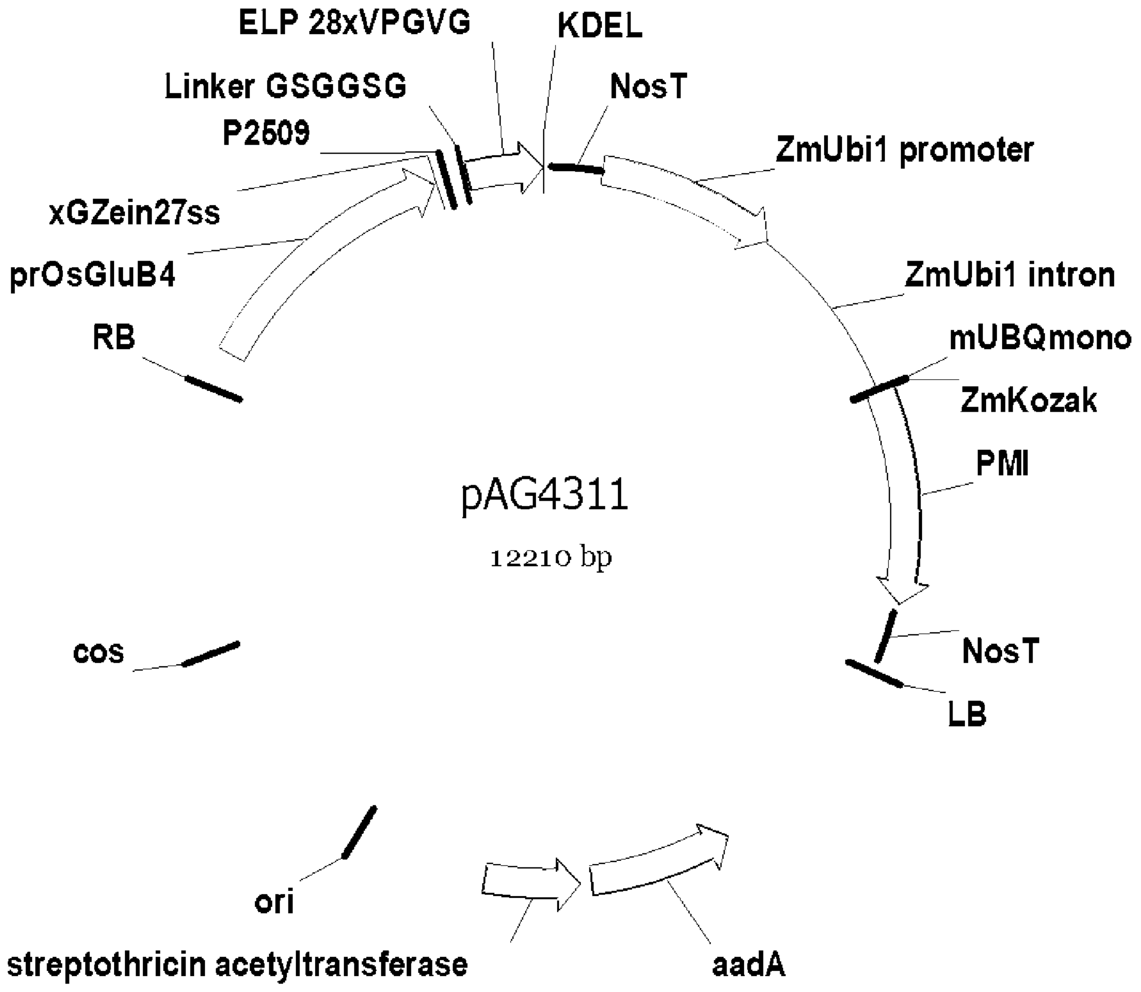
Figure 1F:
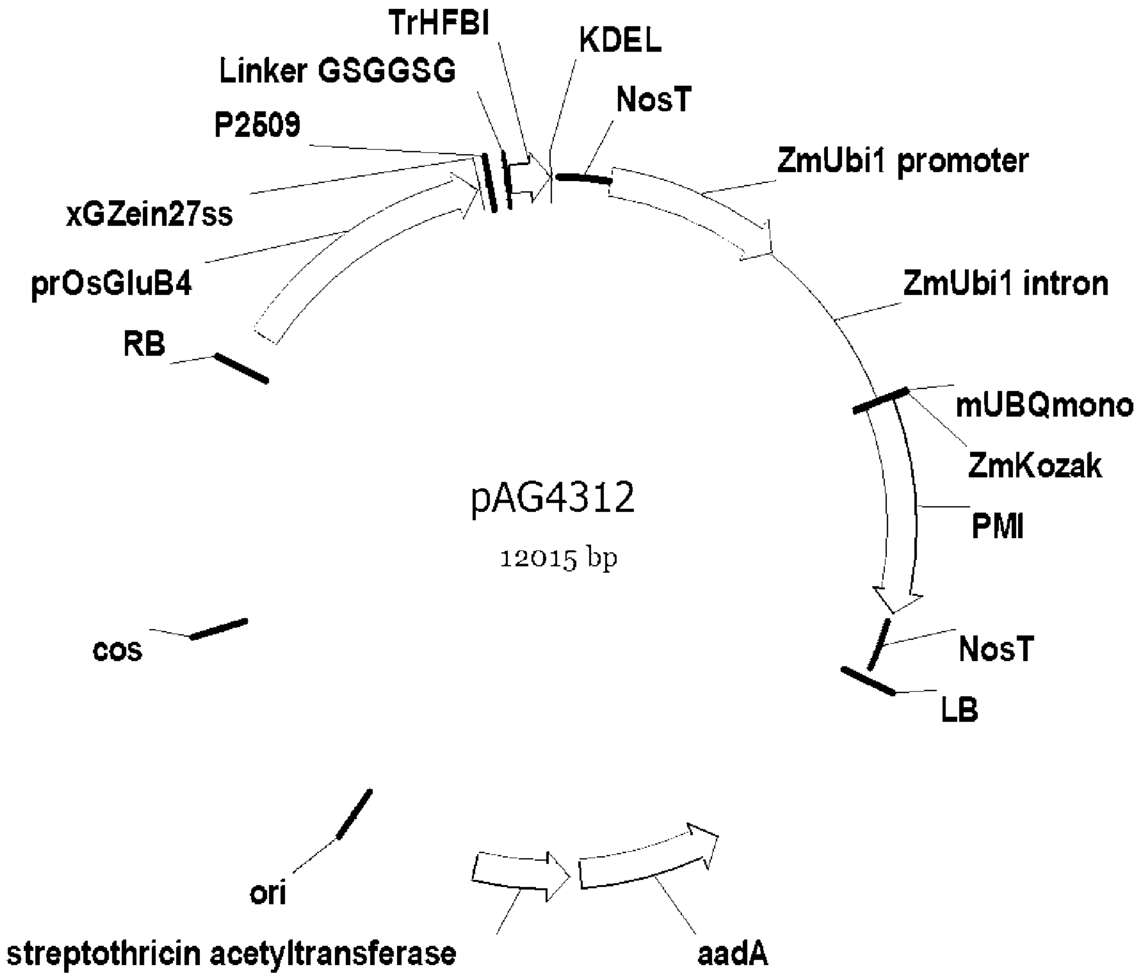

Certain terminology is used in the following description for convenience only and is not limiting.

"Synthetic nucleic acid sequence," "synthetic polynucleotide," "synthetic oligonucleotide," "synthetic DNA," or "synthetic RNA" as used herein refers to a nucleic acid sequence, a polynucleotide, an oligonucleotide, DNA, or RNA that differs from one found in nature by having a different sequence that one found in nature or a chemical modification not found in nature. The definition of synthetic nucleic acid includes but is not limited to a DNA sequence created using biotechnology tools. Such tools include but are not limited to recombinant DNA technology, chemical synthesis, or directed use of nucleases (so called "genome editing" or "gene optimizing" technologies).

"Synthetic protein," "synthetic polypeptide," "synthetic oligopeptide," or "synthetic peptide" as used herein refers to a protein, polypeptide, oligopeptide or peptide that was made through a synthetic process. The synthetic process includes but is not limited to chemical synthesis or recombinant technology.

As used herein, the terms "interleukin 10," "IL10" and "IL-10" are used interchangeably, and refer to cytokine synthesis inhibitory factor, i.e., an anti-inflammatory cytokine. The terms "cIL-10," "cIL10", "chIL10", and "chIL-10" refer to the chicken interleukin 10.

As used herein, the terms "antagonist IL-10R peptide," "antagonist IL10R," "IL10R anatagonist peptide," and "IL-10R antagonist peptide" are used interchangeably, and refer to peptides that are inhibitors of IL-10 receptors (IL-10R). The IL-10R antagonist peptides may be fragments of IL-10, or may differ from the fragments of IL-10. The IL-10R antagonist peptide may be an antagonist derived from the IL-10R. The IL-10R antagonist peptide may be fusion of the peptides, concatenation of the peptides, or any other peptides that are capable of blocking or antagonizing IL-10 receptors. The IL-10R antagonist peptides can block or antagonize receptors in any way, e.g., by blocking the IL-10 binding pockets of the IL-10 receptors, preventing IL-10 from binding to the receptors, blocking IL-10 dimerization, or IL-10 receptor assembly, or allowing IL-10 binding to the receptors but blocking subsequent signal transduction. The IL-10R antagonist peptides can block or antagonize IL-10 receptors by any mechanism or mode of action.

"Antibody" as used herein refers to an immunoglobulin molecule which specifically binds with an antigen.

"Synthetic antibody" as used herein refers to an antibody which is generated using recombinant DNA technology, such as, for example, an antibody expressed by a host engineered to produce the antibody, such as a mammalian cell, microbial cell, or plant as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. A "synthetic antibody" described herein may include fragments and hybrids of antibodies. A "synthetic antibody" described herein may be generated by an organism that is dosed with a specific antigen, and the antibody generated by the organism is isolated and propagated in a second organism.

A "single domain antibody," or sdAB, refers to a synthetic antibody that is a small monomeric antigen-binding fragment of an antibody, i.e., the variable region of an antibody heavy or light chain. sdABs can be derived from antibodies that occur naturally or are generated in camelids, e.g., camels, and llamas, and may be produced by immunizing a camelid with a target antigen, isolating peripheral blood mononucleocytes, isolating their nucleic acids, and cloning sdAB coding regions from specific nucleic acid fragments. sdABs may be also produced in cell culture, by microbial hosts in a fermentation process, or by plants. An antibody described herein may be a sdAB comprising a VHH domain substantially as set out herein. A single domain antibody is a synthetic antibody.

"Antigen" as used herein is defined as a molecule that triggers an immune response. The immune response may involve either antibody production, or the activation of specific immunologically active cells, or both. The antigen may refer to any molecule capable of stimulating an immune response, including macromolecules such as proteins or peptides. The antigen may be synthesized, produced recombinantly in a mammalian, insect, microbial or plant cell, or may be derived from a biological sample, including but not limited to a tissue sample, a cell, or a biological fluid.

"Binding affinity" refers to the sum total noncovalent interaction between members of binding pairs, e.g., an antibody and antigen. The binding affinity of the antibody can be determined based on apparent binding EC50 value. As used herein, the term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing chicken IL-10, as determined by, e.g., an ELISA assay. Thus, reduced or weaker binding is observed with an increased $EC_{50}$, or half maximal effective concentration value.

As used herein, "variant" refers to a protein or DNA molecule that has an amino acid or nucleic acid sequence that differs from the original sequence but retains a biological activity that is the same or substantially similar to that of the original sequence. The variant may be from the same or different species or be a synthetic sequence based on a natural or prior molecule.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

In an embodiment, one or more antagonist IL-10R peptides is provided. The antagonist IL-10R peptide may be expressed separately as one antagonist IL-10R peptide. The antagonist IL-10R peptide may include an amino acid sequence with at least 70, 72, 75, 80, 85, 90, 91, 92, 93, 94, 95, 96, 97, 98, 99 or 100% identity to a reference sequence selected from the group consisting of: SEQ ID NO: 1 [P21], SEQ ID NO: 2 [P22], SEQ ID NO: 3 [P23], SEQ ID NO: 4 [P24], SEQ ID NO: 5 [P25], SEQ ID NO: 6 [P26], SEQ ID NO: 7 [P27], SEQ ID NO: 8 [P28], SEQ ID NO: 9 [P29], SEQ ID NO: 10 [P11], SEQ ID NO: 11 [P30], SEQ ID NO: 12 [P31], and SEQ ID NO: 13 [P32].

An antagonist IL-10R peptide may be expressed in the form of concatenated antagonist IL-10R peptides. The concatenated antagonist IL-10R peptides may comprise a first antagonist IL-10R peptide having an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13 fused to a second antagonist IL-10R peptide having an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13. The first antagonist IL-10R peptide may differ from the second antagonist IL-10R peptide. The first antagonist IL-10R peptide may be similar to the second antagonist IL-10R peptide. The concatenated antagonist IL-10R peptides may have more than two antagonist IL-10R peptides. Each of the first antagonist IL-10R peptide and the second antagonist IL-10R peptide included in the concatenated antagonist IL-10R peptides may have an amino acid sequence with at least 70, 72, 75, 80, 85, 90, 91, 92, 93, 94, 95, 96, 97, 98, 99 or 100% identity to a reference sequence selected from the group consisting of SEQ ID NOS: 1-13. Subsequent antagonist IL-10R peptides may differ from the first and second antagonist IL-10R peptides and from each other. Subsequent antagonist IL-10R peptides may be similar to the first and the second antagonist IL-10R peptide and to each other. The concatenated antagonist IL-10R peptides may comprise an amino acid sequence with at least 70, 72, 75, 80, 85, 90, 91, 92, 93, 94, 95, 96, 97, 98, 99 or 100% identity to a reference sequence selected from the group consisting of SEQ ID NO: 32 [P2501], SEQ ID NO: 33 [P2502], SEQ ID NO: 34 [P2503], SEQ ID NO: 35 [P2504], SEQ ID NO: 36 [P2505], SEQ ID NO: 37 [P2506], SEQ ID NO: 38 [P2507], SEQ ID NO: 39 [P2508], and SEQ ID NO: 40 [P2509]. The first antagonist IL-10R peptide may be linked to the second antagonist IL-10R peptide by a linker. Each of the first, the second and the subsequent antagonist IL-10R peptides may be linked to each other by one or more linkers. The one or more linker may be selected from the group consisting of SEQ ID NOS: 41-44, and 65. The antagonist IL-10R peptide or the concatenated antagonist IL-10R peptides may comprise a signal peptide. The signal peptide may be but is not limited to an amyloplast targeting signal, a cell wall targeting peptide, a mitochondrial targeting peptide, a cytosol localization signal, a chloroplast targeting signal, a nuclear targeting peptide, or a vacuole targeting peptide. The signal peptide may an N-terminal signal peptide or a C-terminal signal peptide. The N-terminal signal peptide may be but is not limited to OsGluB4sp (rice Glu-B4 glutelin signal peptide), BAASS (barley alpha amylase signal sequence), PR1 (pathogenesis related protein), or zein 27 (xGZm27ss) signal peptide. The C-terminal signal peptide may be but is not limited to KDEL (SEQ ID NO: 29), HDEL (SEQ ID NO: 30), SEKDEL (SEQ ID NO: 31), HvVSD from barley polyamine oxidase, or HvAle from barley aleurone (thiol protease). The IL-10R antagonist peptide or the concatenated IL-10R antagonist peptides may be fused to the N-terminal signal peptide or C-terminal signal peptide, or both.

The antagonist IL-10R peptide, or the concatenated antagonist IL-10R peptides may be capable of reducing IL-10 binding to the IL-10R. The antagonist IL-10R peptide, or the concatenated antagonist IL-10R peptides may decrease the production of interferon gamma or nitric oxide when used in a cellular assay comprising cells that are stimulated by IL-10 to increase production of interferon gamma or nitric oxide.

In an embodiment, the antagonist IL-10R peptide having less than 100% identity to its corresponding amino acid sequence of SEQ ID NO: 1-13 or 32-40 may be a variant of the referenced peptide or amino acid. In an embodiment, an isolated peptide having a sequence with at least 70, 75, 80, 85, 90, 91, 92, 93, 94, 95, 96, 97, 98, 99, or 100% identity to a peptide having the sequence of any one of SEQ ID NOS: 1-13 and 32-40 along 7 to 10, 7 to 15, 7 to 30, 7 to 40, 7 to 50, or 7 to all amino acids of a protein having the sequence of any of one any one of SEQ ID NOS: 1-13 and 32-40 is provided. This list of sequence lengths encompasses every full length peptide in SEQ ID NOS: 1-13 and 32-40 and every smaller length within the list, even for peptides that do not include over 50 amino acids. For example, the lengths of 7 to 10, 7 to 20, 7 to 30, and 7 to all amino acids would apply to a sequence with 50 amino acids. A range of amino acid sequence lengths recited herein includes every length of amino sequence within the range, endpoints inclusive. The recited length of amino acids may start at any single position within a reference sequence where enough amino acids follow the single position to accommodate the recited length. The fragment of the antagonist IL-10R peptide may be a subsequence of the polypeptides herein that retain at least 40% of the antagonist IL-10R peptide $EC_{50}$ value when used in a cellular assay comprising cells that are inhibited by IL-10 (in the presence of ConA or PHA) to decrease production of interferon gamma or nitric oxide. The fragment may have 5, 7, 8, 9, 10, 15, 20, 25, 30, 35, 40, 45 or 50 amino acids. The fragments may include 5, 7, 8, 9, 10, 15, 20, 25, 30, 35, 40, 45 or 50 contiguous amino acids. Embodiments also include nucleic acids or polynucleotides, encoding said amino acid sequences. A less than full length amino acid sequence may be selected from any portion of one of the sequences of SEQ ID NOS: 1-13 and 32-40 corresponding to the recited length of amino acids. A less than full length amino acid sequence may be selected from a portion of any one of SEQ ID NOS: 1-13 and 32-40.

In an embodiment, an antagonist IL-10R peptide or concatenated antagonist IL-10R peptides may maintain or improve the body weight, and, or the feed conversion ratio, of poultry fed the peptides relative to poultry fed the same feed lacking the peptides. The antagonist IL-10R peptide or concatenated antagonist IL-10R peptides may be dosed at less than 500 mg per kg of pelleted feed, or more preferably at less than 50 mg per kg of pelleted feed, or even more preferably at less than 5 mg per kg of pelleted feed, or even more preferably at less than 1 mg per kg of pelleted feed. The antagonist IL-10R peptide or concatenated antagonist IL-10R peptides may also improve the body weight or feed conversion ratio of poultry when used in mash (non-pelleted) feed. The antagonist IL-10R peptide or concatenated antagonist IL-10R peptides may maintain their affinity for the IL-10R following incubation in liquid for at least 60 seconds at a temperature less than or equal to 65° C., or 70° C., or 75° C., or 80° C., or 85° C., or 90° C., or 95° C., or 100° C. The antagonist IL-10R peptide or concatenated antagonist IL-10R peptides may maintain their affinity for the IL-10R when heated to a temperature of 70° C. to 90° C. The antagonist IL-10R peptide or concatenated antagonist IL-10R peptides may maintain their affinity for the IL-10R when heated to a temperature in a range between any two of the following values: 70° C., 75° C., 80° C., 85° C., or 90° C.

In an embodiment, the antagonist IL-10R peptide or concatenated antagonist IL-10R peptides may be a peptide or concatenated peptides that are stable to pepsin digestion, may have an increased stability in the animal digestive tract, and may be produced by a microbial host. The antagonist IL-10R peptide or concatenated antagonist IL-10R peptides may be a peptide or concatenated peptides that are readily degradable by pepsin. The readily degradable peptide or concatenated peptides may completely degrade in a time period from 45 minutes to 40 minutes, from 40 minutes to 35 minutes, from 35 minutes to 30 minutes, from 30 minutes to 25 minutes, from 25 minutes to 20 minutes, from 20 minutes to 15 minutes, from 15 minutes to 10 minutes, from 10 minutes to 8 minutes, from 8 minutes to 6 minutes, from 6 minutes to 4 minutes, from 4 minutes to 2 minutes of the pepsin treatment. The time period for degradation may be in a range between any two integer value between 2 minutes and 45 minutes. The complete degradation of the peptide or concatenated peptides by pepsin may occur in 10 minutes.

An embodiment provides an antibody that binds to IL-10, and is referred herein as anti-IL-10 antibody. The anti-IL-10 antibody may bind to the *Gallus gallus* (chicken) IL-10, and is referred herein as an anti-chIL-10 antibody, or chIl10AB. The anti-IL-10 antibody may be a single domain anti-IL-10 antibody (sdAB). Both "single domain anti-IL-10 antibody" and "anti-IL-10 single domain antibody" refer to the same type of antibody and may be used interchangeably herein. An anti-IL-10 single domain antibody may bind to a polypeptide comprising an amino acid sequence of SEQ ID NO: 80. The anti-IL-10 single domain antibody may be capable of reducing IL-10 binding to the IL-10 receptor (IL-10R).

In an embodiment, the anti-IL-10 single domain antibody may have a binding $EC_{50}$ for chicken Il-10 of 30 nM, or less. The anti-IL-10 single domain antibody may have a binding EC50 for chicken IL-10 of about 30 nM, or less, about 25 nM, or less, about 20 nM, or less, about 15 nM, or less, about 10 nM, or less, about 5 nM, or less, or about 1 nM, or less. The anti-IL-10 single domain antibody may have a binding $EC_{50}$ for chicken Il-10 in a range between any two of the following $EC_{50}$ values: 30, 20, 10, 5, or 1 nM. In an embodiment, the $EC_{50}$ of the anti-IL-10 single domain antibody provided herein may be measured by ELISA or any other assay known in the art. The $EC_{50}$ of the anti-IL-10 single domain antibody value may be measured by an ELISA assay described in Example 9 herein.

Without limitations, the anti-IL-10 single domain antibody may be a single domain antibody of any length and of any molecular mass that is capable of reducing IL-10 binding to the IL-10 receptor (IL-10R). The anti-IL-10 single domain antibody may have a molecular mass of 10, 11, 12, 13, 14, 15, 16, 17, 18, 19, or 20 kDa. The anti-IL-10 single domain antibody may have a molecular mass of 14, 15, 16, 17, 18, 19, or 20 kDa. The anti-IL-10 single domain antibody may have a molecular mass in a range between any two of the following molecular masses: 10, 11, 12, 13, 14, 15, 16, 17, 18, 19, or 20 kDa. The anti-Il-10 single domain antibody may have a molecular mass in a range between any two of the following molecular masses: 14, 15, 16, 17, 18, 19, or 20 kDa.

The anti-IL-10 single domain antibody may include an amino acid sequence with at least 70, 72, 75, 80, 85, 90, 91, 92, 93, 94, 95, 96, 97, 98, 99 or 100% identity to a reference sequence selected from the group consisting of: SEQ ID NO: 87 [chIL10sdAB1H5], SEQ ID NO: 88 [chIL10sdAB1E9], SEQ ID NO: 89 [chIL10sdAB1H1], SEQ ID NO: 90 [chIL10sdAB1G6], SEQ ID NO: 91 [chIL10sdAB1C10], SEQ ID NO: 92 [chIL10sdAB1B6], SEQ ID NO: 93 [chIL10sdAB1D12], SEQ ID NO:947 [chIL10sdAB1C2], SEQ ID NO: 95 [chIL10sdAB1B5], SEQ ID NO: 96 [chIL10sdAB1E2], SEQ ID NO: 97 [chIL10sdAB1G7], SEQ ID NO: 98 [chIL10sdAB1G9], SEQ ID NO: 99 [chIL10sdAB1H12], SEQ ID NO: 100 [chIL10sdAB2A9], SEQ ID NO: 101 [chIL10sdAB1E12], SEQ ID NO: 102 [chIL10sdAB1E10], SEQ ID NO: 103 [chIL10sdAB1F12], SEQ ID NO: 104 [chIL10sdAB1A8], SEQ ID NO: 105 [chIL10sdAB1C8], SEQ ID NO: 106 [chIL10sdAB1C12], SEQ ID NO: 107 [chIL10sdAB1B1], SEQ ID NO: 108 [chIL10sdAB1F1], SEQ ID NO: 109 [chIL10sdAB1D11], SEQ ID NO: 110 [chIL10sdAB1E6], SEQ ID NO: 111 [chIL10sdAB1B9], SEQ ID NO: 112 [chIL10sdAB1B10], SEQ ID NO: 113 [chIL10sdAB1F5], SEQ ID NO: 114 [chIL10sdAB1A6], SEQ ID NO: 115 [chIL10sdAB1D5], SEQ ID NO: 116 [chIL10sdAB1D8], SEQ ID NO: 117 [chIL10sdAB1B4], SEQ ID NO: 118 [chIL10sdAB1C7], SEQ ID NO: 119 [chIL10sdAB1B3], SEQ ID NO: 120 [chIL10sdAB1D7], SEQ ID NO: 121 [chIL10sdAB1F7], SEQ ID NO: 122 [chIL10sdAB1F10], SEQ ID NO: 123 [chIL10sdAB1F2], SEQ ID NO: 124 [chIL10sdAB1F3], SEQ ID NO: 125 [chIL10sdAB1F8], SEQ ID NO: 126 [chIL10sdAB1C9], SEQ ID NO: 127 [chIL10sdAB1A12], SEQ ID NO: 128 [chIL10sdAB1C3], SEQ ID NO: 129 [chIL10sdAB1E7], SEQ ID NO: 130 [chIL10sdAB1D9], SEQ ID NO: 131 [chIL10sdAB1A9], SEQ ID NO: 132 [chIL10sdAB1H10], SEQ ID NO: 133 [chIL10sdAB1C1], SEQ ID NO: 134 [chIL10sdAB1D1], SEQ NO: 135 [chIL10sdAB1A11], SEQ ID NO: 136 [chIL10sdAB1G8], SEQ ID NO: 137 [chIL10sdAB1A5], SEQ ID NO: 138 [chIL10sdAB1C5], SEQ ID NO: 139 [chIL10sdAB1H6], SEQ ID NO: 140 [chIL10sdAB2A8], SEQ ID NO: 141 [chIL10sdAB1F9], SEQ ID NO: 142 [chIL10sdAB1E11], SEQ ID NO: 143 [chIL10sdAB1D6], SEQ ID NO: 144 [chIL10sdAB1C4], SEQ ID NO: 145 [chIL10sdAB1H4], SEQ ID NO: 146 [chIL10sdAB1F11], SEQ ID NO: 147 [chIL10sdAB1D3], SEQ ID NO: 148 [chIL10sdAB1A7], SEQ ID NO: 149 [chIL10sdAB1H8], SEQ ID NO: 150 [chIL 10sdAB1H3], SEQ ID NO: 151 [chIL10sdAB1B8], SEQ ID NO: 152 [chIL10sdAB1B2], SEQ ID NO: 153 [chIL10sdAB1D2], and SEQ ID NO: 154 [chIL10sdAB1D10]. The anti-IL-10 single domain antibody may be fused to a signal peptide. The signal peptide may be but is not limited to an amyloplast targeting signal, a cell wall targeting peptide, a mitochondrial targeting peptide, a cytosol localization signal, a chloroplast targeting signal, a nuclear targeting peptide, an endoplasmic reticulum retention signal, or a vacuole targeting peptide. The signal peptide may an N-terminal signal peptide or a C-terminal signal peptide. The N-terminal signal peptide may be but is not limited to OsGluB4sp (rice Glu-B4 glutelin signal peptide), BAASS (barley alpha amylase signal sequence), PR1 (pathogenesis related protein), or zein 27 (xGZm27ss) signal peptide. The C-terminal signal peptide may be but is not limited to KDEL (SEQ ID NO: 29), HDEL (SEQ ID NO: 30), SEKDEL (SEQ ID NO: 31), HvVSD from barley polyamine oxidase, or HvAle from barley aleurone (thiol protease). The anti-IL-10 single domain antibody may be fused to the N-terminal signal peptide or C-terminal signal peptide, or both.

In an embodiment, the anti-IL-10 single domain antibody having less than 100% identity to its corresponding amino acid sequence of one of SEQ ID NO: 87-154 may be a variant of the referenced peptide or amino acid. In an embodiment, an isolated peptide having a sequence with at least 70, 75, 80, 85, 90, 91, 92, 93, 94, 95, 96, 97, 98, 99, or 100% identity to a peptide having the sequence of any one of SEQ ID NOS: 87-154 along 10 to 20, 10 to 25, 10 to 30, 10 to 40, 10 to 50, 10 to 60, 10 to 70, 10 to 80, 10 to 90, 10 to 100, 10 to 110, 10 to 115, 10 to 116, 10 to 117, 10 to 118, 10 to 119, 10 to 120, 10 to 121, 10 to 122, 10 to 123, 10 to 124, 10 to 125, 10 to 126, or 10 to all amino acids of a protein having the sequence of any of one any one of SEQ ID NOS: 87-154 is provided. This list of sequence lengths encompasses every full length peptide in SEQ ID NOS: 87-154 and every smaller length within the list, even for peptides that do not include over 126 amino acids. For example, the lengths of 10 to 20, 10 to 25, 10 to 30, 10 to 40, 10 to 50, 10 to 60, 10 to 70, 10 to 80, 10 to 90, 10 to 100, 10 to 110, 10 to 115, 10 to 116, 10 to 117, 10 to 118, 10 to 119, 10 to 120, 10 to 121, 10 to 122, 10 to 123, 10 to 124, 10 to 125, 10 to 126, or 10 to all amino acids would apply to a sequence with 126 amino acids. A range of amino acid sequence lengths recited herein includes every length of amino sequence within the range, endpoints inclusive. The recited length of amino acids may start at any single position within a reference sequence where enough amino acids follow the single position to accommodate the recited length. The fragment of the anti-IL-10 single domain antibody may be a subsequence of the polypeptides herein that retain at least 40% of the anti-IL-10 single domain antibody's $EC_{50}$ value when used in a cellular assay comprising cells that are inhibited by IL-10 to decrease production of interferon gamma in the presence of ConA, which is described herein in Example 9. The fragment may have 10, 15, 20, 25, 30, 35, 40, 45, 50, 55, 60, 65 70, 75, 80, 85, 90, 95, 100, 115, 116, 117, 118, 19, 120, 121, 122, 123, 124, 124, or 126 amino acids. The fragments may include 10, 15, 20, 25, 30, 35, 40, 45, 50, 55, 60, 65 70, 75, 80, 85, 90, 95, 100, 115, 116, 117, 118, 19, 120, 121, 122, 123, 124, 124, or 126 contiguous amino acids. Embodiments also include nucleic acids or polynucleotides, encoding said amino acid sequences. A less than full length amino acid sequence may be selected from any portion of one of the sequences of SEQ ID NOS: 87-154 corresponding to the recited length of amino acids. A less than full length amino acid sequence may be selected from a portion of any one of SEQ ID NOS: 87-154.

The anti-IL-10 single domain antibody may increase the production of interferon gamma or nitric oxide when used in a cellular assay comprising cells that are inhibited by IL-10 to decrease production of interferon gamma or nitric oxide.

The anti-IL-10 single domain antibody may maintain or improve the body weight, and, or the feed conversion ratio, of poultry fed the antibodies relative to poultry fed the same feed lacking the antibodies. The anti-IL-10 single domain antibody may be dosed at less than 500 mg per kg of pelleted feed, or more preferably at less than 50 mg per kg of pelleted feed, or even more preferably at less than 5 mg per kg of pelleted feed, or even more preferably at less than 1 mg per kg of pelleted feed. The anti-IL-10 single domain antibody may also improve the body weight or feed conversion ratio of poultry when used in mash (non-pelleted) feed. The anti-IL-10 single domain antibody may maintain its affinity for IL-10 following exposure to pelleting process temperature less than or equal to 65° C., or 70° C., or 75° C., or 80° C., or 85° C., or 90° C., or 95° C., or 100° C. The anti-IL-10 single domain antibody may maintain its affinity for IL-10 following incubation in liquid for at least 60 seconds at a temperature less than or equal to 65° C., or 70° C., or 75° C., or 80° C., or 85° C., or 90° C., or 95° C., or 100° C. The anti-IL-10 single domain antibody may have activity when heated to a temperature of 70° C. to 90° C. The anti-IL-10 single domain antibody may have activity when heated to a temperature in a range between any two of the following values: 70° C., 75° C., 80° C., 85° C., or 90° ° C. The anti-IL-10 single domain antibody may be active following exposure of a temperature of 70° C. to 90° C., or any value in between the foregoing values. The anti-IL-10 single domain antibody may be an antibody stable to pepsin digestion, may have an increased stability in the animal digestive tract, and may be produced by a microbial host. The anti-IL-10 single domain antibody may be an antibody that is readily degradable by pepsin. The readily degradable antibody may completely degrade in a time period from 45 minutes to 40 minutes, from 40 minutes to 35 minutes, from 35 minutes to 30 minutes, from 30 minutes to 25 minutes, from 25 minutes to 20 minutes, from 20 minutes to 15 minutes, from 15 minutes to 10 minutes, from 10 minutes to 8 minutes, from 8 minutes to 6 minutes, from 6 minutes to 4 minutes, from 4 minutes to 2 minutes of the pepsin treatment. The time period for degradation may be in a range between any two integer value between 2 minutes and 45 minutes. The complete degradation of the antibody by pepsin may occur in 10 minutes.

An embodiment provides one or more synthetic polynucleotides encoding the anti-IL-10 single domain antibody or their variants described herein. The one or more synthetic polynucleotides may comprise, consist essentially of, or consist of a sequence with at least 70, 72, 75, 80, 85, 90, 91, 92, 93, 94, 95, 96, 97, 98, 99, or 100% identity to a reference sequence of SEQ ID NO: 173 [chIL101A11 coding seq], SEQ ID NO: 174 [chIL101A11B coding seq], SEQ ID NO: 175 [chIL101F11A coding seq], SEQ ID NO: 176 [chIL101F11B coding seq], SEQ ID NO: 177 [chIL101H1A coding seq], or SEQ ID NO: 178 [chIL101H1B coding seq]. The one or more synthetic polynucleotides may be included in the expression cassette to be expressed in a host. The host may be but is not limited to a microorganism, a plant cell, a phage, a virus, a mammalian cell, or an insect cell.

An embodiment provides an expression cassette. The expression cassette may comprise one or more synthetic polynucleotide encoding the antagonist IL-10R peptide, concatenated IL-10R antagonist peptides, anti-IL-10 single domain antibody or their variants described herein.

A polynucleotide sequence in an expression cassette, isolated nucleic acid, vector, or any other DNA construct herein, or utilized in a method herein may be operably connected to one or more regulatory elements. A regulatory element included may be a promoter. The promoter may be a constitutive promoter which provides transcription of the polynucleotide sequences throughout the plant in most cells, tissues and organs and during many but not necessarily all stages of development. The promoter may be an inducible promoter, which initiates transcription of the polynucleotide sequences only when exposed to a particular chemical or environmental stimulus. The promoter may be specific to a host. The promoter may be suitable for expression of the polynucleotide in a plant, a bacterium, yeast, a mammalian cell, or an insect cell. The promoter may be a plant specific promoter. The promoter may be specific to a particular developmental stage, organ or tissue. A tissue specific promoter may be capable of initiating transcription in a particular plant tissue. Plant tissue that may be targeted by a tissue specific promoter may be but is not limited to a stem, leaves, trichomes, anthers, seed, embryo, or endosperm. A constitutive promoter herein may be the maize Ubiquitin promoter, the rice Ubiquitin 3 promoter (OsUbi3P), the switchgrass ubiquitin promoter, the PEPC promoter, the maize Actin promoter, or the rice Actin 1 promoter. Other known constitutive promoters may be used, and include but are not limited to Cauliflower Mosaic Virus (CAMV) 35S promoter, the Cestrum Yellow Leaf Curling Virus promoter (CMP) or the CMP short version (CMPS), and the Rubisco small subunit promoter.

The tissue specific promoter may include the seed-specific promoter. The seed specific promoter may be but is not limited to the maize zein promoter, the rice glutelin (GluB4) promoter, the maize oleosin promoter, or the maize globulin promoter.

The promoter may be a promoter homolog to any one of the previously listed promoters derived from other species, or promoter variants to the previously listed promoters with greater than 80% identity.

The promoter may be suitable for expressing the one or more polynucleotides in a bacterium. The promoter may be the T7 RNA polymerase promoter, the LAC promoter or the arabinose promoter. The promoter may be suitable for expressing the polynucleotide in a yeast. The promoter may be the GAL promoter or the glucose promoter. The promoter may be any prokaryotic promoter. The prokaryotic promoter may be a bacterial promoter, or phage promoter that is active in bacteria. The prokaryotic promoter may be any inducible promoter that is active in bacteria, or any other promoter that is active in bacteria.

Another regulatory element that may be provided is a terminator sequence, which terminates transcription. A terminator sequence may be included at the 3' end of a transcriptional unit of the expression cassette. The terminator may be derived from a variety of genes. The terminator may be from a eukaryote, such as a plant or mammalian cell, or a prokaryote. The terminator may be a terminator sequence from the nopaline synthase or octopine synthase genes of *Agrobacterium tumefaciens*. The terminator may be maize gamma zein 27 terminator. The terminator may be any other terminator sequence.

The one or more synthetic polynucleotide may further include one or more signal polynucleotide sequence encoding any one of the signal peptides described herein. The expression cassette may comprise, consist essentially of, or consist of a synthetic polynucleotide sequence with at least 70, 72, 75, 80, 85, 90, 91, 92, 93, 94, 95, 96, 97, 98, 99, or 100% identity to a reference sequence of SEQ ID NO: 84 [xGZein27ss: chIL10sdAB1A11:KDEL], SEQ ID NO: 85 [xGZein27ss:chIL10 sdAB 1B9:KDEL], SEQ ID NO: 86 [xGZein27ss:chIL10sdAB1F11:KDEL], or SEQ ID NO: 179 [xGZein27ss:chIL10sdAB1H1:KDEL].

The expression cassette including the one or more synthetic polynucleotides may be included in a vector.

An embodiment comprises a vector containing the expression cassette including one or more synthetic polynucleotides encoding the antagonist IL-10R peptide, the concatenated antagonist IL-10R peptides, or the anti-IL-10 single domain antibody of any of the above embodiments. The vector may contain any one of the expression cassettes described in any of the embodiments herein. The vector may be a vector used in plant transformation and that is capable of delivering its DNA into the genome of plant cells. The vector may be a vector used for yeast and fungal expression. The vector may be a vector for expression of the peptides, concatenated peptides or antibodies described herein used in bacterial expression. The vector may be a vector used for mammalian or insect cell expression.

The vector may comprise the expression cassette including synthetic polynucleotides encoding the antagonist IL-10R peptide or concatenated antagonist IL-10R peptides. The vector may comprise a nucleic acid sequence with at least 70, 72, 75, 80, 85, 90, 91, 92, 93, 94, 95, 96, 97, 98, 99, or 100% identity to a reference sequence of SEQ ID NO: 69 [pAG4305], SEQ ID NO: 70 [pAG4306], SEQ ID NO: 71 [pAG4308], SEQ IS NO: 72 [pAG4310], SEQ ID NO: 73 [pAG4311], SEQ ID NO: 74 [pAG4312], SEQ ID NO: 75 [pAG4313], SEQ ID NO: 76 [pAG4981], SEQ ID NO: 77 [pAG4982], SEQ ID NO: 78 [pAG4983], and SEQ ID NO: 79 [pAG4984].

The vector may comprise the expression cassette including the synthetic polynucleotide encoding an anti-IL-10 single domain antibody. The vector may comprise a nucleic acid sequence with at least 70, 72, 75, 80, 85, 90, 91, 92, 93, 94, 95, 96, 97, 98, 99, or 100% identity to a reference sequence of SEQ ID NO: 155 [pAG4314], SEQ ID NO: 156 [pAG4315], SEQ ID NO: 157 [pAG4316], SEQ ID NO: 158 [pAG4317], SEQ ID NO: 159 [pAG4985], SEQ ID NO: 160 [pAG4986], SEQ ID NO: 161 [pAG4987], SEQ ID NO: 162 [pAG4988], SEQ ID NO: 163 [pAG4989], SEQ ID NO: 164 [pAG4990], SEQ ID NO: 165 [pAG4991], SEQ ID NO: 166 [pAG4992], SEQ ID NO: 167 [pAG4993], SEQ ID NO: 168 [pAG4994], SEQ ID NO: 169 [pAG4995], SEQ ID NO: 170 [pAG4996], SEQ ID NO: 171 [pAG4997], or SEQ ID NO: 172 [pAG4998].

An embodiment comprises a polynucleotide comprising, consisting essentially of, or consisting of a sequence that has at least 70, 72, 75, 80, 85, 90, 91, 92, 93, 94, 95, 96, 97, 98, 99, or 100% identity along its length to a contiguous portion of a polynucleotide having any one of the sequences set forth herein or the complements thereof. The contiguous portion may be any length up to the entire length of a sequence set forth herein or the complement thereof.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, a transgenic plant comprising any one of synthetic polynucleotides described herein and expressing any one of the antagonist IL-10R peptides, concatenated antagonist IL-10R peptides or anti-IL-10 single domain antibodies described herein is provided. As used herein, the term "transgenic plants" describes plants transformed with DNA that enables the plant containing the transformed DNA to perform a novel function; usually the transcription of the DNA, potentially at a level different from the level in wild-type plants, and potentially the translation of the transcript into a protein, which may be a novel protein to the plant. The transgenic plant may refer to a whole transgenic plant or tissues thereof. The tissues of transgenic plants may be any portion of a transgenic plant, including but not limited to leaves, stems, flowers, buds, petals, grain, seed, embryo, endosperm, leaves, stalks, roots, pollen, or anthers. The tissues may also refer to liquid extracts made by fractionating any portion of a transgenic plant in an organic or aqueous liquid (for example, extracting protein from transgenic seeds and using the extract as a source of the transgenic protein) and using the separated liquid to feed an animal, or in animal feed, or an animal feed additive. The tissue may be callus from a transgenic plant. The tissue may be seeds from a transgenic plant that accumulate peptides, antagonist IL-10R peptides, concatenated antagonist IL-10R peptides, or anti-IL-10 single domain antibodies described herein. A transgenic plant may be regenerated from tissues of a transgenic plant. A transgenic plant may be a product of sexual crossing of a first transgenic plant and a second transgenic plant or a non-transgenic plant where the product plant retains a synthetic nucleic acid introduced to the first transgenic plant. A transgenic plant may be a product of self-pollination of a first transgenic plant with itself.

An embodiment provides a progeny of any one of the transgenic plants described herein. The transgenic plant may express any one of the antibodies described herein. The antibodies may target endogenous molecules produced by the host animal ingesting the transgenic plant or tissues thereof. The targeted endogenous molecules may be but are not limited to interleukins, cytokines, hormones, peptides, cellular receptors, clusters of differentiation, or related molecules. The transgenic plants of the present disclosure may express other peptides or proteins that impact immune response of an animal fed with the transgenic plant or tissues thereof. The transgenic plant may contain at least one of the expression cassettes that are described herein. The transgenic plant may be produced using the vectors described herein. The transgenic plant may be capable of producing any one of the peptides, antagonist IL-10R peptides, concatenated antagonist IL-10R peptides, or anti-IL-10 single domain antibodies described herein. The transgenic plant expressing peptides, antagonist IL-10R peptides, concatenated antagonist IL-10R peptides, or anti-IL-10 single domain antibodies described herein, may be but is not limited to tobacco plant, corn plants, soy bean plants, or any other plant commonly eaten by animals.

The transgenic plants may express peptides and proteins that modulate, stimulate, or augment the immune system, or immune response of an animal fed the transgenic plants or tissues thereof. The transgenic plants may express antibodies targeting endogenous molecules produced by the host animal ingesting the transgenic plants or tissues thereof. The antibodies expressed by the transgenic plant may bind to molecules such as interleukins, cytokines, hormones, peptides, cellular receptors, clusters of differentiation, or similar molecules. The transgenic plants may express other peptides or proteins that modulate various endogenous immune system pathways, endocrine pathways, or other physiological systems. More specifically, the transgenic plants may express express one or more antibodies that bind to interleukin 10 (IL-10), or one or more peptide or protein antagonists that interfere or block the IL-10 receptor complex (IL-10R), or one or more peptide or protein molecules that otherwise inhibit IL-10 signaling pathways.

The transgenic plants, or tissue thereof may modulate, stimulate, or augment the immune system, or immune response of an animal fed the transgenic plant or tissues thereof. The transgenic plants or tissues thereof may improve the gastrointestinal physiology of an animal eating the plants. The transgenic plants or tissues thereof may decrease the binding of IL-10 with the IL-10 receptor (IL-10R) when fed to poultry. The transgenic plants or tissues thereof may maintain or improve the body weight, and, or the feed conversion ratio, of poultry fed the transgenic plants or tissues thereof, relative to poultry fed the same feed lacking the transgenic plants or tissues thereof. The transgenic plants or tissues thereof may be dosed at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed. The transgenic plants and tissues thereof may also improve the body weight or feed conversion ratio of poultry when used in mash (non-pelleted) feed.

In an embodiment, a method of making any one of the transgenic plants described herein is provided. The method may comprise culturing explants from a target plant and contacting them with a vector that contains at least one expression cassette described herein. The target plant may be a corn or soy bean plant, or it may be wheat, rice, sorghum, tobacco, canola, cotton, switchgrass, or another plant. The method may include contacting the vector with the plant explant, for example, by using biolistic transformation or by using *Agrobacterium* transformation. Once the explant has been contacted by the vector, methods of selecting and regenerating whole plants may be used that are known in the art.

In an embodiment, any one of the antagonist IL-10R peptides, concatenated antagonist IL-10R peptides or anti-IL-10 single domain antibodies may be isolated from the transgenic plant or plant tissue.

In an embodiment, the specific recombinant, engineered or synthetic molecules described herein may be expressed by other hosts and may be isolated from the hosts.

In an embodiment, the transgenic plants or tissues thereof, or the isolated antagonist IL-10R peptides, concatenated antagonist IL-10R peptides or anti-IL-10 single domain antibodies may be included in an animal feed.

In an embodiment, an animal feed that includes any one of the transgenic plants, or tissues thereof described herein is provided. The term "animal feed" refers to any food, feed, feed composition, preparation, additive, supplement, or mixture suitable and intended for intake by animals for their nourishment and growth. The animal feed comprising transgenic plants, or plant tissues, may decrease the binding of IL-10 with the IL-10R when fed to poultry. The animal feed comprising transgenic plants, or plant tissues, may maintain or improve the body weight, and, or the feed conversion ratio, of poultry fed the transgenic plants or tissues thereof, relative to poultry fed the same feed lacking the transgenic plants or tissues thereof. The animal feed may comprise transgenic plants or tissues thereof at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed. The animal feed or animal feed additives comprising transgenic plants and tissues thereof may also improve the body weight or feed conversion ratio of poultry when used in mash (non-pelleted) feed. The animal feed may include an isolated antagonist IL-10R peptide, concatenated antagonist IL-10R peptides or anti-IL-10 single domain antibody. The antagonist IL-10R peptide, concatenated antagonist IL-10R peptides or anti-IL-10 single domain antibodies included in the animal feed may be active in the gastrointestinal environment of animals. The antagonist IL-10R peptide, concatenated antagonist IL-10R peptides or anti-IL-10 single domain antibody included the animal feed may be a peptide or antibody that is stable to pepsin digestion. The antagonist IL-10R peptide, concatenated antagonist IL-10R peptides, anti-IL-10 single domain antibodies included the animal feed may be a peptide or antibody that is digested by pepsin. The animal may be a monogastric animal. The monogastric animal may be but is not limited to a chicken, a turkey, or a duck. The antagonist IL-10R peptide, concatenated antagonist IL-10R peptides or anti-IL-10 single domain antibody may be active after preparation of the animal feed. The temperatures which feeds are exposed to during preparation may be within the range of 20° C. to 70° C., endpoints inclusive. The temperature may be 20° C., 25° C., 30° C., 35° C., 40° C., 45° C., 50° C., 55° C., 60° C., 65° C., 70° C., 20° C., to 25° C., 20° C., to 30° C., 2° C. to 35° C., 20° C. to 40° C., 20° C., to 45° C., 20° C. to 50° C., 20° C. to 55° C., 20° C. to 60° C., 20° C. to 65° C., 20° C. to 70° C., 30° C. to 70° C., 40° C. to 70° C., 50° C. to 70° C., 60° C. to 60° C., or less than 70° C. The temperatures which feeds are exposed to during pelleting may be within the range of 70° C. to 130° C., endpoints inclusive. The temperature may be 70° C., 75° C., 80° C., 85° C., 90° C., 95° C., 100° C., 105° C., 110° C., 115° C., 120° C., 125° C., 130° C., 0° C. to 75° C., 70° C. to 80° C., 70° C. to 85° C., 70° C. to 90° C., 70° C. to 95° C., 70° C. to 100° C., 70° C. to 105° C., 70° C. to 110° C., 70° C. to 115° C., 70° C. to 120° C., 70° C. to 125° C., 70° C. to 130° C., 80° C. to 130° C., 90° C. to 130° C., 100° C. to 130° C., 110° C. to 130° C., 120° C. to 130° C., or less than 130° C.

The antagonist IL-10R peptide, concatenated antagonist IL-10R peptides or anti-IL-10 single domain antibody may have improved thermal stability and may retain activity after being exposed to high temperatures during feed pelleting.

In an embodiment, the animal feed may further include a feed supplement. The feed supplement may be any plant material. The plant material may be a non-transgenic plant or a transgenic plant. The plant material may include a transgenic plant or a mutant plant. The plant material may be a grain that contains starch. The plant material may be a grain that contains fiber. The plant material may be achemically treated forage. The plant material may be a non-transgenic plant or part thereof. The plant material may include at least one component selected from the group consisting of: barley, wheat, rye, oat, corn, rice, triticale, beet, sugar beet, spinach, cabbage, quinoa, corn meal, corn pellets, corn oil, distillers grains, forage, wheat meal, wheat pellets, wheat grain, barley grain, barley pellets, soybean meal, soybean oilcake, lupin meal, rapeseed meal, sorghum grain, sorghum pellets, rapeseed, sunflower seed, and cotton seed.

The feed supplement may be a mineral. The mineral may be a trace mineral. The mineral may be a macro mineral. The mineral may be rock phosphate or a phosphate salt. The mineral may be calcium phosphate. The feed supplement may be at least one vitamin. The at least one vitamin may be a fat-soluble vitamin. The feed supplement may be an amino acid. The feed supplement may include one or more exogenous enzymes. The one or more exogenous enzymes may include a phytase enzyme. The one or more exogenous enzymes may include a hydrolytic enzyme. The hydrolytic enzyme may be an enzyme classified under EC3.4 as hydrolase. The hydrolytic enzymes may be, but are not limited to, xylanases, mannanases, carbohydrases, proteases, peptidases, glucanases, cellulases, lipases, phospholipases, pectinases, galactosidases, laccases, amylases, hemicellulases, or cellobiohydrolases. The enzymes may be expressed in the transgenic plants or parts thereof included in the feed supplement. The feed supplement may include purified enzymes. The feed supplements may be but are not limited to growth improving additives, coloring agents, flavorings, stabilizers, limestone, stearine, starch, saccharides, fatty acids, or a gum. The coloring agents may be carotenoids. The carotenoids may be but are not limited to cantaxanthin, beta-carotene, astaxanthin, or lutein. The fatty acids may be polyunsaturated fatty acids. The polyunsaturated fatty acids may include but are not limited to arachidonic acid, docosohexaenoic acid (DHA), eicosapentaenoic acid (EPA) or gamma-linoleic acid.

The feed supplement may include at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix. The feed supplement may include fish meal, fish oil, bone meal, feather meal and animal fat. The feed supplement may include yeast or yeast extract.

In an embodiment, a method of preparing an animal feed is provided. The method may include producing any one of the antagonist IL-10R peptides, concatenated antagonist IL-10R peptides or anti-IL-10 single domain antibodies described herein by any one of the methods described herein.

An embodiment provides a method of producing an animal feed. The method may include mixing any one of the transgenic plants or tissues thereof described herein, or the progeny thereof with plant material. The transgenic plant may be a progeny of the transgenic plant that include one or more synthetic polynucleotides encoding peptides and antibodies described herein. The one or more polynucleotides may be included in a genetic construct(s) or an expression cassette(s). The method may comprise making any transgenic plant herein. The transgenic plant or its progeny may be the plant expressing a peptide or protein produced by the method herein. The method may further include pelletizing the mixture. The method may further include adding a feed supplement to the mixture. The feed supplement may include at least one exogenous enzyme. The at least one exogenous enzyme may be selected from the group consisting of: phytase, xylanase, mannanase, protease, glucanase, and cellulase. Preparing the animal feed may include combining one or more transgenic plants described herein with any other feed supplement.

An expression cassette having one or more polynucleotides encoding an antagonist IL-10R peptide, concatenated antagonist IL-10R peptides or anti-IL-10 single domain antibody in a plant may be expressed prior to the step of step of mixing the plant, or prior to the step of pelletizing the plant. The expression may be constitutive or the expression may be induced. Upon the expression of the nucleic acid(s), the transgenic plant may have an increased level of the antagonist IL-10R peptide, concatenated antagonist IL-10R peptides or anti-IL-10 single domain antibodies compared to the level of antagonist IL-10R peptide, concatenated antagonist IL-10R peptides or anti-IL-10 single domain antibodies in a non-transgenic plant of the same genetic background but lacking the one or more expression cassettes.

The antagonist IL-10R peptide, concatenated antagonist IL-10R peptides or anti-IL-10 single domain antibodies may be isolated, purified and added to the animal feed as a pure antagonist IL-10R peptide, concatenated antagonist IL-10R peptides or anti-IL-10 single domain antibodies. The antagonist IL-10R peptide, concatenated antagonist IL-10R peptides or anti-IL-10 single domain antibodies may be isolated from the intact host organism and added to the animal feed as an antagonist IL-10R peptide, concatenated antagonist IL-10R peptides or anti-IL-10 single domain antibodies composition. The antagonist IL-10R peptide, concatenated antagonist IL-10R peptides or anti-IL-10 single domain antibodies may be added to the animal feed in admixture with other feed supplements. The transgenic plant including the antagonist IL-10R peptide, concatenated antagonist IL-10R antagonist peptides or anti-IL-10 single domain antibodies or the purified antagonist IL-10R peptide, concatenated antagonist IL-10R peptides or anti-IL-10 single domain antibodies may be combined with other feed supplements to form premixes.

An animal feed may be produced as mash feed. The animal feed may be produced as pelleted feed. The milled feed stuffs may be mixed with the premix that includes any one of the transgenic plants that include an antagonist IL-10R peptide, concatenated antagonist IL-10R peptides or anti-IL-10 single domain antibody. The antagonist IL-10R peptide, concatenated antagonist IL-10R peptides or anti-IL-10 single domain antibody may be an antagonist IL-10R peptide, concatenated antagonist IL-10R peptides or anti-IL-10 single domain antibody that is/are stable to pepsin digestion. The antagonist IL-10R peptide, concatenated antagonist IL-10R peptides or anti-IL-10 single domain antibody may be an antagonist IL-10R peptide, concatenated antagonist IL-10R peptides or anti-IL-10 single domain antibody that is/are digestable by pepsin. The milled feed stuffs may include the plant material and the feed supplements described herein. The feed supplements may include one or more exogenous enzymes described herein. Enzymes may be added as liquid or solid formulations. For mash feed, a solid or liquid peptide formulation may be added before or during the mixing step. For pelleted feed, the peptide preparation may be added before or after the pelleting step. The antagonist IL-10R peptide, concatenated antagonist IL-10R peptides or anti-IL-10 single domain antibody may be included in premix. The premix may also include vitamins and trace minerals. Macro minerals may be added separately to animal feedstock.

An embodiment comprises a method of treating or preventing a gastrointestinal infection in an animal. The gastrointestinal infection may be caused by a gastrointestinal pathogen. As used herein, a gastrointestinal pathogen may include a bacterium, yeast, fungi, archaea, virus, protozoa, or other infectious agent that is capable of replication inside or outside of the infected host animal, and causes irritation, necrosis, cellular disruption, or cellular damage within the infected host animal, or otherwise stimulates or modulates the immune system of the infected host animal. The gastrointestinal pathogen may belong to the genus *Eimeria*. The gastrointestinal pathogen may be but is not limited to *Eimeria tenella, Eimeria acervulina*, or *Eimeria maxima*. The method may include administering to an animal any one of the antagonist IL-10R peptides or anti-IL-10 single domain antibodies described herein. Administering may be performed by any known route, for example, by injection. Administering may be performed by feeding the infected animal with the transgenic plant expressing one or more antibodies that bind to IL-10, or one or more peptide or protein antagonists to the IL-10R, or plant tissues thereof, or animal feed or feed compositions containing the transgenic plants and tissues thereof. The method comprises administering any one of the antagonist IL-10R peptides or anti-IL-10 single domain antibodies described herein in a therapeutically effective amount. As used herein, a therapeutically effective amount of an antagonist IL-10 peptide, concatenated antagonist IL-10 peptides or anti-IL-10 single domain antibody is an amount effective to reduce the symptoms of the gastrointestinal disease in the animal when administered daily for a period of from one week to two months. The therapeutically effective amounts of the antagonist IL-10R peptide or concatenated antagonist IL-10R peptides may be a dose of less than 500 mg per kg of pelleted feed, or more preferably less than 50 mg per kg of pelleted feed, or even more preferably less than 5 mg per kg of pelleted feed, or even more preferably less than 1 mg per kg of pelleted feed.

The therapeutically effective amounts of the anti-IL-10 single domain antibody may be at a dose of less than 500 mg per kg of pelleted feed, or more preferably at a dose of less than 50 mg per kg of pelleted feed, or even more preferably at a dose of less than 5 mg per kg of pelleted feed, or even more preferably at a dose of less than 1 mg per kg of pelleted feed.

The therapeutically effective amounts of the transgenic plants or tissues thereof may be at a dose of less than 700 kg per ton of pelleted feed, or more preferably at a dose of less than 5 kg per ton of pelleted feed, or more preferably at a dose of less than 1 kg per ton of pelleted feed, or even more preferably at a dose of less than 500 g per ton of pelleted feed, or even more preferably at a dose of less than 50 g per ton of pelleted feed, or yet even more preferably at a dose less than 5 g per ton of pelleted feed.

The therapeutically effective amounts of the animal feed may comprise transgenic plants or tissues thereof at less than 700 kg per ton of pelleted feed, or more preferably at less than 5 kg per ton of pelleted feed, or more preferably at less than 1 kg per ton of pelleted feed, or even more preferably at less than 500 g per ton of pelleted feed, or even more preferably at less than 50 g per ton of pelleted feed, or yet even more preferably at less than 5 g per ton of pelleted feed.

An embodiment comprises a method of stimulating or modulating the immune system and improving gastrointestinal physiology of an animal comprising feeding the animal with the transgenic plants or tissues thereof. As used herein, the term "modulate" means to change, or respond to a stimulus. In this context "modulate" could mean to increase a response or decrease a response. With regards to modulating an immune response, it means to stimulate or to decrease an immune response. Words that are used synonymously with decrease as it relates to modulation of a response include blocking, interfering, antagonizing, lowering, alleviating, shutting down, or removing. The term gastrointestinal physiology describes the biological state of an animal's gastrointestinal tract, including the foregut, midgut, and hindgut. The actual anatomical features of the gastrointestinal tract may vary among animal species, but in poultry include the esophagus, crop, proventriculus, ventriculous, gizzard, duodenum, jejunum, ileum, small intestine, large intestine, cloaca, and ceca. The biological state of the gastrointestinal tract may be described as healthy or normal, lacking any abnormal visual or pathological observation, or aberrant histological evaluation. The biological state of the gastrointestinal tract may be described as inflamed, infected, or necrotic, all of which describe a physiological state that is impaired and could be improved to a normal or healthy state.

In an embodiment, a method of improving the gastrointestinal physiology of an animal is provided. The method may comprise feeding the animal any of the transgenic plants, or plant parts, described herein. In an embodiment, the method may comprise feeding the animal any of the anti-IL-10 single domain antibodies, peptides, or antagonist IL-10R s described herein.

In an embodiment, a method of improving animal performance or animal gastrointestinal physiology is provided. The method may comprise feeding the animals any of the transgenic plants expressing one or more antibodies that bind to IL-10, or one or more peptide or protein antagonists to the IL-10R, or plant tissues thereof, or feed, or feed compositions containing the transgenic plants or tissues thereof, or anti-IL-10 single domain antibodies, or the IL-10R antagonists. The method may comprise feeding the animals any one of the transgenic plants, or plant parts described herein. As used herein, animal performance is synonymous with animal growth or animal productivity, and each term can be used interchangeably. Animal performance relates to the weight gain of the animal over time, and to the animal's feed conversion ratio, which is defined as the mass of feed eaten by the animal divided by the weight gain of the animal. These terms may be used to describe either, or both, weight gain and feed conversion ratio, so an improvement in animal performance may indicate an increase in weight gain relative to control animals, and, or, a decrease (less feed eaten per mass of animal growth) in feed conversion ratio. In an embodiment, the method may comprise feeding an animal any of the animal feed or animal feed additives comprising any of the anti-IL-10 single domain antibodies, peptides, IL-10R antagonists, or transgenic plants or tissues thereof, described herein.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

EMBODIMENTS

1. At least one antagonist IL-10R peptide, wherein (i) the at least one antagonist IL-10R peptide is one peptide comprising an amino acid sequence with at least 90% identity to a reference sequence selected from the group consisting of: SEQ ID NOS: 1-13, or (ii) the at least one antagonist IL-10R peptide comprises concatenated peptides comprising an amino acid sequence with at least 90% identity to a reference sequence selected from the group consisting of: SEQ ID NOS: 32-40.
2. The at least one antagonist IL-10R peptide of embodiment 1, wherein each of the concatenated peptides are linked to each other by one or more linkers.
3. The at least one antagonist peptide of any one or both of embodiments 1 and 2, wherein the one or more linkers comprise a sequence selected from the group consisting of SEQ ID NOS: 41-44, and 65.
4. The at least one antagonist IL-10R peptide of any one or more of embodiments 1-3, wherein the at least one peptide or each one of the concatenated peptides comprise an N-terminal signal peptide or C-terminal signal peptide, or both.
5. The at least one antagonist IL-10R peptide of any one or more of embodiments 1-4, wherein the N-terminal signal peptide is selected from a group consisting of: OsGluB4sp (rice Glu-B4 glutelin signal peptide), BAASS (barley alpha amylase signal sequence), PR1 (pathogenesis related protein), or zein 27 (xGZm27ss) signal peptide.
6. The at least one antagonist IL-10R peptide of any one or more of embodiments 1-5, wherein the peptide is stable at a temperature in a range from 70° C. to 90° C.
7. The at least one antagonist IL-10R peptide of any one or more of embodiments 1-6, wherein the peptide is digestible by pepsin.
8. The at least one antagonist IL-10R peptide of any one or more of embodiments 1-6, wherein the peptide is stable to digestion by pepsin.
9. The at least one antagonist IL-10R peptide of any one or more of embodiments 1-8, wherein the C-terminal signal peptide is selected from a group consisting of: KDEL (SEQ ID NO: 29), HDEL (SEQ ID NO: 30), SEKDEL (SEQ ID NO: 31), HvVSD from barley polyamine oxidase, or HvAle from barley aleurone (thiol protease).

10. A synthetic polynucleotide encoding the at least one antagonist IL-10R peptide of any one or more of embodiments 1-9.

11. The synthetic polynucleotide of embodiment 10, wherein the synthetic polynucleotide comprises a sequence with at least 90% identity to a reference sequence selected from the group consisting of: 16-28, and 56.

12. An anti-IL-10 single domain antibody that binds to a polypeptide comprising an amino acid sequence of SEQ ID NO: 80.

13. The anti-IL-10 single domain antibody of embodiment 12, wherein the antibody has a molecular mass in a range of 10 kDa to 20 kDa.

14. The anti-IL-10 single domain antibody of any one or both of embodiments 12 and 13, wherein the antibody is stable at a temperature in a range from 70° C. to 90° C.

15. The anti-IL-10 single domain antibody of any one or more of embodiments 12-14, wherein the antibody binds to chicken Il-10 with an $EC_{50}$ of 30 nM or less in a cell ELISA assay.

16. The anti-IL-10 single domain antibody of any one or more of embodiments 12-15, wherein the antibody comprises an amino acid sequence with at least 90% identity to a sequence selected from the group consisting of SEQ ID NOs: 87-154.

17. The anti-IL-10 single domain antibody of any one or more of embodiments 12-16, wherein the antibody comprises the amino acid sequence with at least 90% identity to a sequence selected from the group consisting of SEQ ID NOs: 89, 135, and 146.

18. The anti-IL-10 single domain antibody of any one or more of embodiments 12-17, wherein the antibody is fused to an N-terminal signal peptide or C-terminal signal peptide, or both.

19. The anti-IL-10 single domain antibody of any one or more of embodiments 12-18, wherein the N-terminal signal peptide is selected from a group consisting of: OsGluB4sp (rice Glu-B4 glutelin signal peptide), BAASS (barley alpha amylase signal sequence), PR1 (pathogenesis related protein), or zein 27 (xGZm27ss) signal peptide.

20. The anti-IL-10 single domain antibody of any one or more of embodiments 12-19, wherein the C-terminal signal peptide is selected from a group consisting of: KDEL (SEQ ID NO: 29), HDEL (SEQ ID NO: 30), SEKDEL (SEQ ID NO: 31), HvVSD from barley polyamine oxidase, or HvAle from barley aleurone (thiol protease).

21. The anti-IL-10 single domain antibody of any one or more of embodiments 12-20, wherein the anti-IL-10 single domain antibody is digestible by pepsin.

22. The anti-IL-10 single domain antibody of any one or more of embodiments 12-20, wherein the anti-IL-10 single domain antibody is stable to digestion by pepsin.

23. The anti-IL-10 single domain antibody of any one or more of embodiments 12-22, wherein the anti-IL-10 single domain antibody is stable to a temperature exposure of greater than 70° C. and less than 100° C.

24. A synthetic polynucleotide encoding the anti-IL-10 single domain antibody of any one or more of embodiments 12-23.

25. The synthetic polynucleotide of embodiment 24, wherein the synthetic polynucleotide comprises a sequence with at least 90% identity to a reference sequence selected from the group consisting of: SEQ ID NOs: 173-178.

26. A transgenic plant or tissues thereof comprising one or more polynucleotides encoding the at least one antagonist IL-10R peptide of any one or more of embodiments 1-9, or the anti-IL-10 single domain antibody of any one or more of embodiments 12-23.

27. A transgenic plant or tissues thereof comprising one or more polynucleotides encoding the at least one antagonist IL-10R peptide, or the anti-IL-10 single domain antibody.

28. The transgenic plant or tissues thereof of embodiment 27, wherein the antagonist IL-10R peptide is one peptide comprising an amino acid sequence with at least 90% identity to a reference sequence selected from the group consisting of: SEQ ID NOS: 1-13.

29. The transgenic plant or tissues thereof of any one or both embodiments 27 and 28, wherein the antagonist IL-10R peptide comprises concatenated antagonist IL-10R peptides comprising an amino acid with at least 90% identity to a reference sequence selected from the group consisting of SEQ ID NOS: 32-40.

30. The transgenic plant or tissues thereof of any one or more of embodiments 27-29, wherein the anti-IL-10 single domain antibody binds to a polypeptide comprising an amino acid sequence of SEQ ID NO: 80.

31. The transgenic plant or tissues thereof of any one or more of embodiments 27-30, wherein the anti-IL-10 single domain antibody has a molecular mass in a range of 10 kDa to 20 kDa.

32. The transgenic plant or tissues thereof of any one or more of embodiments 27-31, wherein the anti-IL-10 single domain antibody is stable at a temperature in a range from 70° C. to 90° C.

33. The transgenic plant or tissues thereof of any one or more of embodiments 27-32, wherein the anti-IL-10 single domain antibody binds to chicken Il-10 with an $EC_{50}$ of 30 nM or less in a cell ELISA assay.

34. The transgenic plant or tissues thereof of any one or more of embodiments 27-33, wherein the anti-IL-10 single domain antibody comprises an amino acid sequence with at least 90% identity to a sequence selected from the group consisting of SEQ ID NOs: 87-154.

35. The transgenic plant or tissues thereof of any one or more of embodiments 27-34, wherein the anti-IL-10 single domain antibody comprises the amino acid sequence with at least 90% identity to a sequence selected from the group consisting of SEQ ID NOs: 89, 135, and 146.

36. The transgenic plant or tissues thereof of any one or more of embodiments 27-35, wherein the one or more polynucleotides comprise a sequence with at least 90% identity to a reference sequence selected from the group consisting of SEQ ID NOS: 16-28, and 56.

37. The transgenic plant or tissues thereof of any one or more of embodiments 27-36, wherein the one or more polynucleotides comprise a sequence with at least 90% identity to a reference sequence selected from the group consisting of SEQ ID NOS: 173-178.

38. The transgenic plant or tissues thereof of any one or more of embodiments 27-37, wherein the anti-IL-10 single domain antibody is digestible by pepsin.
39. The transgenic plant or tissues thereof of any one or more of embodiments 27-37, wherein the anti-IL-10 single domain antibody is stable to digestion by pepsin.
40. The transgenic plant or tissues thereof of any one or more of embodiments 27-39, wherein a plant is selected from the group consisting of: corn, soybean, wheat, rice, sorghum, canola, cotton, and switchgrass.
41. An animal feed comprising the transgenic plant or tissues thereof of any one or more of embodiments 26-40.
42. An animal feed comprising at least one antagonist IL-10R peptide of any one or more of embodiments 1-9, or an anti-IL-10 single domain antibody of any one or more of embodiments 12-23.
43. The animal feed of embodiment 42, wherein the at least one IL-10R antagonist IL-10R peptide, or the anti-IL-10 single domain antibody is active upon expression in the plant and exposure to a temperature in the range from 25° C. to 130° C.
44. The animal feed of any one or more of embodiments 41, or 42-43 further comprising a feed supplement.
45. The animal feed of any one or more of embodiments 41, or 42-44, wherein the feed supplement is plant material.
46. The animal feed of any one or more of embodiments 41, or 42-45, wherein the plant material is a non-transgenic plant or a transgenic plant.
47. The animal feed of any one or more of embodiments 41, or 42-46, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.
48. The animal feed of any one or more of embodiments 41, or 42-47, wherein the feed supplement includes one or more exogenous enzymes.
49. The animal feed of any or more of embodiments 41, or 42-48, wherein the one or more exogenous enzymes includes a hydrolytic enzyme selected from the group consisting of: xylanase, endoglucanase, cellulase, protease, phytase, amylase and mannanase.
50. The animal feed of any one or more of embodiments 41, or 42-49, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.
51. A method of treating or preventing a gastrointestinal infection in an animal comprising feeding the animal the at least one antagonist IL-10R peptide of any one or more of embodiments 1-9, the anti-IL-10 single domain antibody of any or more of embodiments 12-23, the transgenic plant or tissues thereof of any one or more of embodiments 26-40, or the animal feed of any one more of embodiments 41-50.
52. The method of embodiment 51, wherein the gastrointestinal infection is caused by a gastrointestinal pathogen selected from the group consisting of: bacteria, yeast, fungi, archae, virus, and protozoa.
53. The method of any one or both of embodiments 51 and 52, wherein the gastrointestinal pathogen belongs to the genus *Eimeria*.
54. The method any one or more of embodiments 51-53, wherein the gastrointestinal pathogen is selected from the group consisting of: *Eimeria tenella, Eimeria acervulina*, and *Eimeria maxima*.
55. A method of stimulating or modulating the immune system and improving gastrointestinal physiology of an animal comprising feeding the animal the at least one antagonist IL-10R peptide of any one or more of embodiments 1-9, the anti-IL-10 single domain antibody of any or more of embodiments 12-23, the transgenic plant or tissues thereof of any one or more of embodiments 26-40, or the animal feed of any one or more of embodiments 41-50.
56. A method of improving animal performance comprising feeding an animal the at least one antagonist IL-10R peptide of any one or more of embodiments 1-9, the anti-IL-10 single domain antibody of any one or more of embodiments 12-23, the transgenic plant or tissues thereof of any one or more of embodiments 26-40, or the animal feed of any one or more of embodiments 41-50.
57. A method of preparing an animal feed comprising mixing the antagonist IL-10R peptide of any one or more of embodiments 1-9, the anti-IL-10 single domain antibody of any one or more of embodiments 12-23, or the transgenic plant or tissues thereof of any one or more of embodiments 26-40 with plant material to form a mixture.
58. The method of embodiment 57, wherein the method further comprises pelletizing the mixture.
59. The method of any one or both of embodiments 57 and 58, wherein the method further comprises adding a feed supplement to the mixture.
60. The method of any one or more of embodiments 57-59, wherein the plant material is a non-transgenic plant or a transgenic plant.
61. The method of any one or more of embodiments 57-60, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.
62. The method of any one or more of embodiments 57-61, wherein the feed supplement includes one or more exogenous enzymes.
63. The method of any or more of embodiments 57-62, wherein the one or more exogenous enzymes includes a hydrolytic enzyme selected from the group consisting of: xylanase, endoglucanase, cellulase, protease, phytase, amylase and mannanase.
64. The method of any one or more of embodiments 57-63, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

Further embodiments herein may be formed by supplementing an embodiment with one or more elements from any one or more other embodiments herein, and/or substituting one or more elements from one embodiment with one or more elements from one or more other embodiments

EXAMPLES

The following non-limiting examples are provided to illustrate particular embodiments. The embodiments throughout may be supplemented with one or more details from one or more examples below, and/or one or more elements from an embodiment may be substituted with one or more details from one or more examples below.

Example 1. Strategies for Engineering Peptides and Antibodies

While reducing IL-10 levels prior to and during *Eimeria* infection can help control the negative effects of Coccidiosis, the mechanisms known in the art that have been employed to reduce IL-10 levels are expensive and have questionable robustness to be employed broadly in industry. The shortcomings of the existing technologies (using isolated, or partially purified, peptides or antibodies) to control Coccidiosis can be addressed in several important ways using biotechnology to design novel products that target the IL-10 signaling pathway. First, by broadening antibody discovery and development beyond the common target chicken production system, as is currently done by inoculating maternal hens or eggs with conjugated IL-10 peptides, novel antibodies and peptides can be developed that have been specifically tailored to controlling Coccidiosis. The peptides and synthetic antibodies developed herein were engineered to have high affinity (thus reducing dosing levels), improved thermal stability (to survive pelleting when mixed into animal feed), and low molecular weight to promote high-levels of expression (to maximize production economics), properties that are not found in naturally occurring peptides and antibodies and that could not be simply selected for in nature, nor could these properties be efficiently replicated in a hen or egg production system without undue experimentation. Second, by engineering the genes encoding the peptides and antibodies developed herein into plants, their delivery can be made by directly feeding the plants or plant tissues without additional isolation, or purification, or formulation, into the diet. This greatly benefits production and animal administration economics. That such a combination of technologies works effectively in controlling Coccidiosis was unexpected. It was anticipated that antibodies and peptides delivered in whole grain or meal, with no isolation, would either not survive the pelleting process when being mixed in feed (which is often the case when using larger antibodies, such as IgG's or IgY's, and peptides), not diffuse adequately from the plant matrix and be readily available to the animal at sufficient concentrations to modulate the IL-10 signaling pathway, or would be rapidly degraded in the digestive tract. Unexpectedly, the combination of technologies used to make the products described herein, was able to overcome these challenges and address the challenges confronting current methods used in the art for controlling Coccidiosis.

Plant expression of heterologous peptides and proteins is one of the least expensive recombinant protein production systems on the planet. By engineering corn or soy beans to produce anti-IL-10 antibodies, IL-10R peptide antagonists, or other molecules that inhibit IL-10 signaling, these molecules can be made at high concentrations, e.g., a concentration in a range from 0.01 mg of heterologous protein (anti-IL-10 antibodies, IL-10R peptide antagonists, or other proteins or peptides that inhibit IL-10 signaling) per gram of milled grain up to as much as 20 mg of heterologous protein per gram of milled grain. Heterologous proteins and peptides produced in seed tissue are naturally stabilized in the seed as it progresses through its desiccation process following seed development. Antibodies and peptide antagonists produced in corn or soy beans can be delivered directly into poultry diets by simply milling the grain and mixing it with the other ingredients. While other processing and formulation steps may be used, there is no need for additional processing steps that would be required if these products were produced by fermentation or by inoculating eggs, both of which are more expensive processes. Further, because these molecules are encoded by DNA that is stably integrated into the plants' genome, there is the opportunity to further engineer these molecules and endow them with beneficial properties that cannot be implemented when generating antibodies in maternal hens or by inoculating eggs.

Figure 3:
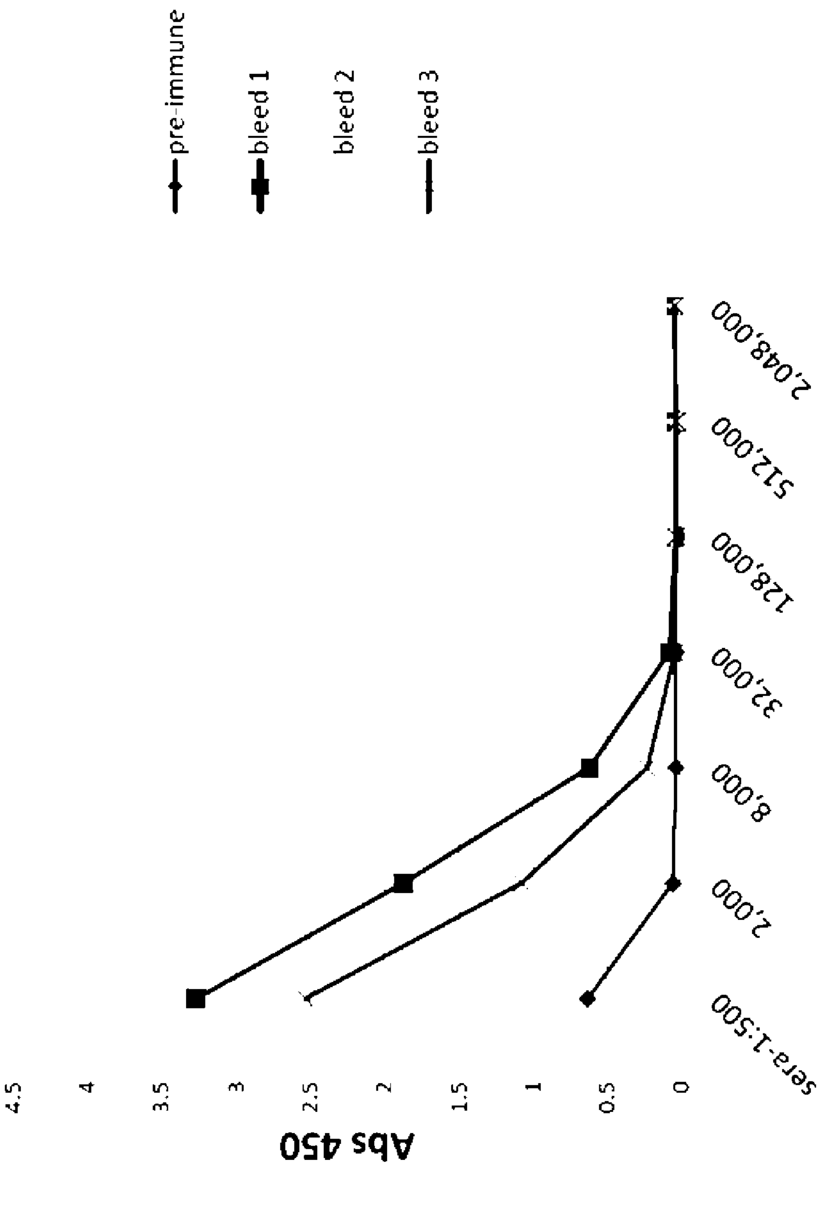
FIG. 3 illustrates the antibody response generated by a llama injected with full-length chicken IL-10. It demonstrates that specific antibodies are produced by the animal that increases the binding of chicken IL-10 post-injection, relative to the pre-immune (that is, pre-injection) state of the animal.

Engineering of antibodies, proteins, and peptides provides additional opportunities to address industry needs in modulating IL-10 signaling pathways. Anti-IL-10 antibodies can be generated by any number of hosts, including camels, calves, chickens, goats, horses, humans, llamas, mice, rabbits, rats, sharks, and many other species. The particular choice of host for generating an antibody may depend on a variety of considerations including the choice of antigen (will the antigen be recognized as self by the host or recognized as foreign and generate an appropriate immune response), the choice of antibody (IgG, IgY, a polyclonal, monoclonal, etc.), ease of working with the host, the amount of antibody desired, the intended species the antibody will be used in, and the type of antibody desired (full length (approximately 120-160 kDa), antibody fragments (Fab that can be approximately 50 kDa, or scFv that can be approximately 25 kDa), or single domain antibodies (that can be approximately 10-20 kDa)). Single domain antibodies are small synthetic antibodies abbreviated by sdAb, sdAB, $V_HH$, or $V_{NAR}$, and have specific features that make them suitable for targeting IL-10 when delivered through feed into an animal's digestive tract. In particular, sdAbs are generally recognized as having improved thermal stability relative to full length and other antibody fragments, and are very susceptible to molecular engineering, which provides the possibility of further improving their thermal stability and affinity, both of which may help in reducing the necessary dose required in the animal feed to modulate the IL-10 signaling pathway (E. R. Goldman, G. P. Anderson, J. L. Liu, J. B. Delehanty, L. J. Sherwood, L. E. Osborn, L. B. Cummins, and A. Hayhurst, 2006, Facile Generation of Heat-Stable Antiviral and Antitoxin Single Domain Antibodies from a Semisynthetic Llama Library, Annal. Chem., 78:8245-8255, which is incorporated herein by reference as if fully set forth). Chicken IL-10 (amino acid residues in positions 2 to 151 of SEQ ID NO: 80) was compared with llama IL-10 (SEQ ID NO: 207). Sequence alignment analysis showed the sequences to be only 48% identical. Based on this analysis, the full-length *Gallus gallus* IL-10 (chicken IL-10 or cIL-10) was selected as the target antigen for generating sdAbs in camels or llamas. Because llamas are not exposed to cIL-10, an endogenous chicken interleukin, and it's only through a biotechnology process that cIL-10 can be made, isolated and dosed into a llama, llamas are naive to cIL-10 and it was found that it's possible to generate a significant immune response as shown in FIG. 3. Further, given that IL-10 is known to dimerize in vivo (K. Asadullah, W. Sterry, H. D. Volk, "Interleukin-10 Theraphy—Review of a New Approach", Pharmacological Reviews, 55 (2):241-269, 2003), using IL-10 peptides as target antigens is challenging because peptide epitopes may be selected that are not normally exposed in the IL-10 dimer in vivo. Thus, library generation and antibody screening may be more readily optimized, and synthetic antibodies developed, using full-length cIL-10. Another advantage of developing a single molecule for expression is that it can be selected from a diversity of molecules made by the inoculated host, allowing for screening and selection of a highly optimized sdAb that can be reproducibly made with great efficiency in corn or another host. In this way, many of the current challenges with modulating the IL-10 pathway in poultry can be addressed to bring this innovation into the marketplace.

Example 2. Peptide Selection

Synthetic peptides were designed by analyzing the crystal structures of human IL-10/IL-10R1 complexes, determining portions of the sequences of the human proteins that contribute to binding, and finding the analogous sequences in the chicken proteins by aligning the sequences of human and chicken IL-10 and IL-10R1, respectively, with Clustal Omega (Diaz-Valdez et al., 2011, Josephson et al., 2001, Naiyer et al., 2013, Ni et al., 2016, Reineke et al., 1998, Yoon et al., 2005, Zdanov et al., 1996). Amino acid sequences were obtained from Pub Med; and the presumed signal peptide, transmembrane, and intracellular sequences were removed from the alignments. All peptide sequences were checked for known allergenic epitopes using the Allergen Online Database.

Human IL-10 residues involved in binding to its receptor as determined by peptide mapping are as follows:

```
Chicken ------ LEPTCLHFSELLPARLRELRVKFEEIKDYFQSRDD
Huma    SPGQGTQSENSCTHFPGNLPNMLRDLRDAFSRVKTFFQMKDQ
        . . * :* ** ** **:** *..:* :** :*:

Chicken ELNIQLLSSELLDEFKGTFGCQSVSEMLRFYTDEVLPRAMQTSTSHQQSMGDLGNMLLGL
Human   -LDNLLLKESLLEDFKGYLGCQALSEMIQFYLEEVMPQAENQDPDIKAHVNSLGENLKTL
        *: **...**::*** :***::***::** :**:*:* : . . : :..**: * *

Chicken KATMRRCHRFFTCEKRSKAIKQIKETFEKMDENGIYKAMGEFDIFINYIEEYLLMRRR- (SEQ ID NO: 80)
Human   RLRLRRCHRFLPCENKSKAVEQVKNAFNKLQEKGIYKAMSEFDIFINYIEAYMTMKIRN (SEQ ID NO: 81)
        : :******: **::***::*:*::*:*::*:******.********** *: *: *
```

Human (AAA63207.1; SEQ ID NO: 81) and chicken (NP_001004414.2; SEQ ID NO: 80) sequences were obtained and edited as described above. Human IL-10 residues that are involved in binding to human IL-10R1 are in boldface and colored gray (Reineke et. al., 1998). Chicken IL-10 sequence alignment with the human IL-10 sequence is also shown.

Human IL-10 residues that bury >5 Å$^2$ surface area in the complex with the receptor (Yoon, et. al., 2005).

```
Chicken ------ LEPTCLHFSELLPARLRELRVKFEEIKDYFQSRDD
Human   SPGQGTQSENSCTHFPGNLPNMLRDLRDAFSRVKTFFQMKDQ
        . . * :* ** ** **:** *..:* :** :*:

Chicken ELNIQLLSSELLDEFKGTFGCQSVSEMLRFYTDEVLPRAMQTSTSHQQSMGDLGNMLLGL
Human   -LDNLLLKESLLEDFKGYLGCQALSEMIQFYLEEVMPQAENQDPDIKAHVNSLGENLKTL
        *: **...**::*** :***::***::** :**:*:* : . . : :..**: * *

Chicken KATMRRCHRFFTCEKRSKAIKQIKETFEKMDENGIYKAMGEFDIFINYIEEYLLMRRR- (SEQ ID NO: 80)
Human   RLRLRRCHRFLPCENKSKAVEQVKNAFNKLQEKGIYKAMSEFDIFINYIEAYMTMKIRN (SEQ ID NO: 81)
        : :******: **::***::*:*::*:*::*:******.********** *: *: *
```

Chicken IL-10 sequence (SEQ ID NO: 80) alignment with the human IL-10 sequence (SEQ ID NO: 81) is shown, with the two segments of the human IL-10 sequence that contribute the majority of binding surface (Diaz-Valdez et al., 2011; Josephson et al., 2001; Naiyer et al., 2013; Ni et al., 2016; Reineke et al., 1998; Yoon et al., 2005; and Zdanov et al., 1996), are indicated in boldface and colored gray. Helical regions are underlined.

Examples of peptide design based on alignment with predicted sequence regions of binding interactions:

```
Chicken ------ LEPTCLHFSELLPARLRELRVKFEEIKDYFQSRDD
Human   SPGQGTQSENSCTHFPGNLPNMLRDLRDAFSRVKTFFQMKDQ
        . . * :* ** ** **:** *..:* :** :*:

Chicken ELNIQLLSSELLDEFKGTFGCQSVSEMLRFYTDEVLPRAMQTSTSHQQSMGDLGNMLLGL
Human   -LDNLLLKESLLEDFKGYLGCQALSEMIQFYLEEVMPQAENQDPDIKAHVNSLGENLKTL
        *: **...**::*** :***::***::** :**:*:* :  .  .  : :..**: * *

Chicken KATMRRCHRFFTCEKRSKAIKQIKETFEKMDENGIYKAMGEFDIFINYIEEYLLMRRR- (SEQ ID NO: 80)
Human   RLRLRRCHRFLPCENKSKAVEQVKNAFNKLQEKGIYKAMSEFDIFINYIEAYMTMKIRN (SEQ ID NO: 81)
        : :******: **::***::*:*::*:*::*:******.********** *: *: *
```

Binding hot spots and helical regions of human IL-10 are designated as shown previously. Sequences within the chicken IL-10 sequence that encompass peptides P25 (SEQ ID NO: 5) and P26 (SEQ ID NO: 6) are designated by boldface italics and colored gray. Peptide P21 (SEQ ID NO: 1) consists of P25, P26, and all of the chicken IL-10 residues between them in the sequence.

Examples of peptide design based on alignment with binding hot spots:

```
Chicken ------ LEPTCLHFSELLPARLRELRVKFEEIKDYFQSRDD
Human   SPGQGTQSENSCTHFPGNLPNMLRDLRDAFSRVKTFFQMKDQ
        . . * :* **  ** **:** *..:* :** :*:

Chicken ELNIQLLSSELLDEFKGTFGCQSVSEMLRFYTDEVLPRAMQTSTSHQQSMGDLGNMLLGL
Human   -LDNLLLKESLLEDFKGYLGCQALSEMIQFYLEEVMPQAENQDPDIKAHVNSLGENLKTL
         *:  **...**::*** :***::***::** :**:*:* :  .  .  :  :..**: *  *

Chicken KATMRRCHRFFTCEKRSKAIKQIKETFEKMD[ENGIYKAMGEFDIFINYIEEYLLMRRR]- (SEQ ID NO: 80)
Human   RLRLRRCHRFLPCENKSKAVEQVKNAFNKLQEKGIYKAMSEFDIFNYIEAYMTMKIRN (SEQ ID NO: 81)
        : :******: **::***::*:*::*:*::*:******.********** *: *: *
```

Binding hot spots and helical regions of human IL-10 are designated as previously shown. Peptide P27 (SEQ ID NO: 7) is designated by boldface, italicized and is colored in gray. Peptide P22 (SEQ ID NO: 2) is designated in boldface and included in a frame. Peptide 27 is the region within the P22 sequence.

Alignment of human (SEQ ID NO: 83) and chicken (SEQ ID NO: 82) IL-10R1 soluble domain sequences:

```
Human IL-10R1    HGTELPSPPSVWFEAEFFHHILHWTPIPNQSESTCYEVALLRYGIE-SWNSISNCSQTLS
Chicken IL-10r1  --ELRLKPTRVRFVAEMVYHLLQWEPGPDAPSDTRYDVEHKIYGTNSPWTAIPNCMKIHG
                       .*  * * **:.:*:*:* *  :  ..* *:*    ** :  *.:* ** :  .

Human IL-10R1    YDLTAVTLDLYHSNGYRARVRAVDGSRHSNWTVTNTRFSVDEVTLTVGSVNLEIHNGFIL
Chicken IL-10R1  HSCDLTYYTLDPSLRYYARVRAVVGNHTSDWKRTNA-FSPQEASLRLSGHSLAVTDNSIH
                 :.   .   *  *  * ****** *.: *:*. **: ** :*.:* :.. .* : :. *

Human IL-10R1    GKIQLPRPKMAPANDTYESIFSHFREYEIAIRKVPGNFTFTHKKVKHENFSLLTSGEVGE
Chicken IL-10R1  VQLQLLL-RAGNRTVKYDDIQKHARRYRVYIRRARDNQTYEVWETAS-EFYIRNLFWNTE
                  ::**   : .  . .*:.* .* *.*.: **:. .* *:   :.   :* : .     *

Human IL-10R1    FCVQVKPSVASRSNKGMWSKEECISLTRQYFTVTN---VIIFFAFVLL---LSGALAYCL (SEQ ID NO: 83)
Chicken IL-10R1  YCISVEPDVASRHIPAMRTAEQCVTIGHRDESAEL (SEQ ID NO: 82)
                 :*:.*:*.****   .* : *:*::: ::  :.
```

Human (NP_001549.2) and chicken (NP_001034686.1) sequences were obtained and edited as described above. Human IL-10R1 residues that are involved in binding to human IL-10 (FIG. 5 of Reineke et. al., 1998) are designated by boldface. Chicken IL-10R1 sequence alignment with the human IL-10R1 sequence is also shown; intracellular and transmembrane domains are omitted for clarity.

Example 3. Peptide Screening

Peptides were chemically synthesized, desalted, and purified to >98% purity by Watsonbio, Inc., Houston TX. Peptide stock solutions were prepared at 10 mM in DMSO and diluted in assay buffer to 0.05 mM. Peptides were screened at Marin Biologic Laboratories, Inc., Novato, CA, by determining their effectiveness at blocking the inhibitory effect of chicken IL-10 on the induction of interferon gamma (IFN-Y) induced by concanavalin A (ConA) (or alternatively phytohemagglutinin (PHA) may be used) in chicken spleen cells (Wu et al. (2016) and Rothwell et al. (2004)). Briefly, lymphocytes and mononuclear cells were isolated from chicken spleens by differential centrifugation on Ficoll-Hypaque. Cells were cultured at $5\times10^6$ cells/mL in wells of a 96-well plate for 72 hours in the presence of peptide, 1.2 μg/mL ConA (or alternatively 12.5 μg/mL PHA), and with or without cIL-10. Spleen cells were also incubated without peptides and/or without ConA (or PHA) as controls. Levels of IFN-Y in the supernatants were determined by ELISA.

The use of peptides derived from IL-10s of several species that can be added to feed to reduce respiratory and intestinal illness in these animals is known in the art. See U.S. Pat. No. 8,652,457 B2 and U.S. patent application publication No. US2016/0280778 A1, which are incorporated by reference herein as if fully set forth. These peptides were designed to elicit an immune response in the animals, which would lead to the production of anti-IL-10 antibodies. In contrast, peptides described herein were designed with the goal of directly interfering with binding of chicken IL-10 to its receptor (that is, as IL-10R antagonists). As a result, the peptides described here were designed in part to mimic sections of either cIL-10 or the R1 subunit of the cIL-10 receptor and to compete with either cIL-10 or cIL-10R for binding to the other species, as opposed to the peptides in the previous patents that were designed to incorporate antigenic features of IL-10.

TABLE 1

Amino acid sequences of peptides

| SEQ ID NO | Description | Sequence |
|---|---|---|
| 1 | P21 | PARLRELRVKFEEIKDYFQSRDDELNIQLLSSEL LDEFKG |
| 2 | P22 | ENGIYKAMGEFDIFINYIEEYLLMRRR |
| 3 | P23 | PARLRELRVKFEEIKDYFQGGGSGGGSQQSMG DLGNMLLGLKATMRR |
| 4 | P24 | GCQSVSEMLRFYTDEVLPRAMQGGGSGGGSKA MGEFDIFINYIEEYLLMR |
| 5 | P25 | PARLRELR |
| 6 | P26 | LSSELLDEFKG |
| 7 | P27 | GEFDIFNYIE |
| 8 | P28 | SLRYYARVRA |
| 9 | P29 | TNAFSPQ |
| 10 | P11 | YDDIQKHARRYRVYIRRARDNQTYEVWET |
| 11 | P30 | IQKHARRY |
| 12 | P31 | NQTYEVWE |
| 13 | P32 | VASRHIPAM |
| 14 | P9* | FFKKFFKKFFKKFFKK |
| 15 | P6* | GTELPSPPSVWFEAEF |

*P9 and P6 are control peptides (Ni et al.)

Example 4. Basic Plant Expression Constructs for Production of IL-10R Antagonist Peptides in Maize The amino acid sequences for IL-10R antagonist peptides and all other sequences in this document have been back translated and codon optimized for expression in the desired host organism. As an example, for plant expression, maize codon usage was used to demonstrate codon optimization, expression cassette assembly, vector assembly, and plant transformation, but other host organisms could also be used. All IL-10R antagonist peptides and antibodies were back translated and codon optimized for expression in maize using the computer program Vector NTI (ThermoFisher Scientific, Waltham, MA). The resulting DNA sequences are presented in Table 2 and at the end of the document.

TABLE 2

IL-10R antagonist peptides and their maize codon optimized DNA coding sequences

| Peptide name | IL-10R antagonist peptide sequence | Maize codon optimized DNA sequence |
|---|---|---|
| P21 | PARLRELRVKFEEIKDY FQSRDDELNIQLLSSEL LDEFKG (SEQ ID NO: 1) | CCGGCCAGGCTGAGGGAGCTGAGGGTGAAG TTCGAGGAGATCAAGGACTACTTCCAGAGC AGGGACGACGAGCTGAACATCCAGCTGCTG AGCAGCGAGCTGCTGGACGAGTTCAAGGGC (SEQ ID NO: 16) |

TABLE 2-continued

IL-10R antagonist peptides and their maize codon optimized DNA coding sequences

| Peptide name | IL-10R antagonist peptide sequence | Maize codon optimized DNA sequence |
|---|---|---|
| P22 | ENGIYKAMGEFDIFINY IEEYLLMRRR (SEQ ID NO: 2) | GAGAACGGCATCTACAAGGCCATGGGCGAG TTCGACATCTTCATCAACTACATCGAGGAGT ACCTGCTGATGAGGAGGAGG (SEQ ID NO: 17) |
| P23 | PARLRELRVKFEEIKDY FQGGGSGGGSQQSMGD LGNMLLGLKATMRR (SEQ ID NO: 3) | CCGGCCAGGCTGAGGGAGCTGAGGGTGAAG TTCGAGGAGATCAAGGACTACTTCCAGGGC GGCGGCAGCGGCGGCGGCAGCCAGCAGAG CATGGGCGACCTGGGCAACATGCTGCTGGG CCTGAAGGCCACCATGAGGAGG (SEQ ID NO: 18) |
| P24 | GCQSVSEMLRFYTDEV LPRAMQGGGSGGGSKA MGEFDIFINYIEEYLLM R (SEQ ID NO: 4) | GGCTGCCAGAGCGTGAGCGAGATGCTGAGG TTCTACACCGACGAGGTGCTGCCGAGGGCC ATGCAGGGCGGCGGCAGCGGCGGCGGCAG CAAGGCCATGGGCGAGTTCGACATCTTCAT CAACTACATCGAGGAGTACCTGCTGATGAG G (SEQ ID NO: 19) |
| P25 | PARLRELR (SEQ ID NO: 5) | CCGGCCAGGCTGAGGGAGCTGAGG (SEQ ID NO: 20) |
| P26 | LSSELLDEFKG (SEQ ID NO: 6) | CTGAGCAGCGAGCTGCTGGACGAGTTCAAG GGC (SEQ ID NO: 21) |
| P27 | GEFDIFNYIE (SEQ ID NO: 7) | GGCGAGTTCGACATCTTCAACTACATCGAG (SEQ ID NO: 22) |
| P28 | SLRYYARVRA (SEQ ID NO: 8) | AGCCTGAGGTACTACGCCAGGGTGAGGGCC (SEQ ID NO: 23) |
| P29 | TNAFSPQ (SEQ ID NO: 9) | ACCAACGCCTTCAGCCCGCAG (SEQ ID NO: 24) |
| P11 | YDDIQKHARRYRVYIRR ARDNQTYEVWET (SEQ ID NO: 10) | TACGACGACATCCAGAAGCACGCCAGGAGG TACAGGGTGTACATCAGGAGGGCCAGGGAC AACCAGACCTACGAGGTGTGGGAGACC (SEQ ID NO: 25) |
| P30 | IQKHARRY (SEQ ID NO: 11) | ATCCAGAAGCACGCCAGGAGGTAC (SEQ ID NO: 26) |
| P31 | NQTYEVWE (SEQ ID NO: 12) | AACCAGACCTACGAGGTGTGGGAG (SEQ ID NO: 27) |
| P32 | VASRHIPAM (SEQ ID NO: 13) | GTGGCCAGCAGGCACATCCCGGCCATG (SEQ ID NO: 28) |

Examples of basic cloning vectors containing individual expression cassettes for P24 IL-10R antagonist peptide are given in Table 3. Analogous vectors could be made for any of the other IL-10R antagonist peptides listed in Table 2, or antibodies, by substituting the P24 peptide transgene with a different peptide or antibody sequence.

TABLE 3

P24 basic expression vectors

| Vector | Promoter | N-terminal signal | C-terminal signal |
|---|---|---|---|
| pAG4305 | prOsGluB4 | xGZein27ss | KDEL (SEQ ID NO: 29) |
| pAG4981 | prZmgZ27 | xGZein27ss | KDEL (SEQ ID NO: 29) |

TABLE 3-continued

P24 basic expression vectors

| Vector | Promoter | N-terminal signal | C-terminal signal |
|---|---|---|---|
| pAG4982 | prGt11 | xGZein27ss | KDEL (SEQ ID NO: 29) |
| pAG4983 | prZmGlb1 | xGZein27ss | KDEL (SEQ ID NO: 29) |
| pAG4984 | prZmOle16 | xGZein27ss | KDEL (SEQ ID NO: 29) |

Figure 1G:
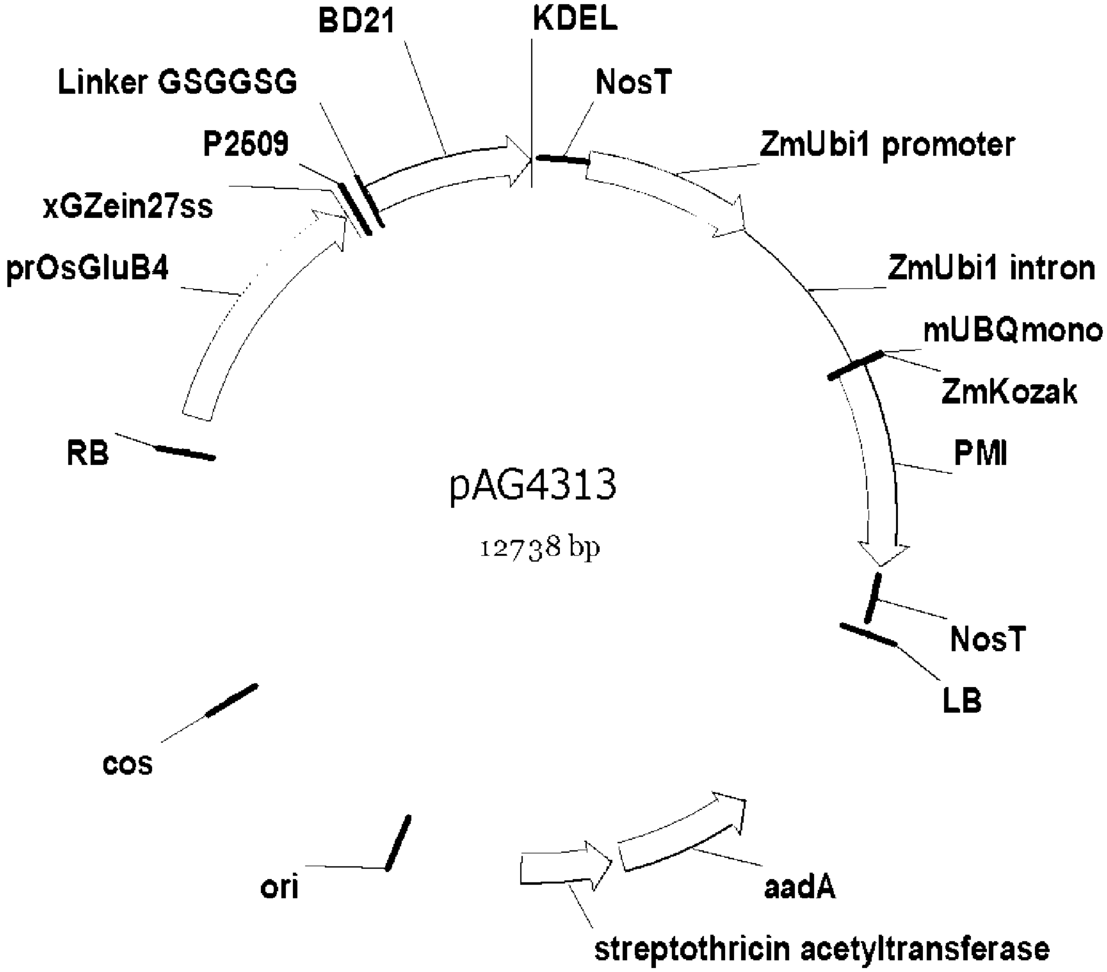

FIGS. 1A-1G illustrate the schematic drawings of the vectors pAG4305 (FIG. 1A), pAG4306 (FIG. 1B), pAG4308 (FIG. 1C), pAG4310 (FIG. 1D), pAG4311 (FIG. 1E), pAG4312 (FIG. 1F), and pAG4313 (FIG. 1G).

Figure 2A:
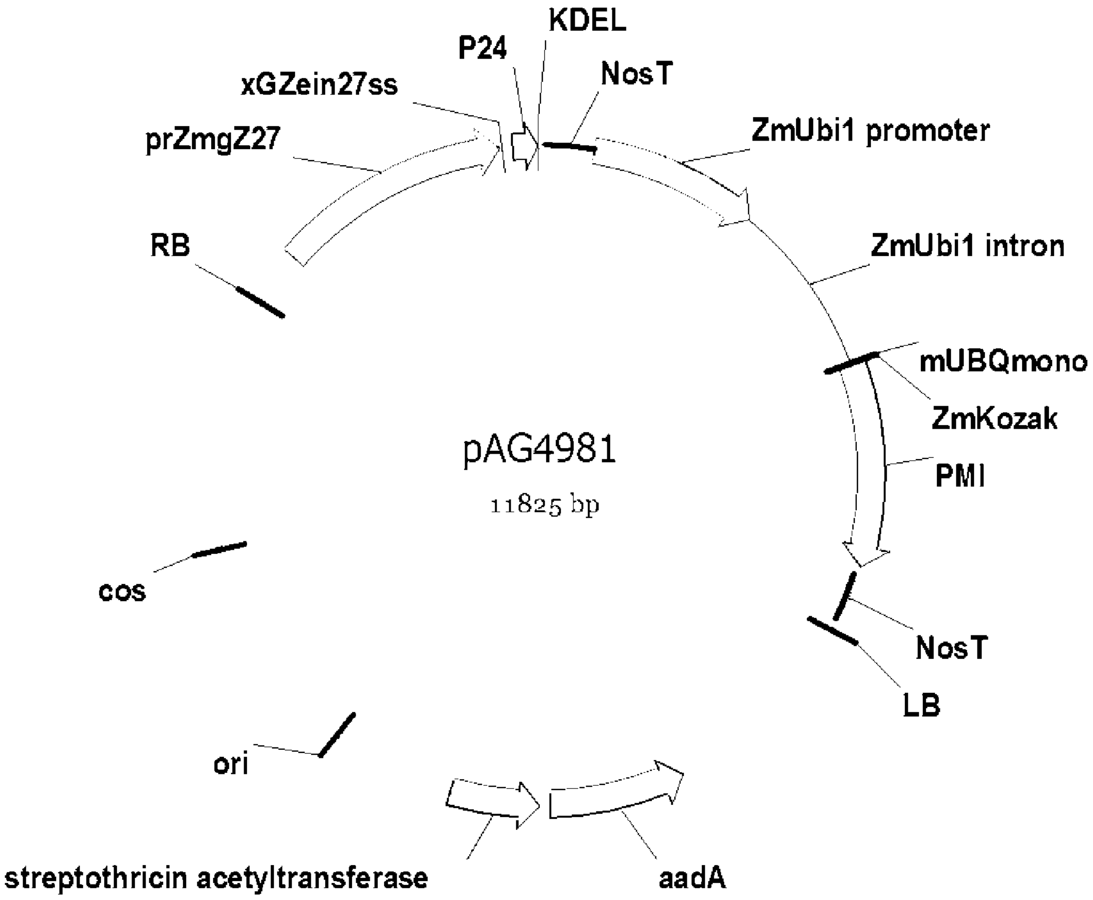
FIGS. 2A-2D are schematic drawings of the vectors pAG4981 (FIG. 2A), pAG4982 (FIG. 2B), pAG4983 (FIG. 2C), and pAG4984 (FIG. 2D).
Figure 2B:
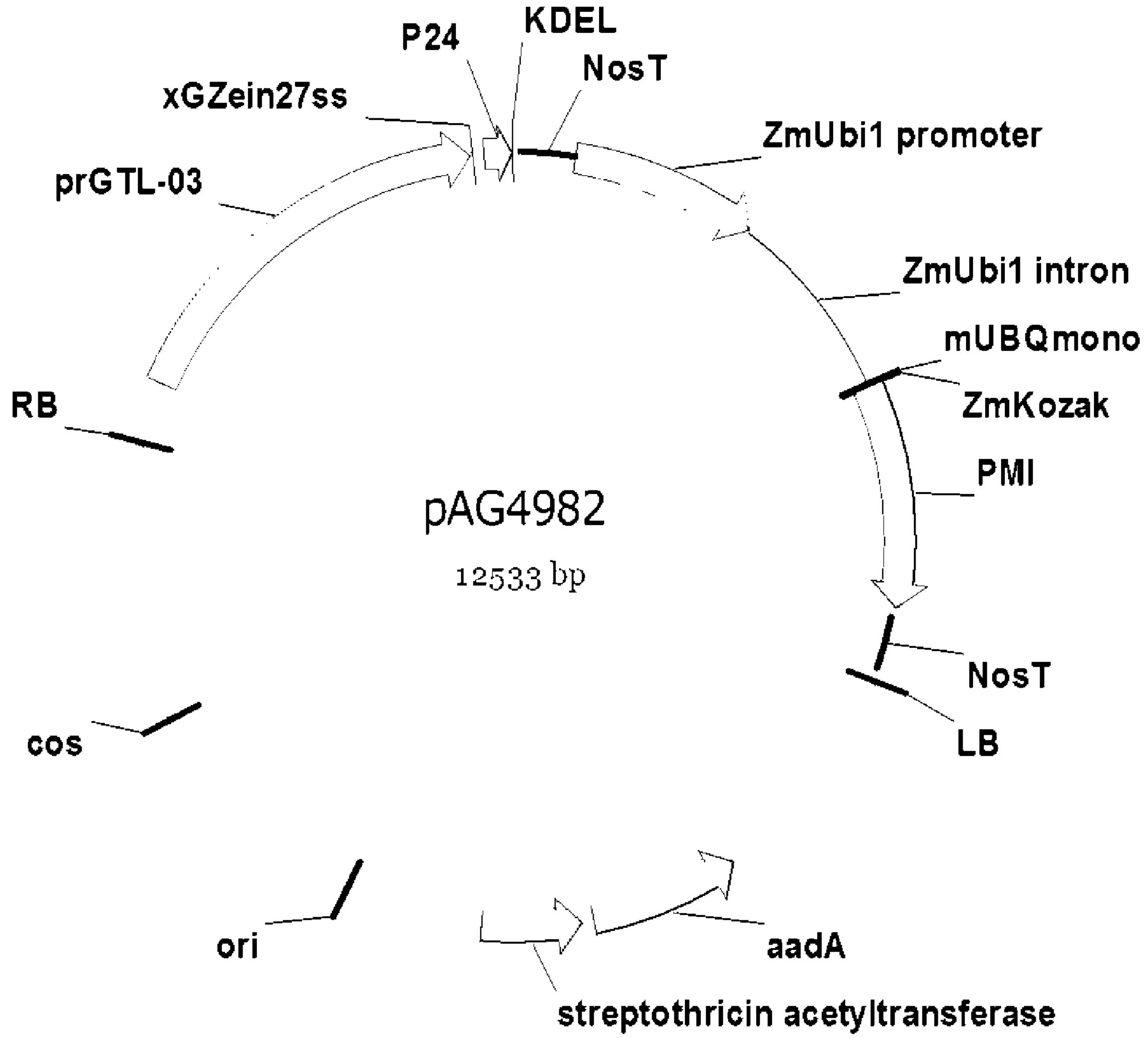
Figure 2C:
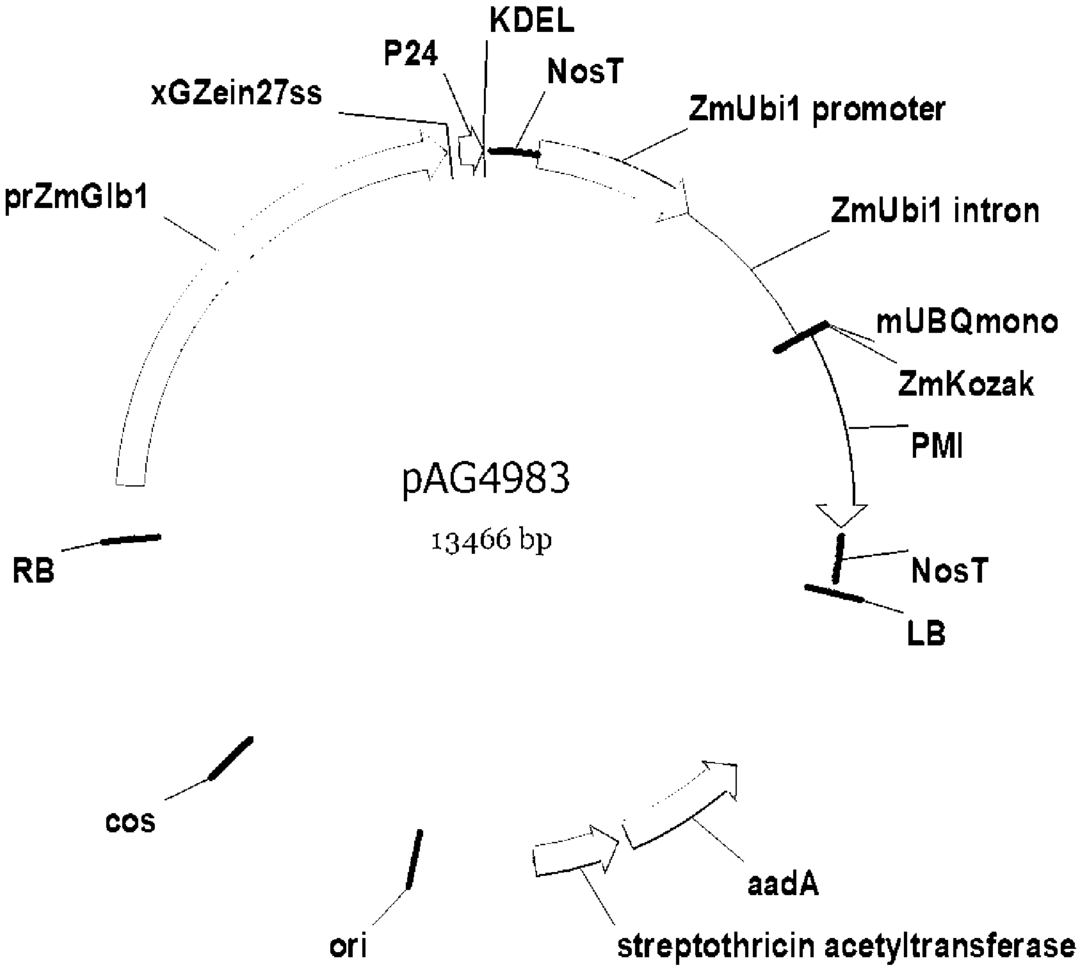
Figure 2D:
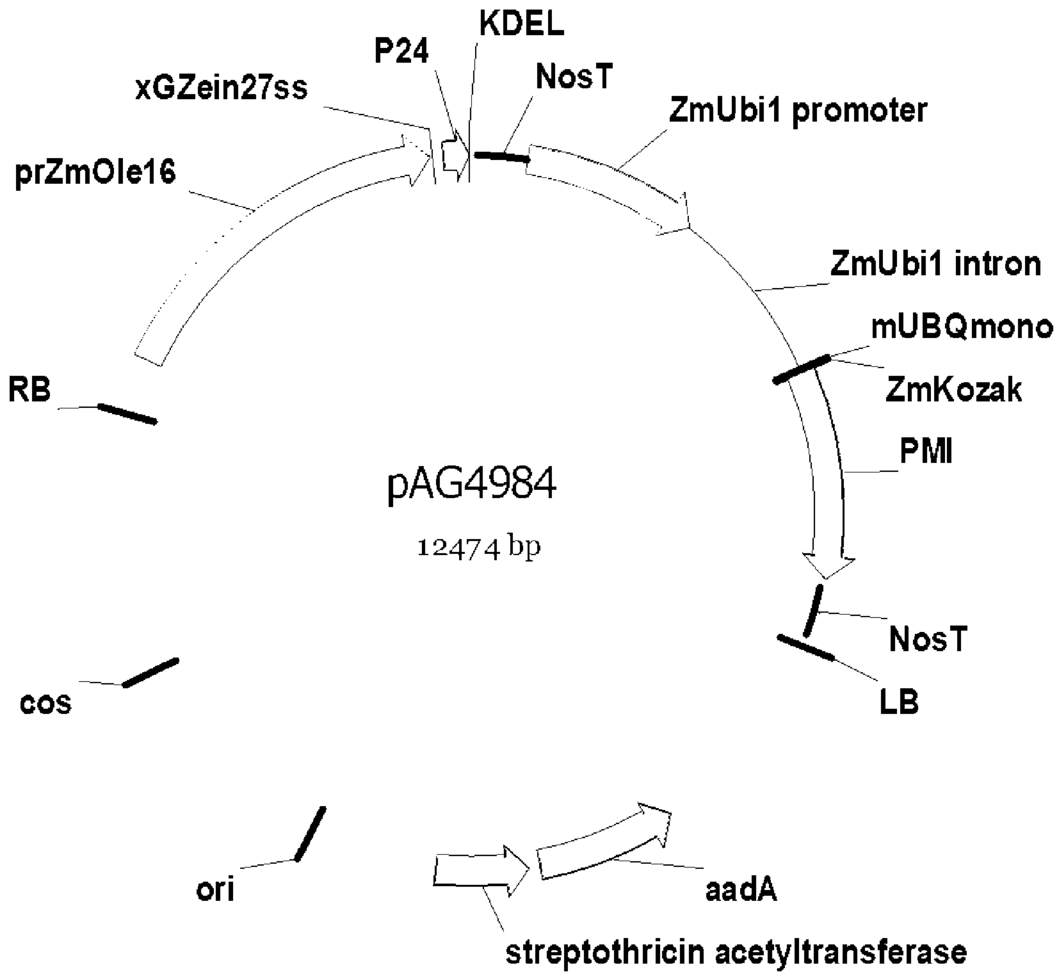

FIGS. 2A-2D illustrate the schematic drawings of the vectors pAG4981 (FIG. 2A), pAG4982 (FIG. 2B), pAG4983 (FIG. 2C), and pAG4984 (FIG. 2D).

Any DNA fragments encoding IL-10R antagonist peptides listed in Table 2, or anti-IL-10 single domain antibodies, can be cloned between desirable promoter and Nos terminator sequence in the basic P24 peptide expression vectors (Table 3), in order to generate required expression cassettes. In addition, amino terminal (N) signal sequences, such as xGZein27ss in maize expression vectors, can be replaced by other signal sequences in order to modulate specific expression and accumulation of IL-10R antagonist peptides or antibodies to desired levels. N-terminal signal sequences include, but not limited to, for example by OsGluB4sp (rice GluB-4 glutelin signal peptide), BAASS (barley alpha amylase signal sequence), or PR1 (pathogenesis related protein). The IL-10R antagonist peptides, or anti-IL-10 single domain antibodies, can be expressed to endoplasmic reticulum (ER) for improved accumulation and glycosylation using carboxyl terminal (C) retention signal sequences such KDEL (SEQ ID NO: 29), HDEL (SEQ ID NO: 30), or SEKDEL. Furthermore, IL-10R antagonist peptides, or anti-IL-10 single domain antibodies, can be expressed and directed to protein storage vacuoles with the help of signal sequences attached to either N-terminal or C-terminal part of the sequence. These storage vacuole signal sequences include HvAle from barley aleurone (thiol protease) or HvVSD from barley polyamine oxidase. If necessary, IL-10R antagonist peptides, or anti-IL-10 singe domain antibodies, can be also expressed from basic P24 vectors without signal sequences for accumulating expressed products in apoplast or cytoplasm. All those mentioned above and other signal sequences of similar functions can be added to or removed from the basic plant expression vectors. Signal sequences described above can be found in the "List of sequences" at the end of this document.

Example 5. Additional Strategies for Expressing IL-10R Antagonist Peptides in Transgenic Maize Peptide Concatenation.

This strategy represents expression of a chimeric IL-10R antagonist sequence that contains multiple, contiguously linked, copies of DNA sequences encoding IL-10R antagonist peptides. The peptide coding sequences in a concatemer could be fused directly to one another or separated by intervening sequences such as AGPA hinges for stabilizing chimeric molecule for expression. Examples of possible variants of concatenated peptide sequences for the eight amino acid long peptide P25 are provided in Table 4. Each P25 concatemer can be synthesized as DNA molecule and cloned into any P24 basic expression vectors thus effectively replacing P24 coding sequence for subsequent expression in maize. In this way, new maize transformation vectors can be developed, such as for example pAG4306, where P2509 concatemer that is composed of three P25 units separated by AGPA hinges is expressed from the rice GluB4 promoter into ER. Nucleotide sequence for P2509 is available in the "List of sequences" section. A similar approach can be used for expressing all other short or all IL-10R antagonist peptides that are listed in Table 2.

TABLE 4

Examples of the P25 IL-10R antagonist peptide and concatemers for expression in maize

| Peptide | Sequence for maize expression |
|---|---|
| P25 | PARLRELR<br>(SEQ ID NO: 5) |
| P2501 | PARLRELRKDEL<br>(SEQ ID NO: 32) |
| P2502 | PARLRELRPARLRELR<br>(SEQ ID NO: 33) |
| P2503 | PARLRELRPARLRELRKDEL<br>(SEQ ID NO: 34) |
| P2504 | PARLRELR**AGPA**PARLRELR<br>(SEQ ID NO: 35) |
| P2505 | PARLRELR**AGPA**PARLRELRKDEL<br>(SEQ ID NO: 36) |
| P2506 | PARLRELRPARLRELRPARLRELR<br>(SEQ ID NO: 37) |
| P2507 | PARLRELRPARLRELRPARLRELRKDEL<br>(SEQ ID NO: 38) |
| P2508 | PARLRELR**AGPA**PARLRELR**AGPA**PARLRELR<br>(SEQ ID NO: 39) |
| P2509 | PARLRELR**AGPA**PARLRELR**AGPA**PARLRELRKDEL<br>(SEQ ID NO: 40) |

Gene Fusions.

Another strategy for expressing IL-10R antagonist peptides in plants can employ chimeric enlargement or gene fusion approach. In this strategy, target peptides can be expressed, for example, as chimeric fusions with parts of the maize gamma-zein 27 kDa. This strategy was used for expressing zeolin and Zera fusion proteins (Mainieri et al., 2007; U.S. Pat. No. 8,802,825; Llop-Tous, 2010, all of which are incorporated herein by reference as if fully set forth). Co-expression of target sequences as gamma-zein fusions allows high level protein accumulation in ER-derived protein bodies. The IL-10R antagonist peptide sequences selected for expression can be fused to maize gamma-zein sequences with the help of linker sequences such as, for example linker GSGGSG (SEQ ID NO: 41). Additional linker sequences, for example linkers similar to those in zeolin fusion protein (GGGGS; SEQ ID NO: 42), Zera fusions (GGGGG; SEQ ID NO: 43), or other linkers can also be exploited (Table 5). All IL-10R antagonist peptides can be expressed with or without C-terminal sequence such as KDEL (SEQ ID NO: 29), HDEL (SEQ ID NO: 30), SEKDEL (SEQ ID NO: 31), HvVSD, or other such sequences. Furthermore, gamma-zein sequences as fusion components of chimeric protein enlargements can be substituted for other protein sequences such as, for example, elastin-like polypeptides (ELP) (Urry, 1992), which were used for expressing human IL-10 in tobacco (Patel et al., 2007) or hydrophobins that were used for transient protein expression in *Nicotiana benthamiana* (Joensuu et al., 2010; Jacquet et al., 2014). When either of the latter two approaches is used, expressed protein fusions form protein bodies. Two constructs that serve as examples for expressing P2509 concatemer fused with maize gamma-zein components are represented by the vectors pAG4308 and pAG4310. The pAG4311 vector is an example of expressing P2509 as a fusion with 28×VPGVG (SEQ ID NO: 44)

elasting-like polypeptide (Conley et al., 2009). Variable number of repeats and sequences such as VPGXG in ELP fusion partner could be used for expressing IL-10R antagonist peptides. The ELP fusion proteins can be purified by nonchromatographic bioseparation of recombinant proteins (Lin et al., 2006). The pAG4312 construct provides an example of expressing P2509 peptide fused to the mature chain of *Trichoderma reesei* HFBI hydrophobin (GenBank Accession #P52754.1). Hydrophobins fusions can be purified by efficient surfactant-based aqueous two-phase system (ATPS) (Joensuu et al., 2010). Other fusion partners for IL-10R antagonist peptides could additionally be exploited such as, fusing P2509 to a thermal stable glucanase enzyme, which is presented in vector pAG4313.

TABLE 5

Linker sequences for developing protein fusions

| Linker sequence | Nucleotide | Description |
|---|---|---|
| GSGGSG (SEQ ID NO: 41) | ggcagcggcggcagcggc (SEQ ID NO: 45) | Linker for expression Phy02opt: BD21 |
| GGGGS (SEQ ID NO: 42) | ggcggcggcggcagc (SEQ ID NO: 46) | Linker used for Zeolin expression (Mainieri et al., 2004) |
| GGGGG (SEQ ID NO: 43) | ggcggcggcggcggc (SEQ ID NO: 47) | Linker used for expressing Zera fusions (Llop-Tous et al., 2011) |

Example 6. Production of Single-Domain Antibodies to IL-10

Camelid single-domain antibodies (sdABs; also known as $V_H$H antibodies) with affinity for cIL-10 were generated by immunizing a llama with full-length, purified recombinant cIL-10 (IBI Scientific, Peosta IA). Full-length IL-10 was selected, as opposed to individual cIL-10 peptides, because cIL-10 is only 48% identical to the llama IL-10 homologue. It was previously unknown whether cIL-10 would generate an adequate immune response in llamas, but given the limited sequence identity, cIL-10 was used to test whether llamas would be naïve, and that the full-length molecule could be used to generate an adequate immune response. Furthermore, IL-10 is known to dimerize, thus using the full-length molecule would bias the generated antibodies towards epitopes that are present in the dimerized molecule. That llamas would not otherwise be exposed to cIL-10, except through injection of isolated or recombinant cIL-10, provided a novel process for generating anti-cIL-10 antibodies. Pre-immune serum was collected from a single llama prior to injection with cIL-10. The first immunization was carried out with 200 μg of cIL-10 in the presence of Complete Freund's Adjuvant (CFA). Subsequent booster immunizations were carried out, each with 100 μg cIL-10, in the presence of Incomplete Freund's Adjuvant (IFA) three weeks, seven weeks and eleven weeks after the initial immunization. Blood samples ("bleeds") were collected from the animal one week after each of the booster immunizations. FIG. 3 illustrates the llama's immune response prior to (pre-immune), and after being dosed with cIL-10.

Figure 4:
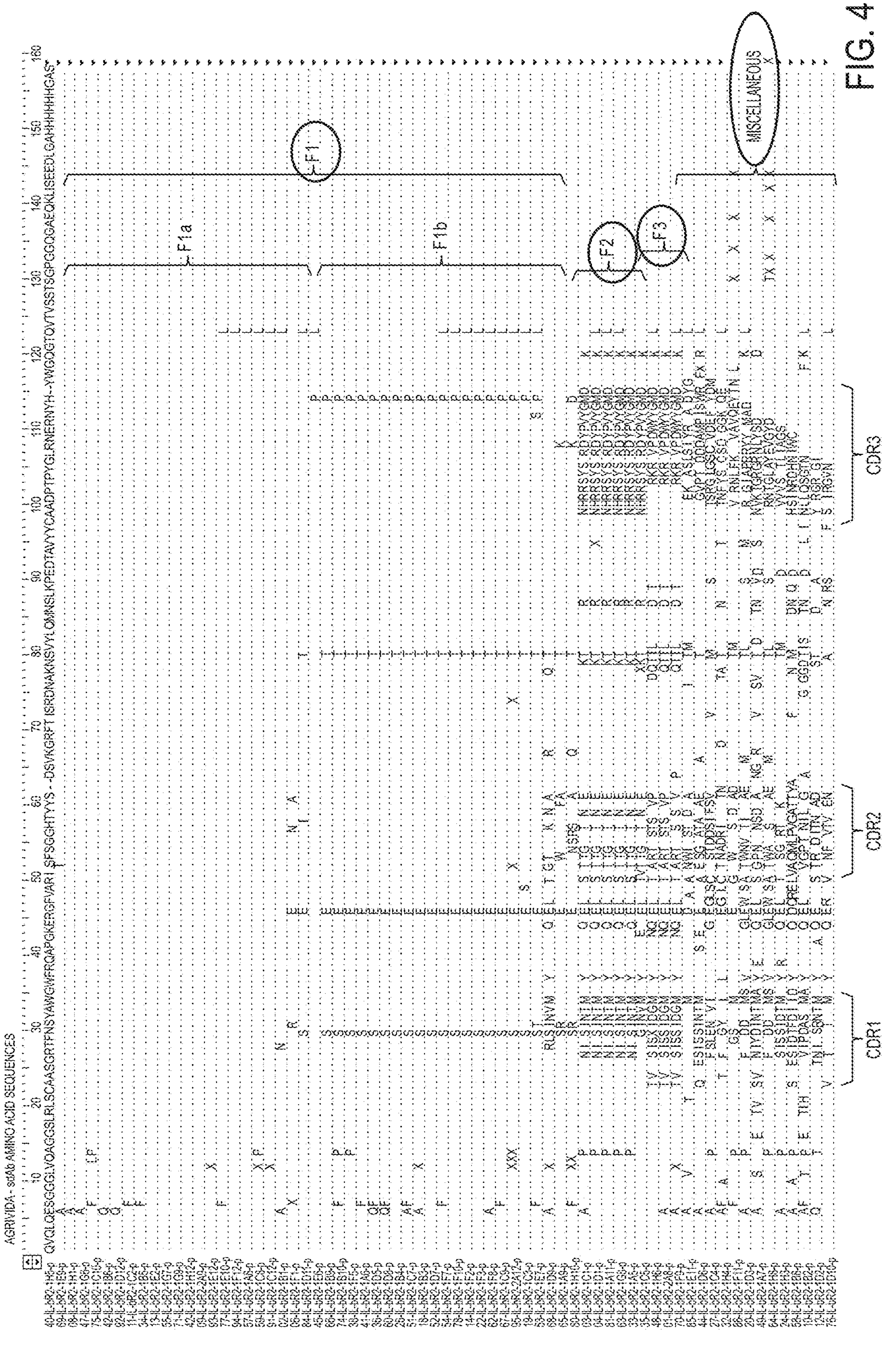
FIG. 4 illustrates the sequencing results from the anti-IL-10 antibody development and inter-relationship among the identified sequences. In this figure, sequences of sdAbs according to embodiments herein are aligned and compared to the sequence of sdAbs 40-IL-bR2-1H5 set forth as SEQ ID NO: 208. The amino acid (AA) positions replaced in the sequence of SEQ ID NO: 208 are as follows: for 68-IL-bR2-1D9, AA 26 to 34 (SEQ ID NO: 209); for 80-IL-bR2-1H10, AA 54 to 57 (SEQ ID NO: 210); for 03-IL-bR2-1C1, 04-IL-bR2-1D1, 81-IL-bR2-1A11, 63-IL-bR2-1G8, and 33-IL-bR2-1A5, AA 30 to 34 (SEQ ID NO: 211), AA 97 to 103 (SEQ ID NO: 212), and AA 105 to 112) SEQ ID NO: 213); for 35-IL-bR2-1C5, AA 30 to 34 (SEQ ID NO: 214), AA 50 to 54 (SEQ ID NO: 215), and AA 97 to 103 (SEQ ID NO: 212); for 48-IL-bR2-1H6, AA 27 to 34 (SEQ ID NO: 216), AA 75 to 79 (SEQ ID NO: 217), and AA 105 to 112 (SEQ ID NO: 218); for 01-IL-bR2-2A8 and 70-IL-bR2-1F9, AA 27 to 34 (SEQ ID NO: 216), AA 105 to 112 (SEQ ID NO: 218), and AA 76 to 79 (SEQ ID NO: 219); for 85-IL-bR2-1E11, AA 102 to 108 (SEQ ID NO: 220); for 44-IL-bR2-1D6, AA 26 to 34 (SEQ ID NO: 221), AA 99 to 102 (SEQ ID NO: 222), and AA 104 to 113 (SEQ ID NO: 223); for 27-IL-bR2-1C4, AA 27 to 31 (SEQ ID NO: 224), AA 46 to 50 (SEQ ID NO: 225), AA 53 to 61 (SEQ ID NO: 226), and AA 98 to 105 (SEQ ID NO: 227); for 32-IL-bR2-1H4, AA 52 to 57 (SEQ ID NO: 228), and AA 98 to 102 (SEQ ID NO: 229); for 86-IL-bR2-1F11, AA 100 to 104 (SEQ ID NO: 230), and AA 107 to 110 (SEQ ID NO: 231); for 20-IL-bR2-ID3, AA 44 to 47 (SEQ ID NO: 232), AA 52 to 55 (SEQ ID NO: 233), and AA 100 to 107 (SEQ ID NO: 234); for 49-IL-bR2-1A7, AA 27 to 35 (SEQ ID NO: 235), and AA 97 to 109 (SEQ ID NO: 236); for 24-IL-bR2-1H3, AA 24 to 37 (SEQ ID NO: 237), AA 98 to 101 (SEQ ID NO: 238), and AA 103 to 108 (SEQ ID NO: 239); for 58-IL-bR2-1B8, AA 26 to 35 (SEQ ID NO: 240), AA 46 to 61 (SEQ ID NO: 241), and AA 97 to 107 (SEQ ID NO: 242); for 10-IL-bR2-1B2, AA 27 to 32 (SEQ ID NO: 243), AA 52 to 59 (SEQ ID NO: 244), AA 75 to 80 (SEQ ID NO: 245), and AA 97 to 104 (SEQ ID NO: 246); for 12-IL-bR2-1D2, AA 30 to 34 (SEQ ID NO: 247), and AA 55 to 58 (SEQ ID NO: 248); and for 76-IL-bR2-1D10, AA 99 to 103 (SEQ ID NO: 249).

The production of antibodies targeting cIL-10 in the animal during this immunization process was evaluated via ELISA using each of the bleeds as shown in FIG. 3, and the bleeds were then used to develop single-domain antibodies. The alignment of the chicken and llama IL-10 homologs shows 48% identity (68% similarity). The preparation of sdABs has been described elsewhere (Goldman et al. 2006; Arbabi Ghahroudi et al. 1997; Liu et al. 2013). Briefly, peripheral blood mononuclear cells (PBMCs) were isolated from the bleeds that were collected during weeks eight and 12 of the immunization protocol. RNA was purified from the PBMCs and used to create phagemid cDNA libraries for expression and screening of sdABs. Notably, sdABs represent only the heavy chain variable region (VHH) from the llama antibodies produced when the host was injected with recombinant cIL-10, and therefore the RNA-derived, DNA coding sequence of sdABs represents a synthetic nucleotide that is produced through a novel process that does not occur in nature. Two rounds of panning against purified recombinant cIL-10 were used to enrich the library for phage displaying sdAB with affinity for the antigen. From the enriched libraries, individual clones were generated, isolated and sequenced. FIG. 4 illustrates the results of the anti-IL-10 sdAB screening and sequencing. FIG. 4 demonstrates that the isolated sdAB amino acid sequences reside in four distinct groups, with a fifth miscellaneous group. The complementarity-determine regions (CDRs) are designated in FIG. 4.

Example 7. Anti-IL-10 sdAbEC50 Measurements and Thermal Stability

Figure 5:
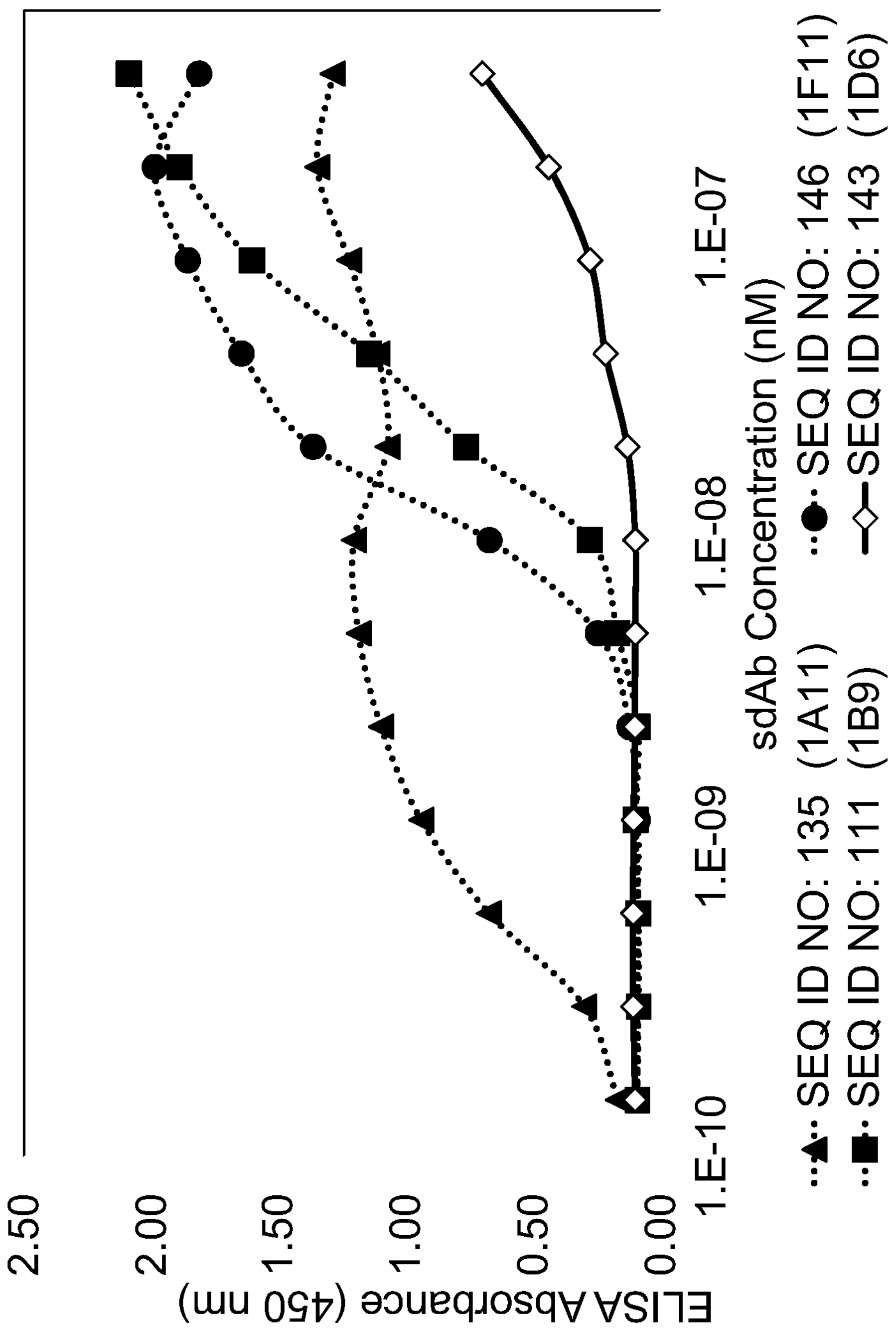
FIG. 5 illustrates apparent binding affinity of anti-IL-10 antibodies to chicken IL-10.

Candidate sdABs were evaluated for their apparent binding affinity against purified cIL-10, as measured by ELISA. Different concentrations of individual isolated sdABs were incubated on cIL-10 ELISA plates, with increasing signals indicative of higher levels of sdAB binding to cIL-10. Apparent EC50 values were estimated by determining the sdAB concentration at which 50% of the maximum signal was observed. FIG. 5 illustrates the ELISA measurements and apparent binding affinity of selected sdAB candidates to chicken IL-10. Among the candidates tested, chIL10sdAB1A11 (SEQ ID NO: 135), chIL10sdAB1F11 (SEQ ID NO: 146), and chIL10sdAB1B9 (SEQ ID NO: 111), had EC50 values of less than 100 nM, with estimated values of 1 nM, 15 nM, and 35 nM, respectively. Another sdAB, chIL10sdAB1D6 (SEQ ID NO: 143), had an estimated EC50 value of 100 nM. Additional sdABs were evaluated in this way for their EC50 values, including chIL10sdAB1H1 (SEQ ID NO: 89) with an EC50 value of 20 nM. Since higher binding affinity is reflected by lower EC50 values, sdABs with low EC50 values, and more divergent sequences were selected for further assessment and development.

Although sdABs are considered to have high specificity for their antigenic target, and do not bind strongly to non-specific peptides, it is often desirable to demonstrate binding specificity to individual epitopes or peptides. The sdABs were prepared using the full-length chIL-10 protein, however individual peptides could also be used in our method. Likewise, counter selecting sdABs that bind the full length chIL-10, but had little or no affinity to specific peptides was also used to identify sdABs that bound desired antigenic peptides, but not others. Counter selection can be made using several different methods, including an ELISA or dot-blot, where the peptides for counter selection are immobilized on a surface and the anti-cIL-10 sdAB are incubated to allow binding, washed to remove unbound sdAB, then incubated with a labeled anti-llama antibody to detect any bound sdAB. Any sdAB that does not bind the immobilized peptides used for counter selection but still bind the full length IL-10, can be further developed with the confidence that they possess the desired binding criteria. Some peptides that were used for counter selection include: DDELNIQL [peptide 1; SEQ ID NO: 180], VLPRAMQT [peptide 2; SEQ ID NO: 181], EKMDENGI [peptide 3; SEQ ID NO: 182], EPTCLHFS [peptide 4; SEQ ID NO: 183], DQMGDLL [peptide 5; SEQ ID NO: 184], DQLHSLL [peptide 6; SEQ ID NO: 185], VMPKAESD [peptide 7; SEQ ID NO: 186], VMPQAENH [peptide 8; SEQ ID NO: 187], SKLQERGV [peptide 9; SEQ ID NO: 188], SELQERGV [peptide 10; SEQ ID NO; 189], ENSCIHFP [peptide 11; SEQ ID NO: 190], DSSCIHLP [peptide 12; SEQ ID NO: 191], DQLNSML [peptide 13; SEQ ID NO: 192], NMLQERGV [peptide 14; SEQ ID NO: 193], DSSCTHFP [peptide 15; SEQ ID NO: 194], DDLEIGL [peptide 16; SEQ ID NO: 195], VLPTAIADMTEE peptide 17; SEQ ID NO: 196], TQMEGKGP [peptide 18; SEQ ID NO: 197], and NQCCRFV [peptide 19; SEQ ID NO: 198].

Internal screening for thermal stability was performed to determine the heat tolerance of sdABs, which may be important for their use in animal feed processing. In particular, thermal stability is a highly desirable property in animal feed pelleting processes, where the molecules may be exposed to temperatures over 70° C., and up to 125° C., depending on the specific process and pelleting equipment used. In order to evaluate the thermal stability, heat treated sdABs were prepared by incubating the sdABs at 70° C., 75° C., 80° C., 85° C., and 90° C. for 30 seconds, 60 seconds, 90 seconds, 120 seconds, 300 seconds and 600 seconds, and were then allowed to equilibrate to room temperature. Control sdABs were incubated at 37° C. or room temperature, for the same period of time that the heat treated sdABs and also allowed to equilibrate to room temperature. The EC50 values of the sdABs were then compared between the control (37° C. or room temperature treated) and treatment (those heated between 70° C. and 90° C. for various amounts of time) sdABs by ELISA. Thermal stability, as expressed by the ratio of the EC50 values of the heat treated sdABs and control sdABs, ranged between 30% to 90%, with higher thermal stability values correlating to lower temperatures and lower exposure times.

Example 8. Anti-IL-10 sdAb Gastric Stability

Simulated gastric fluid (SGF) consisted of 0.084 M HCl, 35 mM NaCl, pH 1.2, containing 2630 Units of pepsin per milliliter. Reaction stop solution was 200 mM sodium carbonate. Protein samples, including bovine serum albumin (BSA), chIL10sdAB1A11 (SEQ ID NO: 135), chIL10sdAB1F11 (SEQ ID NO: 146), chIL10sdAB1H1 (SEQ ID NO: 89), chIL10sdAB1B9 (SEQ ID NO: 111), chIL10sdAB1D6 (SEQ ID NO: 143), chIL10sdAB1E11 (SEQ ID NO: 142) chIL10sdAB1F7 (SEQ ID NO: 121) chIL10sdAB1F9 (SEQ ID NO: 141), and chIL10sdAB2A8 (SEQ ID NO: 140), to be tested were brought to a concentration of 5 mg/mL in storage buffer (50 mM MES, 150 mM NaCl, 40% (v/v) glycerol, pH 6.3).

Figure 6:
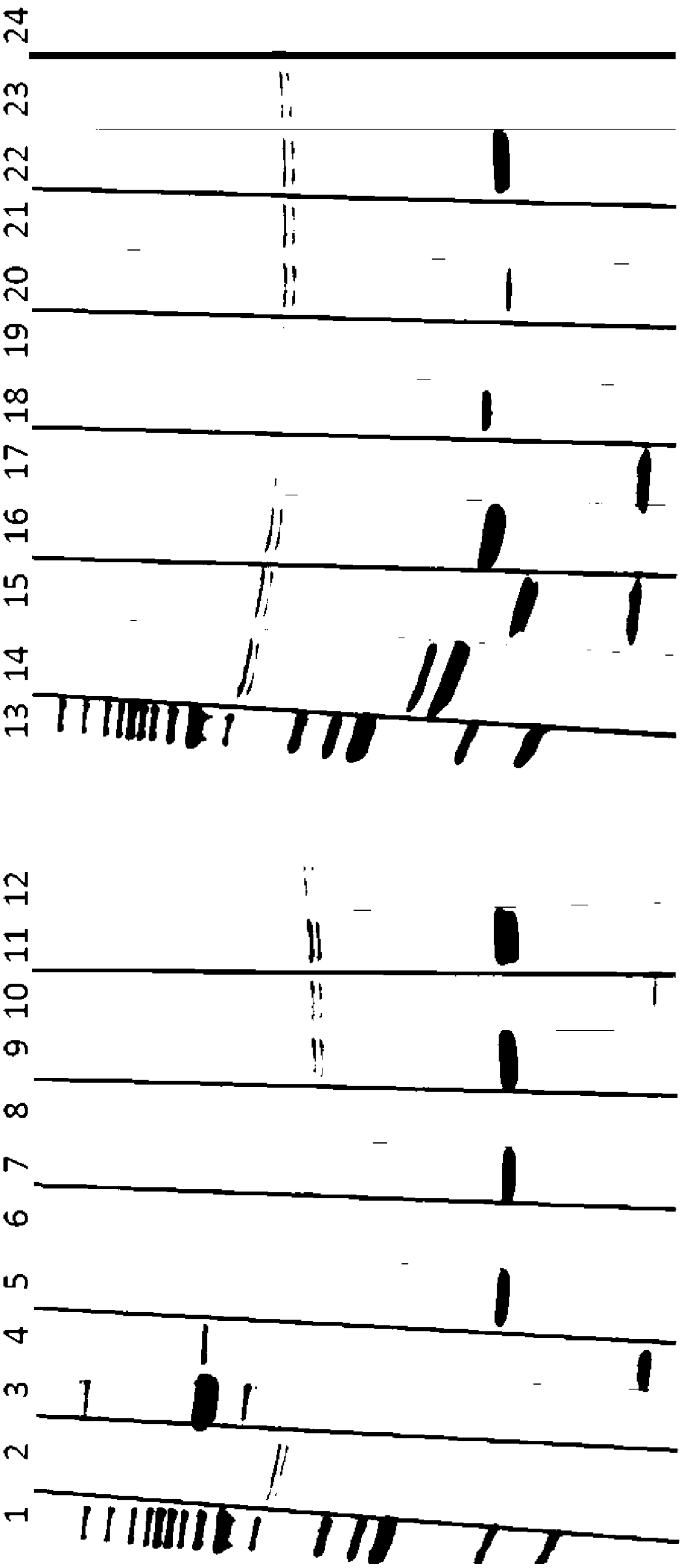
FIG. 6 illustrates results of the anti-IL-10 antibody digestion in the simulated gastric fluid (SGF) test.

Single domain antibody samples (2.5 μL) were dispensed into 200 μL thin-walled PCR tubes and prewarmed on a PCR thermal cycler set to 37° C. Aliquots (100 μL) of SGF were placed into PCR tubes and also prewarmed. For 0 minute digestion samples, 17.5 μL of stop solution was added to the protein samples before adding SGF. Digestions were initiated by the addition of 47.5 μL of prewarmed SGF to the sdAB samples. After 1 minute, 2 minutes, 5 minutes, 10 minutes, and 30 minutes, reactions were terminated by the addition of 17.5 μL stop solution. SDS-PAGE sample-loading buffer (17.5 μL; ThermoFisher catalog #NP0007, with dithiothreitol added to a concentration of approximately 50 mM) was added to each sample. After heating for 10 minutes at 70° C., 15 μL of each sample was loaded onto a protein electrophoresis gel (ThermoFisher catalog #NP0321 or similar) and electrophoresis was performed as directed by the manufacturer. Gels were then stained with Coomassie Blue dye using standard methods. Results are shown in FIG. 6 for the 0 and 10 minute time points. In this figure, lane 1—molecular weight standards; lane 2—pepsin only; lane 3—BSA 0 min; lane 4—BSA 10 min; lane 5—1A11 0 min; lane 6—1A11 10 min; lane 7—1F11 0 min; lane 8—1F11 10 min; lane 9—1H1 0 min; lane 10—1H1 10 min; lane 11—1B9 0 min; lane 12—1B9 10 min; lane 13—molecular weight standards; lane 14—1D6 0 min; lane 15—1D6 10 min; lane 16—1E11 0 min; lane 17—1E11 10 min; lane 18—1F7 0 min; lane 19—1F7 10 min; lane 20—1F9 0 min; lane 21—1F9 10 min; lane 22—2A8 0 min; lane 23—2A8 10 min; and lane 24—pepsin only. FIG. 6 shows that BSA is significantly degraded within a 10 minute digestion in SGF, as are all of the sdABs tested. Given the inherent rapid digestibility of the sdABs, it is unexpected that the sdABs perform well in controlling Coccidiosis and binding IL-10 when dosed into feed. It may have been anticipated that rapid digestion in SGF would underlie poor performance of sdABs in controlling Coccidiosis as they should be quickly degraded and therefore have a limited ability to bind IL-10 and block IL-10 signaling. Given that the sdABs described herein are effective in controlling Coccidiosis suggests that gastric stability is not a dominating factor in oral antibody administration and is a beneficial trait as proteins that are rapidly degraded in SGF pose a lower allergenicity risk than those that are stable in SGF. Given the increased thermal stability of sdABs (see discussion in Example 1, above), it is unusual that the developed sdABs are readily digestible by pepsin, as it is widely regarded that high thermal stability, as demonstrated by sdABs, correlates with high SGF stability, in contrast to the measured digestibility of the developed anti-IL-10 sdABs. The anti-IL-10 sdABs developed herein have good thermal stability and are readily digested in pepsin, which are attributes that support the product's performance and safety profile, which should aid in its regulatory evaluation and eventual customer acceptance.

Example 9. Chicken IL-10 Ligand-Receptor Assay and sdAB IC50 Measurement

An assay was developed to measure how the sdABs bind their target cIL-10, and prevent cIL-10 from binding to its receptor. The soluble domain of the cIL-10 receptor was expressed and immobilized on a biacore probe surface. It was then incubated with cIL-10 and different mixtures of sdABs and cIL-10, and the binding of cIL-10 to the soluble domain of the cIL-10 receptor was measured by surface plasmon resonance.

The amino acid sequence of the soluble domain of the chicken interleukin-10 receptor subunit 1 (cIL-10R1) was deduced by alignment of the amino acid sequence of the human IL-10R alpha receptor subunit (UniProtKB/SwissProt accession number Q13651) with the analogous chicken IL-10 receptor subunit 1 (NCBI reference sequence NP_001034686).

For this assay, the gene coding for the chicken receptor soluble domain (residues 22-231) was synthesized as an upstream fusion to the human $IgG_1$ Fc domain (residues 100-330 of UniProtKB/SwissProt accession number P01857) connected by a linker consisting of IEGRMD [SEQ ID NO: 199] (the final, aggregate expressed molecule comprising the cIL-10R1 fused to IEGRMD [SEQ ID NO: 199] fused to the Fc residues 100-330 will be referred to as "cIL-10R1-Fc"). cIL-10R1-Fc could be directly immobilized to facilitate the surface plasmon resonance binding assay on a biacore instrument. To produce cIL-10R1-Fc, the gene encoding cIL-10R1-Fc was cloned into pGAPZαB (ThermoFisher) via the EcoRI and NotI restriction sites. Pichia pastoris strain GS115 was transformed with the plasmid as directed in the pGAPZαB instruction manual. A high-expressing clone was grown in a 2.5 L fermenter using a fed-batch protocol. Growth medium in the batch phase consisted of 1.5 L of 20 g/L peptone, 10 g/L yeast extract, 13.4 g/L yeast nitrogen base, 10 g/L casamino acids, 10 g/L glycerol, and 100 mM sodium phosphate monobasic. Temperature was maintained at 28° C., pH was maintained at 6.0 by addition of 50% ammonium hydroxide, and dissolved oxygen ($pO_2$) was maintained at 30%. After glycerol was exhausted, as indicated by a spike in dissolved oxygen, temperature was lowered to 25° C. and feeding of 750 mL of 100 g/L glucose, 50 g/L peptone, 25 g/L yeast extract, 10 g/L casamino acids, 0.5% (v/v) Antifoam 204, and 100 µg/mL zeocin was initiated.

Culture supernatant was isolated by centrifugation and sterile filtered through a 0.22 µm filter. Supernatant was taken to 1M ammonium sulfate by the addition of 0.5 volume of 3M ammonium sulfate, 20 mM Tris·HCl, 1 mM EDTA, pH 8. After filtering, the receptor fusion was purified by hydrophobic interaction chromatography (Phenyl Sepharose), affinity chromatography (Protein G Sepharose), anion-exchange chromatography (MonoQ), and size-exclusion chromatography.

Chicken IL-10 was obtained from Kingfisher Biotech, Inc. Camelid VHH domains fused to C-terminal myc- and his-tags were expressed in *E. coli* with expression directed to the periplasmic space by an N-terminal signal peptide. Protein was extracted from the periplasm by osmotic shock and then purified by metal chelation chromatography and size-exclusion chromatography. Protein concentrations were determined by measuring the absorbance at 280 nm, using extinction coefficients calculated from the amino acid sequences.

Affinity and inhibition were measured using a BIAcore T200 surface plasmon resonance instrument (GE Healthcare). Approximately 7000 response units of the cIL-10R1-Fc fusion was covalently coupled to a CM5 sensor chip using EDC/NHS chemistry as directed by the manufacturer. All experiments were conducted at 37° C. in HBS-EP buffer (10 mM HEPES, 150 mM NaCl, 3 mM EDTA, 0.005% [v/v] Tween-20, pH 7.4). Binding affinity ($K_d$) for cIL-10 to immobilized cIL-10R1-Fc was determined by injecting five concentrations of cIL-10 over the sensor chip for 120 seconds at 20 µL/second. After 300 seconds of dissociation, the sensor chip was regenerated with a 10 second pulse of 10 mM sodium acetate, 0.5 mM EDTA, pH 4 followed by a 120 second stabilization phase before making the next injection. The BIAcore evaluation software was used to calculate the maximum bound material ($R_{max}$) for each cIL-10 concentration. $R_{max}$ values were plotted against cIL-10 concentration and fit to the equation for a rectangular hyperbola to calculate $K_d$.

Inhibition of cIL-10 binding to cIL-10R1-Fc by the sdABs was measured by preincubating 10 nM cIL-10 with six concentrations of each sdAB in HBS-EP for at least 20 minutes, followed by injection onto the sensor chip as described above. Calculated $R_{max}$ values for each sdAB concentration were plotted against the sdAB concentration to determine $IC_{50}$ values.

Figure 7:
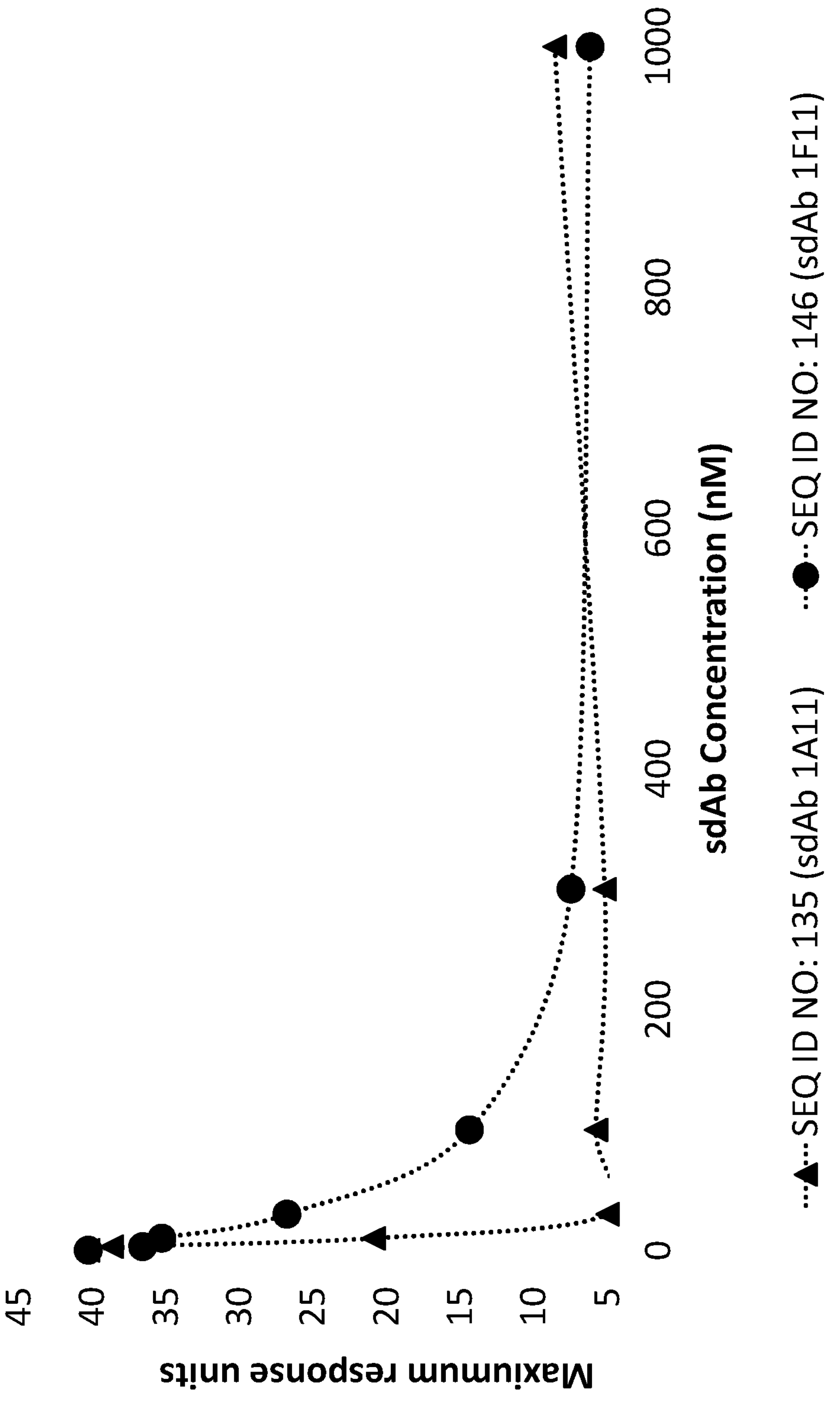
FIG. 7 illustrates the apparent inhibition of IL-10 binding to the IL-10 receptor in the presence of anti-IL10 antibodies chIL10sdAB1A11 (SEQ ID NO: 135) and chIL10sdAB1F11 (SEQ ID NO: 146).

FIG. 7 illustrates anti-IL-10 sdAb IC50 values measured for chIL10sdAB1A11 (SEQ ID NO: 135) and chIL10sdAB1F11 (SEQ ID NO: 146).

Figure 8:
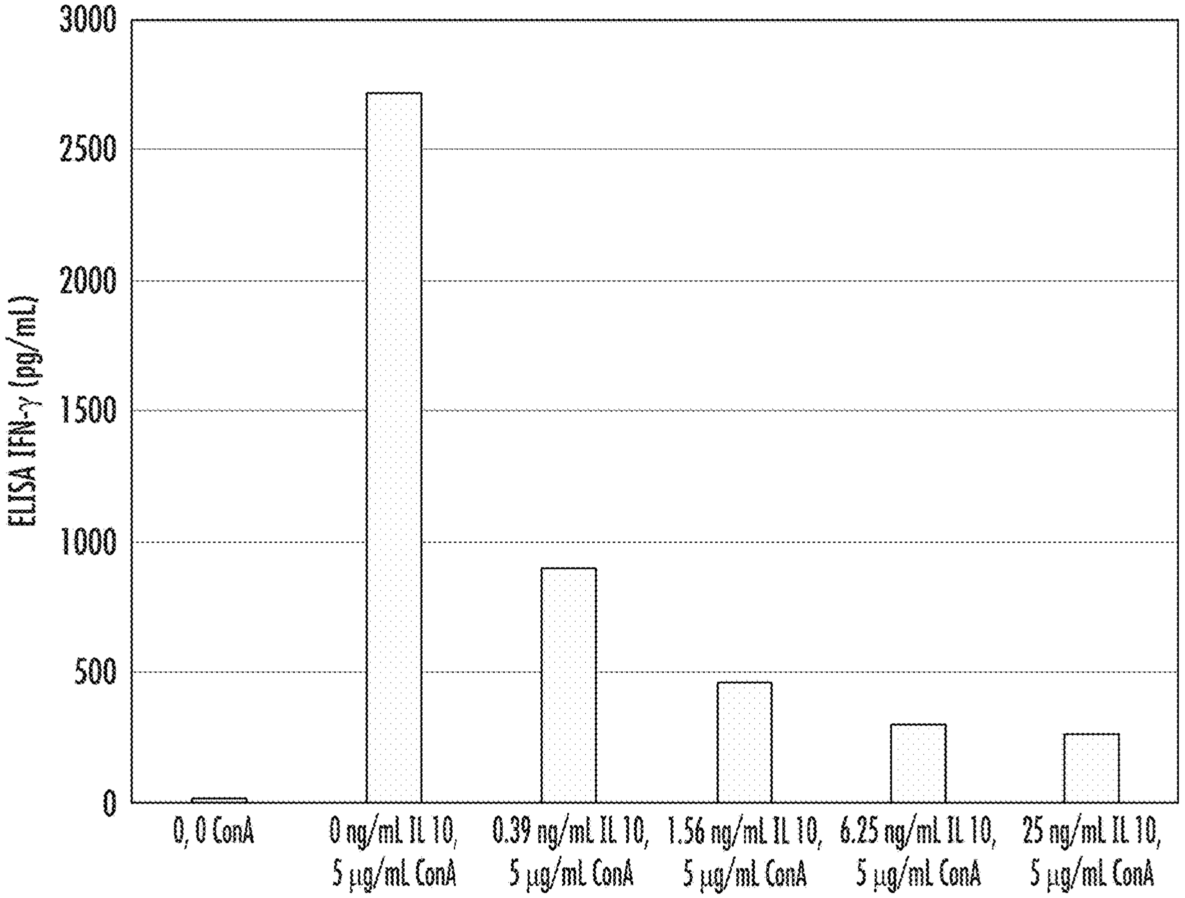
FIG. 8 illustrates IL-10 suppression of Concanavalin A-induced secretion of IFN-γ secretion in primary chicken spleen cells.

Example 10. Cell-Based Assay to Measure the Biological Activity of cIL-10 on Interferon Gamma (IFN-□) Production and Inhibition of cIL-10 by Anti-IL-10 sdAB in Stimulated Primary Chicken Spleenocytes IL-10 is known to be a potent regulator of the immune system that affects many cell types and generally acts to attenuate inflammation and the immune response (Kevin N. Couper, Daniel G. Blount, Eleanor M. Riley, "IL-10: The Master Regulator of Immunity to Infection," The Journal of Immunology, 180:5771-5777, 2008). Primary chicken spleen cells were used to evaluate the use of sdABs in blocking the biological activity of IL-10 in cellular signaling on a relevant target cell type. A cell-based assay was developed to study the inhibitory effect of cIL-10 on the concanavalin A (ConA) dependent induction (or phytohemagglutinin (PHA) dependent induction, both stimulators work with these cells) of interferon gamma (IFN-□) production in chicken spleen cells (Wu et al. (2016) and Rothwell et al. (2004)). Briefly, lymphocytes and mononuclear cells were isolated from chicken spleens by differential centrifugation on Ficoll-Hypaque. Freshly isolated cells were cultured at $5\times10^6$ cells/mL in wells of a 96-well plate for 72 hours in the presence of 1.2 µg/mL ConA (or 12.5 µg/mL PHA) with, or without, cIL-10 at concentrations of 0-25 mg/mL. Levels of IFN-□ in the supernatants of treated cells were determined by ELISA. FIG. 8 shows the IFN-□ response of the cells in the absence of ConA, ConA with no cIL-10, and ConA with 0.39, or 1.56, or 6.25, or 25 ng/mL cIL-10). As seen in FIG. 8, IL-10 suppresses of ConA-induced secretion of IFN-γ in primary chicken spleen cells. FIG. 8 also shows that spleen cells have a dose dependent response in IFN-□ production to chIL-10, as increasing cIL-10 lowers IFN-□ production in a dose-dependent manner.

To test how effective sdABs were in interrupting cIL-10 stimulated production of IFN-□□ primary chicken spleen cells were incubated with and without different concentrations of sdABs ranging from 0.1 nM up to 10 □M, with ConA, and with or without cIL-10. Levels of IFN-□ in the culture supernatants were determined by ELISA. Included in these studies, as control treatments, were spleen cells treated only with 5 µg/mL ConA (positive control for IFN-□ production), cells treated with 5 µg/mL of ConA and 1.5 ng/ml of cIL-10 (positive control for cIL-10 inhibition of ConA-dependent IFN-g production), and cells treated with 5 µg/mL of ConA, 1.5 ng/ml of cIL-10, and either an anti-IL-10 polyclonal antibody ("all10 pAb", positive control antibody) or a non-specific sdAB that did not bind cIL-10 ("aMOP pAb (NC)", a negative control antibody to demonstrate that non-specific binding cannot provide the same effect observed with antibodies that specifically bind cIL-10). Experimental treatments contained 5 µg/mL ConA, 1.5 ng/ml of cIL-10, and varying concentrations of anti-IL-10 sdABs. In these experiments, sdABs were dose at 1 nM, 30 nM, and 1000 nM.

Figure 9:
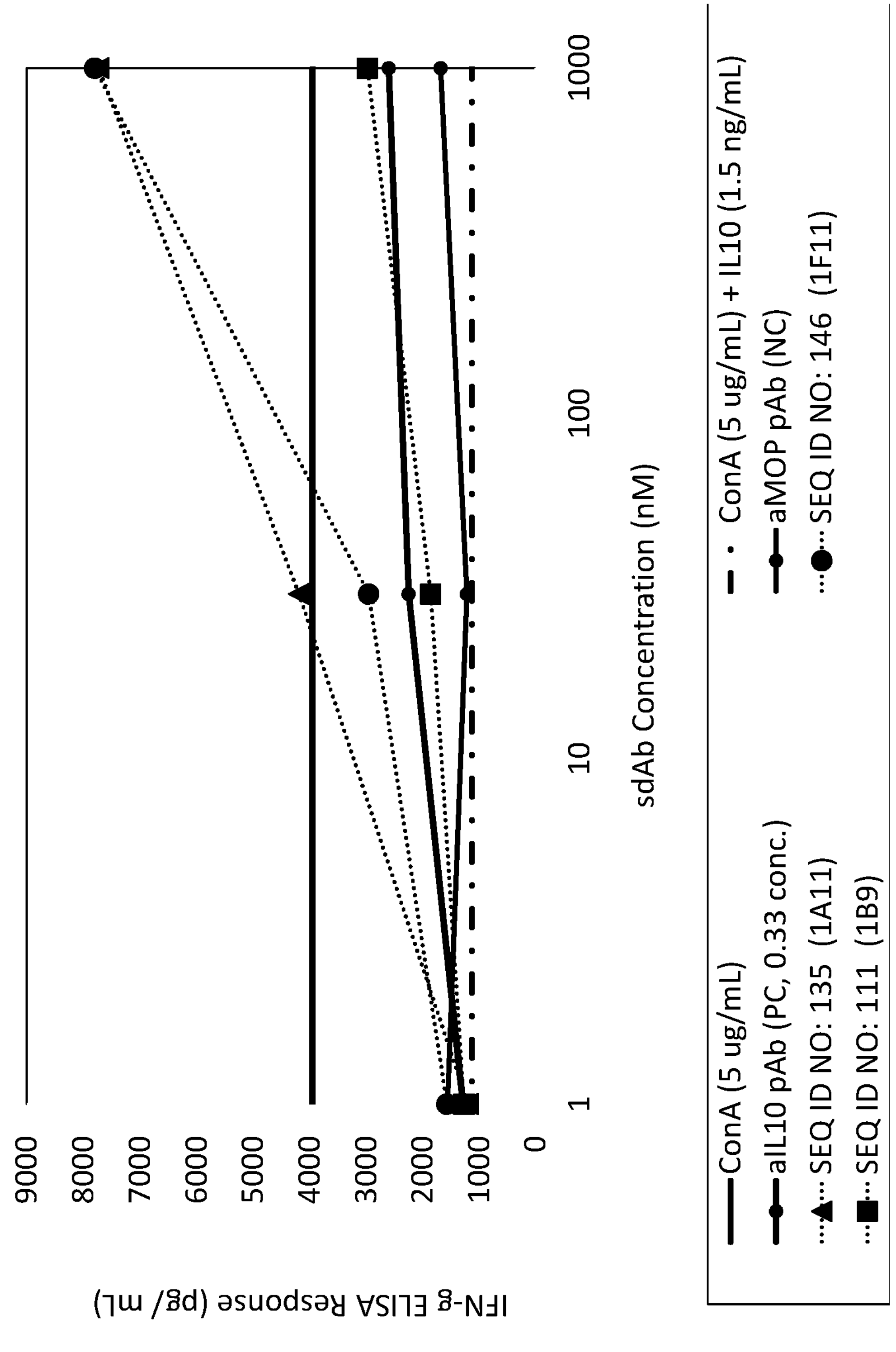
FIG. 9 illustrates recovery of IFN-γ secretion from primary chicken spleen cells treated with Concanavalin A and chicken IL-10, when also treated with the anti-IL-10 antibodies (chIL10sdAB1A11 (SEQ ID NO: 135), chIL10sdAB1B9 (SEQ ID NO: 111), and chIL10sdAB1F11 (SEQ ID NO: 146)).

FIG. 9 illustrates the anti-IL-10 antibodies (chIL10sdAB1A11 (SEQ ID NO: 135), chIL10sdAB1B9

(SEQ ID NO: 111), chIL10sdAB1F11 (SEQ ID NO: 146) effect on the IFN-γ secretion in primary chicken spleen cells. Based on these results, the apparent EC50 values for chIL 10sdAB1A11 (SEQ ID NO: 135), chIL10sdAB1B9 (SEQ ID NO: 111), chIL10sdAB1F11 (SEQ ID NO: 146) were measured to be 25 nM, 40 nM, and 60 nM, respectively. Although higher than the $EC_{50}$ and $IC_{50}$ values measured for binding of the anti-IL-10 sdABs to cIL-10, they are still in relative agreement with these values and further demonstrate the biological efficacy of the anti-IL-10 sdABs in blocking IL-10 signaling and decrease immune system suppression.

Example 11. Plant Expression of Anti-IL-10 Single Domain Antibodies

Antibody expression was demonstrated in transient expression using tobacco and in transgenic corn events. Other plant species can be used to express the anti-IL-10 sdABs, including rice, sorghum, soy beans, and canola. Depending on the final product and intended use, a particular plant species may be more suited for production than other species.

Expression cassettes containing the sequences of anti-IL-10 sdAbs for expression in maize are included in Table 6. In Table 6, some vectors contain single expression cassettes, while other vectors contain multiple expression cassettes, which usually helps increase expression of the sdAB. The DNA sequence of each chicken anti-IL-10 sdAB contained in the expression cassettes listed in Table 6 has been codon optimized for maize gene expression, however, the genes may be optimized for other plant (or microbial) species to improve their expression when a different expression host is desired.

TABLE 6

Plant expression vectors for expression of chicken anti-IL-10 sdABs:

| Vector | Chicken anti-IL-10 sdAb expression cassette(s) |
|---|---|
| pAG4314 | OsGluB4P:xGZein27ss:chIL10sdAB1A11A:KDEL |
| pAG4315 | OsGluB4P:xGZein27ss:chIL10sdAB1B9:KDEL |
| pAG4316 | OsGluB4P:xGZein27ss:chIL10sdAB1F11A:KDEL |
| pAG4317 | OsGluB4P:xGZein27ss:chIL10sdAB1H1A:KDEL |
| pAG4985 | ZmZ27P:xGZein27ss:chIL10sdAB1A11A:KDEL |
| pAG4986 | ZmZ27P:xGZein27ss:chIL10sdAB1B9:KDEL |
| pAG4987 | ZmZ27P:xGZein27ss:chIL10sdAB1F11A:KDEL |
| pAG4988 | ZmZ27P:xGZein27ss:chIL10sdAb1A11A:KDEL + OsGluB4P:xGZein27ss: chIL10sdAB1A11A:KDEL |
| pAG4989 | ZmZ27P:xGZein27ss:chIL10sdAB1B9:KDEL + OsGluB4P:xGZein27ss: chIL10sdAB1B9:KDEL |
| pAG4990 | ZmZ27P:xGZein27ss:chIL10sdAB1F11A:KDEL + OsGluB4P:xGZein27ss: chIL10sdAB1F11A:KDEL |
| pAG4991 | ZmZ27P:xGZein27ss:chIL10sdAB1H1A:KDEL |
| pAG4992 | ZmZ27P:xGZein27ss:chIL10sdAB1H1A:KDEL + OsGluB4P:xGZein27ss: chIL10sdAB1H1A:KDEL |
| pAG4993 | ZmZ27P:xGZein27ss:chIL10sdAB1A11B:KDEL |
| pAG4994 | ZmZ27P:xGZein27ss:chIL10sdAB1F11B:KDEL |
| pAG4995 | ZmZ27P:xGZein27ss:chIL10sdAB1H1B:KDEL |
| pAG4996 | ZmZ27P:xGZein27ss:chIL10sdAB1A11B:KDEL + OsGluB4P:xGZein27ss: chIL10sdAB1A11A:KDEL |
| pAG4997 | ZmZ27P:xGZein27ss:chIL10sdAB1F11B:KDEL + OsGluB4P:xGZein27ss: chIL10sdAB1F11A:KDEL |
| pAG4998 | ZmZ27P:xGZein27ss:chIL10sdAB1H1B:KDEL + OsGluB4P:xGZein27ss: chIL10sdAB1H1A:KDEL |

Figure 10A:
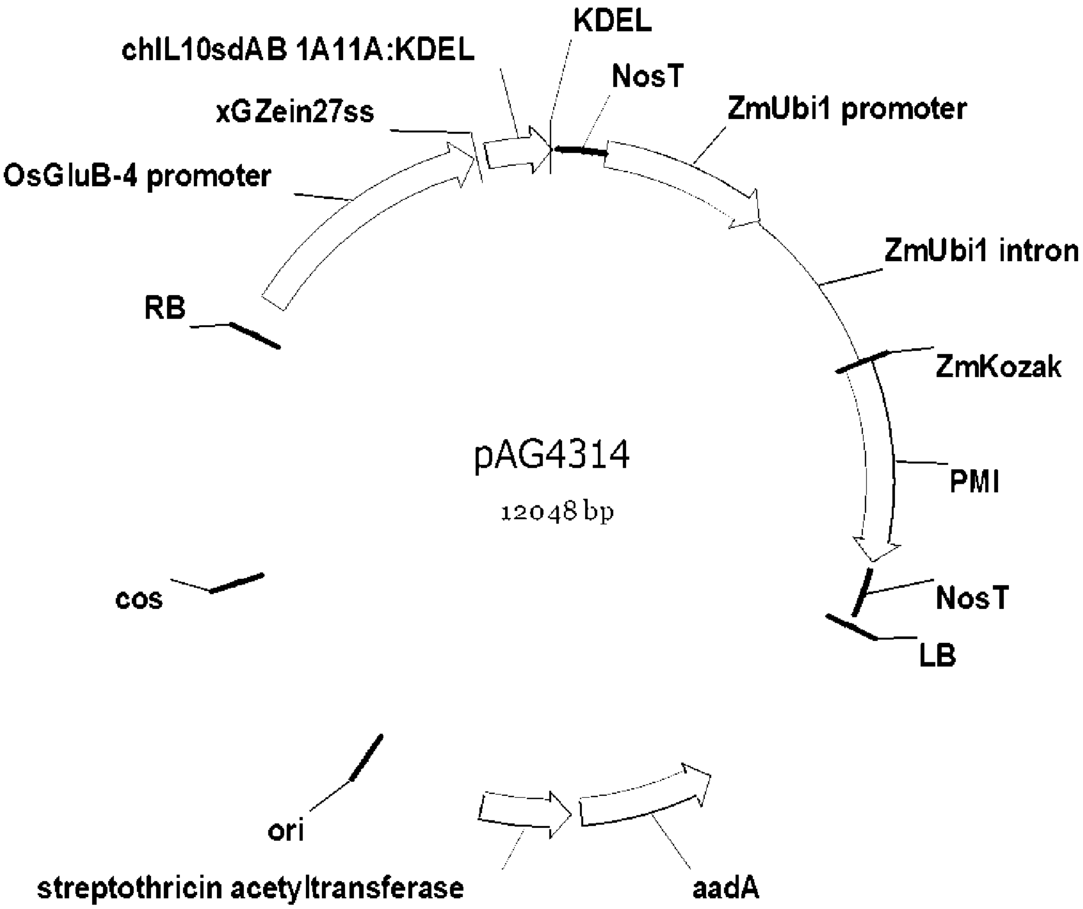
FIG. 10A is a schematic drawing of the vector pAG4314.
Figure 10B:
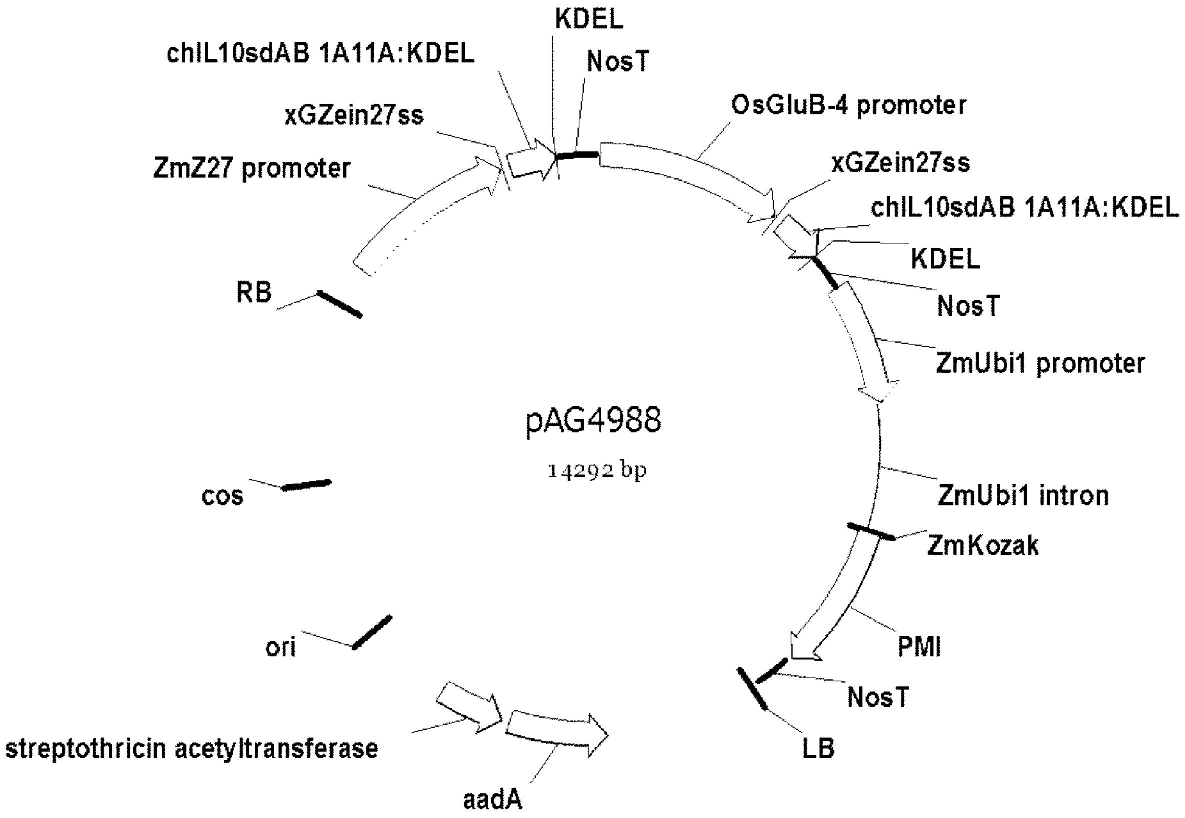
FIG. 10B is a schematic drawing of the vector pAG4988.

FIG. 10A is a schematic drawing of a vector pAG4314 that includes a single expression cassette for an anti-IL-10 sdAB (OsGluB4P:xGZein27ss:chIL10sdAB1A11A:KDEL) and the PMI expression cassette for selection in plants. FIG. 10B is a schematic drawing of a vector pAG4988 that increases the transgene dosage by including two expression cassettes for the same anti-IL-10 sdAB (ZmZ27P: xGZein27ss:chIL10sdAb1A11A:KDEL+OsGluB4P: xGZein27ss:chIL10sdAB1A11A:KDEL). Vector pAG4988 also includes the PMI expression cassette for selection in plant tissues. The T-DNA sequences for the vectors listed in the table are provided below in such a way that each sequence starts with the right border repeat and ends with the left border repeat.

Deduced protein sequences for selected chicken IL10 sdAb are provided with the maize gamma zein 27 signal sequence and KDEL signal sequence, which are underlined at N-terminal and C-terminal ends of the protein, respectively.

Protein Sequences of chIL 10 sdABs Encoded by Plant Expression Cassettes

>xGZein27ss:chIL10sdAb1A11:KDEL (SEQ ID NO: 84)

MRVLLVALALLALAASATSQVQLQESGGGLVQPGGSLRLSCASGNIFSIN

TMGWYRQAPGKQRELVASITTGGTTNYEDSVKGRFTISRDNAKKTVYLQM

NRLKPEDTAVYYCNHRRSYSGRDYPVYGMDYWGKGTLVTVSSKDEL

>xGZein27ss:chIL10sdAb1B9:KDEL (SEQ ID NO: 85)

MRVLLVALALLALAASATSQVQLQESGGGLVQAGGSLRLSCAASGRTFSS

YAWGWFRQAPGKEREFVARISFSGGHTYYSDSVKGRFTISRDNAKNTVYL

QMNSLKPEDTAVYYCAADPTPYGLRNERNYPYWGQGTQVTVSSKDEL

>xGZein27ss:chIL10sdAb1F11:KDEL (SEQ ID NO: 86)

MRVLLVALALLALAASATSQVQLQEFGGGLVQPGGSLRLSCASGRTGSSY

AMGWFRQAPGKEREFVAAISWSGGSTDYADSVKGRFTISRDNAKNTMYLQ

MNSLKPEDTAVYYCAVDRNLFKLRVAVQEYTNLGQGTQVTVSSKDEL

>xGZein27ss:chIL10sdAb1H1:KDEL (SEQ ID NO: 179)

MRVLLVALALLALAASATSQVQLQASGGGLVQAGGSLRLSCAASGRTFNS

YAWGWFRQAPGKERGFVARISFSGGHTYYSDSVKGRFTISRDNAKNSVYL

QMNSLKPEDTAVYYCAADPTPYGLRNERNYHYWGQGTQVTVSSKDEL

The nucleotide sequences encoding chIL10sdAB1A11, chIL10sdAB1F11, and chIL10sdAB1H1 antibodies in vectors and nucleotide sequences were named 1A11A (chIL101A11A), 1F11A (chIL101F11A), and 1H1A (chIL101H1A), respectively, to reflect different coding sequences with altered codon useage. This modification was made in order to avoid any possible confusion in the future due to availability of different variants (for example, "variant A" and "variant B") of the maize codon optimized sequences for maize expression. The deduced protein sequences encoded by the variants "A" and "B" are identical.

Nucleotide sequence alignments of the maize codon optimized variants "A' and "B" of the selected chIL 10 sdABs:

```
CLUSTAL O(1.2.4) multiple sequence alignments
1A11A    CAGGTTCAGCTGCAGGAAAGCGGTGGCGGACTGGTGCAGCCAGGTGGCAGCCTCAGGCTG   60
1A11B    CAGGTGCAGCTCCAGGAGTCCGGCGGCGGCCTCGTGCAGCCGGGCGGCTCCCTCCGCCTG   60
         ***** ***** *****   *** ***** ** ******** ** ***  **** * ***

1A11A    AGCTGCGCTGCTAGCGGCAATATTTTTAGCATTAACACAATGGGTTGGTATAGACAGGCT   120
1A11B    AGCTGCGCCGCGTCCGGCAACATCTTCAGCATCAACACGATGGGCTGGTACAGGCAGGCC   120
         ******** **   ****** ** ** ***** ***** ***** ***** ** *****

1A11A    CCTGGCAAGCAGCGTGAGCTCGTTGCCAGCATTACCACGGGTGGTACAACCAATTATGAA   180
1A11B    CCCGGCAAGCAGCGGGAGCTCGTGGCCTCCATCACCACGGGCGGCACCACGAACTACGAG   180
         ** *********** ******** ***  *** ******** ** ** ** ** ** **

1A11A    GATAGCGTGAAGGGTCGTTTTACCATTAGCAGGGACAATGCTAAGAAGACCGTTTACCTC   240
1A11B    GACAGCGTCAAGGGCCGCTTCACCATCTCCAGGGACAACGCCAAGAAGACGGTGTACCTC   240
         ** ***** ***** ** ** *****   ********* ** ******** ** ******

1A11A    CAGATGAACAGGCTGAAGCCAGAAGATACCGCCGTGTATTACTGCAACCACAGGAGAAGC   300
1A11B    CAGATGAACCGCCTGAAGCCGGAGGACACGGCGGTCTACTACTGCAACCACCGCAGGTCC   300
         ********* * ******** ** ** ** ** ** ** ************ * **   *

1A11A    TATAGCGGAAGAGATTATCCTGTTTACGGTATGGACTACTGGGGCAAGGGAACCCTGGTT   360
1A11B    TACAGCGGCAGGGACTACCCCGTGTACGGCATGGACTACTGGGGCAAGGGCACCCTCGTG   360
         ** ***** ** ** ** ** ** ***** ******************** ***** **

1A11A    ACCGTGAGCAGC 372 [SEQ ID NO: 173]
1A11B    ACCGTGTCCTCC 372 [SEQ ID NO: 174]
         ******  *  *

1F11A    CAGGTTCAGCTCCAGGAGTTTGGTGGCGGACTGGTGCAGCCAGGTGGCAGCCTCAGGCTG   60
1F11B    CAGGTGCAGCTCCAGGAGTTCGGCGGCGGCCTCGTGCAGCCGGGCGGCTCCCTCCGCCTG   60
         ***** ************** ** ***** ** ******** ** ***  **** * ***

1F11A    AGCTGCGCTGCTAGCGGTAGAACCGGCAGCAGCTATGCTATGGGATGGTTTAGACAGGCT   120
1F11B    AGCTGCGCCGCGTCCGGCAGGACGGGCTCCAGCTACGCGATGGGCTGGTTCAGGCAGGCG   120
         ******** **   *** ** ** ***  ****** ** ***** ***** ** *****

1F11A.   CCAGGCAAGGAGCGTGAATTTGTTGCTGCCATTAGCTGGAGCGGAGGTAGCACCGATTAT   180
1F11B    CCCGGCAAGGAGAGGGAGTTCGTGGCGGCCATCTCGTGGAGCGGCGGCAGCACCGACTAC   180
         ** ********* * ** ** ** ** *****    ******** ** ******** **

1F11A    GCTGACAGCGTGAAGGGCAGGTTTACCATTAGCAGAGATAATGCCAAGAACACCATGTAC   240
1F11B    GCTGACTCCGTCAAGGGCCGCTTCACCATCAGCAGGGACAACGCGAAGAACACGATGTAC   240
         ******  *** ****** * ** ***** ***** ** ** ** ******** ******

1F11A    CTCCAGATGAATAGCCTGAAGCCAGAGGATACCGCTGTTTATTACTGCGCCGTGGACCGT   300
1F11B    CTCCAGATGAACTCCCTGAAGCCGGAGGACACCGCCGTGTACTACTGCGCGGTCGACCGC   300
         ***********   ********* ***** ***** ** ** ******** ** *****

1F11A    AATCTCTTTAAGCTGAGGGTTGCTGTGCAGGAATACACCAACCTCGGCCAGGGAACCCAG   360
1F11B    AACCTCTTCAAGCTGAGGGTGGCCGTCCAGGAGTACACCAACCTCGGCCAGGGCACCCAG   360
         ** ***** *********** ** ** ***** ******************** ******

1F11A    GTTACCGTGAGCAGC 373 [SEQ ID NO: 173]
1F11B    GTGACCGTGTCCTCC 373 [SEQ ID NO: 176]
         ** ******  *  *

1H1A     CAGGTTCAGCTCCAGGCTTCGGGCGGCGGGCTCGTCCAGGCGGGCGGCTCGCTCAGGCTC   60
1H1B     CAGGTGCAGCTCCAGGCCTCCGGCGGCGGCCTCGTGCAGGCGGGCGGCTCCCTCCGCCTG   60
         ***** *********** ** ******** ***** ************** *** * **

1H1A     TCGTGCGCGGCGTCGGGGCGGACTTTCAACAGCTACGCTTGGGGCTGGTTCAGGCAGGCG   120
1H1B     AGCTGCGCCGCGTCCGGCAGGACCTTCAACAGCTACGCTTGGGGCTGGTTCAGGCAGGCG   120
            ***** ***** **  **** ************************************

1H1A     CCGGGCAAGGAGCGCGGCTTCGTGGCCAGGATCTCCTTCAGCGGCGGCCACACCTACTAC   180
1H1B     CCGGGCAAGGAGCGCGGCTTCGTGGCCAGGATCTCCTTCAGCGGCGGCCACACCTACTAC   180
         ************************************************************

1H1A     TCCGACAGCGTCAAGGGCCGCTTCACGATCTCCAGGGACAACGCCAAGAACAGCGTGTAC   240
1H1B     TCCGACAGCGTCAAGGGCCGCTTCACGATCAGCAGGGACAACGCCAAGAACTCCGTGTAC   240
         ******************************  *******************  *******

1H1A     CTCCAGATGAACTCCCTGAAGCCCGAGGACACGGCCGTCTACTACTGCGCGGCGGACCCG   300
1H1B     CTCCAGATGAACAGCCTGAAGCCCGAGGACACGGCCGTCTACTACTGCGCGGCGGACCCG   300
         ************  **********************************************
```

-continued

```
1H1A     ACGCCCTACGGCCTCAGGAACGAGCGGAACTACCATTACTGGGGGCAGGGCACGCAGGTC   360
1H1B     ACCCCATACGGCCTCCGCAACGAGAGGAACTACCACTACTGGGGCCAGGGCACCCAGGTG   360
         ** ** ********* * ****** ********** ******** ******** *****

1H1A     ACTGTCTCTTCG 372 [SEQ ID NO: 177]
1H1B     ACCGTGTCCTCC 372 [SEQ ID NO: 178]
         ** ** ** **
```

TABLE 7

| The percentage of nucleotide sequence identity between "A" and "B" variants | | |
|---|---|---|
| Sequence "A" | Sequence "B" | Sequence identity, % |
| 1A11A | 1A11B | 78.2 |
| 1F11A | 1F11B | 79.7 |
| 1H1A | 1H1B | 90.3 |

Figure 11:
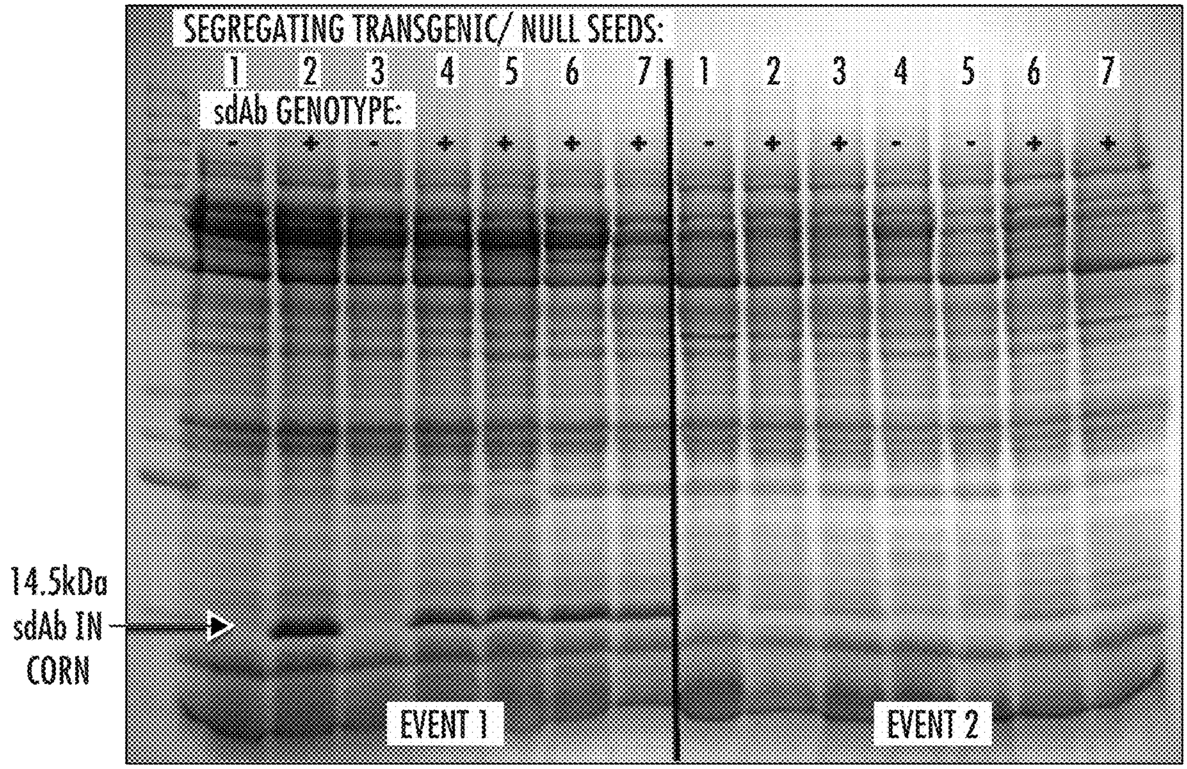
FIG. 11 illustrates that single domain antibodies express at high level in individual corn grain. In both transgenic events, individual grain were genotyped and protein extracted. The presence of the sdAB band in the gel image correlates perfectly with the presence of the sdAB gene as represented at the top of the figure with a "+" if the sdAB gene is present and a "−" if the sdAB gene is absent.

Any polynucleotides encoding anti-IL10 antibodies can be cloned between desirable promoter and terminator sequences in the plant expression vectors described herein (Table 6), in order to generate expression cassettes. In addition, amino terminal (N) signal sequences, such as xGZein27ss in maize expression vectors, can be replaced by other signal sequences in order to modulate specific expression and accumulation of anti-IL-10 antibodies to desired levels. N-terminal signal sequences include, but not limited to, for example by OsGluB4sp (rice GluB-4 glutelin signal peptide), BAASS (barley alpha amylase signal sequence), or PR1 (pathogenesis related protein). The anti-IL-10 antibodies can be expressed to endoplasmic reticulum (ER) for improved accumulation and potential glycosylation using carboxyl terminal (C) retention signal sequences such KDEL (SEQ ID NO: 29), HDEL (SEQ ID NO: 30), or SEKDEL (SEQ ID NO: 31). Furthermore, anti-IL10 antibodies can be expressed and directed to protein storage vacuoles with the help of signal sequences attached to either N-terminal or C-terminal part of the sequence. These storage vacuole signal sequences include HvAle from barley aleurone (thiol protease) or HvVSD from barley polyamine oxidase. If necessary, anti-IL-10 antibodies can be also expressed from expression vectors without signal sequences for accumulating expressed products in apoplast, chloroplast, or cytoplasm. All of the genetic elements mentioned above, including other signal sequences with similar functions, can be added to or removed from the basic plant expression vectors to tailor the expression properties of the anti-IL-10 sdAB. FIG. 11 illustrates that using the genetic elements described herein, sdABs can be expressed at high level in corn grain. In FIG. 11, sdABs expressed in corn were extracted from individual seed from a hemizygous parent, where 50% of the seed contained the expression cassette and 50% of the seed did not contain the expression cassette. In FIG. 11, individual seed from two different transgenic events were genotyped and analyzed for the presence of the expressed sdAB by SDS-PAGE electrophoresis and coomassie staining. As shown in FIG. 11, the presence of the sdAB correlated perfectly with the genotyping result, that is, only seed that tested positive for the gene by PCR produced a protein band at the right size of the sdAB. Further, expression levels of the sdAB in event 1 were estimated at 3 mg per gram of corn grain, which would result in an expression level of 9 mg of sdAB per gram of corn for the fully homozygous event. Expression levels for recombinant proteins, including sdABs, up to 21 mg per gram of corn grain have been observed using the expression cassettes and genetic elements described herein.

Example 12. Transient Expression of Chicken IL10 sdAb 1A11 in Leaves of Tobacco *Nicotiana benthamiana*

Transient protein expression in plants has been used by multiple groups for production of therapeutic proteins and vaccine antigens. Among various plant species, tobacco *Nicotiana benthamiana*, is one of the most suitable production hosts because it can achieve a high level of protein expression in a short timeframe by using a leaf infiltration procedure. Such production attributes are required for economical heterologous protein production.

Genetic Elements and Construction of Vectors

For expression in *N. benthamiana*, the chicken IL-10 sdAb 1A11 (referred to herein as Nb1A11; SEQ ID NO: 202) sequence was codon optimized for *Nicotiana* codon usage and synthesized by GenScript as either an 868 bp NcoI-AvriI DNA fragment, which at 5' end contained 90 bp tobacco PR1a gene sequence [SEQ ID NO: 205] encoding transit peptide, 304 bp first intron of Arabidopsis ubiquitin 10 gene (AtUBQ10i) in Nb1a11 coding region, and at 3' end myc tag, 6×His, and KDEL sequences [SEQ ID NO: 206], or as 564 bp NcoI-AvrII fragment without the AtUBQ10i intron. The Nb1A11:AtUBQ10i sequence is shown below as SEQ ID NO: 203, and the intron sequence is indicated by the bold characters and is underlined.

[SEQ ID NO: 203]

CAAGTTCAGTTACAGGAAAGCGGGGGAGGTTTAGTTCAGCCTGGGGGTTC

ATTGAGGTTGAGTTGTGCAGCAAGTGGAAATATTTTTTCTATTAATACTA

TGGGATGGTATAGACAAGCTCCAGGTAAATTTCTGTGTTCCTTATTCTCT

CAAAATCTTCGATTTTGTTTTCGTTCGATCCCAATTTCGTATATGTTCTT

TGGTTTAGATTCTGTTAATCTTAGATCGAAGACGATTTTCTGGGTTTGAT

CGTTAGATATCATCTTAATTCTCGATTAGGGTTTCATAGATATCATCCGA

TTTGTTCAAATAATTTGAGTTTTGTCGAATAATTACTCTTCGATTTGTGA

TTTCTATCTAGATCTGGTGTTAGTTTCTAGTTTGTGCGATCGAATTTGTC

GATTAATCTGAGTTTTTCTGATTAACAGGAAAGCAAAGAGAACTTGTTGC

AAGTATTACTACTGGAGGAACTACAAATTACGAAGATAGTGTTAAAGGAA

GATTCACTATTTCAAGAGATAATGCTAAGAAAACAGTTTATCTTCAGATG

AATAGATTGAAGCCAGAAGATACAGCAGTTTACTACTGTAATCATAGAAG

ATCATACTCTGGTAGAGATTATCCTGTTTATGGTATGGATTATTGGGGAA

AAGGGACATTAGTTACAGTTAGCAGC

The AtUBQ10i was inserted into Nb1A11 coding region between nucleotides 124 and 125 for dual purpose: 1) monitoring expression of Nb1A11 from plant cells rather than from *Agrobacterium;* 2) potentially enhancing expression of Nb1A11 in tobacco, since positive effects of heterologous introns on gene transcription in plants and other species are well documented in the literature ("Introns increase gene expression in cultured maize cells," J. Callis, M. Fromm, V. Walbot, Genes Dev., 1:1183-1200, 1987; doi: 10.1101/gad. 1.10.1183; "Increased Gene Expression by the First Intron of Maize Shrunken-1 Locus in Grass Species," V. Vasil, M. Clancy, R. J. Ferl, I. K. Vasil, L. C. Hannah, Plant Physiol. 91:1575-1579, 1989; "Intron-mediated enhancement as a method for increasing transgene expression levels in barley," J. G. Bartlett, J. W. Snape, W. A. Harwood, Plant Biotechnology Journal, 7:856-866, 2009, all of which are incorporated herein by reference as if fully set forth). The sequences of myc tag and 6×His were included to facilitate Nb1A11 sdAB detection and purification. The KDEL sequence was added for retaining the expressed 1A11 sdAb in endoplasmic reticulum (ER) for improving accumulation levels of the protein. For transient expression of Nb1A11 sdAB in *N. benthamiana*, a new and previously uncharacterized constitutive ubiquitin 1 gene promoter (prNbUbi1) was used. The sequence of the prNbUbi1 is shown below as SEQ ID NO: 204, wherein the sequence of the intron sequence is indicated by the bold characters and is underlined.

[SEQ ID NO: 204]

CATGAAAGTCCACATCATCAGCTCGTCCCAAACATCACTACTAGACCCAA

CTCGTTCAATCTTCTCGACTACAACAAATGAAATCCGCTCATCAAGGTGT

CTGAGGCTGATCTCAATAAATGGAGGGACTAATTGTATGGATCGAAATCT

GCCCCAAAATATTTAGGGTAAGGTACATTGAAGAAAGAGTCATCGAGGTC

GATCAGGAAACGATCGAGATGTTAACAATGGTCGATGTCGAGCACCGCAT

GTAGAGTTGTAACACCTAGTTTTTAGAATAGGATAATACAAAGAATATTC

TATTGGATATCCTTTACACTTATATTATTAGAGTTTGTTAGGAAAATGAC

CCACATAAATAGGAAAAAAGACAATGAATGGAGACAGGTGACATTTATCT

GATGAGAACAGACTTTTGATAGAAGATATTTTCTCTCTCACTAAGATACA

AACACTACATTTTCATCAAGATTCTTGTTCATATCATTGTACACTTTTCT

ATCAAATCTGAAATAATTTAAATATTCTAGGATTTGTCTGTCACTCATCA

TTGTCAGACGGGATAATCATGTACTCATCCTTTTTTGGCAAACCACTTTT

TCTATTTACTTAAATGCCATTTATTGATATCTATTGCTAGTCATTCCTCC

ACCGTTGCTCATACTTTTTTGCAATAGTATGCATGTTGATATCAATCCAC

CACCAAATCTTCTAACATTAATCATATTTTCACAACTTACATTTATAAAT

ATTATTATTAACTAAGTTTAACTCACTATTATATAAACTCAATTGTTTTA

CTCGAAAGTTACACTATTATATTGAGAATTACGTTTCCAAACTTTTTAAG

CATTTATTGTGTAACCATAAGAGACTTTGATTTTTTAAAAATTATTTAGA

TTTTATTAATGAGAATGGCACAACATTATGGTCAACTATGTATTTCATCA

TTAACTAAATAGTTAGCACTTTGATTCTTTCACATGAATTATGAATTTAT

GATGGGCTCAAATTAAAATTAAATTATTCACAAAAACTTATTTTTATATT

CTACGACACCCACTTTTCTAGCTTTTTCCCGAAGGGGCGTGAGAGTGTCA

CACACGCTCCAAATTTCCCAACCAAACAAGGAAAGGGCAGAGAAAGATAG

CTTTAGCGTGTTGTTTTGGTGCACTACACGTCATTAGGACACGTGTCATG

ATATAATAGGCCAATCCCACGAGGCGGTTTCGTCTTGAGTCGGCCATAGT

-continued

GTCCATAAATGAGGGCTCTCCGTCGGTTTCCCCATCATTCATCAGATTTA

TCTTCTATACTTCATCGCCTTCATATTTCTCTCTCAAGGTTTGAGAATTT

CTTCAATTTCTCGCTTTAGCAGTTCTTTTTTATTGAATCAACGATTTCGG

CATCTAAAGTCCTAATTTTGAAGTTCATTGCTTTAATTGTTTGTTGTTGA

TTTTATATTATTACAG

This promoter was identified by screening *N. benthamiana* Expressed Sequence Tag (EST) database for the most abundant in leaf tissue ubiquitin gene transcript. The database is maintained by the *Nicotiana benthamiana* Genome and Transcriptome Sequencing Consortium (Nakasugi K, Crowhurst R N, Bally J, Wood C C, Hellens R P, Waterhouse P M (2013) De Novo Transcriptome Sequence Assembly and Analysis of RNA Silencing Genes of *Nicotiana benthamiana*. PLOS ONE 8 (3): e59534, which is incorporated by reference herein as if fully set forth). The transcript Nbv6.1trP26199, annotated as putative ubiquitin 1, appeared to contain significantly larger number of ESTs (1196) than other ubiquitin related transcripts. The Nbv6.1trP26199 specific 1466 bp upstream genomic sequence, which included 128 bp 3'UTR positioned intron, was identified in *N. benthamiana* draft genome sequence (v1.0.1) that is available at the Sol Genomics Network at Boyce Thompson Institute for Plant Research (Bombarely, A., H. G. Rosli, J. Vrebalov, P. Moffett, L. A. Mueller, and G. B. Martin (2012). A draft genome sequence of *Nicotiana benthamiana* to enhance molecular plant-microbe biology research. Molecular Plant-Microbe Interactions 25:1523-1530, which is incorporated by reference herein as if fully set forth).

Figure 12:
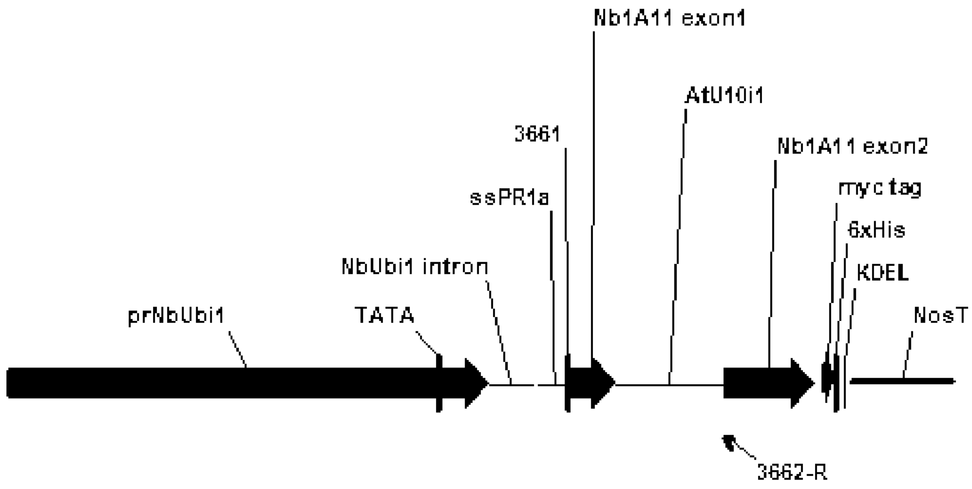
FIG. 12 is a schematic drawing of the pLH1A11int expression cassette.
Figure 13:
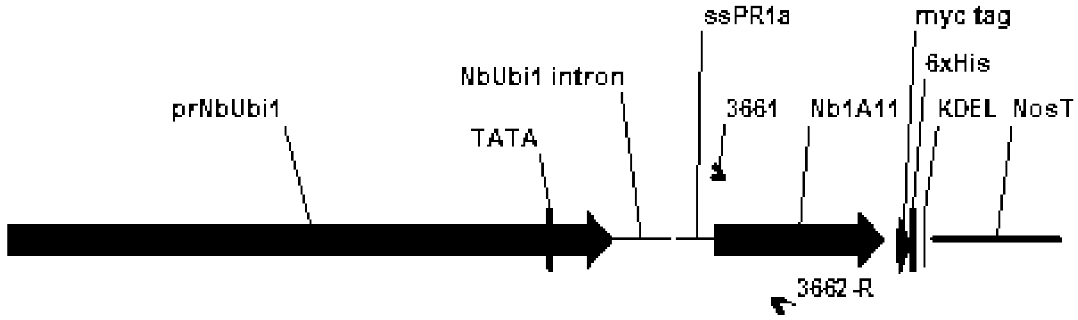
FIG. 13 is a schematic drawing of the pLH1A11 expression cassette.

This 1466 bp sequence in *N. benthamiana* genome has nucleotide coordinates 74703-76169 in the Scaffold No: 5041 and is fused tocoding region of a putative ubiquitin gene that encodes five 76 amino acid long identical ubiquitin monomers. The 1466 bp prNbUbi1 was synthesized by GenScript as NotI-NcoI fragment. The entire Nb1A11+AtUBQ10i or Nb1A11 expression cassettes were cloned into NotI-KpnI sites of the pLH9000 vector, which was kindly provided by Dr. I. Lernomtova (IPK Gatersleben, Germany), and the final constructs were designated as pLH1A11int or pLH1A11 respectively. FIG. 12 illustrates pLH1A11int expression cassette. FIG. 13 illustrates pLH1A11 expression cassette. Subsequently, pLH9000, pLH1A11int and pLH1A11 were electroporated into electrocompetent cells of the *Agrobacterium* strain GV3101. *Agrobacterium* colonies carrying pLH9000, pLH1A11int or pLH1A11 constructs were validated by PCR.

*N. benthamiana* Plant Growing and Inoculation with *Agrobacterium*

The seeds of *N. benthamiana* were acquired from The US *Nicotiana* Germplasm Collection (NC State University). The seeds were sowed into 4"×4' pots containing ProMix soil. After germination the seedlings and the plants were kept at 16 h day and 8 h night light regime. Five weeks old healthy *N. benthamiana* plants were used for syringe infiltration with *Agrobacterium* strains GV3101 harboring either pLH9000 as a negative control, pLH1A11int or pLH1A11 expressing Nb1A11 (chicken IL-10 sdAb1A11 for *N. benthamiana* expression as described above), or with the mixture of two *Agrobacterium* strains, such as GV3101 with pLH1A11int and C58C1 with p19. As used herein, 1A11 sdAB is synonomous with anti-chicken IL-10 sdAB and chicken IL-10 sdAb1A11. The p19 is a tomato bushy stunt virus protein, which is involved into suppression of RNA-dependent gene silencing thus improving expression of heterologous proteins. *Agrobacterium* strains GV3101 and C58C1 with p19 were kindly provided by Dr. I. Lernomtova (IPK Gatersleben, Germany). The *Agrobacterium* strains containing plasmids were grown from single colonies overnight in LB medium supplemented with corresponding antibiotics, the cells were harvested by centrifugation and resuspended to $OD_{600}$=0.4 in 10 mM $MgCl_2$, 10 mM MES-K (pH 5.6). Prior to syringe infiltration of *N. benthamiana* leaves 100 μM Acetosyringone was added to each *Agrobacterium* strain. The leaf tissues for expression analysis of Nb1A11 were harvested on day 4 post infiltration.

RNA Analysis of Nb1A11 Expression

The total plant RNA from *Agrobacterium* infiltrated *N. benthamiana* leaf tissues was isolated with NucleoSpin RNA Plant Kit (Takara) according to manufacturer's protocol. Subsequently, 1 μg of the total RNA was converted into cDNA using iScript CDNA Synthesis Kit (Bio-Rad) and 1.5 μl of each cDNA was used as template in PCR reactions with the following primers:

```
forward primer 3661
(5'- CGTGCCCAAGTTCAGTTACA - 3' [SEQ ID NO: 200 ]),
and

reverse primer 3662
(5'- TTGCAACAAGTTCTCTTTGCTT - 3' [SEQ ID NO: 201]).
```

Figure 14:
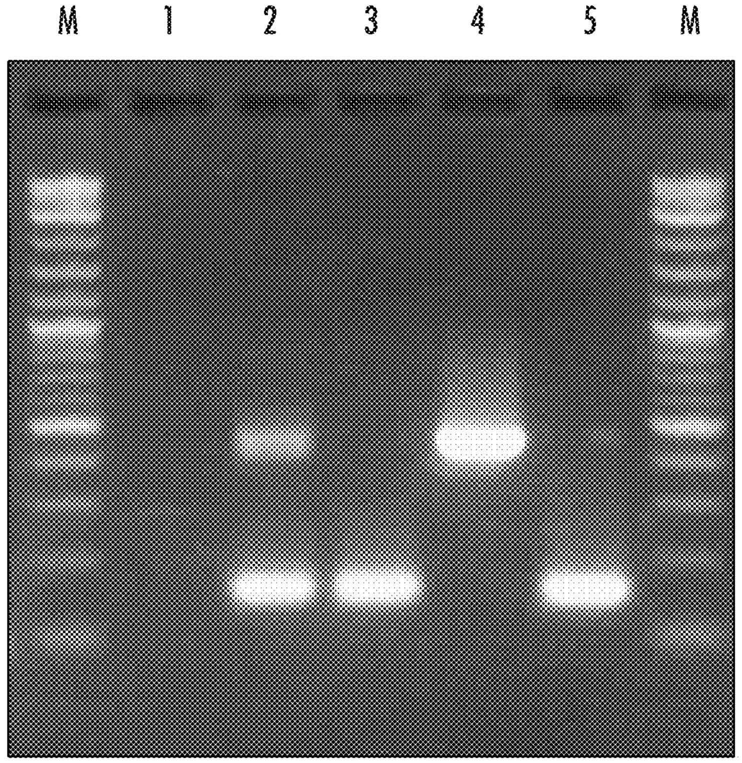
FIG. 14 illustrates end point RT-PCR analysis of transiently expressed Nb1A11 in *N. benthamiana* leaves. Lanes 1-5 contain the following samples: lane 1—GV3101+pLH9000 (negative control); lane 2—GV3101+pLH1A11int; lane 3—GV3101+pLH1A11; lane 4—plasmid pLH1A11int; and lane 5—plasmid pLH1A11.

The primers were positioned to flank intron AtUBQ10i within the coding region of Nb1A11 and allow unambiguous identification of the plant cell expressed 1A11 transcript with the fully spliced out intron. The Platinum Taq DNA Polymerase (Invitrogen) was used to amplify PCR products under conditions recommended by manufacturer with 36 cycles of amplification and primer annealing temperature of 55° C. The PCR products were resolved on 2% agarose gel. FIG. 14 illustrates end point RT-PCR analysis of transiently expressed Nb1A11 in *N. benthamiana* leaves. In this figure, lanes 1-5: lane 1—GV3101+pLH9000 (negative control); lane 2—GV3101+pLH1A11int; lane 3—GV3101+pLH1A11; lane 4—plasmid pLH1A11int; and lane 5—plasmid pLH1A11.

In *N. benthamiana* leaf tissues infiltrated with the negative control plasmid pLH9000 no 1A11 transcripts were amplified (lane 1). Distinct PCR products of the expected 1A11 transcript sizes were amplified from *N. benthamiana* leaf tissues infiltrated with either pLH1A11int or pLH1A11 (lanes 2 and 3 respectively).

Amplified PCR products from plasmids pLH1A11int and pLH1A11 were uses as positive controls and run in lanes 4 and 5. The resulting products in lanes 4 and 5 were observed to have identical sizes to the products in lanes 2 and 3. A lower intensity PCR band corresponding in size to the expected 458 bp fragment containing AtUBQ10i was also detected in lane 2. This fragment could have been amplified from either *N. benthamiana* genomic DNA, which was still lingering in total RNA preparation of the sample despite of its removal by DNase digestion as suggested by manufacturer's instructions, or alternatively, the amplification product is indicative of a fraction of isolated total RNA containing Nb1A11 transcripts with still unspliced AtUBQ10i.

1A11 sdAb Transient Protein Expression Analysis

Figure 15:
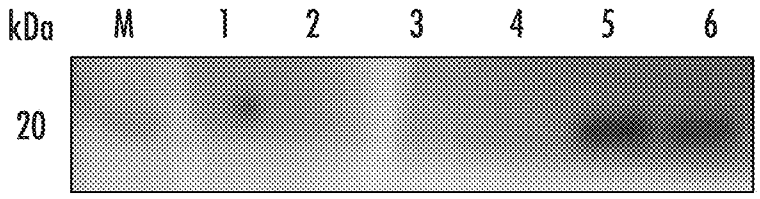
FIG. 15 illustrates sdAB1A11 expression in *Agrobacterium* infiltrated leaves of *N. benthamiana*. The Western blot shows detection of sdAB1A11 in samples 5 and 6.

Based on the results of Nb1A11 RNA transcript analysis in leaves of *N. benthamiana*, the leaf tissue samples that were infiltrated with pLH1A11int and pLH1A11int+p19 were selected for protein isolation and Western blot analysis. *Agrobacterium*-infiltrated leaf tissues were ground in liquid nitrogen and the total protein was isolated using extraction buffer composed of 1 M NaCl, 50 mM Sodium Phosphate pH8.0, 10 mM Imidazole. The extraction buffer was supplemented with 1×Halt Protease Inhibitor Cocktail (ThermoFisher) and 2 mM β-mercaptoethanol. Protein extraction was performed at 4° C. for 1 h with agitation, samples were centrifuged twice to remove plant debris. The 1A11 sdAB containing 6×His tag at its C-terminal end was isolated from the cleared supernatant of the total *N. benthamiana* leaf protein using Ni-NTA spin columns (QIAGEN) according to manufacturer's protocol for native conditions. The 1A11 sdAB was further concentrated using Amicon Ultra-2 centrifugal filters (Millipore-Sigma) and protein concentration was determined by NanoDrop spectrophotometer. Subsequently, 15 μg of 1A11 containing concentrated protein fraction was resolved on 4-12% gradient NuPAGE polyacrylamide gels (ThermoFisher) using 1×MOPS SDS gel running buffer. Biotynylated Protein Ladder (Cell Signalling Technologies) and Precision Plus Protein Kaleidoscope (Bio-Rad) were used as molecular weight standards. The proteins were separated in a polyacrylamide gel and transferred onto PVDF membrane using semi-dry Western blotting procedure. The PVDF membrane bound 1A11 protein was detected using Rabbit Anti-VHH HRP (Invitrogen) as the primary antibody at 1:2500 dilution followed by Anti-Rabbit IgG Peroxidase Goat (Sigma) as the secondary antibody at 1:5000 dilution. Detection of the biotinylated proteins in the protein molecular weight ladder was accomplished by Anti-biotin HRP-liked Ab at 1:15000 dilution (Cell Signaling Technology). The signal detection was achieved using Super Signal West Pico Plus chemiluminescent substrate (ThermoFisher). FIG. 15 illustrates 1A11 protein expression in *Agrobacterium* infiltrated leaves of *N. benthamiana*. The Western blot shows detection of 1A11 sdAb in samples 5, 6. It was demonstrated that the lanes 5 and 6 contain a protein of expected molecular weight of 17.4 kDa that is cross reactive with the Anti-VHH primary antibody, indicating the protein is indeed 1A11 sdAB.

Example 13. Anticoccidial Efficacy of IL-10R Peptide Antagonists and sdABs in Commercial Broiler Chickens Infected with a Mixture of *Eimeria acervulina, E. maxima*, and *E. tenella* Field Isolates The same study design was used to measure the anticoccidial efficacy/sensitivity anti-IL10 antibodies, or IL-10R antagonists against a mixture of *Eimeria acervulina, E. maxima*, and *E. tenella*. In these trials, chickens were separated into multiple control groups that were either exposed to *Eimeria* (Infected, I) or not exposed to *Eimeria* (Non-Infected, NI), and treatment groups that were exposed to *Eimeria* and treated with various diets. The control groups included a negative control group receiving normal feed with and without anti-IL-10 sdAB (or with and without IL-10R antagonist) in the feed, and a positive control group receiving a standard chemical Coccidiostat. Treatment groups were fed diets containing from 50 g to four kilograms of milled grain expressing anti-IL-10 sdAB per kilogram of feed (or IL-10R antagonist peptide doses ranging from 1 milligram of peptide per kilogram of feed to 40 milligrams of IL-10R antagonist peptide per kilogram of feed. Anti-IL-10 sdABs, including SEQ ID NO: 87 (chIL10sdAB1H5), SEQ ID NO: 88 (chIL10sdAB1E9), SEQ ID NO: 89 (chIL10sdAB1H1), SEQ ID NO: 90 (chIL10sdAB1G6), SEQ ID NO: 91 (chIL10sdAB1C10), SEQ ID NO: 92 (chIL10sdAB1B6), SEQ ID NO: 93 (chIL10sdAB1D12), SEQ ID NO: 94 (chIL10sdAB1C2), SEQ ID NO: 95 (chIL10sdAB1B5), SEQ ID NO: 96 (chIL10sdAB1E2), SEQ ID NO: 97 (chIL10sdAB1G7), SEQ ID NO: 98 (chIL10sdAB1G9), SEQ ID NO: 99 (chIL10sdAB1H12), SEQ ID NO: 100 (chIL10sdAB2A9), SEQ ID NO: 101 (chIL10sdAB1E12), SEQ ID NO: 102 (chIL10sdAB1E10), SEQ ID NO: 103 (chIL10sdAB1F12), SEQ ID NO: 104 (chIL10sdAB1A8), SEQ ID NO: 105 (chIL10sdAB1C8), SEQ ID NO: 106 (chIL10sdAB1C12), SEQ ID NO: 107 (chIL10sdAB1B1), SEQ ID NO: 108 (chIL10sdAB1F1), SEQ ID NO: 109 (chIL10sdAB1D11), SEQ ID NO: 110 (chIL10sdAB1E6), SEQ ID NO: 111 (chIL10sdAB1B9), SEQ ID NO: 112 (chIL10sdAB1B10), SEQ ID NO: 113 (chIL10sdAB1F5), SEQ ID NO: 114 (chIL10sdAB1A6), SEQ ID NO: 115 (chIL 10sdAB1D5), SEQ ID NO: 116 (chIL 10sdAB1D8), SEQ ID NO: 117 (chIL10sdAB1B4), SEQ ID NO: 118 (chIL 10sdAB1D7), SEQ ID NO: 119 (chIL10sdAB1B3), SEQ ID NO: 120 (chIL10sdAB1D7), SEQ ID NO: 121 (chIL10sdAB1F7), SEQ ID NO: 122 (chIL10sdAB1F10), SEQ ID NO: 123 (chIL10sdAB1F2), SEQ ID NO: 124 (chIL10sdAB1F3), SEQ ID NO:125 (chIL10sdAB1F8), SEQ ID NO: 126 (chIL10sdAB1C9), SEQ ID NO: 127 (chIL10sdAB1A12), SEQ ID NO: 128 (chIL10sdAB1C3), SEQ ID NO: 129 (chIL10sdAB1E7), SEQ ID NO: 130 (chIL10sdAB1D9), SEQ ID NO: 131 (chIL10sdAB1A9), SEQ ID NO: 132 (chIL10sdAB1H10), SEQ ID NO: 133 (chIL10sdAB1C1), SEQ ID NO: 134 (chIL10sdAB1D1), SEQ ID NO: 135 (chIL10sdAB1A11), SEQ ID NO: 136 (chIL10sdAB1G8), SEQ ID NO: 137 (chIL10sdAB1A5), SEQ ID NO: 138 (chIL10sdAB1C5), SEQ ID NO: 139 (chIL10sdAB1H6), SEQ ID NO: 140 (chIL10sdAB2A8), SEQ ID NO: 141 (chIL10sdAB1F9), SEQ ID NO: 142 (chIL10sdAB1E11), SEQ ID NO: 143 (chIL10sdAB1D6), SEQ ID NO: 144 (chIL10sdAB1C4), SEQ ID NO: 145 (chIL10sdAB1H4), SEQ ID NO: 146 (chIL10sdAB1F11), SEQ ID NO: 147 (chIL10sdAB1D3), SEQ ID NO: 148 (chIL10sdAB1A7), SEQ ID NO: 149 (chIL10sdAB1H8), SEQ ID NO: 150 (chIL10sdAB1H3), SEQ ID NO: 151 (chIL10sdAB1B8), SEQ ID NO: 152 (chIL10sdAB1B2), SEQ ID NO: 153 (chIL10sdAB1D2), or SEQ ID NO: 154 (chIL10sdAB1D10), or peptides of SEQ ID NO: 1 [P21], SEQ ID NO: 2 [P22], SEQ ID NO: 3 [P23], SEQ ID NO: 4 [P24], SEQ ID NO: 5 [P25], SEQ ID NO: 6 [P26], SEQ ID NO: 7 [P27], SEQ ID NO: 8 [P28], SEQ ID NO: 9 [P29], SEQ ID NO: 10 [P11], SEQ ID NO: 11 [P30], SEQ ID NO: 12 [P31], SEQ ID NO: 13 [P32] SEQ or concatenated peptides SEQ ID NO: 32 [P2501], SEQ ID NO: 33 [P2502], SEQ ID NO: 34 [P2503], SEQ ID NO: 35 [P2504], SEQ ID NO: 36 [P2505], SEQ ID NO: 37 [P2506], SEQ ID NO: 38 [P2507], SEQ ID NO: 39 [P2508], or SEQ ID NO: 40 [P2509] were tested in this manner.

These feeding trials are eight days in length and consist of 96 cages, each starting with 8 male chicks. The treatments will be replicated in 8 blocks, randomized within blocks of 8 cages each. A randomization procedure for pen assignment for treatments and blocks was used by the contracting facility.

TABLE 8

Treatment design to test chIL10sdAB expressing corn grain

| Trt | Description | Infected/ Non-Infected | Additive inclusion, g additive/kg feed | Cages/ Trt | Birds/ Cage |
|---|---|---|---|---|---|
| T1 | Nonmedicated (NMNI) | NI | 0 | 8 | 8 |
| T2 | Nonmedicated (NMI, NC) | I | 0 | 8 | 8 |
| T3 | Coccidiostat (PC) | NI | 0.010 | 8 | 8 |
| T4 | Coccidiostat (PC) | I | 0.010 | 8 | 8 |
| T5 | SEQ ID NO: 135 (chIL10sdAB1A11) | I | 4000 | 8 | 8 |
| T6 | SEQ ID NO: 135 (chIL10sdAB1A11) | I | 4000 | 8 | 8 |
| T7 | SEQ ID NO: 135 (chIL10sdAB1A11) | I | 1 | 8 | 8 |
| T8 | SEQ ID NO: 135 (chIL10sdAB1A11) | I | 40 | 8 | 8 |
| T9 | SEQ ID NO: 135 (chIL10sdAB1A11) | I | 500 | 8 | 8 |
| T10 | SEQ ID NO: 135 (chIL10sdAB1A11) | I | 300 | 8 | 8 |
| T11 | SEQ ID NO: 135 (chIL10sdAB1A11) | I | 150 | 8 | 8 |
| T12 | SEQ ID NO: 135 (chIL10sdAB1A11) | I | 50 | 8 | 8 |

Other sdABs were tested using the same trial design, same grain loadings, but different chIL10sdAB expressing corn grain. In a similar way, the same trial design was used to test IL-10R peptide antagonists as shown in Table 9.

TABLE 9

Treatment design to test IL-10R antagonist peptides

| Trt | Description | Infected/ Non-Infected | Additive inclusion, g additive/kg feed | Cages/ Trt | Birds/ Cage |
|---|---|---|---|---|---|
| T1 | Nonmedicated (NMNI, NC) | NI | 0 | 8 | 8 |
| T2 | Nonmedicated (NMI, NC) | I | 0 | 8 | 8 |
| T3 | Coccidiostat (PC) | NI | 0.010 | 8 | 8 |
| T4 | Coccidiostat (PC) | I | 0.010 | 8 | 8 |
| T5 | P21 | NI | 0.070 | 8 | 8 |
| T6 | P21 | I | 0.070 | 8 | 8 |
| T7 | P21 | I | 0.050 | 8 | 8 |
| T8 | P21 | I | 0.035 | 8 | 8 |
| T9 | P21 | I | 0.020 | 8 | 8 |
| T10 | P21 | I | 0.015 | 8 | 8 |
| T11 | P21 | I | 0.010 | 8 | 8 |
| T12 | P21 | I | 0.001 | 8 | 8 |

At the start of every trial, the facility was checked to ensure that all cages have water and feed available in each cage, which was provided to animal ad libitum. The building temperature was maintained as appropriate for the age of the birds. Even, continuous illumination was provided by fluorescent lamps hung vertically along the wall. Cages will be checked twice daily, and observations including availability of feed, water, temperature and any unusual conditions were recorded. Mortality birds were removed from cages, and the cage number, date, weight of the bird, sex and probable cause of death were recorded.

As part of the trial, an unmedicated commercial starter ration compounded with basal feedstuffs was formulated. This ration was used to formulate the study's negative and positive control rations, and experimental diets, which were all fed ad libitum from the date of chick arrival until completion of the study. Quantities of all basal feed and test articles used to prepare treatment batches were documented and tested as part of the trial quality control procedures. Treatment diets were mixed to a uniform distribution of test article. The mixer was flushed between control and treatment diets, and in between each treatment diet. Each treatment feed was then distributed among cages of the corresponding treatment.

Day of hatch male chicks (Cobb 500) were used in the study. Upon arrival, chicks will be colony raised in Coccidia free battery cages. At 12 days of age (trial day 0) chicks will grouped into sets of 8, weighed, and placed into an assigned cage. Birds were weighed by cage on day of trial 0 and 8.

On day of trial 2, all non-infected birds received 1 ml of distilled water by oral pipette. All other birds will receive the coccidial inoculum diluted to a 1 ml volume and dosed by oral pipette. The inoculum was a mixture of *Eimeria acervulina, E. maxima*, and *E. tenella* field isolates, which produces a mild infection with all species.

Data were collected after starting the study on days 0, 2, 7, and 8. On day 0, birds were weighed and allocated to their cages for the study. On Day 2, designated birds were inoculated with coccidian. On Day 7, dropping pans were cleaned to prepare for droppings collection on Day 8, and subsequent analysis. On Day 8, birds were weighed by cage, along with the remaining feed, and fecal matter. Feces collected from each cage were thoroughly mixed and prepared for fecal floatation, and each sample was examined to determine the number of oocysts per gram of fecal matter. All birds were scored for coccidian lesions on day 8 using the method of Johnson and Reid (1970). During the trial death weights were recorded and clinical observations were recorded twice each day throughout the study.

Feed in-take, body weight gain, feed conversion, opgs, coccidian lesion scores, and mortality were measured for each group and analyzed by standard statistical methods. The effect of sdAB (or peptide) supplementation was compared between groups treated with *Eimeria* and not treated with *Eimeria*, between treatment groups treated with *Eimeria* and antibody (or peptide) and control groups treated and not treated with *Eimeria*, control groups treated with *Eimeria* and no antibody (or peptide) or Coccidiostat, and control groups treated with *Eimeria* and also treated with a Coccidiostat.

Additionally the minimum effective dose was determined by seeing which antibody (or peptide) dose reduced fecal oocyst counts or lesion scores relative to the control birds that were infected but not treated with antibody (or peptide) or Coccidiostat. Using this design the extent of oocyst and lesion scoring reduction were determined as a function of dose.

REFERENCES

Arbabi Ghahroudi, M. et al., 1997. Selection and identification of single domain antibody fragments from camel heavy-chain antibodies. *FEBS Letters,* 414 (3), pp. 521-526.

Cervantes, H., 2002. Incidence of pathological conditions in clinically normal broilers from different regions of the USA. 51st Western Poultry Disease Conference, May 1-4, Casa Magna Marriott Resort, Puerto Vallart, Jalisco, Mexico, 220-223.

Cervantes, H., 2006. Incidence of subclinical diseases and pathological conditions in clinically normal broilers from 3 production complexes sorted by sex and age. 143rd Annual Convention of the American Veterinary Medical Association and 50th Annual Meeting of the American Association of Avian Pathologists, July 15-19, Hawaii Convention Center, Honolulu, Hawaii.

Cook, M. E., Sand, J. M., McGuirk, S. M., Rieman, J. E., and Raabis, S. M. (2015), U.S. patent application No. US2016/0280778 A1

Diaz-Valdes, N., Manterola, L., Belsue, V., Riezu-Boj, J. I., Larrea, E., Echeverria, I., LLopiz, D., Lopez-Sagaseta, J., Lerat, H., Pawlotsky, J.-M., Prieto, J., Lasarte, J. J., Borras-Cuesta, F., and Sarobe, P. (2011), Hepatology 53, 23-31.

Goldman, E. R. et al., 2006. Facile Generation of Heat Stable Antiviral and Antitoxin Single Domain Antibodies from a Semi-synthetic Llama Library., 78 (24), pp. 8245-8255.

Josephson, K., Logsdon, N. J., and Walter, M. W. (2001), Immunity 14, 35-46.

Liu, J. L. et al., 2013. Selection and evaluation of single domain antibodies toward MS2 phage and coat protein. *Molecular Immunology,* 53 (1-2), pp. 118-125.

Naiyer, M. M., Saha, S., Hemke, V., Roy, S., Singh, S., Musti, K. V., and Saha, B. (2013), Human Immunology 74, 28-31.

Ni, G., Chen, S., Yang, Y., Cummins, S. F., Zhan, J., Li, Z., Zhu, B., Mounsey, K., Walton, S., Wei, M. Q., Wang, Y., Zhou, Y., Wang, T., and Liu, X. (2016), PLOSOne, Apr. 21, 2016.

Reineke, U., Sabat, R., Volk, H.-D., and Schneider-Mergener, J. (1998), Protein Sci. 7, 951-960.

Rothwell, L., Young, J. R., Zoorob, R., Whittaker, C. A., Hesketh, P., Archer, A., Smith, A. L., and Kaiser, P. (2004), J. Immunol. 173, 2675-2682.

Sand, J. M, and Cook, M. E. (2014), U.S. Pat. No. 8,652,457 B2.

Wu, Z., Hu, T., Rothwell, L., Vervelde, L., Kaiser, P., Boulton, K., Nolan, M. J., Tomley, F. M., Blake, D. P., and Hume, D. A. (2016), Devel. Comp. Immunol. 63, 206-212.

Yoon, I. L., Jones, B. C., Logsdon, N. J., and Walter, M. R. (2005), Structure 13, 551-564.

Zdanov, A., Schalk-Hihi, C., and Wlodawer, A. (1996), Protein Sci. 5, 1955-1962.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

SEQUENCE LISTING

```
Sequence total quantity: 249
SEQ ID NO: 1            moltype = AA  length = 40
FEATURE                 Location/Qualifiers
REGION                  1..40
                        note = Synthetic construct, P21
```

-continued

```
source                  1..40
                        mol_type = protein
                        organism = synthetic construct
SEQUENCE: 1
PARLRELRVK FEEIKDYFQS RDDELNIQLL SSELLDEFKG                        40

SEQ ID NO: 2            moltype = AA  length = 27
FEATURE                 Location/Qualifiers
REGION                  1..27
                        note = Synthetic construct, P22
source                  1..27
                        mol_type = protein
                        organism = synthetic construct
SEQUENCE: 2
ENGIYKAMGE FDIFINYIEE YLLMRRR                                      27

SEQ ID NO: 3            moltype = AA  length = 47
FEATURE                 Location/Qualifiers
REGION                  1..47
                        note = Synthetic construct, P23
source                  1..47
                        mol_type = protein
                        organism = synthetic construct
SEQUENCE: 3
PARLRELRVK FEEIKDYFQG GGSGGGSQQS MGDLGNMLLG LKATMRR                47

SEQ ID NO: 4            moltype = AA  length = 50
FEATURE                 Location/Qualifiers
REGION                  1..50
                        note = Synthetic construct, P24
source                  1..50
                        mol_type = protein
                        organism = synthetic construct
SEQUENCE: 4
GCQSVSEMLR FYTDEVLPRA MQGGGSGGGS KAMGEFDIFI NYIEEYLLMR             50

SEQ ID NO: 5            moltype = AA  length = 8
FEATURE                 Location/Qualifiers
REGION                  1..8
                        note = Synthetic construct, P25
source                  1..8
                        mol_type = protein
                        organism = synthetic construct
SEQUENCE: 5
PARLRELR                                                           8

SEQ ID NO: 6            moltype = AA  length = 11
FEATURE                 Location/Qualifiers
REGION                  1..11
                        note = Synthetic construct, P26
source                  1..11
                        mol_type = protein
                        organism = synthetic construct
SEQUENCE: 6
LSSELLDEFK G                                                       11

SEQ ID NO: 7            moltype = AA  length = 10
FEATURE                 Location/Qualifiers
REGION                  1..10
                        note = Synthetic construct, P27
source                  1..10
                        mol_type = protein
                        organism = synthetic construct
SEQUENCE: 7
GEFDIFNYIE                                                         10

SEQ ID NO: 8            moltype = AA  length = 10
FEATURE                 Location/Qualifiers
REGION                  1..10
                        note = Synthetic construct, P28
source                  1..10
                        mol_type = protein
                        organism = synthetic construct
SEQUENCE: 8
SLRYYARVRA                                                         10

SEQ ID NO: 9            moltype = AA  length = 7
FEATURE                 Location/Qualifiers
REGION                  1..7
```

```
                      note = Synthetic construct, P29
source                1..7
                      mol_type = protein
                      organism = synthetic construct
SEQUENCE: 9
TNAFSPQ                                                        7

SEQ ID NO: 10         moltype = AA  length = 29
FEATURE               Location/Qualifiers
REGION                1..29
                      note = Synthetic construct, P11
source                1..29
                      mol_type = protein
                      organism = synthetic construct
SEQUENCE: 10
YDDIQKHARR YRVYIRRARD NQTYEVWET                                29

SEQ ID NO: 11         moltype = AA  length = 8
FEATURE               Location/Qualifiers
REGION                1..8
                      note = Synthetic construct, P30
source                1..8
                      mol_type = protein
                      organism = synthetic construct
SEQUENCE: 11
IQKHARRY                                                       8

SEQ ID NO: 12         moltype = AA  length = 8
FEATURE               Location/Qualifiers
REGION                1..8
                      note = Synthetic construct, P31
source                1..8
                      mol_type = protein
                      organism = synthetic construct
SEQUENCE: 12
NQTYEVWE                                                       8

SEQ ID NO: 13         moltype = AA  length = 9
FEATURE               Location/Qualifiers
REGION                1..9
                      note = Synthetic construct, P32
source                1..9
                      mol_type = protein
                      organism = synthetic construct
SEQUENCE: 13
VASRHIPAM                                                      9

SEQ ID NO: 14         moltype = AA  length = 16
FEATURE               Location/Qualifiers
REGION                1..16
                      note = Synthetic construct, P9
source                1..16
                      mol_type = protein
                      organism = synthetic construct
SEQUENCE: 14
FFKKFFKKFF KKFFKK                                              16

SEQ ID NO: 15         moltype = AA  length = 16
FEATURE               Location/Qualifiers
REGION                1..16
                      note = Synthetic construct, P6
source                1..16
                      mol_type = protein
                      organism = synthetic construct
SEQUENCE: 15
GTELPSPPSV WFEAEF                                              16

SEQ ID NO: 16         moltype = DNA  length = 120
FEATURE               Location/Qualifiers
misc_feature          1..120
                      note = Synthetic construct, P21 coding sequence
source                1..120
                      mol_type = other DNA
                      organism = synthetic construct
SEQUENCE: 16
ccggccaggc tgagggagct gagggtgaag ttcgaggaga tcaaggacta cttccagagc  60
agggacgacg agctgaacat ccagctgctg agcagcgagc tgctggacga gttcaagggc  120

SEQ ID NO: 17         moltype = DNA  length = 81
```

```
FEATURE                Location/Qualifiers
misc_feature           1..81
                       note = Synthetic construct, P22 coding sequence
source                 1..81
                       mol_type = other DNA
                       organism = synthetic construct
SEQUENCE: 17
gagaacggca tctacaaggc catgggcgag ttcgacatct tcatcaacta catcgaggag  60
tacctgctga tgaggaggag g                                            81

SEQ ID NO: 18          moltype = DNA  length = 141
FEATURE                Location/Qualifiers
misc_feature           1..141
                       note = Synthetic construct, P23 coding sequence
source                 1..141
                       mol_type = other DNA
                       organism = synthetic construct
SEQUENCE: 18
ccggccaggc tgagggagct gagggtgaag ttcgaggaga tcaaggacta cttccagggc  60
ggcggcagcg gcggcggcag ccagcagagc atgggcgacc tgggcaacat gctgctgggc  120
ctgaaggcca ccatgaggag g                                            141

SEQ ID NO: 19          moltype = DNA  length = 150
FEATURE                Location/Qualifiers
misc_feature           1..150
                       note = Synthetic construct, P24 coding sequence
source                 1..150
                       mol_type = other DNA
                       organism = synthetic construct
SEQUENCE: 19
ggctgccaga gcgtgagcga gatgctgagg ttctacaccg acgaggtgct gccgagggcc  60
atgcagggcg gcggcagcgg cggcggcagc aaggccatgg gcgagttcga catcttcatc  120
aactacatcg aggagtacct gctgatgagg                                   150

SEQ ID NO: 20          moltype = DNA  length = 24
FEATURE                Location/Qualifiers
misc_feature           1..24
                       note = Synthetic construct, P25 coding sequence
source                 1..24
                       mol_type = other DNA
                       organism = synthetic construct
SEQUENCE: 20
ccggccaggc tgagggagct gagg                                         24

SEQ ID NO: 21          moltype = DNA  length = 33
FEATURE                Location/Qualifiers
misc_feature           1..33
                       note = Synthetic construct, P26 coding sequence
source                 1..33
                       mol_type = other DNA
                       organism = synthetic construct
SEQUENCE: 21
ctgagcagcg agctgctgga cgagttcaag ggc                               33

SEQ ID NO: 22          moltype = DNA  length = 30
FEATURE                Location/Qualifiers
misc_feature           1..30
                       note = Synthetic construct, P27 coding sequence
source                 1..30
                       mol_type = other DNA
                       organism = synthetic construct
SEQUENCE: 22
ggcgagttcg acatcttcaa ctacatcgag                                   30

SEQ ID NO: 23          moltype = DNA  length = 30
FEATURE                Location/Qualifiers
misc_feature           1..30
                       note = Synthetic construct, P28 coding sequence
source                 1..30
                       mol_type = other DNA
                       organism = synthetic construct
SEQUENCE: 23
agcctgaggt actacgccag ggtgagggcc                                   30

SEQ ID NO: 24          moltype = DNA  length = 21
FEATURE                Location/Qualifiers
misc_feature           1..21
                       note = Synthetic construct, P29 coding sequence
source                 1..21
```

```
                        mol_type = other DNA
                        organism = synthetic construct
SEQUENCE: 24
accaacgcct tcagcccgca g                                             21

SEQ ID NO: 25           moltype = DNA  length = 87
FEATURE                 Location/Qualifiers
misc_feature            1..87
                        note = Synthetic construct, P11 coding sequence
source                  1..87
                        mol_type = other DNA
                        organism = synthetic construct
SEQUENCE: 25
tacgacgaca tccagaagca cgccaggagg tacagggtgt acatcaggag ggccagggac  60
aaccagacct acgaggtgtg ggagacc                                       87

SEQ ID NO: 26           moltype = DNA  length = 24
FEATURE                 Location/Qualifiers
misc_feature            1..24
                        note = Synthetic construct, P30 coding sequence
source                  1..24
                        mol_type = other DNA
                        organism = synthetic construct
SEQUENCE: 26
atccagaagc acgccaggag gtac                                          24

SEQ ID NO: 27           moltype = DNA  length = 24
FEATURE                 Location/Qualifiers
misc_feature            1..24
                        note = Synthetic construct, P31 coding sequence
source                  1..24
                        mol_type = other DNA
                        organism = synthetic construct
SEQUENCE: 27
aaccagacct acgaggtgtg ggag                                          24

SEQ ID NO: 28           moltype = DNA  length = 27
FEATURE                 Location/Qualifiers
misc_feature            1..27
                        note = Synthetic construct, P32 coding sequence
source                  1..27
                        mol_type = other DNA
                        organism = synthetic construct
SEQUENCE: 28
gtggccagca ggcacatccc ggccatg                                       27

SEQ ID NO: 29           moltype = AA  length = 4
FEATURE                 Location/Qualifiers
REGION                  1..4
                        note = Synthetic construct, KDEL
source                  1..4
                        mol_type = protein
                        organism = synthetic construct
SEQUENCE: 29
KDEL                                                                4

SEQ ID NO: 30           moltype = AA  length = 4
FEATURE                 Location/Qualifiers
REGION                  1..4
                        note = Synthetic construct, HDEL
source                  1..4
                        mol_type = protein
                        organism = synthetic construct
SEQUENCE: 30
HDEL                                                                4

SEQ ID NO: 31           moltype = AA  length = 6
FEATURE                 Location/Qualifiers
REGION                  1..6
                        note = Synthetic construct, SEKDEL
source                  1..6
                        mol_type = protein
                        organism = synthetic construct
SEQUENCE: 31
SEKDEL                                                              6

SEQ ID NO: 32           moltype = AA  length = 12
FEATURE                 Location/Qualifiers
REGION                  1..12
```

-continued

```
                        note = Synthetic construct, P2501
source                  1..12
                        mol_type = protein
                        organism = synthetic construct
SEQUENCE: 32
PARLRELRKD EL                                                     12

SEQ ID NO: 33           moltype = AA  length = 16
FEATURE                 Location/Qualifiers
REGION                  1..16
                        note = Synthetic construct, P2502
source                  1..16
                        mol_type = protein
                        organism = synthetic construct
SEQUENCE: 33
PARLRELRPA RLRELR                                                 16

SEQ ID NO: 34           moltype = AA  length = 20
FEATURE                 Location/Qualifiers
REGION                  1..20
                        note = Synthetic construct, P2503
source                  1..20
                        mol_type = protein
                        organism = synthetic construct
SEQUENCE: 34
PARLRELRPA RLRELRKDEL                                             20

SEQ ID NO: 35           moltype = AA  length = 20
FEATURE                 Location/Qualifiers
REGION                  1..20
                        note = Synthetic construct, P2504
source                  1..20
                        mol_type = protein
                        organism = synthetic construct
SEQUENCE: 35
PARLRELRAG PAPARLRELR                                             20

SEQ ID NO: 36           moltype = AA  length = 24
FEATURE                 Location/Qualifiers
REGION                  1..24
                        note = Synthetic construct, P2505
source                  1..24
                        mol_type = protein
                        organism = synthetic construct
SEQUENCE: 36
PARLRELRAG PAPARLRELR KDEL                                        24

SEQ ID NO: 37           moltype = AA  length = 24
FEATURE                 Location/Qualifiers
REGION                  1..24
                        note = Synthetic construct, P2506
source                  1..24
                        mol_type = protein
                        organism = synthetic construct
SEQUENCE: 37
PARLRELRPA RLRELRPARL RELR                                        24

SEQ ID NO: 38           moltype = AA  length = 28
FEATURE                 Location/Qualifiers
REGION                  1..28
                        note = Syntheict construct, P2507
source                  1..28
                        mol_type = protein
                        organism = synthetic construct
SEQUENCE: 38
PARLRELRPA RLRELRPARL RELRKDEL                                    28

SEQ ID NO: 39           moltype = AA  length = 32
FEATURE                 Location/Qualifiers
REGION                  1..32
                        note = Synthetic construct, P2508
source                  1..32
                        mol_type = protein
                        organism = synthetic construct
SEQUENCE: 39
PARLRELRAG PAPARLRELR AGPAPARLRE LR                               32

SEQ ID NO: 40           moltype = AA  length = 36
FEATURE                 Location/Qualifiers
```

-continued

```
REGION                1..36
                      note = Synthetic construct, P2509
source                1..36
                      mol_type = protein
                      organism = synthetic construct
SEQUENCE: 40
PARLRELRAG PAPARLRELR AGPAPARLRE LRKDEL                                36

SEQ ID NO: 41         moltype = AA  length = 6
FEATURE               Location/Qualifiers
REGION                1..6
                      note = Synthetic construct, GSGGSG linker
source                1..6
                      mol_type = protein
                      organism = synthetic construct
SEQUENCE: 41
GSGGSG                                                                 6

SEQ ID NO: 42         moltype = AA  length = 5
FEATURE               Location/Qualifiers
REGION                1..5
                      note = Synthetic construct, zeolin linker
source                1..5
                      mol_type = protein
                      organism = synthetic construct
SEQUENCE: 42
GGGGS                                                                  5

SEQ ID NO: 43         moltype = AA  length = 5
FEATURE               Location/Qualifiers
REGION                1..5
                      note = Synthetic construct, Zera fusion
source                1..5
                      mol_type = protein
                      organism = synthetic construct
SEQUENCE: 43
GGGGG                                                                  5

SEQ ID NO: 44         moltype = AA  length = 5
FEATURE               Location/Qualifiers
REGION                1..5
                      note = Synthetic construct, VPGVG
source                1..5
                      mol_type = protein
                      organism = synthetic construct
SEQUENCE: 44
VPGVG                                                                  5

SEQ ID NO: 45         moltype = DNA  length = 18
FEATURE               Location/Qualifiers
misc_feature          1..18
                      note = Synthetic construct, GSSGGSG coding seq
source                1..18
                      mol_type = other DNA
                      organism = synthetic construct
SEQUENCE: 45
ggcagcggcg gcagcggc                                                    18

SEQ ID NO: 46         moltype = DNA  length = 15
FEATURE               Location/Qualifiers
misc_feature          1..15
                      note = Synthetic construct, zeolin linker coding seq
source                1..15
                      mol_type = other DNA
                      organism = synthetic construct
SEQUENCE: 46
ggcggcggcg gcagc                                                       15

SEQ ID NO: 47         moltype = DNA  length = 15
FEATURE               Location/Qualifiers
misc_feature          1..15
                      note = Synthetic construct, Zera linker coding seq
source                1..15
                      mol_type = other DNA
                      organism = synthetic construct
SEQUENCE: 47
ggcggcggcg gcggc                                                       15

SEQ ID NO: 48         moltype = DNA  length = 72
```

```
FEATURE                Location/Qualifiers
misc_feature           1..72
                       note = Synthetic construct, BAAS coding seq
source                 1..72
                       mol_type = other DNA
                       organism = synthetic construct
SEQUENCE: 48
atggcgaaca aacatttgtc cctctccctc ttcctcgtcc tccttggcct gtcggccagc  60
ttggcctccg gg                                                      72

SEQ ID NO: 49          moltype = DNA  length = 72
FEATURE                Location/Qualifiers
misc_feature           1..72
                       note = Synthetic construct, OsGluB4sp coding seq
source                 1..72
                       mol_type = other DNA
                       organism = synthetic construct
SEQUENCE: 49
atggccacca tcgctttctc ccgcttgtcc atctacttct gcgtgcttct cctgtgccac  60
ggctccatgg cc                                                      72

SEQ ID NO: 50          moltype = DNA  length = 93
FEATURE                Location/Qualifiers
misc_feature           1..93
                       note = Synthetic construct, PR1 coding seq
source                 1..93
                       mol_type = other DNA
                       organism = synthetic construct
SEQUENCE: 50
atgggcttcg tgctcttctc ccagctgcct tccttccttc ttgtctccac cctgctcttg  60
ttcctcgtga tctcccactc ctgccgcgcc cag                               93

SEQ ID NO: 51          moltype = DNA  length = 12
FEATURE                Location/Qualifiers
misc_feature           1..12
                       note = Synthetic construct, KDEL coding seq
source                 1..12
                       mol_type = other DNA
                       organism = synthetic construct
SEQUENCE: 51
aaggacgagc tg                                                      12

SEQ ID NO: 52          moltype = DNA  length = 12
FEATURE                Location/Qualifiers
misc_feature           1..12
                       note = Synthetic construct, HDEL coding seq
source                 1..12
                       mol_type = other DNA
                       organism = synthetic construct
SEQUENCE: 52
cacgacgagc tg                                                      12

SEQ ID NO: 53          moltype = DNA  length = 18
FEATURE                Location/Qualifiers
misc_feature           1..18
                       note = Synthetic construct, SEKDEL coding seq
source                 1..18
                       mol_type = other DNA
                       organism = synthetic construct
SEQUENCE: 53
tccgagaagg acgagctg                                                18

SEQ ID NO: 54          moltype = DNA  length = 129
FEATURE                Location/Qualifiers
misc_feature           1..129
                       note = Synthetic construct, HvAle coding seq
source                 1..129
                       mol_type = other DNA
                       organism = synthetic construct
SEQUENCE: 54
atggcccacg cccgcgtcct cctcctggcg ctcgccgtcc tggccaccgc cgccgtcgcc  60
gtcgcctcct cctcctcctt cgccgactcc aacccgatcc gcccggtgac cgaccgcgcc  120
gcctccacc                                                          129

SEQ ID NO: 55          moltype = DNA  length = 24
FEATURE                Location/Qualifiers
misc_feature           1..24
                       note = Synthetic construct, HvVSD coding seq
source                 1..24
```

-continued

```
                        mol_type = other DNA
                        organism = synthetic construct
SEQUENCE: 55
gacgagctga aggccgaggc caag                                        24

SEQ ID NO: 56           moltype = DNA  length = 108
FEATURE                 Location/Qualifiers
misc_feature            1..108
                        note = Synthetic construct, P2509 coding seq
source                  1..108
                        mol_type = other DNA
                        organism = synthetic construct
SEQUENCE: 56
ccggccaggc tgagggagct gagggccggc ccggccccgg ccaggctgag ggagctgagg  60
gccggcccgg ccccggccag gctgagggag ctgaggaagg acgagctg              108

SEQ ID NO: 57           moltype = AA  length = 223
FEATURE                 Location/Qualifiers
REGION                  1..223
                        note = Synthetic construct, ZmZ27
source                  1..223
                        mol_type = protein
                        organism = synthetic construct
SEQUENCE: 57
MRVLLVALAL LALAASATST HTSGGCGCQP PPPVHLPPPV HLPPPVHLPP PVHLPPPVHL  60
PPPVHLPPPV HVPPPVHLPP PPCHYPTQPP RPQPHPQPHP CPCQQPHPSP CQLQGTCGVG  120
STPILGQCVE FLRHQCSPTA TPYCSPQCQS LRQQCCQQLR QVEPQHRYQA IFGLVLQSIL  180
QQQPQSGQVA GLLAAQIAQQ LTAMCGLQQP TPCPYAAAGG VPH                   223

SEQ ID NO: 58           moltype = DNA  length = 672
FEATURE                 Location/Qualifiers
misc_feature            1..672
                        note = Synthetic construct, ZmZ27 coding seq
source                  1..672
                        mol_type = other DNA
                        organism = synthetic construct
SEQUENCE: 58
atgagggtgt tgctcgttgc cctcgctctc ctggctctcg ctgcgagcgc cacctccacg  60
catacaagcg gcggctgcgg ctgccagcca ccgccgccgg ttcatctacc gccgccggtg  120
catctgccac ctccggttca cctgccacct ccggtgcatc tcccaccgcc ggtccacctg  180
ccgccgccgg tccacctgcc accgccggtc catgtgccgc cgccggttca tctgccgccg  240
ccaccatgcc actaccctac tcaaccgccc cggcctcagc ctcatcccca gccacaccca  300
tgcccgtgcc aacagccgca tccaagcccg tgccagctgc agggaacctg cggcgttggc  360
agcaccccga tcctgggcca gtgcgtcgag ttcctgaggc atcagtgcag cccgacggcg  420
acgccctact gctcgcctca gtgccagtcg ttgcggcagc agtgttgcca gcagctcagg  480
caggtggagc cgcagcaccg gtaccaggcg atcttcggct tggtcctcca gtccatcctg  540
cagcagcagc cgcaaagcgg ccaggtcgcg gggctgttgg cggcgcagat agcgcagcaa  600
ctgacggcga tgtgcggcct gcagcagccg actccatgcc cctacgctgc tgccggcggt  660
gtcccccact ga                                                     672

SEQ ID NO: 59           moltype = AA  length = 89
FEATURE                 Location/Qualifiers
REGION                  1..89
                        note = Synthetic construct, ZmZ27_AA24-112
source                  1..89
                        mol_type = protein
                        organism = synthetic construct
SEQUENCE: 59
GGCGCQPPPP VHLPPPVHLP PPVHLPPPVH LPPPVHLPPP VHLPPPVHVP PPVHLPPPPC  60
HYPTQPPRPQ PHPQPHPCPC QQPHPSPCQ                                   89

SEQ ID NO: 60           moltype = DNA  length = 267
FEATURE                 Location/Qualifiers
misc_feature            1..267
                        note = Synthetic construct, ZmZ27_AA24-112 coding seq
source                  1..267
                        mol_type = other DNA
                        organism = synthetic construct
SEQUENCE: 60
ggcggctgcg gctgccagcc accgccgccg gttcatctac cgccgccggt gcatctgcca  60
cctccggttc acctgccacc tccggtgcat ctcccaccgc cggtccacct gccgccgccg  120
gtccacctgc caccgccggt ccatgtgccg ccgccggttc atctgccgcc gccaccatgc  180
cactacccta ctcaaccgcc ccggcctcag cctcatcccc agccacaccc atgcccgtgc  240
caacagccgc atccaagccc gtgccag                                     267

SEQ ID NO: 61           moltype = AA  length = 112
FEATURE                 Location/Qualifiers
REGION                  1..112
                        note = Synthetic construct, Zera_AA1-112
```

-continued

```
source                  1..112
                        mol_type = protein
                        organism = synthetic construct
SEQUENCE: 61
MRVLLVALAL LALAASATST HTSGGCGCQP PPPVHLPPPV HLPPPVHLPP PVHLPPPVHL  60
PPPVHLPPPV HVPPPVHLPP PPCHYPTQPP RPQPHPQPHP CPCQQPHPSP CQ         112

SEQ ID NO: 62           moltype = DNA  length = 336
FEATURE                 Location/Qualifiers
misc_feature            1..336
                        note = Synthetic construct, Zera coding seq
source                  1..336
                        mol_type = other DNA
                        organism = synthetic construct
SEQUENCE: 62
atgagggtgt tgctcgttgc cctcgctctc ctggctctcg ctgcgagcgc cacctccacg  60
catacaagcg gcggctgcgg ctgccagcca ccgccgccgg ttcatctacc gccgccggtg  120
catctgccac ctccggttca cctgccacct ccggtgcatc tcccaccgcc ggtccacctg  180
ccgccgccgg tccacctgcc accgccggtc catgtgccgc cgccggttca tctgccgccg  240
ccaccatgcc actaccctac tcaaccgccc cggcctcagc ctcatcccca gccacaccca  300
tgcccgtgcc aacagccgca tccaagcccg tgccag                            336

SEQ ID NO: 63           moltype = DNA  length = 450
FEATURE                 Location/Qualifiers
misc_feature            1..450
                        note = Synthetic construct, ZeraP2508 coding seq
source                  1..450
                        mol_type = other DNA
                        organism = synthetic construct
SEQUENCE: 63
atgagggtgt tgctcgttgc cctcgctctc ctggctctcg ctgcgagcgc cacctccacg  60
catacaagcg gcggctgcgg ctgccagcca ccgccgccgg ttcatctacc gccgccggtg  120
catctgccac ctccggttca cctgccacct ccggtgcatc tcccaccgcc ggtccacctg  180
ccgccgccgg tccacctgcc accgccggtc catgtgccgc cgccggttca tctgccgccg  240
ccaccatgcc actaccctac tcaaccgccc cggcctcagc ctcatcccca gccacaccca  300
tgcccgtgcc aacagccgca tccaagcccg tgccagggca gcggcggcag cggcccggcc  360
aggctgaggg agctgagggc cggcccggcc ccggccaggc tgagggagct gagggccggc  420
ccggccccgg ccaggctgag ggagctgagg                                   450

SEQ ID NO: 64           moltype = DNA  length = 462
FEATURE                 Location/Qualifiers
misc_feature            1..462
                        note = Synthetic construct, ZeraP2509KDEL coding seq
source                  1..462
                        mol_type = other DNA
                        organism = synthetic construct
SEQUENCE: 64
atgagggtgt tgctcgttgc cctcgctctc ctggctctcg ctgcgagcgc cacctccacg  60
catacaagcg gcggctgcgg ctgccagcca ccgccgccgg ttcatctacc gccgccggtg  120
catctgccac ctccggttca cctgccacct ccggtgcatc tcccaccgcc ggtccacctg  180
ccgccgccgg tccacctgcc accgccggtc catgtgccgc cgccggttca tctgccgccg  240
ccaccatgcc actaccctac tcaaccgccc cggcctcagc ctcatcccca gccacaccca  300
tgcccgtgcc aacagccgca tccaagcccg tgccagggca gcggcggcag cggcccggcc  360
aggctgaggg agctgagggc cggcccggcc ccggccaggc tgagggagct gagggccggc  420
ccggccccgg ccaggctgag ggagctgagg aaggacgagc tg                     462

SEQ ID NO: 65           moltype = AA  length = 140
FEATURE                 Location/Qualifiers
REGION                  1..140
                        note = Synthetic construct, 28xVPGVG
source                  1..140
                        mol_type = protein
                        organism = synthetic construct
SEQUENCE: 65
VPGVGVPGVG VPGVGVPGVG VPGVGVPGVG VPGVGVPGVG VPGVGVPGVG VPGVGVPGVG  60
VPGVGVPGVG VPGVGVPGVG VPGVGVPGVG VPGVGVPGVG VPGVGVPGVG VPGVGVPGVG  120
VPGVGVPGVG VPGVGVPGVG                                              140

SEQ ID NO: 66           moltype = DNA  length = 420
FEATURE                 Location/Qualifiers
misc_feature            1..420
                        note = Synthetic construct, 28xVPGVG coding seq
source                  1..420
                        mol_type = other DNA
                        organism = synthetic construct
SEQUENCE: 66
gtgccgggcg tgggcgtgcc gggcgtgggc gtgccgggcg tgggcgtgcc gggcgtgggc  60
gtgccgggcg tgggcgtgcc gggcgtgggc gtgccgggcg tgggcgtgcc gggcgtgggc  120
gtgccgggcg tgggcgtgcc gggcgtgggc gtgccgggcg tgggcgtgcc gggcgtgggc  180
```

```
gtgccgggcg tgggcgtgcc gggcgtgggc gtgccgggcg tgggcgtgcc gggcgtgggc  240
gtgccgggcg tgggcgtgcc gggcgtgggc gtgccgggcg tgggcgtgcc gggcgtgggc  300
gtgccgggcg tgggcgtgcc gggcgtgggc gtgccgggcg tgggcgtgcc gggcgtgggc  360
gtgccgggcg tgggcgtgcc gggcgtgggc gtgccgggcg tgggcgtgcc gggcgtgggc  420

SEQ ID NO: 67          moltype = AA  length = 75
FEATURE                Location/Qualifiers
REGION                 1..75
                       note = Synthetic construct, HFBI
source                 1..75
                       mol_type = protein
                       organism = synthetic construct
SEQUENCE: 67
SNGNGNVCPP GLFSNPQCCA TQVLGLIGLD CKVPSQNVYD GTDFRNVCAK TGAQPLCCVA  60
PVAGQALLCQ TAVGA                                                   75

SEQ ID NO: 68          moltype = DNA  length = 225
FEATURE                Location/Qualifiers
misc_feature           1..225
                       note = Synthetic construct, HFBI coding seq
source                 1..225
                       mol_type = other DNA
                       organism = synthetic construct
SEQUENCE: 68
agcaacggca acggcaacgt gtgcccgccg ggcctgttca gcaacccgca gtgctgcgcc  60
acccaggtgc tgggcctgat cggcctggac tgcaaggtgc cgagccagaa cgtgtacgac  120
ggcaccgact tcaggaacgt gtgcgccaag accggcgccc agccgctgtg ctgcgtggcc  180
ccggtggccg gccaggccct gctgtgccag accgccgtgg gcgcc                  225

SEQ ID NO: 69          moltype = DNA  length = 11826
FEATURE                Location/Qualifiers
misc_feature           1..11826
                       note = Synthetic construct, pAG4305
source                 1..11826
                       mol_type = other DNA
                       organism = synthetic construct
SEQUENCE: 69
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagtttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
```

-continued

```
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc ccccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
```

-continued

```
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ggctgccaga gcgtgagcga gatgctgagg ttctacaccg  11700
acgaggtgct gccgagggcc atgcagggcg gcggcagcgg cggcggcagc aaggccatgg  11760
gcgagttcga catcttcatc aactacatcg aggagtacct gctgatgagg aaggacgagc  11820
tgtaac                                                             11826
```

SEQ ID NO: 70 moltype = DNA length = 11772

-continued

```
FEATURE                Location/Qualifiers
misc_feature           1..11772
                       note = Synthetic construct, pAG4306
source                 1..11772
                       mol_type = other DNA
                       organism = synthetic construct
SEQUENCE: 70
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
```

-continued

```
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggccc aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc cccctttgg  4620
ggtgtagaac atcctttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga acccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
```

```
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc ttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttctta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggaagg  11760
acgagctgta ac                                                      11772

SEQ ID NO: 71           moltype = DNA  length = 12069
FEATURE                 Location/Qualifiers
misc_feature            1..12069
                        note = Synthetic construct, pAG4308
source                  1..12069
                        mol_type = other DNA
                        organism = synthetic construct
SEQUENCE: 71
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc ccccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
```

-continued

```
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
tttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc cccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
```

-continued

```
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatcttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
```

```
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc acgcatacaa gcggcggctg cggctgccag ccaccgccgc  11700
cggttcatct accgccgccg gtgcatctgc cacctccggt tcacctgcca cctccggtgc  11760
atctcccacc gccggtccac ctgccgccgc cggtccacct gccaccgccg gtccatgtgc  11820
cgccgccggt tcatctgccg ccgccaccat gccactaccc tactcaaccg ccccggcctc  11880
agcctcatcc ccagccacac ccatgcccgt gccaacagcc gcatccaagc ccgtgccagg  11940
gcagcggcgg cagcggcccg gccaggctga gggagctgag ggccggcccg gccccggcca  12000
ggctgaggga gctgagggcc ggcccggccc cggccaggct gagggagctg aggaaggacg  12060
agctgtaac                                                         12069
```

```
SEQ ID NO: 72           moltype = DNA  length = 12057
FEATURE                 Location/Qualifiers
misc_feature            1..12057
                        note = Synthetic construct, pAG4310
source                  1..12057
                        mol_type = other DNA
                        organism = synthetic construct
SEQUENCE: 72
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct ccttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagtttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
```

-continued

```
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc cccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
```

```
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac ctttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggggca  11760
gcggcggcag cggcggcggc tgcggctgcc agccaccgcc gccggttcat ctaccgccgc  11820
cggtgcatct gccacctccg gttcacctgc cacctccggt gcatctccca ccgccggtcc  11880
acctgccgcc gccggtccac ctgccaccgc cggtccatgt gccgccgccg gttcatctgc  11940
cgccgccacc atgccactac cctactcaac cgcccccggcc tcagcctcat ccccagccac  12000
acccatgccc gtgccaacag ccgcatccaa gcccgtgcca gaaggacgag ctgtaac      12057
```

```
SEQ ID NO: 73           moltype = DNA  length = 12210
FEATURE                 Location/Qualifiers
misc_feature            1..12210
                        note = Synthetic construct, pAG4311
source                  1..12210
                        mol_type = other DNA
```

organism = synthetic construct
SEQUENCE: 73
ctaggtcccc gaatttcccc gatcgttcaa acatttggca ataaagtttc ttaagattga 60
atcctgttgc cggtcttgcg atgattatca tataatttct gttgaattac gttaagcatg 120
taataattaa catgtaatgc atgacgttat ttatgagatg ggtttttatg attagagtcc 180
cgcaattata catttaatac gcgatagaaa acaaaatata gcgcgcaaac taggataaat 240
tatcgcgcgc ggtgtcatct atgttactag atcgggaatt ggaattcctg cagtgcagcg 300
tgacccggtc gtgcccctct ctagagataa tgagcattgc atgtctaagt tataaaaaat 360
taccacatat ttttttgtc acacttgttt gaagtgcagt ttatctatct ttatacatat 420
atttaaactt tactctacga ataatataat ctatagtact acaataatat cagtgtttta 480
gagaatcata taaatgaaca gttagacatg gtctaaagga caattgagta ttttgacaac 540
aggactctac agttttatct ttttagtgtg catgtgttct ccttttttt tgcaaatagc 600
ttcacctata taatacttca tccattttat tagtacatcc atttagggtt tagggttaat 660
ggtttttata gactaatttt tttagtacat ctattttatt ctattttagc ctctaaatta 720
agaaaactaa aactctattt tagtttttt atttaataat ttagatataa aatagaataa 780
aataaagtga ctaaaaatta aacaaatacc ctttaagaaa ttaaaaaaac taaggaaaca 840
tttttcttgt ttcgagtaga taatgccagc ctgttaaacg ccgtcgacga gtctaacgga 900
caccaaccag cgaaccagca gcgtcgcgtc gggccaagcg aagcagacgg cacggcatct 960
ctgtcgctgc ctctggaccc ctctcgagag ttccgctcca ccgttggact tgctccgctg 1020
tcggcatcca gaaattgcgt ggcggagcgg cagacgtgag ccggcacggc aggcggcctc 1080
ctcctcctct cacggcacgg cagctacggg ggattccttt cccaccgctc cttcgctttc 1140
ccttcctcgc ccgccgtaat aaatagacac cccctccaca ccctctttcc ccaacctcgt 1200
gttgttcgga gcgcacacac acacaaccag atctccccca aatccacccg tcggcacctc 1260
cgcttcaagg tacgccgctc gtcctccccc cccccccctc tctaccttct ctagatcggc 1320
gttccggtcc atggttaggg cccggtagtt ctacttctgt tcatgtttgt gttagatccg 1380
tgtttgtgtt agatccgtgc tgctagcgtt cgtacacgga tgcgacctgt acgtcagaca 1440
cgttctgatt gctaacttgc cagtgtttct ctttggggaa tcctgggatg gctctagccg 1500
ttccgcagac gggatcgatt tcatgatttt ttttgtttcg ttgcataggg tttggtttgc 1560
ccttttcctt tatttcaata tatgccgtgc acttgtttgt cgggtcatct tttcatgctt 1620
ttttttgtct tggttgtgat gatgtggtct ggttgggcgg tcgttctaga tcggagtaga 1680
attctgtttc aaactacctg gtggatttat taattttgga tctgtatgtg tgtgccatac 1740
atattcatag ttacgaattg aagatgatgg atggaaatat cgatctagga taggtataca 1800
tgttgatgcg ggttttactg atgcatatac agagatgctt tttgttcgct tggttgtgat 1860
gatgtggtgt ggttgggcgg tcgttcattc gttctagatc ggagtagaat actgtttcaa 1920
actacctggt gtatttatta attttggaac tgtatgtgtg tgtcatacat cttcatagtt 1980
acgagtttaa gatggatgga aatatcgatc taggataggt atacatgttg atgtgggttt 2040
tactgatgca tatacatgat ggcatatgca gcatctattc atatgctcta accttgagta 2100
cctatctatt ataataaaca agtatgtttt ataattattt tgatcttgat atacttggat 2160
gatggcatat gcagcagcta tatgtggatt tttttagccc tgccttcata cgctatttat 2220
ttgcttggta ctgtttcttt tgtcgatgct caccctgttg tttggtgtta cttctgcaga 2280
tccagatcta aaccatgcag aaactcatta actcagtgca aaactatgcc tggggcagca 2340
aaacggcgtt gactgaactt tatggtatgg aaaatccgtc cagccagccg atggccgagc 2400
tgtggatggg cgcacatccg aaaagcagtt cacgagtgca gaatgccgcc ggagatatcg 2460
tttcactgcg tgatgtgatt gagagtgata aatcgactct gctcggagag gccgttgcca 2520
aacgctttgg cgaactgcct ttcctgttca aagtattatg cgcagcacag ccactctcca 2580
ttcaggttca tccaaacaaa cacaattctg aaatcggttt tgccaaagaa aatgccgcag 2640
gtatcccgat ggatgccgcc gagcgtaact ataaagatcc taaccacaag ccggagctgg 2700
tttttgcgct gacgcctttc cttgcgatga acgcgtttcg tgaattttcc gagattgtct 2760
ccctactcca gccggtcgca ggtgcacatc cggcgattgc tcacttttta caacagcctg 2820
atgccgaacg tttaagcgaa ctgttcgcca gcctgttgaa tatgcagggt gaagaaaaat 2880
cccgcgcgct ggcgatttta aaatcggccc tcgatagcca gcagggtgaa ccgtggcaaa 2940
cgattcgttt aatttctgaa ttttacccgg aagacagcgg tctgttctcc ccgctattgc 3000
tgaatgtggt gaaattgaac cctggcgaag cgatgttcct gttcgctgaa acaccgcacg 3060
cttacctgca aggcgtggcg ctggaagtga tggcaaactc cgataacgtg ctgcgtgcgg 3120
gtctgacgcc taaatacatt gatattccgg aactggttgc caatgtgaaa ttcgaagcca 3180
aaccggctaa ccagttgttg acccagccgg tgaaacaagg tgcagaactg gacttcccga 3240
ttccagtgga tgattttgcc ttctcgctgc atgaccttag tgataaagaa accaccatta 3300
gccagcagag tgccgccatt ttgttctgcg tcgaaggcga tgcaacgttg tggaaaggtt 3360
ctcagcagtt acagcttaaa ccgggtgaat cagcgtttat tgccgccaac gaatcaccgg 3420
tgactgtcaa aggccacggc cgtttagcgc gtgtttacaa caagctgtaa gagcttactg 3480
aaaaaattaa catctcttgc taagctggga gctctagatc cccgaatttc cccgatcgtt 3540
caaacatttg gcaataaagt ttcttaagat tgaatcctgt tgccggtctt gcgatgatta 3600
tcatataatt tctgttgaat tacgttaagc atgtaataat taacatgtaa tgcatgacgt 3660
tatttatgag atgggttttt atgattagag tcccgcaatt atacatttaa tacgcgatag 3720
aaaacaaaat atagcgcgca aactaggata aattatcgcg cgcggtgtca tctatgttac 3780
tagatcggga attggcgagc tcgaattaat tcagtacatt aaaaacgtcc gcaatgtgtt 3840
attaagttgt ctaagcgtca atttgtttac accacaatat atcctgccac cagccagcca 3900
acagctcccc gaccggcagc tcggcacaaa atcaccactc gatacaggca gcccatcagt 3960
ccgggacggc gtcagcggga gagccgttgt aaggcggcag actttgctca tgttaccgat 4020
gctattcgga agaacggcaa ctaagctgcc gggtttgaaa cacggatgat ctcgcggagg 4080
gtagcatgtt gattgtaacg atgacagagc gttgctgcct gtgatcaaat atcatctccc 4140
tcgcagagat ccgaattatc agccttctta ttcatttctc gcttaaccgt gacaggctgt 4200
cgatcttgag aactatgccg acataatagg aaatcgctgg ataaagccgc tgaggaagct 4260
gagtggcgct atttctttag aagtgaacgt tgacgatcgt cgaccgtacc ccgatgaatt 4320
aattcggacg tacgttctga acacagctgg atacttactt gggcgattgt catacatgac 4380
atcaacaatg tacccgtttg tgtaaccgtc tcttggaggt tcgtatgaca ctagtggttc 4440
ccctcagctt gcgactagat gttgaggcct aacattttat tagagagcag gctagttgct 4500
tagatacatg atcttcaggc cgttatctgt cagggcaagc gaaaattggc catttatgac 4560
gaccaatgcc ccgcagaagc tcccatcttt gccgccatag acgccgcgcc cccttttgg 4620

-continued

```
ggtgtagaac atcctttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taacccttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
```

```
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc ttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggcccccgg  11700
ccaggctgag ggagctgagg gccggcccgg ccccggccag gctgagggag ctgaggggca  11760
gcggcggcag cggcgtgccg ggcgtgggcg tgccgggcgt gggcgtgccg ggcgtgggcg  11820
tgccgggcgt gggcgtgccg ggcgtgggcg tgccgggcgt gggcgtgccg ggcgtgggcg  11880
tgccgggcgt gggcgtgccg ggcgtgggcg tgccgggcgt gggcgtgccg ggcgtgggcg  11940
tgccgggcgt gggcgtgccg ggcgtgggcg tgccgggcgt gggcgtgccg ggcgtgggcg  12000
tgccgggcgt gggcgtgccg ggcgtgggcg tgccgggcgt gggcgtgccg ggcgtgggcg  12060
tgccgggcgt gggcgtgccg ggcgtgggcg tgccgggcgt gggcgtgccg ggcgtgggcg  12120
tgccgggcgt gggcgtgccg ggcgtgggcg tgccgggcgt gggcgtgccg ggcgtgggcg  12180
tgccgggcgt gggcaaggac gagctgtaac                                  12210

SEQ ID NO: 74          moltype = DNA  length = 12015
FEATURE                Location/Qualifiers
misc_feature           1..12015
                       note = Synthetic construct, pAG4312
source                 1..12015
                       mol_type = other DNA
                       organism = synthetic construct
SEQUENCE: 74
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagtttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
```

-continued

```
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc ccccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
```

-continued

```
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
```

-continued

```
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggggca  11760
gcggcggcag cggcagcaac ggcaacggca acgtgtgccc gccgggcctg ttcagcaacc  11820
cgcagtgctg cgccacccag gtgctgggcc tgatcggcct ggactgcaag gtgccgagcc  11880
agaacgtgta cgacggcacc gacttcagga acgtgtgcgc caagaccggc gcccagccgc  11940
tgtgctgcgt ggccccggtg gccggccagg ccctgctgtg ccagaccgcc gtgggcgcca  12000
aggacgagct gtaac                                                   12015

SEQ ID NO: 75          moltype = DNA  length = 12738
FEATURE                Location/Qualifiers
misc_feature           1..12738
                       note = Synthetic construct, pAG4313
source                 1..12738
                       mol_type = other DNA
                       organism = synthetic construct
SEQUENCE: 75
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcactttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
```

-continued

```
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc ccccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
```

-continued

```
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcttaatt aagtctaact cgagttactg gtacgtatac agggttcctt gcgtgaagaa  10140
gggtggcctg cggttcacca ttaacggtca cgactacttc cagctagtac tggtgaccaa  10200
cgtcgcggcg gcagggtcaa tcaagtccat ggaggttatg ggttccaaca cagcggattg  10260
gatgccgatg gcacgtaact ggggcgccca atggcactca ctggcctacc tcaccggtca  10320
aggtctatcc tttagggtca ccaacacaga tgaccaaacg ctcgtcttca ccaacgtcgt  10380
gccaccagga tggaagtttg gccagacatt tgcaagcaag ctgcagttca agtgagagga  10440
gaagcctgaa ttgataccgg agcgtttctt ttgggagtaa catctctggt tgcctagcaa  10500
acatatgatt gtatataagt ttcgttgtgc gtttattctt tcggtgtgta aaataacata  10560
catgctttcc tgatattttc ttgtatatat gtacacacac acgacaaatc cttccatttc  10620
tattattatt gaacaattta attgcgaggg cgagtacttg tctgtttacc tttttttttt  10680
cagatggcat tttatagttt aacctttcat ggaccggcag tagttctaac catgaatgaa  10740
aagaaatcat agtccacacc acgcagggac attgtggtca ttttagacaa gacgatttga  10800
ttaatgtctt gtatgatatg gtcgacagtg aggactaaca aacatatggc atattttatt  10860
accggcgagt taaataaatt tatgtcacag taataaactg cctaataaat gcacgccaga  10920
aaatataatg ataaaaaaaa gaaaagatac ataagtccat tgcttctact tttttaaaaa  10980
ttaaatccaa cattttctat tttttggtat aaacttggaa gtactagttg gatatgcaaa  11040
atcatctaac ctccatatat ttcatcaatt tgtttacttt acatatggga gaggatagta  11100
tgtcaaagaa aatgacaaca agcttacaag tttcttattt taaaagttcc gctaacttat  11160
caagcatagt gtgccacgca aaactgacaa caaaccaaca aatttaagga gcgcctaact  11220
tatcatctat gacataccgc acaaaaatgat aacatactag agaaacttta ttgcacaaaa  11280
ggaaatttat ccataaggca aaggaacatc ttaaggcttt ggatatacat ttaccaacaa  11340
gcattgtttg tattacccct aaagcgcaag acatgtcatc catgagtcat agtgtgtata  11400
tctcaacatt gcaaagctac cttttttcta ttatactttt cgcattatag gctagatatt  11460
atctatacat gtcaacaaac tctatcccta cgtcatatct gaagattctt ttcttcacta  11520
tataagttgg cttccctgtc attgaactca catcaaccag cccaagtttc caataacatc  11580
ctcaaatagc tggatcctaa accatgaggg tgttgctcgt tgccctcgct ctcctggctc  11640
tcgctgcgag cgccacctcc ccggccaggc tgagggagct gagggccggc ccggccccgg  11700
ccaggctgag ggagctgagg gccggcccgg ccccggccag gctgagggag ctgaggggca  11760
gcggcggcag cggcggcgtg gacccgttcg agaggaacaa gatcctgggc aggggcatca  11820
acatcggcaa cgccctggag gccccgaacg agggcgactg gggcgtggtg atcaaggacg  11880
agttcttcga catcatcaag gaggccggct tcagccacgt gagaatcccg atcaggtgga  11940
gcacccacgc ccaggccttc ccgccgtaca agatcgagcc gagcttcttc aagagggtgg  12000
acgaggtgat caacggcgcc ctgaagaggg gcctggccgt ggtgatcaac atccaccact  12060
acgaggagct gatgaacgac ccggaggagc acaaggagag gttcctggcc ctgtggaagc  12120
agatcgccga caggtacaag gactacccgg agaccctgtt cttcgagatc ctgaacgagc  12180
cgcacggcaa cctgaccccg gagaagtgga acgagctgct ggaggaggcc ctgaaggtga  12240
tcaggagcat cgacaagaag cacaccgtga tcatcggcac cgccgagtgg ggcggcatca  12300
gcgccctgga gaagctgagg gtgccgaagt gggagaagaa cgccatcgtg accatccact  12360
actacaaccc gttcgagttc acccaccagg gcgccgagtg ggtgccgggc agcgagaagt  12420
```

```
ggctgggcag gaagtggggc agcccggacg accagaagca cctgatcgag gagttcaact  12480
tcatcgagga gtggagcaag aagaacaaga ggccgatcta catcggcgag ttcggcgcct  12540
acaggaaggc cgacctggag agcaggatca agtggaccag cttcgtggtg agggaggccg  12600
agaagagggg ctggagctgg gcctactggg agttctgcag cggcttcggc gtgtacgacc  12660
cgctgaggaa gcagtggaac aaggacctgc tggaggccct gatcggcggc gacagcatcg  12720
agaaggacga gctgtaac                                                12738

SEQ ID NO: 76           moltype = DNA  length = 11825
FEATURE                 Location/Qualifiers
misc_feature            1..11825
                        note = Synthetic construct, pAG4981
source                  1..11825
                        mol_type = other DNA
                        organism = synthetic construct
SEQUENCE: 76
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
```

-continued

```
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc ccccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgctat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
```

-continued

```
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtaccaaa gtaatcatat tattttatgt gtgaatcttc  10260
tttacttttt catttgatta tgattatgaa ggtatgacct tcataacctt cgtccgaaat  10320
ccattatatc caaaggaaaa taatgcttcg aaggacgaag gattttgata tttaacattt  10380
tatgttgcct tgttcttaat tcatagcatt tgagaacaag tccccaacac caatctttat  10440
ctttactata ttaaagcacc agttcaacga tcgtctcgtg tcaatattat taaaaaactc  10500
ctacatttct ttataatcaa cccgcactct tataatctct tctcttacta ctataataag  10560
agagtttatg tacaaaataa ggtgaaatta tgtataagtg ttctggacct tggttgttgg  10620
ctcatattca cacaacctaa tcaatagaaa acatatgttt tattaaaaca aaatttatca  10680
tatatatata tatatatata tatatatata tatatatata taatataaac cgtagcaatg  10740
cacaggcata tgactagtgg caacttaata ccatgtgtgt attaagatga ataagaggta  10800
tccaaataaa taacttgttc gcttacgtct ggatcgaaag gggttggaaa cgattaaatc  10860
tcttcctagt caaaattaaa tagaaggaga tttaatcgat ttctcccaat ccccttcgat  10920
ccaggtgcaa ccgaataagt ccttaaatgt tgaggaacac gaaacaacca tgcattggca  10980
tgtaaagctc caagaattcg ttgtatcctt aacaactcac agaacatcaa ccaaaattgc  11040
acgtcaaggg tattgggtaa gaaacaatca aacaaatcct ctctgtgtgc aaagaaacac  11100
ggtgagtcat gccgagatca tactcatctg atatacatgc ttacagctca caagacatta  11160
caaacaactc atattgcatt acaaagatcg tttcatgaaa aataaaatag gccggaacag  11220
gacaaaaatc cttgacgtgt aaagtaaatt tacaacaaaa aaaaagccat atgtcaagct  11280
aaatctaatt cgttttacgt agatcaacaa cctgtagaag gcaacaaaac tgagccacgc  11340
agaagtacag aatgattcca gatgaaccat cgacgtgcta cgtaaagaga gtgacgagtc  11400
atatacattt ggcaagaaac catgaagctg cctacagccg tctcggtggc ataagaacac  11460
aagaaattgt gttaattaat caaagctata aataacgctc gcatgcctgt gcacttctcc  11520
atcaccacca ctgggtcttc agaccattag ctttatctac tccagagcgc agaagaaccc  11580
gatcgacacc ggatcctaaa ccatgagggt gttgctcgtt gccctcgctc tcctggctct  11640
cgctgcgagc gccacctccg gctgccagag cgtgagcgag atgctgaggt tctacaccga  11700
cgaggtgctg ccgagggcca tgcagggcgg cggcagcggc ggcggcagca aggccatggg  11760
cgagttcgac atcttcatca actacatcga ggagtacctg ctgatgagga aggacgagct  11820
gtaac                                                              11825
```

```
SEQ ID NO: 77          moltype = DNA  length = 12533
FEATURE                Location/Qualifiers
misc_feature           1..12533
                       note = Synthetic construct, pAG4982
source                 1..12533
                       mol_type = other DNA
                       organism = synthetic construct
SEQUENCE: 77
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
```

-continued

```
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc cccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
tttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc cccctttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
```

-continued

```
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtacctcc atgctgtcct actacttgct tcatcccctt  10260
ctacatttg ttctggtttt tggcctgcat ttcggatcat gatgtatgtg atttccaatc  10320
tgctgcaata tgaatggaga ctctgtgcta accatcaaca acatgaaatg cttatgaggc  10380
```

-continued

```
ctttgctgag cagccaatct tgcctgtgtt tatgtcttca caggccgaat tcctctgttt  10440
tgtttttcac cctcaatatt tggaaacatt tatctaggtt gtttgtgtcc aggcctataa  10500
atcatacatg atgttgtcgt attggatgtg aatgtggtgg cgtgttcagt gccttggatt  10560
tgagtttgat gagagttgct tctgggtcac cactcaccat tatcgatgct cctcttcagc  10620
ataaggtaaa agtcttccct gtttacgtta ttttacccac tatggttgct tgggttggtt  10680
ttttcctgat tgcttatgcc atggaaagtc atttgatatg ttgaacttga attaactgta  10740
gaattgtata catgttccat ttgtgttgta cttccttctt ttctattagt agcctcagat  10800
gagtgtgaaa aaaacagatt atataacttg ccctataaat catttgaaaa aaatattgta  10860
cagtgagaaa ttgatatata gtgaattttt aagagcatgt tttcctaaag aagtatatat  10920
tttctatgta caaaggccat tgaagtaatt gtagatacag gataatgtag actttttgga  10980
cttacactgc tacctttaag taacaatcat gagcaatagt gttgcaatga tatttaggct  11040
gcattcgttt actctcttga tttccatgag cacgcttccc aaactgttaa actctgtgtt  11100
ttttgccaaa aaaaaatgca taggaaagtt gcttttaaaa aatcatatca atccattttt  11160
taagttatag ctaatactta attaatcatg cgctaataag tcactctgtt tttcgtacta  11220
gagagattgt tttgaaccag cactcaagaa cacagcctta acccagccaa ataatgctac  11280
aacctaccag tccacacctc ttgtaaagca tttgttgcat ggaaaagcta agatgacagc  11340
aacctgttca ggaaaacaac tgacaaggtc atagggagag ggagcttttg gaaaggtgcc  11400
gtgcagttca aacaattagt tagcagtagg gtgttggttt ttgctcacag caataagaag  11460
ttaatcatgg tgtaggcaac ccaaataaaa caccaaaata tgcacaaggc agtttgttgt  11520
attctgtagt acagacaaaa ctaaaagtaa tgaaagaaga tgtggtgtta gaaaaggaaa  11580
caatatcatg agtaatgtgt gggcattatg ggaccacgaa ataaaaagaa cattttgatg  11640
agtcgtgtat cctcgatgag cctcaaaagt tctctcaccc cggataagaa acccttaagc  11700
aatgtgcaaa gtttgcattc tccactgaca taatgcaaaa taagatatca tcgatgacat  11760
agcaactcat gcatcatatc atgcctctct caacctattc attcctactc atctacataa  11820
gtatcttcag ctaaatgtta gaacataaac ccataagtca cgtttgatga gtattaggcg  11880
tgacacatga caaatcacag actcaagcaa gataaagcaa aatgatgtgt acataaaact  11940
ccagagctat atgtcatatt gcaaaaagag gagagcttat aagacaaggc atgactcaca  12000
aaaattcatt tgcctttcgt gtcaaaaaga ggagggcttt acattatcca tgtcatattg  12060
caaaagaaag agagaaagaa caacacaatg ctgcgtcaat tatacatatc tgtatgtcca  12120
tcattattca tccacctttc gtgtaccaca cttcatatat catgagtcac ttcatgtctg  12180
gacattaaca aactctatct taacatttag atgcaagagc ctttatctca ctataaatgc  12240
acgatgattt ctcattgttt ctcacaaaaa gcattcagtt cattagtcct acaacaacgg  12300
atcctaaacc atgagggtgt tgctcgttgc cctcgctctc ctggctctcg ctgcgagcgc  12360
cacctccggc tgccagagcg tgagcgagat gctgaggttc tacaccgacg aggtgctgcc  12420
gagggccatg cagggcggcg gcagcggcgg cggcagcaag gccatgggcg agttcgacat  12480
cttcatcaac tacatcgagg agtacctgct gatgaggaag gacgagctgt aac         12533
```

```
SEQ ID NO: 78          moltype = DNA  length = 13466
FEATURE                Location/Qualifiers
misc_feature           1..13466
                       note = Synthetic construct, pAG4983
source                 1..13466
                       mol_type = other DNA
                       organism = synthetic construct
SEQUENCE: 78
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat ttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc ccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
```

-continued

```
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc cccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
```

-continued

```
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatcttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtacccgg tatgaatttg gaaacaaatt cagtactttt  10260
aaaaaaattt gttgtaggga gcaaataata cataaaataa tttatgcatt attttatttt  10320
ttatttgtaa taatatgctt gaaacgataa ttcagtatgc atgttgtgcc agtgtactac  10380
acgggcgggg ggaggggatt gagtgggcca gcgcggtgcg tagggtagat gggctgaaat  10440
tgataactca agtccgacta ggttctcttt ttatttccct tcctttccta ttttcctttc  10500
ttttaatttt catgctttca aactaaattc aaattcgagt tttgaatttc agcttctaaa  10560
ttgtacacta aaattatatg ataaggtaac ccctactatt acttttaatt tttttattct  10620
accccatatt gtttacttag gggagaataa ttgacttaat cacattcttc cttaggtttc  10680
aattctcaat ctttcaaatc cacattttta gatttctatt ttgaatttaa ataccagttt  10740
ggatttagag ttcaatttca aaatacacaa ccaaaatacc agcatgaatg caaatatatt  10800
ttatgtttat gtatttactt ttcttttata ctttgctcaa aatagttatt ttcatgtatg  10860
aaactcaata agcaaggaac tcacgttatt atataaccta ataggaataa tttaggtaac  10920
ataatttatc atcctcttga tttaaaagag atatgcctcc agaataagac acatactaaa  10980
aataactcta atattgaata actaaagtcg tacaaatctc tactattatt cctataaaat  11040
aataaagaac tagctacaac ttctttaagg cattattcag ggtttacagc ttgagaggca  11100
tgaacccatc ctgtatactc ctggacttgg aagacaaaat gtcaaccaaa gtgaaaggtt  11160
ttcttatggt tgctgctaag agatagattg aacactagat ctctcctaag acgtcagggc  11220
atgcgtttag actcctacac atgcgaaaac tgcatcttac agttggaaga aactatatct  11280
caccacttcc tgcggtgtaa ctttgcccaa agatgttggc tcactgttgg aatcactccg  11340
ccccgaactt tggatctaac gcttgcagtg ctacatatta gagcaagact aacaatgccg  11400
tggagaatgg aaggtattat aaccatgtca tggtgcatat ggaaatgtcg aaataactgg  11460
atattcgaaa acataccgcc aacggtggcg gcctgcaagg aaatgttcaa gactgaaatg  11520
```

```
aactacatct gctaccaagt taagctcgag acaggagcta aaagtagaaa ctggatacaa  11580
cactttgtaa catagtgaca ctccccttt cctttctttt accttagaac tatacataca  11640
atccacattc aataaaaatt tgtaggtacg ccatacacac taccggaatc cggctctttg  11700
ccgagtgtga ggcgctttgt cgagtgcttt ttgtccagca ctcggcaaaa aagtctttgc  11760
catgtgccgc actcggcaaa gtcctgctct cggtaacgac cgcgtttacc gagagcagga  11820
ctctcgacac agaaatacac tcgacaaaga aatctttgcc gagagccaaa cactcggcga  11880
acggcagcgc tcggcaaagg gtcgtcagcc gccgtctaaa gctgacggtc gttatctttg  11940
tcgagtgccc cctcgtccga cactcagtag agcaagcttg ccgagtgcca tccttggaca  12000
ctcgataaag tatattttat ttttttttat tttgccaacc aaactttttg tggtatgttc  12060
ctacactatg tagatctaca tgtaccattt tggcacaatt acaaaaatgt tttctataac  12120
tattagattt agttcgttta tttgaatttc ttcggaaaat tcacatatga actgcaagtc  12180
actcgaaaca tgaaaaaccg tgcatgcaaa ataaatgata tgcatgttat ctagcacaag  12240
ttacgaccga attcagaagc agaccagaat cttcaagcac catgctcact aaacatgacc  12300
gtgaacttgt tatccagttg tttaaaaatt gtataaaaca caaataaagt cagaaattaa  12360
tgaaacttgt ccacatgtca tgatatcata tatagaggtt gtgataaaaa tttgataatg  12420
tttcggtaaa gttgtgacgt actatgtgta gaaacctaag tgacctacac ataaaatcat  12480
agagtttcaa tgtagttcac tcgacaaaga ctttgtcaag tgtccgataa aaagtattca  12540
gcaaagaagc cgttgtcgat ttactgttcg tcgagatctc tttgccgagt gtcacactag  12600
gcaaagtctt tacggagtgt ttttcaggct ttgacactcg gcaaagcgct cgattccagt  12660
agtgacagta atttgcatca aaaatagccg agagatttaa aatgagtcaa ctaatagacc  12720
aactaattat tagctattag tcgttagctt ctttaatcta agctaaaacc aactaatagc  12780
ttatttgttg aattacaatt agctcaacgg aattctctgt tttttctata aaaaaaaggg  12840
aaactgcccc tcatttacag caaactgtcc gctgcctgtc gtccagatac aatgaacgta  12900
cctagtagga actcttttac acgctcggtc gctcgccgcg gatcggagtc ccaggaacac  12960
gacaccactg tggaacacga caaagtctgc tcagaggcgg ccacaccctg gcgtgcaccg  13020
agccggagcc cggataagca cggtaaggag agtacggcgg gacgtggcga cccgtgtgtc  13080
tgctgccacg cagccttcct ccacgtagcc gcgcggccgc gccacgtacc agggcccggc  13140
gctggtataa atgcgcgcca cctccgcttt agttctgcat acagccaacc caacacacac  13200
ccgagcatat cacagtgaca gacactacac gggatcctaa accatgaggg tgttgctcgt  13260
tgccctcgct ctcctggctc tcgctgcgag cgccacctcc ggctgccaga gcgtgagcga  13320
gatgctgagg ttctacaccg acgaggtgct gccgagggcc atgcagggcg gcggcagcgg  13380
cggcggcagc aaggccatgg gcgagttcga catcttcatc aactacatcg aggagtacct  13440
gctgatgagg aaggacgagc tgtaac                                      13466
```

```
SEQ ID NO: 79          moltype = DNA  length = 12474
FEATURE                Location/Qualifiers
misc_feature           1..12474
                       note = Synthetic construct, pAG4984
source                 1..12474
                       mol_type = other DNA
                       organism = synthetic construct
SEQUENCE: 79
ctaggtcccc gaatttcccc gatcgttcaa acatttggca ataaagtttc ttaagattga  60
atcctgttgc cggtcttgcg atgattatca tataatttct gttgaattac gttaagcatg  120
taataattaa catgtaatgc atgacgttat ttatgagatg ggtttttatg attagagtcc  180
cgcaattata catttaatac gcgatagaaa acaaaatata gcgcgcaaac taggataaat  240
tatcgcgcgc ggtgtcatct atgttactag atcgggaatt ggaattcctg cagtgcagcg  300
tgacccggtc gtgcccctct ctagagataa tgagcattgc atgtctaagt tataaaaaat  360
taccacatat tttttttgtc acacttgttt gaagtgcagt ttatctatct ttatacatat  420
atttaaactt tactctacga ataatataat ctatagtact acaataatat cagtgtttta  480
gagaatcata taaatgaaca gttagacatg gtctaaagga caattgagta ttttgacaac  540
aggactctac agttttatct ttttagtgtg catgtgttct cctttttttt tgcaaatagc  600
ttcacctata taatacttca tccattttat tagtacatcc atttagggtt tagggttaat  660
ggtttttata gactaatttt tttagtacat ctattttatt ctattttagc ctctaaatta  720
agaaaactaa aactctattt tagttttttt atttaataat ttagatataa aatagaataa  780
aataaagtga ctaaaaatta aacaaatacc ctttaagaaa ttaaaaaaac taaggaaaca  840
tttttcttgt ttcgagtaga taatgccagc ctgttaaacg ccgtcgacga gtctaacgga  900
caccaaccag cgaaccagca gcgtcgcgtc gggccaagcg aagcagacgg cacggcatct  960
ctgtcgctgc ctctggaccc ctctcgagag ttccgctcca ccgttggact tgctccgctg  1020
tcggcatcca gaaattgcgt ggcggagcgg cagacgtgag ccggcacggc aggcggcctc  1080
ctcctcctct cacggcacgg cagctacggg ggattccttt cccaccgctc cttcgctttc  1140
ccttcctcgc ccgccgtaat aaatagacac cccctccaca ccctctttcc ccaacctcgt  1200
gttgttcgga gcgcacacac acacaaccag atctccccca aatccacccg tcggcacctc  1260
cgcttcaagg tacgccgctc gtcctccccc ccccccctc tctaccttct ctagatcggc  1320
gttccggtcc atggttaggg cccggtagtt ctacttctgt tcatgtttgt gttagatccg  1380
tgtttgtgtt agatccgtgc tgctagcgtt cgtacacgga tgcgacctgt acgtcagaca  1440
cgttctgatt gctaacttgc cagtgtttct ctttggggaa tcctgggatg gctctagccg  1500
ttccgcagac gggatcgatt tcatgatttt ttttgtttcg ttgcataggg tttggtttgc  1560
ccttttcctt tatttcaata tatgccgtgc acttgtttgt cgggtcatct tttcatgctt  1620
ttttttgtct tggttgtgat gatgtggtct ggttgggcgg tcgttctaga tcggagtaga  1680
attctgtttc aaactacctg gtggatttat taattttgga tctgtatgtg tgtgccatac  1740
atattcatag ttacgaattg aagatgatgg atggaaatat cgatctagga taggtataca  1800
tgttgatgcg ggttttactg atgcatatac agagatgctt tttgttcgct tggttgtgat  1860
gatgtggtgt ggttgggcgg tcgttcattc gttctagatc ggagtagaat actgtttcaa  1920
actacctggt gtatttatta attttggaac tgtatgtgtg tgtcatacat cttcatagtt  1980
acgagtttaa gatggatgga aatatcgatc taggataggt atacatgttg atgtgggttt  2040
tactgatgca tatacatgat ggcatatgca gcatctattc atatgctcta accttgagta  2100
cctatctatt ataataaaca agtatgtttt ataattattt tgatcttgat atacttggat  2160
gatggcatat gcagcagcta tatgtggatt tttttagccc tgccttcata cgctatttat  2220
```

-continued

```
ttgcttggta ctgtttcttt tgtcgatgct caccctgttg tttggtgtta cttctgcaga  2280
tccagatcta aaccatgcag aaactcatta actcagtgca aaactatgcc tggggcagca  2340
aaacggcgtt gactgaactt tatggtatgg aaaatccgtc cagccagccg atggccgagc  2400
tgtggatggg cgcacatccg aaaagcagtt cacgagtgca gaatgccgcc ggagatatcg  2460
tttcactgcg tgatgtgatt gagagtgata aatcgactct gctcggagag gccgttgcca  2520
aacgctttgg cgaactgcct ttcctgttca aagtattatg cgcagcacag ccactctcca  2580
ttcaggttca tccaaacaaa cacaattctg aaatcggttt tgccaaagaa aatgccgcag  2640
gtatcccgat ggatgccgcc gagcgtaact ataaagatcc taaccacaag ccggagctgg  2700
tttttgcgct gacgcctttc cttgcgatga acgcgtttcg tgaattttcc gagattgtct  2760
ccctactcca gccggtcgca ggtgcacatc cggcgattgc tcacttttta caacagcctg  2820
atgccgaacg tttaagcgaa ctgttcgcca gcctgttgaa tatgcagggt gaagaaaaat  2880
cccgcgcgct ggcgatttta aaatcggccc tcgatagcca gcagggtgaa ccgtggcaaa  2940
cgattcgttt aatttctgaa ttttacccgg aagacagcgg tctgttctcc ccgctattgc  3000
tgaatgtggt gaaattgaac cctggcgaag cgatgttcct gttcgctgaa acaccgcacg  3060
cttacctgca aggcgtggcg ctggaagtga tggcaaactc cgataacgtg ctgcgtgcgg  3120
gtctgacgcc taaatacatt gatattccgg aactggttgc caatgtgaaa ttcgaagcca  3180
aaccggctaa ccagttgttg acccagccgg tgaaacaagg tgcagaactg gacttcccga  3240
ttccagtgga tgattttgcc ttctcgctgc atgaccttag tgataaagaa accaccatta  3300
gccagcagag tgccgccatt ttgttctgcg tcgaaggcga tgcaacgttg tggaaaggtt  3360
ctcagcagtt acagcttaaa ccgggtgaat cagcgtttat tgccgccaac gaatcaccgg  3420
tgactgtcaa aggccacggc cgtttagcgc gtgtttacaa caagctgtaa gagcttactg  3480
aaaaaattaa catctcttgc taagctggga gctctagatc cccgaatttc cccgatcgtt  3540
caaacatttg gcaataaagt ttcttaagat tgaatcctgt tgccggtctt gcgatgatta  3600
tcatataatt tctgttgaat tacgttaagc atgtaataat taacatgtaa tgcatgacgt  3660
tatttatgag atgggttttt atgattagag tcccgcaatt atacatttaa tacgcgatag  3720
aaaacaaaat atagcgcgca aactaggata aattatcgcg cgcggtgtca tctatgttac  3780
tagatcggga attggcgagc tcgaattaat tcagtacatt aaaaacgtcc gcaatgtgtt  3840
attaagttgt ctaagcgtca atttgtttac accacaatat atcctgccac cagccagcca  3900
acagctcccc gaccggcagc tcggcacaaa atcaccactc gatacaggca gcccatcagt  3960
ccgggacggc gtcagcggga gagccgttgt aaggcggcag actttgctca tgttaccgat  4020
gctattcgga agaacggcaa ctaagctgcc gggtttgaaa cacggatgat ctcgcggagg  4080
gtagcatgtt gattgtaacg atgacagagc gttgctgcct gtgatcaaat atcatctccc  4140
tcgcagagat ccgaattatc agccttctta ttcatttctc gcttaaccgt gacaggctgt  4200
cgatcttgag aactatgccg acataatagg aaatcgctgg ataaagccgc tgaggaagct  4260
gagtggcgct atttctttag aagtgaacgt tgacgatcgt cgaccgtacc ccgatgaatt  4320
aattcggacg tacgttctga acacagctgg atacttactt gggcgattgt catacatgac  4380
atcaacaatg tacccgtttg tgtaaccgtc tcttggaggt tcgtatgaca ctagtggttc  4440
ccctcagctt gcgactagat gttgaggcct aacattttat tagagagcag gctagttgct  4500
tagatacatg atcttcaggc cgttatctgt cagggcaagc gaaaattggc catttatgac  4560
gaccaatgcc ccgcagaagc tcccatcttt gccgccatag acgccgcgcc ccccttttgg  4620
ggtgtagaac atccttttgc cagatgtgga aaagaagttc gttgtcccat tgttggcaat  4680
gacgtagtag ccggcgaaag tgcgagaccc atttgcgcta tatataagcc tacgatttcc  4740
gttgcgacta ttgtcgtaat tggatgaact attatcgtag ttgctctcag agttgtcgta  4800
atttgatgga ctattgtcgt aattgcttat ggagttgtcg tagttgcttg gagaaatgtc  4860
gtagttggat ggggagtagt catagggaag acgagcttca tccactaaaa caattggcag  4920
gtcagcaagt gcctgccccg atgccatcgc aagtacgagg cttagaacca ccttcaacag  4980
atcgcgcata gtcttcccca gctctctaac gcttgagtta agccgcgccg cgaagcggcg  5040
tcggcttgaa cgaattgtta gacattattt gccgactacc ttggtgatct cgcctttcac  5100
gtagtgaaca aattcttcca actgatctgc gcgcgaggcc aagcgatctt cttgtccaag  5160
ataagcctgc ctagcttcaa gtatgacggg ctgatactgg gccggcaggc gctccattgc  5220
ccagtcggca gcgacatcct tcggcgcgat tttgccggtt actgcgctgt accaaatgcg  5280
ggacaacgta agcactacat ttcgctcatc gccagcccag tcgggcggcg agttccatag  5340
cgttaaggtt tcatttagcg cctcaaatag atcctgttca ggaaccggat caaagagttc  5400
ctccgccgct ggacctacca aggcaacgct atgttctctt gcttttgtca gcaagatagc  5460
cagatcaatg tcgatcgtgg ctggctcgaa gatacctgca agaatgtcat tgcgctgcca  5520
ttctccaaat tgcagttcgc gcttagctgg ataacgccac ggaatgatgt cgtcgtgcac  5580
aacaatggtg acttctacag cgcggagaat ctcgctctct ccaggggaag ccgaagtttc  5640
caaaaggtcg ttgatcaaag ctcgccgcgt tgtttcatca agccttacgg tcaccgtaac  5700
cagcaaatca atatcactgt gtggcttcag gccgccatcc actgcggagc cgtacaaatg  5760
tacggccagc aacgtcggtt cgagatggcg ctcgatgacg ccaactacct ctgatagttg  5820
agtcgatact tcggcgatca ccgcttccct catgatgttt aactcctgaa ttaagccgcg  5880
ccgcgaagcg gtgtcggctt gaatgaattg ttaggcgtca tcctgtgctc ccgagaacca  5940
gtaccagtac atcgctgttt cgttcgagac ttgaggtcta gttttatacg tgaacaggtc  6000
aatgccgccg agagtaaagc cacattttgc gtacaaattg caggcaggta cattgttcgt  6060
ttgtgtctct aatcgtatgc caaggagctg tctgcttagt gcccactttt tcgcaaattc  6120
gatgagactg tgcgcgactc ctttgcctcg gtgcgtgtgc gacacaacaa tgtgttcgat  6180
agaggctaga tcgttccatg ttgagttgag ttcaatcttc ccgacaagct cttggtcgat  6240
gaatgcgcca tagcaagcag agtcttcatc agagtcatca tccgagatgt aatccttccg  6300
gtaggggctc acacttctgg tagatagttc aaagccttgg tcggataggt gcacatcgaa  6360
cacttcacga acaatgaaat ggttctcagc atccaatgtt tccgccacct gctcagggat  6420
caccgaaatc ttcatatgac gcctaacgcc tggcacagcg gatcgcaaac ctggcgcggc  6480
ttttggcaca aaaggcgtga caggtttgcg aatccgttgc tgccacttgt taaccctttt  6540
gccagatttg gtaactataa tttatgttag aggcgaagtc ttgggtaaaa actggcctaa  6600
aattgctggg gatttcagga aagtaaacat caccttccgg ctcgatgtct attgtagata  6660
tatgtagtgt atctacttga tcgggggatc tgctgcctcg cgcgtttcgg tgatgacggt  6720
gaaaacctct gacacatgca gctcccggag acggtcacag cttgtctgta agcggatgcc  6780
gggagcagac aagcccgtca gggcgcgtca gcgggtgttg gcgggtgtcg gggcgcagcc  6840
atgacccagt cacgtagcga tagcggagtg tatactggct taactatgcg gcatcagagc  6900
agattgtact gagagtgcac catatgcggt gtgaaatacc gcacagatgc gtaaggagaa  6960
```

```
aataccgcat caggcgctct tccgcttcct cgctcactga ctcgctgcgc tcggtcgttc  7020
ggctgcggcg agcggtatca gctcactcaa aggcggtaat acggttatcc acagaatcag  7080
gggataacgc aggaaagaac atgtgagcaa aaggccagca aaaggccagg aaccgtaaaa  7140
aggccgcgtt gctggcgttt ttccataggc tccgcccccc tgacgagcat cacaaaaatc  7200
gacgctcaag tcagaggtgg cgaaacccga caggactata aagataccag gcgtttcccc  7260
ctggaagctc cctcgtgcgc tctcctgttc cgaccctgcc gcttaccgga tacctgtccg  7320
cctttctccc ttcgggaagc gtggcgcttt ctcatagctc acgctgtagg tatctcagtt  7380
cggtgtaggt cgttcgctcc aagctgggct gtgtgcacga accccccgtt cagcccgacc  7440
gctgcgcctt atccggtaac tatcgtcttg agtccaaccc ggtaagacac gacttatcgc  7500
cactggcagc agccactggt aacaggatta gcagagcgag gtatgtaggc ggtgctacag  7560
agttcttgaa gtggtggcct aactacggct acactagaag gacagtattt ggtatctgcg  7620
ctctgctgaa gccagttacc ttcggaaaaa gagttggtag ctcttgatcc ggcaaacaaa  7680
ccaccgctgg tagcggtggt ttttttgttt gcaagcagca gattacgcgc agaaaaaaag  7740
gatctcaaga agatcctttg atcttttcta cggggtctga cgctcagtgg aacgaaaact  7800
cacgttaagg gattttggtc atgagattat caaaaaggat cttcacctag atccttttaa  7860
attaaaaatg aagttttaaa tcaatctaaa gtatatatga gtaaacttgg tctgacagtt  7920
accaatgctt aatcagtgag gcacctatct cagcgatctg tctatttcgt tcatccatag  7980
ttgcctgact ccccgtcgtg tagataacta cgatacggga gggcttacca tctggcccca  8040
gtgctgcaat gataccgcga gacccacgct caccggctcc agatttatca gcaataaacc  8100
agccagccgg aagggccgag cgcagaagtg gtcctgcaac tttatccgcc tccatccagt  8160
ctattaattg ttgccgggaa gctagagtaa gtagttcgcc agttaatagt ttgcgcaacg  8220
ttgttgccat tgctgcaggg gggggggggg gggggttcca ttgttcattc cacggacaaa  8280
aacagagaaa ggaaacgaca gaggccaaaa agctcgcttt cagcacctgt cgtttccttt  8340
cttttcagag ggtattttaa ataaaaacat taagttatga cgaagaagaa cggaaacgcc  8400
ttaaaccgga aaattttcat aaatagcgaa aacccgcgag gtcgccgccc cgtaacctgt  8460
cggatcaccg gaaaggaccc gtaaagtgat aatgattatc atctacatat cacaacgtgc  8520
gtggaggcca tcaaaccacg tcaaataatc aattatgacg caggtatcgt attaattgat  8580
ctgcatcaac ttaacgtaaa aacaacttca gacaatacaa atcagcgaca ctgaatacgg  8640
ggcaacctca tgtccccccc cccccccccc tgcaggcatc gtggtgtcac gctcgtcgtt  8700
tggtatggct tcattcagct ccggttccca acgatcaagg cgagttacat gatcccccat  8760
gttgtgcaaa aaagcggtta gctccttcgg tcctccgatc gttgtcagaa gtaagttggc  8820
cgcagtgtta tcactcatgg ttatggcagc actgcataat tctcttactg tcatgccatc  8880
cgtaagatgc ttttctgtga ctggtgagta ctcaaccaag tcattctgag aatagtgtat  8940
gcggcgaccg agttgctctt gcccggcgtc aacacgggat aataccgcgc cacatagcag  9000
aactttaaaa gtgctcatca ttggaaaacg ttcttcgggg cgaaaactct caaggatctt  9060
accgctgttg agatccagtt cgatgtaacc cactcgtgca cccaactgat cttcagcatc  9120
ttttactttc accagcgttt ctgggtgagc aaaaacagga aggcaaaatg ccgcaaaaaa  9180
gggaataagg gcgacacgga aatgttgaat actcatactc ttcctttttc aatattattg  9240
aagcatttat cagggttatt gtctcatgag cggatacata tttgaatgta tttagaaaaa  9300
taaacaaata ggggttccgc gcacatttcc ccgaaaagtg ccacctgacg tctaagaaac  9360
cattattatc atgacattaa cctataaaaa taggcgtatc acgaggccct ttcgtcttca  9420
agaattggtc gacgatcttg ctgcgttcgg atattttcgt ggagttcccg ccacagaccc  9480
ggattgaagg cgagatccag caactcgcgc cagatcatcc tgtgacggaa ctttggcgcg  9540
tgatgactgg ccaggacgtc ggccgaaaga gcgacaagca gatcacgctt ttcgacagcg  9600
tcggatttgc gatcgaggat ttttcggcgc tgcgctacgt ccgcgaccgc gttgagggat  9660
caagccacag cagcccactc gaccttctag ccgacccaga cgagccaagg gatctttttg  9720
gaatgctgct ccgtcgtcag gctttccgac gtttgggtgg ttgaacagaa gtcattatcg  9780
cacggaatgc caagcactcc cgaggggaac cctgtggttg gcatgcacat acaaatggac  9840
gaacggataa accttttcac gcccttttaa atatccgatt attctaataa acgctctttt  9900
ctcttaggtt tacccgccaa tatatcctgt caaacactga tagtttaaac tgaaggcggg  9960
aaacgacaac ctgatcatga gcggagaatt aagggagtca cgttatgacc cccgccgatg  10020
acgcgggaca agccgtttta cgtttggaac tgacagaacc gcaacgttga aggagccact  10080
cagcctaagc ggccgcattg gacttaatta agtgaggccg gccaagcgtc gatttaaatg  10140
taccacatgg cgcgccaact atcatgcgat cgcttcatgt ctaactcgag ttactggtac  10200
gtaccaaatc catggaatca aggtaccatc aatcccggga taaaatttta gtgaagctaa  10260
agcggtgaaa gattatagaa tttgatgtgc cagattaata aatcgattaa ctcctaaagt  10320
tcaagccgag actacagaca catgagctac ataaatgagc caaggactcg agcaaagaca  10380
aatcgacaca gacattataa ttcaagtcat tctagaagat tcatgagaag agtatcattt  10440
atttaaatca atgacttgat caaataagac ctaggagcta ctattgataa tatatatcat  10500
gggtatctag atcaagcatt atgaagaaga gcctaagtag aaggccccat gggctcgacc  10560
acaaacccaa ggactcgaca ataaagtcta ggagggatcc catagctaaa aggactctag  10620
aagtgtatgt atggtaaaga ttttatcgag acaagaaata cgataaagat cttaacagaa  10680
tcggagtcat acttgtaaaa atagagttgg actcgtgtac aacttggtct tcgacttagt  10740
tcggtcatga attcagtaac cgactagata tgtaccatgg aacccctagg gcatgaggct  10800
atgagccata ggatcatcag atccaaacat acaccaacaa atccatcaca caccgaagat  10860
ccatattaac aagggattag ctactttaca atttcagagt aacaaataga gccaaactca  10920
tagcacaggg gaacttcata tcacaaatgg aggcattgaa ttgatataaa aagctaaagt  10980
tctaaaaagt ttgaagtgct gaaacttcaa agccgctaac tagtgaagca ccgaagcctt  11040
ccggggagag aagacataca cgacacgtta gggacgtaaa atgacgaaat tatacaacta  11100
cctctatatg taacacttat gtaatagaaa agacagaatc catatgaaga tgtataatgg  11160
atcaaccata taaatagata aacaatatat ctgctatggg gattggcatt cttgtatccc  11220
tacgcctgta tatcccctgt ttagagaacc tccgaaggta tatgatgctg aagattattg  11280
ttgtcttgtc tttcatcata tatcgagtct ttccctagga tattattatt cgcaatgtgc  11340
attacatggt taatcgattg agagaacatg catctcacct ttagctgata aacgataatc  11400
catgttttac acttcgtagc tactcatgag tttcgatata caaatttgtt ttctggacta  11460
cgtaccattc catcctctta ggagaggaga ggaagtgtcc tcgatttaat tatgttgtca  11520
ttttgtagtt cttcacaaaa tctcaacagg taccaaacac attgtttcca caagacatat  11580
tttagtcaca acaaatctat attattatta atcactaaaa ctatactgag gctcagatgc  11640
ttttactagc tcttgctagt atgtgatgta ggtctctttc gacatcattc catcaaaatc  11700
```

-continued

```
atatgattag cccataccaa acatttctat accattcaga gaccagaata gtcttttcta  11760
atagaaaaaa ggaaaataga gtgggccgac gacgacacaa attactgcgt ggaccagaaa  11820
atagtgagac acggaagaca aaagaagtaa aagaggcaag gactacggcc cacatgagat  11880
tcggccccgc cacctccggc aaccagcggc cgatccaacg gcagtgcatc ctcaacggcg  11940
cgcgcgcgcg cgcgcgcgca caacctcgta tatatcgccg cgcggaagcg gcgcgaccga  12000
ggaagccttg tcctcgacac cccctacaca ggtgtcgcgc tgcccccgac acgagtcccg  12060
catgcgtccc acgcggccgc gccagatccc gcctccgcgc gttgccacgc cctctataaa  12120
cacccagctc tctccctcgc cctcatctat cgcactcgta gtcgtagctc aagcatcagc  12180
ggcaggagct ctgggcagcg tgcgcacgtg gggtacctag ctcgctctgc tagcctaccg  12240
gatcctaaac catgagggtg ttgctcgttg ccctcgctct cctggctctc gctgcgagcg  12300
ccacctccgg ctgccagagc gtgagcgaga tgctgaggtt ctacaccgac gaggtgctgc  12360
cgagggccat gcagggcggc ggcagcggcg gcggcagcaa ggccatgggc gagttcgaca  12420
tcttcatcaa ctacatcgag gagtacctgc tgatgaggaa ggacgagctg taac        12474

SEQ ID NO: 80          moltype = AA  length = 153
FEATURE                Location/Qualifiers
REGION                 1..153
                       note = MISC_FEATURE - chicken IL-10
source                 1..153
                       mol_type = protein
                       organism = Gallus gallus
SEQUENCE: 80
LEPTCLHFSE LLPARLRELR VKFEEIKDYF QSRDDELNIQ LLSSELLDEF KGTFGCQSVS  60
EMLRFYTDEV LPRAMQTSTS HQQSMGDLGN MLLGLKATMR RCHRFFTCEK RSKAIKQIKE  120
TFEKMDENGI YKAMGEFDIF INYIEEYLLM RRR                              153

SEQ ID NO: 81          moltype = AA  length = 160
FEATURE                Location/Qualifiers
REGION                 1..160
                       note = MISC_FEATURE - IL-10
source                 1..160
                       mol_type = protein
                       organism = Homo sapiens
SEQUENCE: 81
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                       160

SEQ ID NO: 82          moltype = AA  length = 233
FEATURE                Location/Qualifiers
REGION                 1..233
                       note = MISC_FEATURE - IL-10R1
REGION                 1..233
                       note = MISC_FEATURE - human IL-10R1
source                 1..233
                       mol_type = protein
                       organism = Homo sapiens
SEQUENCE: 82
HGTELPSPPS VWFEAEFFHH ILHWTPIPNQ SESTCYEVAL LRYGIESWNS ISNCSQTLSY  60
DLTAVTLDLY HSNGYRARVR AVDGSRHSNW TVTNTRFSVD EVTLTVGSVN LEIHNGFILG  120
KIQLPRPKMA PANDTYESIF SHFREYEIAI RKVPGNFTFT HKKVKHENFS LLTSGEVGEF  180
CVQVKPSVAS RSNKGMWSKE ECISLTRQYF TVTNVIIFFA FVLLLSGALA YCL        233

SEQ ID NO: 83          moltype = AA  length = 210
FEATURE                Location/Qualifiers
REGION                 1..210
                       note = MISC_FEATURE - huan IL-10R1
REGION                 1..210
                       note = MISC_FEATURE - chicken IL-10R1
source                 1..210
                       mol_type = protein
                       organism = Gallus gallus
SEQUENCE: 83
ELRLKPTRVR FVAEMVYHLL QWEPGRDAPS DTRYDVEHKI YGTNSPWTAI PNCMKIHGHS  60
CDLTYYTLDP SLRYYARVRA VVGNHTSDWK RTNAFSPQEA SLRLSGHSLA VTDNSIHVQL  120
QLLLRAGNRT VKYDDIQKHA RRYRVYIRRA RDNQTYEVWE TASEFYIRNL FWNTEYCISV  180
EPDVASRHIP AMRTAEQCVT IGHRDESAEL                                  210

SEQ ID NO: 84          moltype = AA  length = 147
FEATURE                Location/Qualifiers
REGION                 1..147
                       note = Synthetic construct, xGZein27ss:chIL10sdAb1A11:KDEL
source                 1..147
                       mol_type = protein
                       organism = synthetic construct
SEQUENCE: 84
MRVLLVALAL LALAASATSQ VQLQESGGGL VQPGGSLRLS CAASGNIFSI NTMGWYRQAP  60
GKQRELVASI TTGGTTNYED SVKGRFTISR DNAKKTVYLQ MNRLKPEDTA VYYCNHRRSY  120
SGRDYPVYGM DYWGKGTLVT VSSKDEL                                     147
```

```
SEQ ID NO: 85           moltype = AA  length = 147
FEATURE                 Location/Qualifiers
REGION                  1..147
                        note = Synthetic construct, xGZein27ss:chIL10sdAb1B9:KDEL
source                  1..147
                        mol_type = protein
                        organism = synthetic construct
SEQUENCE: 85
MRVLLVALAL LALAASATSQ VQLQESGGGL VQAGGSLRLS CAASGRTFSS YAWGWFRQAP  60
GKEREFVARI SFSGGHTYYS DSVKGRFTIS RDNAKNTVYL QMNSLKPEDT AVYYCAADPT  120
PYGLRNERNY PYWGQGTQVT VSSKDEL                                     147

SEQ ID NO: 86           moltype = AA  length = 148
FEATURE                 Location/Qualifiers
REGION                  1..148
                        note = Synthetic construct, xGZein27ss:chIL10sdAb1F11:KDEL
source                  1..148
                        mol_type = protein
                        organism = synthetic construct
SEQUENCE: 86
MRVLLVALAL LALAASATSQ VQLQEFGGGL VQPGGSLRLS CAASGRTGSS YAMGWFRQAP  60
GKEREFVAAI SWSGGSTDYA DSVKGRFTIS RDNAKNTMYL QMNSLKPEDT AVYYCAVDRN  120
LFKLRVAVQE YTNLGQGTQV TVSSKDEL                                    148

SEQ ID NO: 87           moltype = AA  length = 125
FEATURE                 Location/Qualifiers
REGION                  1..125
                        note = Synthetic construct, chIL10sdAB1H5
source                  1..125
                        mol_type = protein
                        organism = synthetic construct
SEQUENCE: 87
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 88           moltype = AA  length = 125
FEATURE                 Location/Qualifiers
REGION                  1..125
                        note = Synthetic construct, chIL10sdAB1E9
source                  1..125
                        mol_type = protein
                        organism = synthetic construct
SEQUENCE: 88
MQVQLQASGG GLVQAGGSLR LSCAASGRTF NSYAWGWFRQ APGKERGFVA RITFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 89           moltype = AA  length = 125
FEATURE                 Location/Qualifiers
REGION                  1..125
                        note = Synthetic construct, chIL10sdAB1H1
source                  1..125
                        mol_type = protein
                        organism = synthetic construct
SEQUENCE: 89
MQVQLQASGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 90           moltype = AA  length = 125
FEATURE                 Location/Qualifiers
REGION                  1..125
                        note = Synthetic construct, chIL10sdAB1G6
source                  1..125
                        mol_type = protein
                        organism = synthetic construct
SEQUENCE: 90
MQVQLQASGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 91           moltype = AA  length = 125
FEATURE                 Location/Qualifiers
REGION                  1..125
                        note = Synthetic construct, chIL10sdAB1C10
source                  1..125
                        mol_type = protein
```

```
                         organism = synthetic construct
SEQUENCE: 91
MQVQLQEFGG GLVLPGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 92            moltype = AA  length = 125
FEATURE                  Location/Qualifiers
REGION                   1..125
                         note = Synthetic construct, chIL10sdAB1B6
source                   1..125
                         mol_type = protein
                         organism = synthetic construct
SEQUENCE: 92
MQVQLQQSGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 93            moltype = AA  length = 125
FEATURE                  Location/Qualifiers
REGION                   1..125
                         note = Synthetic construct, chIL10sdAB1D12
source                   1..125
                         mol_type = protein
                         organism = synthetic construct
SEQUENCE: 93
MQVQLQQSGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 94            moltype = AA  length = 125
FEATURE                  Location/Qualifiers
REGION                   1..125
                         note = Synthetic construct, chIL10sdAB1C2
source                   1..125
                         mol_type = protein
                         organism = synthetic construct
SEQUENCE: 94
MQVQLQEFGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 95            moltype = AA  length = 125
FEATURE                  Location/Qualifiers
REGION                   1..125
                         note = Synthetic construct, chIL10sdAB1B5
source                   1..125
                         mol_type = protein
                         organism = synthetic construct
SEQUENCE: 95
MQVQLQEFGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 96            moltype = AA  length = 125
FEATURE                  Location/Qualifiers
REGION                   1..125
                         note = Synthetic construct, chIL10sdAB1E2
source                   1..125
                         mol_type = protein
                         organism = synthetic construct
SEQUENCE: 96
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 97            moltype = AA  length = 125
FEATURE                  Location/Qualifiers
REGION                   1..125
                         note = Synthetic construct, chIL10sdAB1G7
source                   1..125
                         mol_type = protein
                         organism = synthetic construct
SEQUENCE: 97
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                              125

SEQ ID NO: 98            moltype = AA  length = 125
```

```
FEATURE              Location/Qualifiers
REGION               1..125
                     note = Synthetic construct, chIL10sdAB1G9
source               1..125
                     mol_type = protein
                     organism = synthetic construct
SEQUENCE: 98
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 99        moltype = AA  length = 125
FEATURE              Location/Qualifiers
REGION               1..125
                     note = Synthetic construct, chIL10sdAB1H12
source               1..125
                     mol_type = protein
                     organism = synthetic construct
SEQUENCE: 99
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 100       moltype = AA  length = 125
FEATURE              Location/Qualifiers
REGION               1..125
                     note = Synthetic construct, chIL10sdAB2A9
source               1..125
                     mol_type = protein
                     organism = synthetic construct
SEQUENCE: 100
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 101       moltype = AA  length = 125
FEATURE              Location/Qualifiers
REGION               1..125
                     note = Synthetic construct, chIL10sdAB1E12
source               1..125
                     mol_type = protein
                     organism = synthetic construct
SEQUENCE: 101
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTQ  120
VTVSS                                                             125

SEQ ID NO: 102       moltype = AA  length = 125
FEATURE              Location/Qualifiers
REGION               1..125
                     note = Synthetic construct, chIL10sdAB1E10
source               1..125
                     mol_type = protein
                     organism = synthetic construct
SEQUENCE: 102
MQVQLQEFGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                             125

SEQ ID NO: 103       moltype = AA  length = 125
FEATURE              Location/Qualifiers
REGION               1..125
                     note = Synthetic construct, chIL10sdAB1F12
source               1..125
                     mol_type = protein
                     organism = synthetic construct
SEQUENCE: 103
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                             125

SEQ ID NO: 104       moltype = AA  length = 125
FEATURE              Location/Qualifiers
REGION               1..125
                     note = Synthetic construct, chIL10sdAB1A8
source               1..125
                     mol_type = protein
                     organism = synthetic construct
SEQUENCE: 104
```

```
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                              125

SEQ ID NO: 105          moltype = AA  length = 125
FEATURE                 Location/Qualifiers
REGION                  1..125
                        note = Synthetic construct, chIL10sdAB1C8
source                  1..125
                        mol_type = protein
                        organism = synthetic construct
SEQUENCE: 105
MQVQLQESGG GLVQPGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                              125

SEQ ID NO: 106          moltype = AA  length = 125
FEATURE                 Location/Qualifiers
REGION                  1..125
                        note = Synthetic construct, chIL10sdAB1C12
source                  1..125
                        mol_type = protein
                        organism = synthetic construct
SEQUENCE: 106
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                              125

SEQ ID NO: 107          moltype = AA  length = 125
FEATURE                 Location/Qualifiers
REGION                  1..125
                        note = Synthetic construct, chIL10sdAB1B1
source                  1..125
                        mol_type = protein
                        organism = synthetic construct
SEQUENCE: 107
MQVQLQASGG GLVQAGGSLR LSCAASGRNF NSYAWGWFRQ APGKERGFVA RISFSGGHTY  60
YSDSVKGRFT ISRDNAKNSV YLQMNSLKPE DTAVYYCAAD PTPYGLRNER NYHYWGQGTL  120
VTVSS                                                              125

SEQ ID NO: 108          moltype = AA  length = 125
FEATURE                 Location/Qualifiers
REGION                  1..125
                        note = Synthetic construct, chIL10sdAB1F1
source                  1..125
                        mol_type = protein
                        organism = synthetic construct
SEQUENCE: 108
MQVQLQESGG GLVQAGGSLR LSCAASGRTF NRYAWGWFRQ APGKEREFVA RISFSGGNTY  60
YADSVKGRFT ISRDNAKNSV YLQMNSLKPE DTAVYYCAAD PTPYGLRNER NYHYWGQGTQ  120
VTVSS                                                              125

SEQ ID NO: 109          moltype = AA  length = 125
FEATURE                 Location/Qualifiers
REGION                  1..125
                        note = Synthetic construct, chIL10sdAB1D11
source                  1..125
                        mol_type = protein
                        organism = synthetic construct
SEQUENCE: 109
MQVQLQESGG GLVQAGGSLR LSCAASGRTF SSYAWGWFRQ APGKEREFVA RISFSGGHIY  60
YSDSVKGRFT ISRDNAKNTV YLQMNSLKPE DTAVYYCAAD PTPYGLRNER NYHYWGQGTL  120
VTVSS                                                              125

SEQ ID NO: 110          moltype = AA  length = 125
FEATURE                 Location/Qualifiers
REGION                  1..125
                        note = Synthetic construct, chIL10sdAB1E6
source                  1..125
                        mol_type = protein
                        organism = synthetic construct
SEQUENCE: 110
MQVQLQESGG GLVQAGGSLR LSCAASGRTF NSYAWGWFRQ APGKERGFVA RISFSGGHTY  60
YSDSVKGRFT ISRDNAKNSV YLQMNSLKPE DTAVYYCAAD PTPYGLRNER NYPYWGQGTL  120
VTVSS                                                              125

SEQ ID NO: 111          moltype = AA  length = 125
FEATURE                 Location/Qualifiers
REGION                  1..125
```

```
                         note = Synthetic construct, chIL10sdAB1B9
source                   1..125
                         mol_type = protein
                         organism = synthetic construct
SEQUENCE: 111
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 112           moltype = AA  length = 125
FEATURE                  Location/Qualifiers
REGION                   1..125
                         note = Synthetic construct, chIL10sdAB1B10
source                   1..125
                         mol_type = protein
                         organism = synthetic construct
SEQUENCE: 112
MQVQLQEFGG GLVQPGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 113           moltype = AA  length = 125
FEATURE                  Location/Qualifiers
REGION                   1..125
                         note = Synthetic construct, chIL10sdAB1F5
source                   1..125
                         mol_type = protein
                         organism = synthetic construct
SEQUENCE: 113
MQVQLQESGG GLVQPGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 114           moltype = AA  length = 125
FEATURE                  Location/Qualifiers
REGION                   1..125
                         note = Synthetic construct, chIL10sdAB1A6
source                   1..125
                         mol_type = protein
                         organism = synthetic construct
SEQUENCE: 114
MQVQLQEFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 115           moltype = AA  length = 125
FEATURE                  Location/Qualifiers
REGION                   1..125
                         note = Synthetic construct, chIL10sdAB1D5
source                   1..125
                         mol_type = protein
                         organism = synthetic construct
SEQUENCE: 115
MQVQLQQFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 116           moltype = AA  length = 125
FEATURE                  Location/Qualifiers
REGION                   1..125
                         note = Synthetic construct, chIL10sdAB1D8
source                   1..125
                         mol_type = protein
                         organism = synthetic construct
SEQUENCE: 116
MQVQLQQFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                              125

SEQ ID NO: 117           moltype = AA  length = 125
FEATURE                  Location/Qualifiers
REGION                   1..125
                         note = Synthetic construct, chIL10sdAB1B4
source                   1..125
                         mol_type = protein
                         organism = synthetic construct
SEQUENCE: 117
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
```

```
VTVSS                                                         125

SEQ ID NO: 118          moltype = AA  length = 125
FEATURE                 Location/Qualifiers
REGION                  1..125
                        note = Synthetic construct, chIL10sdAB1C7
source                  1..125
                        mol_type = protein
                        organism = synthetic construct
SEQUENCE: 118
MQVQLQAFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                         125

SEQ ID NO: 119          moltype = AA  length = 125
FEATURE                 Location/Qualifiers
REGION                  1..125
                        note = Synthetic construct, chIL10sdAB1B3
source                  1..125
                        mol_type = protein
                        organism = synthetic construct
SEQUENCE: 119
MQVQLQASGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                         125

SEQ ID NO: 120          moltype = AA  length = 125
FEATURE                 Location/Qualifiers
REGION                  1..125
                        note = Synthetic construct, chIL10sdAB1D7
source                  1..125
                        mol_type = protein
                        organism = synthetic construct
SEQUENCE: 120
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTQ  120
VTVSS                                                         125

SEQ ID NO: 121          moltype = AA  length = 125
FEATURE                 Location/Qualifiers
REGION                  1..125
                        note = Synthetic construct, chIL10sdAB1F7
source                  1..125
                        mol_type = protein
                        organism = synthetic construct
SEQUENCE: 121
MQVQLQEFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                         125

SEQ ID NO: 122          moltype = AA  length = 125
FEATURE                 Location/Qualifiers
REGION                  1..125
                        note = Synthetic construct, chIL10sdAB1F10
source                  1..125
                        mol_type = protein
                        organism = synthetic construct
SEQUENCE: 122
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                         125

SEQ ID NO: 123          moltype = AA  length = 125
FEATURE                 Location/Qualifiers
REGION                  1..125
                        note = Synthetic construct, chIL10sdAB1F2
source                  1..125
                        mol_type = protein
                        organism = synthetic construct
SEQUENCE: 123
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                         125

SEQ ID NO: 124          moltype = AA  length = 125
FEATURE                 Location/Qualifiers
REGION                  1..125
                        note = Synthetic construct, chIL10sdAB1F3
source                  1..125
```

```
                         mol_type = protein
                         organism = synthetic construct
SEQUENCE: 124
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                             125

SEQ ID NO: 125           moltype = AA  length = 125
FEATURE                  Location/Qualifiers
REGION                   1..125
                         note = Synthetic construct, chIL10sdAB1F8
source                   1..125
                         mol_type = protein
                         organism = synthetic construct
SEQUENCE: 125
MQVQLQASGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                             125

SEQ ID NO: 126           moltype = AA  length = 125
FEATURE                  Location/Qualifiers
REGION                   1..125
                         note = Synthetic construct, chIL10sdAB1C9
source                   1..125
                         mol_type = protein
                         organism = synthetic construct
SEQUENCE: 126
MQVQLQEFGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                             125

SEQ ID NO: 127           moltype = AA  length = 125
FEATURE                  Location/Qualifiers
REGION                   1..125
                         note = Synthetic construct, chIL10sdAB1A12
source                   1..125
                         mol_type = protein
                         organism = synthetic construct
SEQUENCE: 127
MQVQLQESGG GLVQAGGSLR LSCAASGRTF SSYAWGWFRQ APGKEREFVA RISFSGGHTY  60
YSDSVKGRFT ISRDNAKNTV YLQMNSLKPE DTAVYYCAAD PTPYGLRNER NYPYWGQGTL  120
VTVSS                                                             125

SEQ ID NO: 128           moltype = AA  length = 125
FEATURE                  Location/Qualifiers
REGION                   1..125
                         note = Synthetic construct, chIL10sdAB1C3
source                   1..125
                         mol_type = protein
                         organism = synthetic construct
SEQUENCE: 128
MQVQLQESGG GLVQAGGSLR LSCAASGRTF SSYAWGWFRQ APGKEREFVS RISFSGGHTY  60
YSDSVKGRFT ISRDNAKNTV YLQMNSLKPE DTAVYYCAAD PTPYGLRNER NYPYWGQGTL  120
VTVSS                                                             125

SEQ ID NO: 129           moltype = AA  length = 125
FEATURE                  Location/Qualifiers
REGION                   1..125
                         note = Synthetic construct, chIL10sdAB1E7
source                   1..125
                         mol_type = protein
                         organism = synthetic construct
SEQUENCE: 129
MQVQLQEFGG GLVQAGGSLR LSCAASGRTF STYAWGWFRQ APGKEREFVA RISFSGGHTY  60
YSDSVKGRFT ISRDNAKNTV YLQMNSLKPE DTAVYYCAAD PTPYGLRNER SYPYWGQGTL  120
VTVSS                                                             125

SEQ ID NO: 130           moltype = AA  length = 124
FEATURE                  Location/Qualifiers
REGION                   1..124
                         note = Synthetic construct, chIL10sdAB1D9
source                   1..124
                         mol_type = protein
                         organism = synthetic construct
SEQUENCE: 130
MQVQLQASGG GLVQAGGSLR LSCAASGRRL SINVMGWYRQ APGKQRELVA TIGTSGKTNY  60
ADSVRGRFTI SRDNAQNTVY LQMNSLKPED TAVYYCAADP TPYGLRNERN YHYWGQGTQV  120
TVSS                                                              124
```

-continued

```
SEQ ID NO: 131         moltype = AA  length = 125
FEATURE                Location/Qualifiers
REGION                 1..125
                       note = Synthetic construct, chIL10sdAB1A9
source                 1..125
                       mol_type = protein
                       organism = synthetic construct
SEQUENCE: 131
MQVQLQESGG GLVQAGGSLR LSCAASGRTF SRYAWGWFRQ APGKEREFVA RISWSGGHTY  60
FADSVKGRFT ISRDNAKNTV YLQMNSLKPE DTAVYYCAAD PTPYGLKNER NYHYWGQGTQ  120
VTVSS                                                              125

SEQ ID NO: 132         moltype = AA  length = 125
FEATURE                Location/Qualifiers
REGION                 1..125
                       note = Synthetic construct, chIL10sdAB1H10
source                 1..125
                       mol_type = protein
                       organism = synthetic construct
SEQUENCE: 132
MQVQLQEFGG GLVQAGGSLR LSCAASGRTF SRYAWGWFRQ APGKEREFVA RISFNSRSTY  60
YADSVQGRFT ISRDNAKNTV YLQMNSLKPE DTAVYYCAAD PTPYGLKNER NYDYWGQGTQ  120
VTVSS                                                              125

SEQ ID NO: 133         moltype = AA  length = 125
FEATURE                Location/Qualifiers
REGION                 1..125
                       note = Synthetic construct, chIL10sdAB1C1
source                 1..125
                       mol_type = protein
                       organism = synthetic construct
SEQUENCE: 133
MQVQLQASGG GLVQPGGSLR LSCAASGNIF SINTMGWYRQ APGKQRELVA SITTGGTTNY  60
EDSVKGRFTI SRDNAKKTVY LQMNRLKPED TAVYYCNHRR SYSGRDYPVY GMDYWGKGTQ  120
VTVSS                                                              125

SEQ ID NO: 134         moltype = AA  length = 125
FEATURE                Location/Qualifiers
REGION                 1..125
                       note = Synthetic construct, chIL10sdAB1D1
source                 1..125
                       mol_type = protein
                       organism = synthetic construct
SEQUENCE: 134
MQVQLQESGG GLVQPGGSLR LSCAASGNIF SINTMGWYRQ APGKQRELVA SITTGGTTNY  60
EDSVKGRFTI SRDNAKKTVY LQMNRLKPED TAVYYCNHRR SYSGRDYPVY GMDYWGKGTL  120
VTVSS                                                              125

SEQ ID NO: 135         moltype = AA  length = 125
FEATURE                Location/Qualifiers
REGION                 1..125
                       note = Synthetic construct, chIL10sdAB1A11
source                 1..125
                       mol_type = protein
                       organism = synthetic construct
SEQUENCE: 135
MQVQLQESGG GLVQPGGSLR LSCAASGNIF SINTMGWYRQ APGKQRELVA SITTGGTTNY  60
EDSVKGRFTI SRDNAKKTVY LQMNRLKPED TAVYYCNHRR SYSGRDYPVY GMDYWGKGTL  120
VTVSS                                                              125

SEQ ID NO: 136         moltype = AA  length = 125
FEATURE                Location/Qualifiers
REGION                 1..125
                       note = Synthetic construct, chIL10sdAB1G8
source                 1..125
                       mol_type = protein
                       organism = synthetic construct
SEQUENCE: 136
MQVQLQESGG GLVQPGGSLR LSCAASGNIF SINTMGWYRQ APGKQRELVA SITTGGTTNY  60
EDSVKGRFTI SRDNAKKTVY LQMNRLKPED TAVYYCNHRR SYSGRDYPVY GMDYWGKGTL  120
VTVSS                                                              125

SEQ ID NO: 137         moltype = AA  length = 125
FEATURE                Location/Qualifiers
REGION                 1..125
                       note = Synthetic construct, chIL10sdAB1A5
source                 1..125
                       mol_type = protein
                       organism = synthetic construct
```

-continued

```
SEQUENCE: 137
MQVQLQESGG GLVQPGGSLR LSCAASGNIF SINTMGWYRQ APGKQRELVA SITTGGTTNY  60
EDSVKGRFTI SRDNAKKTVY LQMNRLKPED TAVYYCNHRR SYSGRDYPVY GMDYWGKGTQ  120
VTVSS                                                              125

SEQ ID NO: 138         moltype = AA  length = 125
FEATURE                Location/Qualifiers
REGION                 1..125
                       note = Synthetic construct, chIL10sdAB1C5
source                 1..125
                       mol_type = protein
                       organism = synthetic construct
SEQUENCE: 138
MQVQLQESGG GLVQAGGSLR LSCAASGRTF GINVMGWYRQ APGEERELVA TVTTGGTTNY  60
EDSVKGRFTI SRDNAKKTVY LQMNRLKPED TAVYYCNHRR SYSGRDYPVY GMDYWGKGTQ  120
VTVSS                                                              125

SEQ ID NO: 139         moltype = AA  length = 125
FEATURE                Location/Qualifiers
REGION                 1..125
                       note = Synthetic construct, chIL10sdAB1H6
source                 1..125
                       mol_type = protein
                       organism = synthetic construct
SEQUENCE: 139
MQVQLQESGG GLVQAGGSLR LSCTVSGSIS SIDGMGWYRQ APGNQRELVA TIARTGSTSY  60
VPSVKGRFTI SRDNDQTTLY LQMNDLTPED TAVYYCAADP RKRGVPDWYY GMDYWGKGTL  120
VTVSS                                                              125

SEQ ID NO: 140         moltype = AA  length = 125
FEATURE                Location/Qualifiers
REGION                 1..125
                       note = Synthetic construct, chIL10sdAB2A8
source                 1..125
                       mol_type = protein
                       organism = synthetic construct
SEQUENCE: 140
MQVQLQASGG GLVQAGGSLR LSCTVSGSIS SIDGMGWYRQ APGNQRELVA TIARTGSTSY  60
VPSVKGRFTI SRDNAQTTLY LQMNDLTPED TAVYYCAADP RKRGVPDWYY GMDYWGKGTQ  120
VTVSS                                                              125

SEQ ID NO: 141         moltype = AA  length = 125
FEATURE                Location/Qualifiers
REGION                 1..125
                       note = Synthetic construct, chIL10sdAB1F9
source                 1..125
                       mol_type = protein
                       organism = synthetic construct
SEQUENCE: 141
MQVQLQASGG GLVQAGGSLR LSCTVSGSIS SIDGMGWYRQ APGNQRELVA TIARTGSTSY  60
VPSVKGRFTI SRDNAQTTLY LQMNDLTPED TAVYYCAADP RKRGVPDWYY GMDYWGKGTL  120
VTVSS                                                              125

SEQ ID NO: 142         moltype = AA  length = 124
FEATURE                Location/Qualifiers
REGION                 1..124
                       note = Synthetic construct, chIL10sdAB1E11
source                 1..124
                       mol_type = protein
                       organism = synthetic construct
SEQUENCE: 142
MQVQLQASGG GVVQAGGSLR LTCAASGRTY AMGWFRQAPG KERDFAAAIN WIGSTTDYAD  60
SVKGRFTISR DIAKNTMYLQ MNSLKPEDTA VYYCAAEKTA SLSIYRRAYD YGYWGQGTLV  120
TVSS                                                               124

SEQ ID NO: 143         moltype = AA  length = 125
FEATURE                Location/Qualifiers
REGION                 1..125
                       note = Synthetic construct, chIL10sdAB1D6
source                 1..125
                       mol_type = protein
                       organism = synthetic construct
SEQUENCE: 143
MQVQLQASGG GLVQAGGSLR LSCQASESIS SINTMGWFRQ ASGEEREFVA AIESGGATAY  60
AESAKGRFTI SRDNAKNTVY LQMNSLKPED TAVYYCAAGV PTYDDDAMPI SWRFWGRGTL  120
VTVSS                                                              125

SEQ ID NO: 144         moltype = AA  length = 126
FEATURE                Location/Qualifiers
```

```
REGION                 1..126
                       note = Synthetic construct, chIL10sdAB1C4
source                 1..126
                       mol_type = protein
                       organism = synthetic construct
SEQUENCE: 144
MQVQLQASGG GLVQPGGSLR LSCAASGFSL ENYVIGWFRQ APGKGREGLS CISSTDDSIF  60
SVDSVKGRFT VSRDNAKNMV YLQMNSLKSE DTAVYYCATS RGLGSCRVDE FYYDMWGQGT  120
QVTVSS                                                             126

SEQ ID NO: 145         moltype = AA  length = 125
FEATURE                Location/Qualifiers
REGION                 1..125
                       note = Synthetic construct, chIL10sdAB1H4
source                 1..125
                       mol_type = protein
                       organism = synthetic construct
SEQUENCE: 145
MQVQLQAFGG ALVQAGGSLR LSCATSGFTF GYYAIGWLRQ APGKEREGVL CITNADRITY  60
YTNSVKDRFT ISRDNTANTV YLQMNNLKPE DTATYYCATN FYSYCSDNGG KYQEWGQGTL  120
VTVSS                                                              125

SEQ ID NO: 146         moltype = AA  length = 126
FEATURE                Location/Qualifiers
REGION                 1..126
                       note = Synthetic construct, chIL10sdAB1F11
source                 1..126
                       mol_type = protein
                       organism = synthetic construct
SEQUENCE: 146
MQVQLQEFGG GLVQPGGSLR LSCAASGRTG SSYAMGWFRQ APGKEREFVA AISWSGGSTD  60
YADSVKGRFT ISRDNAKNTM YLQMNSLKPE DTAVYYCAVD RNLFKLRVAV QEYTNLGQGT  120
QVTVSS                                                             126

SEQ ID NO: 147         moltype = AA  length = 123
FEATURE                Location/Qualifiers
REGION                 1..123
                       note = Synthetic construct, chIL10sdAB1D3
source                 1..123
                       mol_type = protein
                       organism = synthetic construct
SEQUENCE: 147
MQVQLQASGG GLVQPGGSLR LSCAASGFTF DDYAMSWVRQ APGKGLEWVS AITWNVGTIY  60
YAESMKGRFT ISRDNAKNTL YLQMNSLKSE DTAMYYCARD GIAPRRYYEM ADWGKGTLVT  120
VSS                                                                123

SEQ ID NO: 148         moltype = AA  length = 120
FEATURE                Location/Qualifiers
REGION                 1..120
                       note = Synthetic construct, chIL10sdAB1A7
source                 1..120
                       mol_type = protein
                       organism = synthetic construct
SEQUENCE: 148
MQVQLQASGG GSVQAGESLT VSCSVSGNIY DINTMAWYRE APGKQRELVA SIGPNGNSDY  60
ANGVRGRFTV SRDSVKNTVD LQMTNLKVDD TASYYCNVKT GRGRNLYSDW GDGTQVTVSS  120

SEQ ID NO: 149         moltype = AA  length = 122
FEATURE                Location/Qualifiers
REGION                 1..122
                       note = Synthetic construct, chIL10sdAB1H8
source                 1..122
                       mol_type = protein
                       organism = synthetic construct
SEQUENCE: 149
MQVQLQESGG GLVQPGGSLR LSCAASGFTF DDYAMSWVRQ APGKGLEWVS AITWAGGSTY  60
YAESMKGRFT ISRDNAKNTL YLQMNSLKSE DTAVYYCARN TGLAYEVGYD YWGQGTQVTV  120
SS                                                                 122

SEQ ID NO: 150         moltype = AA  length = 119
FEATURE                Location/Qualifiers
REGION                 1..119
                       note = Synthetic construct, chIL10sdAB1H3
source                 1..119
                       mol_type = protein
                       organism = synthetic construct
SEQUENCE: 150
MQVQLQASGG GLVQPGGSLR LSCAASGSIS SIDTMGWYRR APGKQRELVA TISSGGRTTY  60
KDSVKGRFTI SRDNAKNTMY LQMNSLKPDD TAVYYCAVVV SPTLIAGSWG QGTQVTVSS   119
```

```
SEQ ID NO: 151          moltype = AA  length = 119
FEATURE                 Location/Qualifiers
REGION                  1..119
                        note = Synthetic construct, chIL10sdAB1B8
source                  1..119
                        mol_type = protein
                        organism = synthetic construct
SEQUENCE: 151
MQVQLQASGG ALVQPGGSLR LSCSASESID TFDIIDWYRQ APGKQRDQRE LVAQMLPVGA  60
TTYADSVKGR FTFSRDNANN MVYLQMDNLQ PDDTAVYYCH SINRDHNIWC QGTQVTVSS   119

SEQ ID NO: 152          moltype = AA  length = 116
FEATURE                 Location/Qualifiers
REGION                  1..116
                        note = Synthetic construct, chIL10sdAB1B2
source                  1..116
                        mol_type = protein
                        organism = synthetic construct
SEQUENCE: 152
MQVQLQAFGG GTVQPGESLT IHCAASGVIP DASAMAWYRQ APGKQRELVA RIVGPTNILY  60
GASVKGRFTI SRGNGGDTIS LQMTNLKPDD TALYICNLLQ SGTNYFGKGT LVTVSS      116

SEQ ID NO: 153          moltype = AA  length = 116
FEATURE                 Location/Qualifiers
REGION                  1..116
                        note = Synthetic construct, chIL10sdAB1D2
source                  1..116
                        mol_type = protein
                        organism = synthetic construct
SEQUENCE: 153
MQVQLQQSGG GLVQTGGSLR LSCAASTNIF SRNTMGWYRQ APAKQREFVA SITRSDITNY  60
ADSVKGRFTI SRDNAKSTVY LQMDSLKAED TAVYYCYARG RPGIYWGQGT QVTVSS      116

SEQ ID NO: 154          moltype = AA  length = 115
FEATURE                 Location/Qualifiers
REGION                  1..115
                        note = Synthetic construct, chIL10sdAB1D10
source                  1..115
                        mol_type = protein
                        organism = synthetic construct
SEQUENCE: 154
MQVQLQESGG GLVQAGGSLR LSCVASGITF NTYAMGWYRQ APGKQRERVA VISNFGVTVY  60
ENSVKGRFTI SRDNAKNAVY LQMNNLRSED TAVYFCSAIR GVNYWGQGTL VTVSS       115

SEQ ID NO: 155          moltype = DNA  length = 6030
FEATURE                 Location/Qualifiers
misc_feature            1..6030
                        note = Synthetic construct, pAG4314
source                  1..6030
                        mol_type = other DNA
                        organism = synthetic construct
SEQUENCE: 155
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagctta  180
attaagtcta actcgagtta ctggtacgta tacagggttc cttgcgtgaa gaagggtggc  240
ctgcggttca ccattaacgg tcacgactac ttccagctag tactggtgac caacgtcgcg  300
gcggcagggt caatcaagtc catggaggtt atgggttcca acacagcgga ttggatgccg  360
atggcacgta actggggcgc ccaatggcac tcactggcct acctcaccgg tcaaggtcta  420
tcctttaggg tcaccaacac agatgaccaa acgctcgtct tcaccaacgt cgtgccacca  480
ggatggaagt ttggccagac atttgcaagc aagctgcagt tcaagtgaga ggagaagcct  540
gaattgatac cggagcgttt cttttgggag taacatctct ggttgcctag caaacatatg  600
attgtatata agtttcgttg tgcgtttatt ctttcggtgt gtaaaataac atacatgctt  660
tcctgatatt ttcttgtata tatgtacaca cacacgacaa atccttccat ttctattatt  720
attgaacaat ttaattgcga gggcgagtac ttgtctgttt acctttttt tttcagatgg  780
cattttatag tttaaccttt catggaccgg cagtagttct aaccatgaat gaaaagaaat  840
catagtccac accacgcagg gacattgtgg tcattttaga caagacgatt tgattaatgt  900
cttgtatgat atggtcgaca gtgaggacta acaaacatat ggcatatttt attaccggcg  960
agttaaataa atttatgtca cagtaataaa ctgcctaata aatgcacgcc agaaaatata  1020
atgataaaaa aaagaaaaga tacataagtc cattgcttct acttttttaa aaattaaatc  1080
caacattttc tattttttgg tataaacttg gaagtactag ttggatatgc aaaatcatct  1140
aacctccata tatttcatca atttgtttac tttacatatg ggagaggata gtatgtcaaa  1200
gaaaatgaca acaagcttac aagtttctta ttttaaaagt tccgctaact tatcaagcat  1260
agtgtgccac gcaaaactga caacaaacca acaaatttaa ggagcgccta acttatcatc  1320
tatgacatac cgcacaaaat gataacatac tagagaaact ttattgcaca aaaggaaatt  1380
tatccataag gcaaaggaac atcttaaggc tttggatata catttaccaa caagcattgt  1440
ttgtattacc cctaaagcgc aagacatgtc atccatgagt catagtgtgt atatctcaac  1500
attgcaaagc tacctttttt ctattatact tttcgcatta taggctagat attatctata  1560
```

```
catgtcaaca aactctatcc ctacgtcata tctgaagatt cttttcttca ctatataagt  1620
tggcttccct gtcattgaac tcacatcaac cagcccaagt ttccaataac atcctcaaat  1680
agctggatcc taaaccatga gggtgttgct cgttgccctc gctctcctgg ctctcgctgc  1740
gagcgccacc tcccaggttc agctgcagga aagcggtggc ggactggtgc agccaggtgg  1800
cagcctcagg ctgagctgcg ctgctagcgg caatattttt agcattaaca caatgggttg  1860
gtatagacag gctcctggca agcagcgtga gctcgttgcc agcattacca cgggtggtac  1920
aaccaattat gaagatagcg tgaagggtcg ttttaccatt agcagggaca atgctaagaa  1980
gaccgtttac ctccagatga acaggctgaa gccagaagat accgccgtgt attactgcaa  2040
ccacaggaga agctatagcg gaagagatta tcctgtttac ggtatggact actggggcaa  2100
gggaaccctg gttaccgtga gcagcaagga cgagctgtaa cctaggtccc cgaatttccc  2160
cgatcgttca aacatttggc aataaagttt cttaagattg aatcctgttg ccggtcttgc  2220
gatgattatc atataatttc tgttgaatta cgttaagcat gtaataatta acatgtaatg  2280
catgacgtta tttatgagat gggtttttat gattagagtc ccgcaattat acatttaata  2340
cgcgatagaa aacaaaatat agcgcgcaaa ctaggataaa ttatcgcgcg cggtgtcatc  2400
tatgttacta gatcgggaat tggaattcct gcagtgcagc gtgacccggt cgtgcccctc  2460
tctagagata atgagcattg catgtctaag ttataaaaaa ttaccacata tttttttgt  2520
cacacttgtt tgaagtgcag tttatctatc tttatacata tatttaaact ttactctacg  2580
aataatataa tctatagtac tacaataata tcagtgtttt agagaatcat ataaatgaac  2640
agttagacat ggtctaaagg acaattgagt attttgacaa caggactcta cagttttatc  2700
tttttagtgt gcatgtgttc tcctttttt ttgcaaatag cttcacctat ataatacttc  2760
atccatttta ttagtacatc catttagggt ttagggttaa tggtttttat agactaattt  2820
ttttagtaca tctattttat tctattttag cctctaaatt aagaaaacta aaactctatt  2880
ttagtttttt tatttaataa tttagatata aaatagaata aaataaagtg actaaaaatt  2940
aaacaaatac cctttaagaa attaaaaaaa ctaaggaaac atttttcttg tttcgagtag  3000
ataatgccag cctgttaaac gccgtcgacg agtctaacgg acaccaacca gcgaaccagc  3060
agcgtcgcgt cgggccaagc gaagcagacg gcacggcatc tctgtcgctg cctctggacc  3120
cctctcgaga gttccgctcc accgttggac ttgctccgct gtcggcatcc agaaattgcg  3180
tggcggagcg gcagacgtga gccggcacgg caggcggcct cctcctcctc tcacggcacg  3240
gcagctacgg gggattcctt tcccaccgct ccttcgcttt cccttcctcg cccgccgtaa  3300
taaatagaca ccccctccac accctctttc cccaacctcg tgttgttcgg agcgcacaca  3360
cacacaacca gatctccccc aaatccaccc gtcggcacct ccgcttcaag gtacgccgct  3420
cgtcctcccc cccccccct ctctaccttc tctagatcgg cgttccggtc catggttagg  3480
gcccggtagt tctacttctg ttcatgtttg tgttagatcc gtgtttgtgt tagatccgtg  3540
ctgctagcgt tcgtacacgg atgcgacctg tacgtcagac acgttctgat tgctaacttg  3600
ccagtgtttc tctttgggga atcctgggat ggctctagcc gttccgcaga cgggatcgat  3660
ttcatgattt tttttgtttc gttgcatagg gtttggtttg cccttttcct ttatttcaat  3720
atatgccgtg cacttgtttg tcgggtcatc ttttcatgct tttttttgtc ttggttgtga  3780
tgatgtggtc tggttgggcg gtcgttctag atcggagtag aattctgttt caaactacct  3840
ggtggattta ttaattttgg atctgtatgt gtgtgccata catattcata gttacgaatt  3900
gaagatgatg gatggaaata tcgatctagg ataggtatac atgttgatgc gggttttact  3960
gatgcatata cagagatgct ttttgttcgc ttggttgtga tgatgtggtg tggttgggcg  4020
gtcgttcatt cgttctagat cggagtagaa tactgtttca aactacctgg tgtatttatt  4080
aattttggaa ctgtatgtgt gtgtcataca tcttcatagt tacgagttta agatggatgg  4140
aaatatcgat ctaggatagg tatacatgtt gatgtgggtt ttactgatgc atatacatga  4200
tggcatatgc agcatctatt catatgctct aaccttgagt acctatctat tataataaac  4260
aagtatgttt tataattatt ttgatcttga tatacttgga tgatggcata tgcagcagct  4320
atatgtggat ttttttagcc ctgccttcat acgctattta tttgcttggt actgtttctt  4380
ttgtcgatgc tcaccctgtt gtttggtgtt acttctgcag atccagatct aaaccatgca  4440
gaaactcatt aactcagtgc aaaactatgc ctggggcagc aaaacggcgt tgactgaact  4500
ttatggtatg gaaaatccgt ccagccagcc gatggccgag ctgtggatgg gcgcacatcc  4560
gaaaagcagt tcacgagtgc agaatgccgc cggagatatc gtttcactgc gtgatgtgat  4620
tgagagtgat aaatcgactc tgctcggaga ggccgttgcc aaacgctttg gcgaactgcc  4680
tttcctgttc aaagtattat gcgcagcaca gccactctcc attcaggttc atccaaacaa  4740
acacaattct gaaatcggtt ttgccaaaga aaatgccgca ggtatcccga tggatgccgc  4800
cgagcgtaac tataaagatc ctaaccacaa gccggagctg gtttttgcgc tgacgccttt  4860
ccttgcgatg aacgcgtttc gtgaattttc cgagattgtc tccctactcc agccggtcgc  4920
aggtgcacat ccggcgattg ctcacttttt acaacagcct gatgccgaac gtttaagcga  4980
actgttcgcc agcctgttga atatgcaggg tgaagaaaaa tcccgcgcgc tggcgatttt  5040
aaaatcggcc ctcgatagcc agcagggtga accgtggcaa acgattcgtt taatttctga  5100
attttacccg gaagacagcg gtctgttctc cccgctattg ctgaatgtgg tgaaattgaa  5160
ccctggcgaa gcgatgttcc tgttcgctga aacaccgcac gcttacctgc aaggcgtggc  5220
gctggaagtg atggcaaact ccgataacgt gctgcgtgcg ggtctgacgc ctaaatacat  5280
tgatattccg gaactggttg ccaatgtgaa attcgaagcc aaaccggcta accagttgtt  5340
gacccagccg gtgaaacaag gtgcagaact ggacttcccg attccagtgg atgattttgc  5400
cttctcgctg catgacctta gtgataaaga aaccaccatt agccagcaga gtgccgccat  5460
tttgttctgc gtcgaaggcg atgcaacgtt gtggaaaggt tctcagcagt tacagcttaa  5520
accgggtgaa tcagcgttta ttgccgccaa cgaatcaccg gtgactgtca aaggccacgg  5580
ccgtttagcg cgtgtttaca acaagctgta agagcttact gaaaaaatta acatctcttg  5640
ctaagctggg agctctagat ccccgaattt ccccgatcgt tcaaacattt ggcaataaag  5700
tttcttaaga ttgaatcctg ttgccggtct tgcgatgatt atcatataat ttctgttgaa  5760
ttacgttaag catgtaataa ttaacatgta atgcatgacg ttatttatga gatgggtttt  5820
tatgattaga gtcccgcaat tatacattta atacgcgata gaaaacaaaa tatagcgcgc  5880
aaactaggat aaattatcgc gcgcggtgtc atctatgtta ctagatcggg aattggcgag  5940
ctcgaattaa ttcagtacat taaaaacgtc cgcaatgtgt tattaagttg tctaagcgtc  6000
aatttgttta caccacaata tatcctgcca                                  6030

SEQ ID NO: 156          moltype = DNA  length = 6030
FEATURE                 Location/Qualifiers
misc_feature            1..6030
```

```
                         note = Synthetic construct, pAG4315
source                   1..6030
                         mol_type = other DNA
                         organism = synthetic construct
SEQUENCE: 156
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagctta  180
attaagtcta actcgagtta ctggtacgta tacagggttc cttgcgtgaa gaagggtggc  240
ctgcggttca ccattaacgg tcacgactac ttccagctag tactggtgac caacgtcgcg  300
gcggcagggt caatcaagtc catggaggtt atgggttcca acacagcgga ttggatgccg  360
atggcacgta actggggcgc ccaatggcac tcactggcct acctcaccgg tcaaggtcta  420
tcctttaggg tcaccaacac agatgaccaa acgctcgtct tcaccaacgt cgtgccacca  480
ggatggaagt ttggccagac atttgcaagc aagctgcagt tcaagtgaga ggagaagcct  540
gaattgatac cggagcgttt cttttgggag taacatctct ggttgcctag caaacatatg  600
attgtatata agtttcgttg tgcgtttatt ctttcggtgt gtaaaataac atacatgctt  660
tcctgatatt ttcttgtata tatgtacaca cacacgacaa atccttccat ttctattatt  720
attgaacaat ttaattgcga gggcgagtac ttgtctgttt accttttttt tttcagatgg  780
cattttatag tttaaccttt catggaccgg cagtagttct aaccatgaat gaaaagaaat  840
catagtccac accacgcagg gacattgtgg tcattttaga caagacgatt tgattaatgt  900
cttgtatgat atggtcgaca gtgaggacta acaaacatat ggcatatttt attaccggcg  960
agttaaataa atttatgtca cagtaataaa ctgcctaata aatgcacgcc agaaaatata  1020
atgataaaaa aaagaaaaga tacataagtc cattgcttct actttttttaa aaattaaatc  1080
caacattttc tattttttgg tataaacttg gaagtactag ttggatatgc aaaatcatct  1140
aacctccata tatttcatca atttgtttac tttacatatg ggagaggata gtatgtcaaa  1200
gaaaatgaca acaagcttac aagtttctta ttttaaaagt tccgctaact tatcaagcat  1260
agtgtgccac gcaaaactga caacaaacca acaaatttaa ggagcgccta acttatcatc  1320
tatgacatac cgcacaaaat gataacatac tagagaaact ttattgcaca aaaggaaatt  1380
tatccataag gcaaaggaac atcttaaggc tttggatata catttaccaa caagcattgt  1440
ttgtattacc cctaaagcgc aagacatgtc atccatgagt catagtgtgt atatctcaac  1500
attgcaaagc tacctttttt ctattatact tttcgcatta taggctagat attatctata  1560
catgtcaaca aactctatcc ctacgtcata tctgaagatt cttttcttca ctatataagt  1620
tggcttccct gtcattgaac tcacatcaac cagcccaagt ttccaataac atcctcaaat  1680
agctggatcc taaaccatga gggtgttgct cgttgccctc gctctcctgg ctctcgctgc  1740
gagcgccacc tcccaggttc agctgcagga aagcggtggc ggactggtgc aggctggtgg  1800
cagcctcagg ctgagctgcg ctgctagcgg cagaaccttt agcagctatg cttggggttg  1860
gtttaggcag gccccaggca aggagcgtga atttgttgcc aggattagct ttagcggagg  1920
tcacacctat tacagcgata gcgtgaaggg aaggtttacc attagccgtg acaatgctaa  1980
gaacaccgtt tatctccaga tgaatagcct gaagccagag gataccgccg tgtattactg  2040
cgctgccgac ccaacccctt acggtctcag gaatgagaga aactatcctt actggggcca  2100
gggaacccag gttaccgtga gcagcaagga cgagctgtaa cctaggtccc cgaatttccc  2160
cgatcgttca aacatttggc aataaagttt cttaagattg aatcctgttg ccggtcttgc  2220
gatgattatc atataatttc tgttgaatta cgttaagcat gtaataatta acatgtaatg  2280
catgacgtta tttatgagat gggtttttat gattagagtc ccgcaattat acatttaata  2340
cgcgatagaa aacaaaatat agcgcgcaaa ctaggataaa ttatcgcgcg cggtgtcatc  2400
tatgttacta gatcgggaat tggaattcct gcagtgcagc gtgacccggt cgtgcccctc  2460
tctagagata atgagcattg catgtctaag ttataaaaaa ttaccacata tttttttgt  2520
cacacttgtt tgaagtgcag tttatctatc tttatacata tatttaaact ttactctacg  2580
aataatataa tctatagtac tacaataata tcagtgtttt agagaatcat ataaatgaac  2640
agttagacat ggtctaaagg acaattgagt attttgacaa caggactcta cagttttatc  2700
tttttagtgt gcatgtgttc tcctttttt ttgcaaatag cttcacctat ataatacttc  2760
atccatttta ttagtacatc catttagggt ttagggttaa tggtttttat agactaattt  2820
ttttagtaca tctattttat tctattttag cctctaaatt aagaaaacta aaactctatt  2880
ttagtttttt tatttaataa tttagatata aaatagaata aaataaagtg actaaaaatt  2940
aaacaaatac cctttaagaa attaaaaaaa ctaaggaaac atttttcttg tttcgagtag  3000
ataatgccag cctgttaaac gccgtcgacg agtctaacgg acaccaacca gcgaaccagc  3060
agcgtcgcgt cgggccaagc gaagcagacg gcacggcatc tctgtcgctg cctctggacc  3120
cctctcgaga gttccgctcc accgttggac ttgctccgct gtcggcatcc agaaattgcg  3180
tggcggagcg gcagacgtga gccggcacgg caggcggcct cctcctcctc tcacggcacg  3240
gcagctacgg gggattcctt tcccaccgct ccttcgcttt cccttcctcg cccgccgtaa  3300
taaatagaca cccctccac acctctttc cccaacctcg tgttgttcgg agcgcacaca  3360
cacacaacca gatctccccc aaatccaccc gtcggcacct ccgcttcaag gtacgccgct  3420
cgtcctcccc cccccccct ctctaccttc tctagatcgg cgttccggtc catggttagg  3480
gcccggtagt tctacttctg ttcatgtttg tgttagatcc gtgtttgtgt tagatccgtg  3540
ctgctagcgt tcgtacacgg atgcgacctg tacgtcagac acgttctgat tgctaacttg  3600
ccagtgtttc tctttgggga atcctgggat ggctctagcc gttccgcaga cgggatcgat  3660
ttcatgattt tttttgtttc gttgcatagg gtttggtttg cccttttcct ttatttcaat  3720
atatgccgtg cacttgtttg tcgggtcatc ttttcatgct ttttttgtc ttggttgtga  3780
tgatgtggtc tggttgggcg gtcgttctag atcggagtag aattctgttt caaactacct  3840
ggtggattta ttaattttgg atctgtatgt gtgtgccata catattcata gttacgaatt  3900
gaagatgatg gatggaaata tcgatctagg ataggtatac atgttgatgc gggttttact  3960
gatgcatata cagagatgct tttgttcgc ttggttgtga tgatgtggtg tggttgggcg  4020
gtcgttcatt cgttctagat cggagtagaa tactgtttca aactacctgg tgtatttatt  4080
aattttggaa ctgtatgtgt gtgtcataca tcttcatagt tacgagttta agatggatgg  4140
aaatatcgat ctaggatagg tatacatgtt gatgtgggtt ttactgatgc atatacatga  4200
tggcatatgc agcatctatt catatgctct aaccttgagt acctatctat tataataaac  4260
aagtatgttt tataattatt ttgatcttga tatacttgga tgatggcata tgcagcagct  4320
atatgtggat ttttttagcc ctgccttcat acgctattta tttgcttggt actgtttctt  4380
ttgtcgatgc tcaccctgtt gtttggtgtt acttctgcag atccagatct aaaccatgca  4440
```

-continued

```
gaaactcatt aactcagtgc aaaactatgc ctggggcagc aaaacggcgt tgactgaact  4500
ttatggtatg gaaaatccgt ccagccagcc gatggccgag ctgtggatgg gcgcacatcc  4560
gaaaagcagt tcacgagtgc agaatgccgc cggagatatc gtttcactgc gtgatgtgat  4620
tgagagtgat aaatcgactc tgctcggaga ggccgttgcc aaacgctttg gcgaactgcc  4680
tttcctgttc aaagtattat gcgcagcaca gccactctcc attcaggttc atccaaacaa  4740
acacaattct gaaatcggtt ttgccaaaga aaatgccgca ggtatcccga tggatgccgc  4800
cgagcgtaac tataaagatc ctaaccacaa gccggagctg gtttttgcgc tgacgccttt  4860
ccttgcgatg aacgcgtttc gtgaattttc cgagattgtc tccctactcc agccggtcgc  4920
aggtgcacat ccggcgattg ctcacttttt acaacagcct gatgccgaac gtttaagcga  4980
actgttcgcc agcctgttga atatgcaggg tgaagaaaaa tcccgcgcgc tggcgatttt  5040
aaaatcggcc ctcgatagcc agcagggtga accgtggcaa acgattcgtt taatttctga  5100
attttacccg gaagacagcg gtctgttctc cccgctattg ctgaatgtgg tgaaattgaa  5160
ccctggcgaa gcgatgttcc tgttcgctga aacaccgcac gcttacctgc aaggcgtggc  5220
gctggaagtg atggcaaact ccgataacgt gctgcgtgcg ggtctgacgc ctaaatacat  5280
tgatattccg gaactggttg ccaatgtgaa attcgaagcc aaaccggcta accagttgtt  5340
gacccagccg gtgaaacaag gtgcagaact ggacttcccg attccagtgg atgattttgc  5400
cttctcgctg catgacctta gtgataaaga aaccaccatt agccagcaga gtgccgccat  5460
tttgttctgc gtcgaaggcg atgcaacgtt gtggaaaggt tctcagcagt tacagcttaa  5520
accgggtgaa tcagcgttta ttgccgccaa cgaatcaccg gtgactgtca aaggccacgg  5580
ccgtttagcg cgtgtttaca acaagctgta agagcttact gaaaaaatta acatctcttg  5640
ctaagctggg agctctagat ccccgaattt ccccgatcgt tcaaacattt ggcaataaag  5700
tttcttaaga ttgaatcctg ttgccggtct tgcgatgatt atcatataat ttctgttgaa  5760
ttacgttaag catgtaataa ttaacatgta atgcatgacg ttatttatga gatgggtttt  5820
tatgattaga gtcccgcaat tatacattta atacgcgata gaaaacaaaa tatagcgcgc  5880
aaactaggat aaattatcgc gcgcggtgtc atctatgtta ctagatcggg aattggcgag  5940
ctcgaattaa ttcagtacat taaaaacgtc cgcaatgtgt tattaagttg tctaagcgtc  6000
aatttgttta caccacaata tatcctgcca                                   6030
```

```
SEQ ID NO: 157         moltype = DNA  length = 6033
FEATURE                Location/Qualifiers
misc_feature           1..6033
                       note = Synthetic construct, pAG4316
source                 1..6033
                       mol_type = other DNA
                       organism = synthetic construct
SEQUENCE: 157
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagctta  180
attaagtcta actcgagtta ctggtacgta tacagggttc cttgcgtgaa gaagggtggc  240
ctgcggttca ccattaacgg tcacgactac ttccagctag tactggtgac caacgtcgcg  300
gcggcagggt caatcaagtc catggaggtt atgggttcca acacagcgga ttggatgccg  360
atggcacgta actggggcgc ccaatggcac tcactggcct acctcaccgg tcaaggtcta  420
tcctttaggg tcaccaacac agatgaccaa acgctcgtct tcaccaacgt cgtgccacca  480
ggatggaagt ttggccagac atttgcaagc aagctgcagt tcaagtgaga ggagaagcct  540
gaattgatac cggagcgttt cttttgggag taacatctct ggttgcctag caaacatatg  600
attgtatata agtttcgttg tgcgtttatt ctttcggtgt gtaaaataac atacatgctt  660
tcctgatatt ttcttgtata tatgtacaca cacacgacaa atccttccat ttctattatt  720
attgaacaat ttaattgcga gggcgagtac ttgtctgttt accttttttt tttcagatgg  780
cattttatag tttaaccttt catggaccgg cagtagttct aaccatgaat gaaaagaaat  840
catagtccac accacgcagg gacattgtgg tcattttaga caagacgatt tgattaatgt  900
cttgtatgat atggtcgaca gtgaggacta acaaacatat ggcatatttt attaccggcg  960
agttaaataa atttatgtca cagtaataaa ctgcctaata aatgcacgcc agaaaatata  1020
atgataaaaa aaagaaaaga tacataagtc cattgcttct acttttttaa aaattaaatc  1080
caacattttc tatttttttgg tataaacttg gaagtactag ttggatatgc aaaatcatct  1140
aacctccata tatttcatca atttgtttac tttacatatg ggagaggata gtatgtcaaa  1200
gaaaatgaca acaagcttac aagtttctta ttttaaaagt tccgctaact tatcaagcat  1260
agtgtgccac gcaaaactga caacaaacca acaaatttaa ggagcgccta acttatcatc  1320
tatgacatac cgcacaaaat gataacatac tagagaaact ttattgcaca aaaggaaatt  1380
tatccataag gcaaaggaac atcttaaggc tttggatata catttaccaa caagcattgt  1440
ttgtattacc cctaaagcgc aagacatgtc atccatgagt catagtgtgt atatctcaac  1500
attgcaaagc taccttttt ctattatact tttcgcatta taggctagat attatctata  1560
catgtcaaca aactctatcc ctacgtcata tctgaagatt cttttcttca ctatataagt  1620
tggcttccct gtcattgaac tcacatcaac cagcccaagt ttccaataac atcctcaaat  1680
agctggatcc taaaccatga gggtgttgct cgttgccctc gctctcctgg ctctcgctgc  1740
gagcgccacc tcccaggttc agctccagga gtttggtggc ggactggtgc agccaggtgg  1800
cagcctcagg ctgagctgcg ctgctagcgg tagaaccggc agcagctatg ctatgggatg  1860
gtttagacag gctccaggca aggagcgtga atttgttgct gccattagct ggagcggagg  1920
tagcaccgat tatgctgaca gcgtgaaggg caggtttacc attagcagag ataatgccaa  1980
gaacaccatg tacctccaga tgaatagcct gaagccagag gataccgctg tttattactg  2040
cgccgtggac cgtaatctct ttaagctgag ggttgctgtg caggaataca ccaacctcgg  2100
ccagggaacc caggttaccg tgagcagcaa ggacgagctg taacctaggt ccccgaattt  2160
ccccgatcgt tcaaacattt ggcaataaag tttcttaaga ttgaatcctg ttgccggtct  2220
tgcgatgatt atcatataat ttctgttgaa ttacgttaag catgtaataa ttaacatgta  2280
atgcatgacg ttatttatga gatgggtttt tatgattaga gtcccgcaat tatacattta  2340
atacgcgata gaaaacaaaa tatagcgcgc aaactaggat aaattatcgc gcgcggtgtc  2400
atctatgtta ctagatcggg aattggaatt cctgcagtgc agcgtgaccc ggtcgtgccc  2460
ctctctagag ataatgagca ttgcatgtct aagttataaa aaattaccac atattttttt  2520
tgtcacactt gtttgaagtg cagtttatct atctttatac atatatttaa actttactct  2580
```

```
acgaataata taatctatag tactacaata atatcagtgt tttagagaat catataaatg  2640
aacagttaga catggtctaa aggacaattg agtattttga caacaggact ctacagtttt  2700
atctttttag tgtgcatgtg ttctcctttt tttttgcaaa tagcttcacc tatataatac  2760
ttcatccatt ttattagtac atccatttag ggtttagggt taatggtttt tatagactaa  2820
tttttttagt acatctattt tattctattt tagcctctaa attaagaaaa ctaaaactct  2880
attttagttt ttttatttaa taatttagat ataaaataga ataaaataaa gtgactaaaa  2940
attaaacaaa taccctttaa gaaattaaaa aaactaagga aacatttttc ttgtttcgag  3000
tagataatgc cagcctgtta aacgccgtcg acgagtctaa cggacaccaa ccagcgaacc  3060
agcagcgtcg cgtcgggcca agcgaagcag acggcacggc atctctgtcg ctgcctctgg  3120
acccctctcg agagttccgc tccaccgttg gacttgctcc gctgtcggca tccagaaatt  3180
gcgtggcgga gcggcagacg tgagccggca cggcaggcgg cctcctcctc ctctcacggc  3240
acggcagcta cgggggattc ctttcccacc gctccttcgc tttcccttcc tcgcccgccg  3300
taataaatag acaccccctc cacaccctct ttccccaacc tcgtgttgtt cggagcgcac  3360
acacacacaa ccagatctcc cccaaatcca cccgtcggca cctccgcttc aaggtacgcc  3420
gctcgtcctc cccccccccc cctctctacc ttctctagat cggcgttccg gtccatggtt  3480
agggcccggt agttctactt ctgttcatgt ttgtgttaga tccgtgtttg tgttagatcc  3540
gtgctgctag cgttcgtaca cggatgcgac ctgtacgtca gacacgttct gattgctaac  3600
ttgccagtgt ttctctttgg ggaatcctgg gatggctcta gccgttccgc agacgggatc  3660
gatttcatga ttttttttgt ttcgttgcat agggtttggt ttgccctttt cctttatttc  3720
aatatatgcc gtgcacttgt ttgtcgggtc atcttttcat gctttttttt gtcttggttg  3780
tgatgatgtg gtctggttgg gcggtcgttc tagatcggag tagaattctg tttcaaacta  3840
cctggtggat ttattaattt tggatctgta tgtgtgtgcc atacatattc atagttacga  3900
attgaagatg atggatggaa atatcgatct aggataggta tacatgttga tgcgggtttt  3960
actgatgcat atacagagat gctttttgtt cgcttggttg tgatgatgtg gtgtggttgg  4020
gcggtcgttc attcgttcta gatcggagta gaatactgtt tcaaactacc tggtgtattt  4080
attaattttg gaactgtatg tgtgtgtcat acatcttcat agttacgagt ttaagatgga  4140
tggaaatatc gatctaggat aggtatacat gttgatgtgg gttttactga tgcatataca  4200
tgatggcata tgcagcatct attcatatgc tctaaccttg agtacctatc tattataata  4260
aacaagtatg ttttataatt attttgatct tgatatactt ggatgatggc atatgcagca  4320
gctatatgtg gatttttta gccctgcctt catacgctat ttatttgctt ggtactgttt  4380
cttttgtcga tgctcaccct gttgtttggt gttacttctg cagatccaga tctaaaccat  4440
gcagaaactc attaactcag tgcaaaacta tgcctggggc agcaaaacgg cgttgactga  4500
actttatggt atggaaaatc cgtccagcca gccgatggcc gagctgtgga tgggcgcaca  4560
tccgaaaagc agttcacgag tgcagaatgc cgcccggagat atcgtttcac tgcgtgatgt  4620
gattgagagt gataaatcga ctctgctcgg agaggccgtt gccaaacgct ttggcgaact  4680
gcctttcctg ttcaaagtat tatgcgcagc acagccactc tccattcagg ttcatccaaa  4740
caaacacaat tctgaaatcg gttttgccaa agaaaatgcc gcaggtatcc cgatggatgc  4800
cgccgagcgt aactataaag atcctaacca caagccggag ctggtttttg cgctgacgcc  4860
tttccttgcg atgaacgcgt ttcgtgaatt ttccgagatt gtctccctac tccagccggt  4920
cgcaggtgca catccggcga ttgctcactt tttacaacag cctgatgccg aacgtttaag  4980
cgaactgttc gccagcctgt tgaatatgca gggtgaagaa aaatcccgcg cgctggcgat  5040
tttaaaatcg gccctcgata gccagcaggg tgaaccgtgg caaacgattc gtttaatttc  5100
tgaattttac ccggaagaca gcggtctgtt ctccccgcta ttgctgaatg tggtgaaatt  5160
gaaccctggc gaagcgatgt tcctgttcgc tgaaacaccg cacgcttacc tgcaaggcgt  5220
ggcgctggaa gtgatggcaa actccgataa cgtgctgcgt gcgggtctga cgcctaaata  5280
cattgatatt ccggaactgg ttgccaatgt gaaattcgaa gccaaaccgg ctaaccagtt  5340
gttgacccag ccggtgaaac aaggtgcaga actggacttc ccgattccag tggatgattt  5400
tgccttctcg ctgcatgacc ttagtgataa agaaaccacc attagccagc agagtgccgc  5460
cattttgttc tgcgtcgaag gcgatgcaac gttgtggaaa ggttctcagc agttacagct  5520
taaaccgggt gaatcagcgt ttattgccgc caacgaatca ccggtgactg tcaaaggcca  5580
cggccgttta gcgcgtgttt acaacaagct gtaagagctt actgaaaaaa ttaacatctc  5640
ttgctaagct gggagctcta gatccccgaa tttccccgat cgttcaaaca tttggcaata  5700
aagtttctta agattgaatc ctgttgccgg tcttgcgatg attatcatat aatttctgtt  5760
gaattacgtt aagcatgtaa taattaacat gtaatgcatg acgttattta tgagatgggt  5820
ttttatgatt agagtcccgc aattatacat ttaatacgcg atagaaaaca aaatatagcg  5880
cgcaaactag gataaattat cgcgcgcggt gtcatctatg ttactagatc gggaattggc  5940
gagctcgaat taattcagta cattaaaaac gtccgcaatg tgttattaag ttgtctaagc  6000
gtcaatttgt ttacaccaca atatatcctg cca                               6033
```

```
SEQ ID NO: 158          moltype = DNA  length = 6030
FEATURE                 Location/Qualifiers
misc_feature            1..6030
                        note = Synthetic construct, pAG4317
source                  1..6030
                        mol_type = other DNA
                        organism = synthetic construct
SEQUENCE: 158
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagctta  180
attaagtcta actcgagtta ctggtacgta tacagggttc cttgcgtgaa gaagggtggc  240
ctgcggttca ccattaacgg tcacgactac ttccagctag tactggtgac caacgtcgcg  300
gcggcagggt caatcaagtc catggaggtt atgggttcca acacagcgga ttggatgccg  360
atggcacgta actggggcgc ccaatggcac tcactggcct acctcaccgg tcaaggtcta  420
tcctttaggg tcaccaacac agatgaccaa acgctcgtct tcaccaacgt cgtgccacca  480
ggatggaagt ttggccagac atttgcaagc aagctgcagt tcaagtgaga ggagaagcct  540
gaattgatac cggagcgttt cttttgggag taacatctct ggttgcctag caaacatatg  600
attgtatata agtttcgttg tgcgtttatt ctttcggtgt gtaaaataac atacatgctt  660
tcctgatatt ttcttgtata tatgtacaca cacacgacaa atccttccat ttctattatt  720
```

-continued

```
attgaacaat ttaattgcga gggcgagtac ttgtctgttt accttttttt tttcagatgg  780
cattttatag tttaaccttt catggaccgg cagtagttct aaccatgaat gaaaagaaat  840
catagtccac accacgcagg gacattgtgg tcattttaga caagacgatt tgattaatgt  900
cttgtatgat atggtcgaca gtgaggacta acaaacatat ggcatatttt attaccggcg  960
agttaaataa atttatgtca cagtaataaa ctgcctaata aatgcacgcc agaaaatata  1020
atgataaaaa aaagaaaaga tacataagtc cattgcttct actttttttaa aaattaaatc  1080
caacattttc tattttttgg tataaacttg gaagtactag ttggatatgc aaaatcatct  1140
aacctccata tatttcatca atttgtttac tttacatatg ggagaggata gtatgtcaaa  1200
gaaaatgaca acaagcttac aagtttctta ttttaaaagt tccgctaact tatcaagcat  1260
agtgtgccac gcaaaactga caacaaacca acaaatttaa ggagcgccta acttatcatc  1320
tatgacatac cgcacaaaat gataacatac tagagaaact ttattgcaca aaaggaaatt  1380
tatccataag gcaaaggaac atcttaaggc tttggatata catttaccaa caagcattgt  1440
ttgtattacc cctaaagcgc aagacatgtc atccatgagt catagtgtgt atatctcaac  1500
attgcaaagc tacctttttt ctattatact tttcgcatta taggctagat attatctata  1560
catgtcaaca aactctatcc ctacgtcata tctgaagatt cttttcttca ctatataagt  1620
tggcttccct gtcattgaac tcacatcaac cagcccaagt ttccaataac atcctcaaat  1680
agctggatcc taaaccatga gggtgttgct cgttgccctc gctctcctgg ctctcgctgc  1740
gagcgccacc tcccaggttc agctccaggc ttcgggcggc gggctcgtcc aggcgggcgg  1800
ctcgctcagg ctctcgtgcg cggcgtcggg gcggactttc aacagctacg cttggggctg  1860
gttcaggcag gcgccgggca aggagcgcgg cttcgtggcc aggatctcct tcagcggcgg  1920
ccacacctac tactccgaca gcgtcaaggg ccgcttcacg atctccaggg acaacgccaa  1980
gaacagcgtg tacctccaga tgaactccct gaagcccgag gacacggccg tctactactg  2040
cgcggcggac ccgacgccct acggcctcag gaacgagcgg aactaccatt actgggggca  2100
gggcacgcag gtcactgtct cttcgaagga cgagctgtaa cctaggtccc cgaatttccc  2160
cgatcgttca aacatttggc aataaagttt cttaagattg aatcctgttg ccggtcttgc  2220
gatgattatc atataatttc tgttgaatta cgttaagcat gtaataatta acatgtaatg  2280
catgacgtta tttatgagat gggtttttat gattagagtc ccgcaattat acatttaata  2340
cgcgatagaa aacaaaatat agcgcgcaaa ctaggataaa ttatcgcgcg cggtgtcatc  2400
tatgttacta gatcgggaat tggaattcct gcagtgcagc gtgacccggt cgtgcccctc  2460
tctagagata atgagcattg catgtctaag ttataaaaaa ttaccacata tttttttttgt  2520
cacacttgtt tgaagtgcag tttatctatc tttatacata tatttaaact ttactctacg  2580
aataatataa tctatagtac tacaataata tcagtgtttt agagaatcat ataaatgaac  2640
agttagacat ggtctaaagg acaattgagt attttgacaa caggactcta cagttttatc  2700
tttttagtgt gcatgtgttc tccttttttt ttgcaaatag cttcacctat ataatacttc  2760
atccatttta ttagtacatc catttagggt ttagggttaa tggtttttat agactaattt  2820
ttttagtaca tctattttat tctattttag cctctaaatt aagaaaacta aaactctatt  2880
ttagtttttt tatttaataa tttagatata aaatagaata aaataaagtg actaaaaatt  2940
aaacaaatac cctttaagaa attaaaaaaa ctaaggaaac atttttcttg tttcgagtag  3000
ataatgccag cctgttaaac gccgtcgacg agtctaacgg acaccaacca gcgaaccagc  3060
agcgtcgcgt cgggccaagc gaagcagacg gcacggcatc tctgtcgctg cctctggacc  3120
cctctcgaga gttccgctcc accgttggac ttgctccgct gtcggcatcc agaaattgcg  3180
tggcggagcg gcagacgtga gccggcacgg caggcggcct cctcctcctc tcacggcacg  3240
gcagctacgg gggattcctt tcccaccgct ccttcgcttt cccttcctcg cccgccgtaa  3300
taaatagaca cccccctccac accctctttc cccaacctcg tgttgttcgg agcgcacaca  3360
cacacaacca gatctccccc aaatccaccc gtcggcacct ccgcttcaag gtacgccgct  3420
cgtcctcccc cccccccct ctctaccttc tctagatcgg cgttccggtc catggttagg  3480
gcccggtagt tctacttctg ttcatgtttg tgttagatcc gtgtttgtgt tagatccgtg  3540
ctgctagcgt tcgtacacgg atgcgacctg tacgtcagac acgttctgat tgctaacttg  3600
ccagtgtttc tctttgggga atcctgggat ggctctagcc gttccgcaga cgggatcgat  3660
ttcatgattt tttttgtttc gttgcatagg gtttggtttg cccttttcct ttatttcaat  3720
atatgccgtg cacttgtttg tcgggtcatc ttttcatgct tttttttgtc ttggttgtga  3780
tgatgtggtc tggttgggcg gtcgttctag atcggagtag aattctgttt caaactacct  3840
ggtggattta ttaattttgg atctgtatgt gtgtgccata catattcata gttacgaatt  3900
gaagatgatg gatggaaata tcgatctagg ataggtatac atgttgatgc gggttttact  3960
gatgcatata cagagatgct tttgttcgc ttggttgtga tgatgtggtg tggttgggcg  4020
gtcgttcatt cgttctagat cggagtagaa tactgtttca aactacctgg tgtatttatt  4080
aattttggaa ctgtatgtgt gtgtcataca tcttcatagt tacgagttta agatggatgg  4140
aaatatcgat ctaggatagg tatacatgtt gatgtgggtt ttactgatgc atatacatga  4200
tggcatatgc agcatctatt catatgctct aaccttgagt acctatctat tataataaac  4260
aagtatgttt tataattatt ttgatcttga tatacttgga tgatggcata tgcagcagct  4320
atatgtggat tttttttagcc ctgccttcat acgctattta tttgcttggt actgtttctt  4380
ttgtcgatgc tcaccctgtt gtttggtgtt acttctgcag atccagatct aaaccatgca  4440
gaaactcatt aactcagtgc aaaactatgc ctggggcagc aaaacggcgt tgactgaact  4500
ttatggtatg gaaaatccgt ccagccagcc gatggccgag ctgtggatgg gcgcacatcc  4560
gaaaagcagt tcacgagtgc agaatgccgc cggagatatc gtttcactgc gtgatgtgat  4620
tgagagtgat aaatcgactc tgctcggaga ggccgttgcc aaacgctttg gcgaactgcc  4680
tttcctgttc aaagtattat gcgcagcaca gccactctcc attcaggttc atccaaacaa  4740
acacaattct gaaatcggtt ttgccaaaga aaatgccgca ggtatcccga tggatgccgc  4800
cgagcgtaac tataaagatc ctaaccacaa gccggagctg gtttttgcgc tgacgccttt  4860
ccttgcgatg aacgcgtttc gtgaattttc cgagattgtc tccctactcc agccggtcgc  4920
aggtgcacat ccggcgattg ctcacttttt acaacagcct gatgccgaac gtttaagcga  4980
actgttcgcc agcctgttga atatgcaggg tgaagaaaaa tcccgcgcgc tggcgatttt  5040
aaaatcggcc ctcgatagcc agcagggtga accgtggcaa acgattcgtt taatttctga  5100
attttacccg gaagacagcg gtctgttctc cccgctattg ctgaatgtgg tgaaattgaa  5160
ccctggcgaa gcgatgttcc tgttcgctga aacaccgcac gcttacctgc aaggcgtggc  5220
gctggaagtg atggcaaact ccgataacgt gctgcgtgcg ggtctgacgc ctaaatacat  5280
tgatattccg gaactggttg ccaatgtgaa attcgaagcc aaaccggcta accagttgtt  5340
gacccagccg gtgaaacaag gtgcagaact ggacttcccg attccagtgg atgattttgc  5400
cttctcgctg catgacctta gtgataaaga aaccaccatt agccagcaga gtgccgccat  5460
```

```
tttgttctgc gtcgaaggcg atgcaacgtt gtggaaaggt tctcagcagt tacagcttaa  5520
accgggtgaa tcagcgttta ttgccgccaa cgaatcaccg gtgactgtca aaggccacgg  5580
ccgtttagcg cgtgtttaca acaagctgta agagcttact gaaaaaatta acatctcttg  5640
ctaagctggg agctctagat ccccgaattt ccccgatcgt tcaaacattt ggcaataaag  5700
tttcttaaga ttgaatcctg ttgccggtct tgcgatgatt atcatataat ttctgttgaa  5760
ttacgttaag catgtaataa ttaacatgta atgcatgacg ttatttatga gatgggtttt  5820
tatgattaga gtcccgcaat tatacattta atacgcgata gaaaacaaaa tatagcgcgc  5880
aaactaggat aaattatcgc gcgcggtgtc atctatgtta ctagatcggg aattggcgag  5940
ctcgaattaa ttcagtacat taaaaacgtc cgcaatgtgt tattaagttg tctaagcgtc  6000
aatttgttta caccacaata tatcctgcca                                   6030

SEQ ID NO: 159          moltype = DNA  length = 6029
FEATURE                 Location/Qualifiers
misc_feature            1..6029
                        note = Synthetic construct, pAG4985
source                  1..6029
                        mol_type = other DNA
                        organism = synthetic construct
SEQUENCE: 159
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctgcaggaa agcggtggcg gactggtgca gccaggtggc  1800
agcctcaggc tgagctgcgc tgctagcggc aatattttta gcattaacac aatgggttgg  1860
tatagacagg ctcctggcaa gcagcgtgag ctcgttgcca gcattaccac gggtggtaca  1920
accaattatg aagatagcgt gaagggtcgt tttaccatta gcagggacaa tgctaagaag  1980
accgtttacc tccagatgaa caggctgaag ccagaagata ccgccgtgta ttactgcaac  2040
cacaggagaa gctatagcgg aagagattat cctgtttacg gtatggacta ctggggcaag  2100
ggaaccctgg ttaccgtgag cagcaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt ggaattcctg cagtgcagcg tgacccggtc gtgcccctct  2460
ctagagataa tgagcattgc atgtctaagt tataaaaaat taccacatat ttttttgtc  2520
acacttgttt gaagtgcagt ttatctatct ttatacatat atttaaactt tactctacga  2580
ataatataat ctatagtact acaataatat cagtgtttta gagaatcata taaatgaaca  2640
gttagacatg gtctaaagga caattgagta ttttgacaac aggactctac agttttatct  2700
ttttagtgtg catgtgttct ccttttttt tgcaaatagc ttcacctata taatacttca  2760
tccattttat tagtacatcc atttagggtt tagggttaat ggtttttata gactaatttt  2820
tttagtacat ctattttatt ctattttagc ctctaaatta agaaaactaa aactctattt  2880
tagttttttt atttaataat ttagatataa aatagaataa aataaagtga ctaaaaatta  2940
aacaaatacc ctttaagaaa ttaaaaaaac taaggaaaca tttttcttgt ttcgagtaga  3000
taatgccagc ctgttaaacg ccgtcgacga gtctaacgga caccaaccag cgaaccagca  3060
gcgtcgcgtc gggccaagcg aagcagacgg cacggcatct ctgtcgctgc ctctggaccc  3120
ctctcgagag ttccgctcca ccgttggact tgctccgctg tcggcatcca gaaattgcgt  3180
ggcggagcgg cagacgtgag ccggcacggc aggcggcctc ctcctcctct cacggcacgg  3240
cagctacggg ggattccttt cccaccgctc cttcgctttc ccttcctcgc ccgccgtaat  3300
aaatagacac cccctccaca ccctctttcc ccaacctcgt gttgttcgga gcgcacacac  3360
acacaaccag atctccccca aatccacccg tcggcacctc cgcttcaagg tacgccgctc  3420
gtcctccccc cccccccctc tctaccttct ctagatcggc gttccggtcc atggttaggg  3480
cccggtagtt ctacttctgt tcatgtttgt gttagatccg tgtttgtgtt agatccgtgc  3540
tgctagcgtt cgtacacgga tgcgacctgt acgtcagaca cgttctgatt gctaacttgc  3600
```

```
cagtgtttct ctttggggaa tcctgggatg gctctagccg ttccgcagac gggatcgatt  3660
tcatgatttt ttttgtttcg ttgcataggg tttggtttgc ccttttcctt tatttcaata  3720
tatgccgtgc acttgtttgt cgggtcatct tttcatgctt ttttttgtct tggttgtgat  3780
gatgtggtct ggttgggcgg tcgttctaga tcggagtaga attctgtttc aaactacctg  3840
gtggatttat taattttgga tctgtatgtg tgtgccatac atattcatag ttacgaattg  3900
aagatgatgg atggaaatat cgatctagga taggtataca tgttgatgcg ggttttactg  3960
atgcatatac agagatgctt tttgttcgct tggttgtgat gatgtggtgt ggttgggcgg  4020
tcgttcattc gttctagatc ggagtagaat actgtttcaa actacctggt gtatttatta  4080
attttggaac tgtatgtgtg tgtcatacat cttcatagtt acgagtttaa gatggatgga  4140
aatatcgatc taggataggt atacatgttg atgtgggttt tactgatgca tatacatgat  4200
ggcatatgca gcatctattc atatgctcta accttgagta cctatctatt ataataaaca  4260
agtatgtttt ataattattt tgatcttgat atacttggat gatggcatat gcagcagcta  4320
tatgtggatt tttttagccc tgccttcata cgctatttat ttgcttggta ctgtttcttt  4380
tgtcgatgct caccctgttg tttggtgtta cttctgcaga tccagatcta aaccatgcag  4440
aaactcatta actcagtgca aaactatgcc tggggcagca aaacggcgtt gactgaactt  4500
tatggtatgg aaaatccgtc cagccagccg atggccgagc tgtggatggg cgcacatccg  4560
aaaagcagtt cacgagtgca gaatgccgcc ggagatatcg tttcactgcg tgatgtgatt  4620
gagagtgata aatcgactct gctcggagag gccgttgcca aacgctttgg cgaactgcct  4680
ttcctgttca aagtattatg cgcagcacag ccactctcca ttcaggttca tccaaacaaa  4740
cacaattctg aaatcggttt tgccaaagaa aatgccgcag gtatcccgat ggatgccgcc  4800
gagcgtaact ataaagatcc taaccacaag ccggagctgg tttttgcgct gacgcctttc  4860
cttgcgatga acgcgtttcg tgaattttcc gagattgtct ccctactcca gccggtcgca  4920
ggtgcacatc cggcgattgc tcacttttta caacagcctg atgccgaacg tttaagcgaa  4980
ctgttcgcca gcctgttgaa tatgcagggt gaagaaaaat cccgcgcgct ggcgatttta  5040
aaatcggccc tcgatagcca gcagggtgaa ccgtggcaaa cgattcgttt aatttctgaa  5100
ttttacccgg aagacagcgg tctgttctcc ccgctattgc tgaatgtggt gaaattgaac  5160
cctggcgaag cgatgttcct gttcgctgaa acaccgcacg cttacctgca aggcgtggcg  5220
ctggaagtga tggcaaactc cgataacgtg ctgcgtgcgg gtctgacgcc taaatacatt  5280
gatattccgg aactggttgc caatgtgaaa ttcgaagcca aaccggctaa ccagttgttg  5340
acccagccgg tgaaacaagg tgcagaactg gacttcccga ttccagtgga tgattttgcc  5400
ttctcgctgc atgaccttag tgataaagaa accaccatta gccagcagag tgccgccatt  5460
ttgttctgcg tcgaaggcga tgcaacgttg tggaaaggtt ctcagcagtt acagcttaaa  5520
ccgggtgaat cagcgtttat tgccgccaac gaatcaccgg tgactgtcaa aggccacggc  5580
cgtttagcgc gtgtttacaa caagctgtaa gagcttactg aaaaaattaa catctcttgc  5640
taagctggga gctctagatc cccgaatttc cccgatcgtt caaacatttg gcaataaagt  5700
ttcttaagat tgaatcctgt tgccggtctt gcgatgatta tcatataatt tctgttgaat  5760
tacgttaagc atgtaataat taacatgtaa tgcatgacgt tatttatgag atgggttttt  5820
atgattagag tcccgcaatt atacatttaa tacgcgatag aaaacaaaat atagcgcgca  5880
aactaggata aattatcgcg cgcggtgtca tctatgttac tagatcggga attggcgagc  5940
tcgaattaat tcagtacatt aaaaacgtcc gcaatgtgtt attaagttgt ctaagcgtca  6000
atttgtttac accacaatat atcctgcca                                    6029

SEQ ID NO: 160         moltype = DNA  length = 6029
FEATURE                Location/Qualifiers
misc_feature           1..6029
                       note = Synthetic construct, pAG4986
source                 1..6029
                       mol_type = other DNA
                       organism = synthetic construct
SEQUENCE: 160
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggatttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
```

-continued

```
agcgccacct cccaggttca gctgcaggaa agcggtggcg gactggtgca ggctggtggc  1800
agcctcaggc tgagctgcgc tgctagcggc agaaccttta gcagctatgc ttggggttgg  1860
tttaggcagg ccccaggcaa ggagcgtgaa tttgttgcca ggattagctt tagcggaggt  1920
cacacctatt acagcgatag cgtgaaggga aggtttacca ttagccgtga caatgctaag  1980
aacaccgttt atctccagat gaatagcctg aagccagagg ataccgccgt gtattactgc  2040
gctgccgacc caacccctta cggtctcagg aatgagagaa actatcctta ctggggccag  2100
ggaacccagg ttaccgtgag cagcaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt ggaattcctg cagtgcagcg tgacccggtc gtgcccctct  2460
ctagagataa tgagcattgc atgtctaagt tataaaaaat taccacatat ttttttgtc  2520
acacttgttt gaagtgcagt ttatctatct ttatacatat atttaaactt tactctacga  2580
ataatataat ctatagtact acaataatat cagtgtttta gagaatcata taaatgaaca  2640
gttagacatg gtctaaagga caattgagta ttttgacaac aggactctac agttttatct  2700
ttttagtgtg catgtgttct ccttttttt tgcaaatagc ttcacctata taatacttca  2760
tccattttat tagtacatcc atttagggtt tagggttaat ggtttttata gactaatttt  2820
tttagtacat ctattttatt ctattttagc ctctaaatta agaaaactaa aactctattt  2880
tagtttttt atttaataat ttagatataa aatagaataa aataaagtga ctaaaaatta  2940
aacaaatacc ctttaagaaa ttaaaaaaac taaggaaaca tttttcttgt ttcgagtaga  3000
taatgccagc ctgttaaacg ccgtcgacga gtctaacgga caccaaccag cgaaccagca  3060
gcgtcgcgtc gggccaagcg aagcagacgg cacggcatct ctgtcgctgc ctctggaccc  3120
ctctcgagag ttccgctcca ccgttggact tgctccgctg tcggcatcca gaaattgcgt  3180
ggcggagcgg cagacgtgag ccggcacggc aggcggcctc ctcctcctct cacggcacgg  3240
cagctacggg ggattccttt cccaccgctc cttcgcttc ccttcctcgc ccgccgtaat  3300
aaatagacac cccctccaca ccctctttcc ccaacctcgt gttgttcgga gcgcacacac  3360
acacaaccag atctccccca aatccacccg tcggcacctc cgcttcaagg tacgccgctc  3420
gtcctccccc cccccccctc tctaccttct ctagatcggc gttccggtcc atggttaggg  3480
cccggtagtt ctacttctgt tcatgtttgt gttagatccg tgtttgtgtt agatccgtgc  3540
tgctagcgtt cgtacacgga tgcgacctgt acgtcagaca cgttctgatt gctaacttgc  3600
cagtgtttct ctttggggaa tcctgggatg gctctagccg ttccgcagac gggatcgatt  3660
tcatgatttt ttttgtttcg ttgcataggg tttggtttgc ccttttcctt tatttcaata  3720
tatgccgtgc acttgtttgt cgggtcatct tttcatgctt tttttgtct tggttgtgat  3780
gatgtggtct ggttgggcgg tcgttctaga tcggagtaga attctgtttc aaactacctg  3840
gtggatttat taattttgga tctgtatgtg tgtgccatac atattcatag ttacgaattg  3900
aagatgatgg atggaaatat cgatctagga taggtataca tgttgatgcg ggttttactg  3960
atgcatatac agagatgctt tttgttcgct tggttgtgat gatgtggtgt ggttgggcgg  4020
tcgttcattc gttctagatc ggagtagaat actgtttcaa actacctggt gtatttatta  4080
attttggaac tgtatgtgtg tgtcatacat cttcatagtt acgagtttaa gatggatgga  4140
aatatcgatc taggataggt atacatgttg atgtgggttt tactgatgca tatacatgat  4200
ggcatatgca gcatctattc atatgctcta accttgagta cctatctatt ataataaaca  4260
agtatgtttt ataattattt tgatcttgat atacttggat gatggcatat gcagcagcta  4320
tatgtggatt tttttagccc tgccttcata cgctatttat ttgcttggta ctgtttcttt  4380
tgtcgatgct caccctgttg tttggtgtta cttctgcaga tccagatcta aaccatgcag  4440
aaactcatta actcagtgca aaactatgcc tggggcagca aaacggcgtt gactgaactt  4500
tatggtatgg aaaatccgtc cagccagccg atggccgagc tgtggatggg cgcacatccg  4560
aaaagcagtt cacgagtgca gaatgccgcc ggagatatcg tttcactgcg tgatgtgatt  4620
gagagtgata aatcgactct gctcggagag gccgttgcca aacgctttgg cgaactgcct  4680
ttcctgttca aagtattatg cgcagcacag ccactctcca ttcaggttca tccaaacaaa  4740
cacaattctg aaatcggttt tgccaaagaa aatgccgcag gtatcccgat ggatgccgcc  4800
gagcgtaact ataaagatcc taaccacaag ccggagctgg tttttgcgct gacgcctttc  4860
cttgcgatga acgcgtttcg tgaattttcc gagattgtct ccctactcca gccggtcgca  4920
ggtgcacatc cggcgattgc tcactttta caacagcctg atgccgaacg tttaagcgaa  4980
ctgttcgcca gcctgttgaa tatgcagggt gaagaaaaat cccgcgcgct ggcgatttta  5040
aaatcggccc tcgatagcca gcagggtgaa ccgtggcaaa cgattcgttt aatttctgaa  5100
ttttacccgg aagacagcgg tctgttctcc ccgctattgc tgaatgtggt gaaattgaac  5160
cctggcgaag cgatgttcct gttcgctgaa acaccgcacg cttacctgca aggcgtggcg  5220
ctggaagtga tggcaaactc cgataacgtg ctgcgtgcgg gtctgacgcc taaatacatt  5280
gatattccgg aactggttgc caatgtgaaa ttcgaagcca aaccggctaa ccagttgttg  5340
acccagccgg tgaaacaagg tgcagaactg gacttcccga ttccagtgga tgattttgcc  5400
ttctcgctgc atgaccttag tgataaagaa accaccatta gccagcagag tgccgccatt  5460
ttgttctgcg tcgaaggcga tgcaacgttg tggaaaggtt ctcagcagtt acagcttaaa  5520
ccgggtgaat cagcgtttat tgccgccaac gaatcaccgg tgactgtcaa aggccacggc  5580
cgtttagcgc gtgtttacaa caagctgtaa gagcttactg aaaaaattaa catctcttgc  5640
taagctggga gctctagatc cccgaatttc cccgatcgtt caaacatttg gcaataaagt  5700
ttcttaagat tgaatcctgt tgccggtctt gcgatgatta tcatataatt tctgttgaat  5760
tacgttaagc atgtaataat taacatgtaa tgcatgacgt tatttatgag atgggttttt  5820
atgattagag tcccgcaatt atacatttaa tacgcgatag aaaacaaaat atagcgcgca  5880
aactaggata aattatcgcg cgcggtgtca tctatgttac tagatcggga attggcgagc  5940
tcgaattaat tcagtacatt aaaaacgtcc gcaatgtgtt attaagttgt ctaagcgtca  6000
atttgtttac accacaatat atcctgcca                                    6029
```

```
SEQ ID NO: 161         moltype = DNA  length = 6032
FEATURE                Location/Qualifiers
misc_feature           1..6032
                       note = Synthetic construct, pAG4987
source                 1..6032
                       mol_type = other DNA
```

-continued organism = synthetic construct
SEQUENCE: 161
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggttca gctccaggag tttggtggcg gactggtgca gccaggtggc 1800
agcctcaggc tgagctgcgc tgctagcggt agaaccggca gcagctatgc tatgggatgg 1860
tttagacagg ctccaggcaa ggagcgtgaa tttgttgctg ccattagctg gagcggaggt 1920
agcaccgatt atgctgacag cgtgaagggc aggtttacca ttagcagaga taatgccaag 1980
aacaccatgt acctccagat gaatagcctg aagccagagg ataccgctgt ttattactgc 2040
gccgtggacc gtaatctctt taagctgagg gttgctgtgc aggaatacac caacctcggc 2100
cagggaaccc aggttaccgt gagcagcaag gacgagctgt aacctaggtc cccgaatttc 2160
cccgatcgtt caaacatttg gcaataaagt ttcttaagat tgaatcctgt tgccggtctt 2220
gcgatgatta tcatataatt tctgttgaat tacgttaagc atgtaataat taacatgtaa 2280
tgcatgacgt tatttatgag atgggttttt atgattagag tcccgcaatt atacatttaa 2340
tacgcgatag aaaacaaaat atagcgcgca aactaggata aattatcgcg cgcggtgtca 2400
tctatgttac tagatcggga attggaattc ctgcagtgca gcgtgacccg gtcgtgcccc 2460
tctctagaga taatgagcat tgcatgtcta agttataaaa aattaccaca tatttttttt 2520
gtcacacttg tttgaagtgc agtttatcta tctttataca tatatttaaa ctttactcta 2580
cgaataatat aatctatagt actacaataa tatcagtgtt ttagagaatc atataaatga 2640
acagttagac atggtctaaa ggacaattga gtattttgac aacaggactc tacagtttta 2700
tctttttagt gtgcatgtgt tctccttttt ttttgcaaat agcttcacct atataatact 2760
tcatccattt tattagtaca tccatttagg gtttagggtt aatggttttt atagactaat 2820
ttttttagta catctatttt attctatttt agcctctaaa ttaagaaaac taaaactcta 2880
ttttagtttt tttatttaat aatttagata taaaatagaa taaaataaag tgactaaaaa 2940
ttaaacaaat accctttaag aaattaaaaa aactaaggaa acatttttct tgtttcgagt 3000
agataatgcc agcctgttaa acgccgtcga cgagtctaac ggacaccaac cagcgaacca 3060
gcagcgtcgc gtcgggccaa gcgaagcaga cggcacggca tctctgtcgc tgcctctgga 3120
cccctctcga gagttccgct ccaccgttgg acttgctccg ctgtcggcat ccagaaattg 3180
cgtggcggag cggcagacgt gagccggcac ggcaggcggc ctcctcctcc tctcacggca 3240
cggcagctac gggggattcc tttcccaccg ctccttcgct ttcccttcct cgcccgccgt 3300
aataaataga caccccctcc acaccctctt tccccaacct cgtgttgttc ggagcgcaca 3360
cacacacaac cagatctccc ccaaatccac ccgtcggcac ctccgcttca aggtacgccg 3420
ctcgtcctcc cccccccccc ctctctacct tctctagatc ggcgttccgg tccatggtta 3480
gggcccggta gttctacttc tgttcatgtt tgtgttagat ccgtgtttgt gttagatccg 3540
tgctgctagc gttcgtacac ggatgcgacc tgtacgtcag acacgttctg attgctaact 3600
tgccagtgtt tctctttggg gaatcctggg atggctctag ccgttccgca gacgggatcg 3660
atttcatgat tttttttgtt tcgttgcata gggtttggtt tgcccttttc ctttatttca 3720
atatatgccg tgcacttgtt tgtcgggtca tcttttcatg cttttttttg tcttggttgt 3780
gatgatgtgg tctggttggg cggtcgttct agatcggagt agaattctgt ttcaaactac 3840
ctggtggatt tattaatttt ggatctgtat gtgtgtgcca tacatattca tagttacgaa 3900
ttgaagatga tggatggaaa tatcgatcta ggataggtat acatgttgat gcgggtttta 3960
ctgatgcata tacagagatg ctttttgttc gcttggttgt gatgatgtgg tgtggttggg 4020
cggtcgttca ttcgttctag atcggagtag aatactgttt caaactacct ggtgtattta 4080
ttaattttgg aactgtatgt gtgtgtcata catcttcata gttacgagtt taagatggat 4140
ggaaatatcg atctaggata ggtatacatg ttgatgtggg ttttactgat gcatatacat 4200
gatggcatat gcagcatcta ttcatatgct ctaaccttga gtacctatct attataataa 4260
acaagtatgt tttataatta ttttgatctt gatatacttg gatgatggca tatgcagcag 4320
ctatatgtgg atttttttag ccctgccttc atacgctatt tatttgcttg gtactgtttc 4380
ttttgtcgat gctcaccctg ttgtttggtg ttacttctgc agatccagat ctaaaccatg 4440
cagaaactca ttaactcagt gcaaaactat gcctggggca gcaaaacggc gttgactgaa 4500
ctttatggta tggaaaatcc gtccagccag ccgatggccg agctgtggat gggcgcacat 4560
ccgaaaagca gttcacgagt gcagaatgcc gccggagata tcgtttcact gcgtgatgtg 4620

```
attgagagtg ataaatcgac tctgctcgga gaggccgttg ccaaacgctt tggcgaactg  4680
cctttcctgt tcaaagtatt atgcgcagca cagccactct ccattcaggt tcatccaaac  4740
aaacacaatt ctgaaatcgg ttttgccaaa gaaaatgccg caggtatccc gatggatgcc  4800
gccgagcgta actataaaga tcctaaccac aagccggagc tggtttttgc gctgacgcct  4860
ttccttgcga tgaacgcgtt tcgtgaattt tccgagattg tctccctact ccagccggtc  4920
gcaggtgcac atccggcgat tgctcacttt ttacaacagc ctgatgccga acgtttaagc  4980
gaactgttcg ccagcctgtt gaatatgcag ggtgaagaaa aatcccgcgc gctggcgatt  5040
ttaaaatcgg ccctcgatag ccagcagggt gaaccgtggc aaacgattcg tttaatttct  5100
gaattttacc cggaagacag cggtctgttc tccccgctat tgctgaatgt ggtgaaattg  5160
aaccctggcg aagcgatgtt cctgttcgct gaaacaccgc acgcttacct gcaaggcgtg  5220
gcgctggaag tgatggcaaa ctccgataac gtgctgcgtg cgggtctgac gcctaaatac  5280
attgatattc cggaactggt tgccaatgtg aaattcgaag ccaaaccggc taaccagttg  5340
ttgacccagc cggtgaaaca aggtgcagaa ctggacttcc cgattccagt ggatgatttt  5400
gccttctcgc tgcatgacct tagtgataaa gaaaccacca ttagccagca gagtgccgcc  5460
attttgttct gcgtcgaagg cgatgcaacg ttgtggaaag gttctcagca gttacagctt  5520
aaaccgggtg aatcagcgtt tattgccgcc aacgaatcac cggtgactgt caaaggccac  5580
ggccgtttag cgcgtgttta caacaagctg taagagctta ctgaaaaaat taacatctct  5640
tgctaagctg ggagctctag atccccgaat ttccccgatc gttcaaacat ttggcaataa  5700
agtttcttaa gattgaatcc tgttgccggt cttgcgatga ttatcatata atttctgttg  5760
aattacgtta agcatgtaat aattaacatg taatgcatga cgttatttat gagatgggtt  5820
tttatgatta gagtcccgca attatacatt taatacgcga tagaaaacaa aatatagcgc  5880
gcaaactagg ataaattatc gcgcgcggtg tcatctatgt tactagatcg ggaattggcg  5940
agctcgaatt aattcagtac attaaaaacg tccgcaatgt gttattaagt tgtctaagcg  6000
tcaatttgtt tacaccacaa tatatcctgc ca                                6032
```

```
SEQ ID NO: 162          moltype = DNA  length = 8274
FEATURE                 Location/Qualifiers
misc_feature            1..8274
                        note = Synthetic construct, pAG4988
source                  1..8274
                        mol_type = other DNA
                        organism = synthetic construct
SEQUENCE: 162
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctgcaggaa agcggtggcg gactggtgca gccaggtggc  1800
agcctcaggc tgagctgcgc tgctagcggc aatattttta gcattaacac aatgggttgg  1860
tatagacagg ctcctggcaa gcagcgtgag ctcgttgcca gcattaccac gggtggtaca  1920
accaattatg aagatagcgt gaagggtcgt tttaccatta gcagggacaa tgctaagaag  1980
accgtttacc tccagatgaa caggctgaag ccagaagata ccgccgtgta ttactgcaac  2040
cacaggagaa gctatagcgg aagagattat cctgtttacg gtatggacta ctggggcaag  2100
ggaaccctgg ttaccgtgag cagcaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt gttaattaag tctaactcga gttactggta cgtatacagg  2460
gttccttgcg tgaagaaggg tggcctgcgg ttcaccatta acggtcacga ctacttccag  2520
ctagtactgg tgaccaacgt cgcggcggca gggtcaatca agtccatgga ggttatgggt  2580
tccaacacag cggattggat gccgatggca cgtaactggg gcgcccaatg gcactcactg  2640
gcctacctca ccggtcaagg tctatccttt agggtcacca acacagatga ccaaacgctc  2700
gtcttcacca acgtcgtgcc accaggatgg aagtttggcc agacatttgc aagcaagctg  2760
```

-continued cagttcaagt gagaggagaa gcctgaattg ataccggagc gtttcttttg ggagtaacat 2820
ctctggttgc ctagcaaaca tatgattgta tataagtttc gttgtgcgtt tattctttcg 2880
gtgtgtaaaa taacatacat gctttcctga tattttcttg tatatatgta cacacacacg 2940
acaaatcctt ccatttctat tattattgaa caatttaatt gcgagggcga gtacttgtct 3000
gtttaccttt ttttttcag atggcatttt atagtttaac ctttcatgga ccggcagtag 3060
ttctaaccat gaatgaaaag aaatcatagt ccacaccacg cagggacatt gtggtcattt 3120
tagacaagac gatttgatta atgtcttgta tgatatggtc gacagtgagg actaacaaac 3180
atatggcata ttttattacc ggcgagttaa ataaatttat gtcacagtaa taaactgcct 3240
aataaatgca cgccagaaaa tataatgata aaaaaaagaa aagatacata agtccattgc 3300
ttctactttt ttaaaaatta aatccaacat tttctatttt ttggtataaa cttggaagta 3360
ctagttggat atgcaaaatc atctaacctc catatatttc atcaatttgt ttactttaca 3420
tatgggagag gatagtatgt caaagaaaat gacaacaagc ttacaagttt cttattttaa 3480
aagttccgct aacttatcaa gcatagtgtg ccacgcaaaa ctgacaacaa accaacaaat 3540
ttaaggagcg cctaacttat catctatgac ataccgcaca aaatgataac atactagaga 3600
aactttattg cacaaaagga aatttatcca taaggcaaag gaacatctta aggctttgga 3660
tatacattta ccaacaagca ttgtttgtat taccccctaaa gcgcaagaca tgtcatccat 3720
gagtcatagt gtgtatatct caacattgca aagctacctt ttttctatta tacttttcgc 3780
attataggct agatattatc tatacatgtc aacaaactct atccctacgt catatctgaa 3840
gattcttttc ttcactatat aagttggctt ccctgtcatt gaactcacat caaccagccc 3900
aagtttccaa taacatcctc aaatagctgg atcctaaacc atgagggtgt tgctcgttgc 3960
cctcgctctc ctggctctcg ctgcgagcgc cacctcccag gttcagctgc aggaaagcgg 4020
tggcggactg gtgcagccag gtggcagcct caggctgagc tgcgctgcta gcggcaatat 4080
ttttagcatt aacacaatgg gttggtatag acaggctcct ggcaagcagc gtgagctcgt 4140
tgccagcatt accacgggtg gtacaaccaa ttatgaagat agcgtgaagg gtcgttttac 4200
cattagcagg gacaatgcta agaagaccgt ttacctccag atgaacaggc tgaagccaga 4260
agataccgcc gtgtattact gcaaccacag gagaagctat agcggaagag attatcctgt 4320
ttacggtatg gactactggg gcaagggaac cctggttacc gtgagcagca aggacgagct 4380
gtaacctagg tccccgaatt tccccgatcg ttcaaacatt tggcaataaa gtttcttaag 4440
attgaatcct gttgccggtc ttgcgatgat tatcatataa tttctgttga attacgttaa 4500
gcatgtaata attaacatgt aatgcatgac gttatttatg agatgggttt ttatgattag 4560
agtcccgcaa ttatacattt aatacgcgat agaaaacaaa atatagcgcg caaactagga 4620
taaattatcg cgcgcggtgt catctatgtt actagatcgg gaattggaat tcctgcagtg 4680
cagcgtgacc cggtcgtgcc cctctctaga gataatgagc attgcatgtc taagttataa 4740
aaaattacca catatttttt ttgtcacact tgtttgaagt gcagtttatc tatctttata 4800
catatattta aactttactc tacgaataat ataatctata gtactacaat aatatcagtg 4860
ttttagagaa tcatataaat gaacagttag acatggtcta aaggacaatt gagtattttg 4920
acaacaggac tctacagttt tatcttttta gtgtgcatgt gttctccttt ttttttgcaa 4980
atagcttcac ctatataata cttcatccat tttattagta catccattta gggtttaggg 5040
ttaatggttt ttatagacta attttttag tacatctatt ttattctatt ttagcctcta 5100
aattaagaaa actaaaactc tattttagtt tttttattta ataatttaga tataaaatag 5160
aataaaataa agtgactaaa aattaaacaa ataccctta agaaattaaa aaaactaagg 5220
aaacattttt cttgtttcga gtagataatg ccagcctgtt aaacgccgtc gacgagtcta 5280
acggacacca accagcgaac cagcagcgtc gcgtcgggcc aagcgaagca gacggcacgg 5340
catctctgtc gctgcctctg gacccctctc gagagttccg ctccaccgtt ggacttgctc 5400
cgctgtcggc atccagaaat tgcgtggcgg agcggcagac gtgagccggc acggcaggcg 5460
gcctcctcct cctctcacgg cacggcagct acgggggatt cctttcccac cgctccttcg 5520
ctttcccttc ctcgcccgcc gtaataaata gacacccct ccacaccctc tttccccaac 5580
ctcgtgttgt tcggagcgca cacacacaca accagatctc ccccaaatcc acccgtcggc 5640
acctccgctt caaggtacgc cgctcgtcct cccccccccc ccctctctac cttctctaga 5700
tcggcgttcc ggtccatggt tagggcccgg tagttctact tctgttcatg tttgtgttag 5760
atccgtgttt gtgttagatc cgtgctgcta gcgttcgtac acggatgcga cctgtacgtc 5820
agacacgttc tgattgctaa cttgccagtg tttctctttg gggaatcctg ggatggctct 5880
agccgttccg cagacgggat cgatttcatg atttttttg tttcgttgca tagggtttgg 5940
tttgcccttt tcctttattt caatatatgc cgtgcacttg tttgtcgggt catcttttca 6000
tgcttttttt tgtcttggtt gtgatgatgt ggtctggttg ggcggtcgtt ctagatcgga 6060
gtagaattct gtttcaaact acctggtgga tttattaatt ttggatctgt atgtgtgtgc 6120
catacatatt catagttacg aattgaagat gatggatgga aatatcgatc taggataggt 6180
atacatgttg atgcgggttt tactgatgca tatacagaga tgcttttttgt tcgcttggtt 6240
gtgatgatgt ggtgtggttg ggcggtcgtt cattcgttct agatcggagt agaatactgt 6300
ttcaaactac ctggtgtatt tattaatttt ggaactgtat gtgtgtgtca tacatcttca 6360
tagttacgag tttaagatgg atggaaatat cgatctagga taggtataca tgttgatgtg 6420
ggttttactg atgcatatac atgatggcat atgcagcatc tattcatatg ctctaacctt 6480
gagtacctat ctattataat aaacaagtat gttttataat tattttgatc ttgatatact 6540
tggatgatgg catatgcagc agctatatgt ggattttttt agccctgcct tcatacgcta 6600
tttatttgct tggtactgtt tcttttgtcg atgctcaccc tgttgtttgg tgttacttct 6660
gcagatccag atctaaacca tgcagaaact cattaactca gtgcaaaact atgcctgggg 6720
cagcaaaacg gcgttgactg aactttatgg tatggaaaat ccgtccagcc agccgatggc 6780
cgagctgtgg atgggcgcac atccgaaaag cagttcacga gtgcagaatg ccgccggaga 6840
tatcgtttca ctgcgtgatg tgattgagag tgataaatcg actctgctcg gagaggccgt 6900
tgccaaacgc tttggcgaac tgcctttcct gttcaaagta ttatgcgcag cacagccact 6960
ctccattcag gttcatccaa acaaacacaa ttctgaaatc ggttttgcca aagaaaatgc 7020
cgcaggtatc ccgatggatg ccgccgagcg taactataaa gatcctaacc acaagccgga 7080
gctggttttt gcgctgacgc ctttccttgc gatgaacgcg tttcgtgaat tttccgagat 7140
tgtctcccta ctccagccgg tcgcaggtgc acatccggcg attgctcact tttacaaca 7200
gcctgatgcc gaacgtttaa gcgaactgtt cgccagcctg ttgaatatgc agggtgaaga 7260
aaaatcccgc gcgctggcga ttttaaaatc ggccctcgat agccagcagg gtgaaccgtg 7320
gcaaacgatt cgtttaattt ctgaatttta cccggaagac agcggtctgt tctccccgct 7380
attgctgaat gtggtgaaat tgaaccctgg cgaagcgatg ttcctgttcg ctgaaacacc 7440
gcacgcttac ctgcaaggcg tggcgctgga agtgatggca aactccgata acgtgctgcg 7500

```
tgcgggtctg acgcctaaat acattgatat tccggaactg gttgccaatg tgaaattcga  7560
agccaaaccg gctaaccagt tgttgaccca gccggtgaaa caaggtgcag aactggactt  7620
cccgattcca gtggatgatt ttgccttctc gctgcatgac cttagtgata aagaaaccac  7680
cattagccag cagagtgccg ccattttgtt ctgcgtcgaa ggcgatgcaa cgttgtggaa  7740
aggttctcag cagttacagc ttaaaccggg tgaatcagcg tttattgccg ccaacgaatc  7800
accggtgact gtcaaaggcc acggccgttt agcgcgtgtt tacaacaagc tgtaagagct  7860
tactgaaaaa attaacatct cttgctaagc tgggagctct agatccccga atttccccga  7920
tcgttcaaac atttggcaat aaagtttctt aagattgaat cctgttgccg gtcttgcgat  7980
gattatcata taatttctgt tgaattacgt taagcatgta ataattaaca tgtaatgcat  8040
gacgttattt atgagatggg tttttatgat tagagtcccg caattataca tttaatacgc  8100
gatagaaaac aaaatatagc gcgcaaacta ggataaatta tcgcgcgcgg tgtcatctat  8160
gttactagat cgggaattgg cgagctcgaa ttaattcagt acattaaaaa cgtccgcaat  8220
gtgttattaa gttgtctaag cgtcaatttg tttacaccac aatatatcct gcca        8274

SEQ ID NO: 163         moltype = DNA  length = 8274
FEATURE                Location/Qualifiers
misc_feature           1..8274
                       note = Synthetic construct, pAG4989
source                 1..8274
                       mol_type = other DNA
                       organism = synthetic construct
SEQUENCE: 163
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctgcaggaa agcggtggcg gactggtgca ggctggtggc  1800
agcctcaggc tgagctgcgc tgctagcggc agaaccttta gcagctatgc ttggggttgg  1860
tttaggcagg ccccaggcaa ggagcgtgaa tttgttgcca ggattagctt tagcggaggt  1920
cacacctatt acagcgatag cgtgaaggga aggtttacca ttagccgtga caatgctaag  1980
aacaccgttt atctccagat gaatagcctg aagccagagg ataccgccgt gtattactgc  2040
gctgccgacc caacccctta cggtctcagg aatgagagaa actatcctta ctggggccag  2100
ggaacccagg ttaccgtgag cagcaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt gttaattaag tctaactcga gttactggta cgtatacagg  2460
gttccttgcg tgaagaaggg tggcctgcgg ttcaccatta acggtcacga ctacttccag  2520
ctagtactgg tgaccaacgt cgcggcggca gggtcaatca agtccatgga ggttatgggt  2580
tccaacacag cggattggat gccgatggca cgtaactggg gcgcccaatg gcactcactg  2640
gcctacctca ccggtcaagg tctatccttt agggtcacca acacagatga ccaaacgctc  2700
gtcttcacca acgtcgtgcc accaggatgg aagtttggcc agacatttgc aagcaagctg  2760
cagttcaagt gagaggagaa gcctgaattg ataccggagc gtttcttttg ggagtaacat  2820
ctctggttgc ctagcaaaca tatgattgta tataagtttc gttgtgcgtt tattctttcg  2880
gtgtgtaaaa taacatacat gctttcctga tattttcttg tatatatgta cacacacacg  2940
acaaatcctt ccatttctat tattattgaa caatttaatt gcgagggcga gtacttgtct  3000
gtttaccttt ttttttttcag atggcatttt atagtttaac ctttcatgga ccggcagtag  3060
ttctaaccat gaatgaaaag aaatcatagt ccacaccacg cagggacatt gtggtcattt  3120
tagacaagac gatttgatta atgtcttgta tgatatggtc gacagtgagg actaacaaac  3180
atatggcata ttttattacc ggcgagttaa ataaatttat gtcacagtaa taaactgcct  3240
aataaatgca cgccagaaaa tataatgata aaaaaaagaa aagatacata agtccattgc  3300
ttctactttt ttaaaaatta aatccaacat tttctatttt ttggtataaa cttggaagta  3360
ctagttggat atgcaaaatc atctaacctc catatatttc atcaatttgt ttactttaca  3420
```

```
tatgggagag gatagtatgt caaagaaaat gacaacaagc ttacaagttt cttattttaa  3480
aagttccgct aacttatcaa gcatagtgtg ccacgcaaaa ctgacaacaa accaacaaat  3540
ttaaggagcg cctaacttat catctatgac ataccgcaca aaatgataac atactagaga  3600
aactttattg cacaaaagga aatttatcca taaggcaaag gaacatctta aggctttgga  3660
tatacattta ccaacaagca ttgtttgtat taccoctaaa gcgcaagaca tgtcatccat  3720
gagtcatagt gtgtatatct caacattgca aagctacctt ttttctatta tacttttcgc  3780
attataggct agatattatc tatacatgtc aacaaactct atccctacgt catatctgaa  3840
gattcttttc ttcactatat aagttggctt ccctgtcatt gaactcacat caaccagccc  3900
aagtttccaa taacatcctc aaatagctgg atcctaaacc atgagggtgt tgctcgttgc  3960
cctcgctctc ctggctctcg ctgcgagcgc cacctcccag gttcagctgc aggaaagcgg  4020
tggcggactg gtgcaggctg gtggcagcct caggctgagc tgcgctgcta gcggcagaac  4080
ctttagcagc tatgcttggg gttggtttag gcaggcccca ggcaaggagc gtgaatttgt  4140
tgccaggatt agctttagcg gaggtcacac ctattacagc gatagcgtga agggaaggtt  4200
taccattagc cgtgacaatg ctaagaacac cgtttatctc cagatgaata gcctgaagcc  4260
agaggatacc gccgtgtatt actgcgctgc cgacccaacc ccttacggtc tcaggaatga  4320
gagaaactat ccttactggg gccagggaac ccaggttacc gtgagcagca aggacgagct  4380
gtaacctagg tccccgaatt tccccgatcg ttcaaacatt tggcaataaa gtttcttaag  4440
attgaatcct gttgccggtc ttgcgatgat tatcatataa tttctgttga attacgttaa  4500
gcatgtaata attaacatgt aatgcatgac gttatttatg agatgggttt ttatgattag  4560
agtcccgcaa ttatacattt aatacgcgat agaaaacaaa atatagcgcg caaactagga  4620
taaattatcg cgcgcggtgt catctatgtt actagatcgg gaattggaat tcctgcagtg  4680
cagcgtgacc cggtcgtgcc cctctctaga gataatgagc attgcatgtc taagttataa  4740
aaaattacca catatttttt ttgtcacact tgtttgaagt gcagtttatc tatctttata  4800
catatattta aactttactc tacgaataat ataatctata gtactacaat aatatcagtg  4860
ttttagagaa tcatataaat gaacagttag acatggtcta aaggacaatt gagtattttg  4920
acaacaggac tctacagttt tatcttttta gtgtgcatgt gttctccttt ttttttgcaa  4980
atagcttcac ctatataata cttcatccat tttattagta catccattta gggtttaggg  5040
ttaatggttt ttatagacta atttttttag tacatctatt ttattctatt ttagcctcta  5100
aattaagaaa actaaaactc tattttagtt tttttattta ataatttaga tataaaatag  5160
aataaaataa agtgactaaa aattaaacaa ataccettta agaaattaaa aaaactaagg  5220
aaacattttt cttgtttcga gtagataatg ccagcctgtt aaacgccgtc gacgagtcta  5280
acggacacca accagcgaac cagcagcgtc gcgtcgggcc aagcgaagca gacggcacgg  5340
catctctgtc gctgcctctg gacccctctc gagagttccg ctccaccgtt ggacttgctc  5400
cgctgtcggc atccagaaat tgcgtggcgg agcggcagac gtgagccggc acggcaggcg  5460
gcctcctcct cctctcacgg cacggcagct acgggggatt cctttcccac cgctccttcg  5520
ctttcccttc ctcgcccgcc gtaataaata gacacccct ccacaccctc tttccccaac  5580
ctcgtgttgt tcggagcgca cacacacaca accagatctc ccccaaatcc acccgtcggc  5640
acctccgctt caaggtacgc cgctcgtcct cccccccccc ccctctctac cttctctaga  5700
tcggcgttcc ggtccatggt tagggcccgg tagttctact tctgttcatg tttgtgttag  5760
atccgtgttt gtgttagatc cgtgctgcta gcgttcgtac acggatgcga cctgtacgtc  5820
agacacgttc tgattgctaa cttgccagtg tttctctttg gggaatcctg ggatggctct  5880
agccgttccg cagacgggat cgatttcatg attttttttg tttcgttgca tagggtttgg  5940
tttgcccttt tcctttattt caatatatgc cgtgcacttg tttgtcgggt catcttttca  6000
tgcttttttt tgtcttggtt gtgatgatgt ggtctggttg ggcggtcgtt ctagatcgga  6060
gtagaattct gtttcaaact acctggtgga tttattaatt ttggatctgt atgtgtgtgc  6120
catacatatt catagttacg aattgaagat gatggatgga aatatcgatc taggataggt  6180
atacatgttg atgcgggttt tactgatgca tatacagaga tgctttttgt tcgcttggtt  6240
gtgatgatgt ggtgtggttg ggcggtcgtt cattcgttct agatcggagt agaatactgt  6300
ttcaaactac ctggtgtatt tattaatttt ggaactgtat gtgtgtgtca tacatcttca  6360
tagttacgag tttaagatgg atggaaatat cgatctagga taggtataca tgttgatgtg  6420
ggttttactg atgcatatac atgatggcat atgcagcatc tattcatatg ctctaacctt  6480
gagtacctat ctattataat aaacaagtat gttttataat tattttgatc ttgatatact  6540
tggatgatgg catatgcagc agctatatgt ggattttttt agccctgcct tcatacgcta  6600
tttatttgct tggtactgtt tcttttgtcg atgctcaccc tgttgtttgg tgttacttct  6660
gcagatccag atctaaacca tgcagaaact cattaactca gtgcaaaact atgcctgggg  6720
cagcaaaacg gcgttgactg aactttatgg tatggaaaat ccgtccagcc agccgatggc  6780
cgagctgtgg atgggcgcac atccgaaaag cagttcacga gtgcagaatg ccgccggaga  6840
tatcgtttca ctgcgtgatg tgattgagag tgataaatcg actctgctcg gagaggccgt  6900
tgccaaacgc tttggcgaac tgcctttcct gttcaaagta ttatgcgcag cacagccact  6960
ctccattcag gttcatccaa acaaacacaa ttctgaaatc ggttttgcca aagaaaatgc  7020
cgcaggtatc ccgatggatg ccgccgagcg taactataaa gatcctaacc acaagccgga  7080
gctggttttt gcgctgacgc ctttccttgc gatgaacgcg tttcgtgaat tttccgagat  7140
tgtctcccta ctccagccgg tcgcaggtgc acatccggcg attgctcact ttttacaaca  7200
gcctgatgcc gaacgtttaa gcgaactgtt cgccagcctg ttgaatatgc agggtgaaga  7260
aaaatcccgc gcgctggcga ttttaaaatc ggccctcgat agccagcagg gtgaaccgtg  7320
gcaaacgatt cgtttaattt ctgaatttta cccggaagac agcggtctgt tctccccgct  7380
attgctgaat gtggtgaaat tgaaccctgg cgaagcgatg ttcctgttcg ctgaaacacc  7440
gcacgcttac ctgcaaggcg tggcgctgga agtgatggca aactccgata acgtgctgcg  7500
tgcgggtctg acgcctaaat acattgatat tccggaactg gttgccaatg tgaaattcga  7560
agccaaaccg gctaaccagt tgttgaccca gccggtgaaa caaggtgcag aactggactt  7620
cccgattcca gtggatgatt ttgccttctc gctgcatgac cttagtgata aagaaaccac  7680
cattagccag cagagtgccg ccattttgtt ctgcgtcgaa ggcgatgcaa cgttgtggaa  7740
aggttctcag cagttacagc ttaaaccggg tgaatcagcg tttattgccg ccaacgaatc  7800
accggtgact gtcaaaggcc acggccgttt agcgcgtgtt tacaacaagc tgtaagagct  7860
tactgaaaaa attaacatct cttgctaagc tgggagctct agatccccga atttccccga  7920
tcgttcaaac atttggcaat aaagtttctt aagattgaat cctgttgccg gtcttgcgat  7980
gattatcata taatttctgt tgaattacgt taagcatgta ataattaaca tgtaatgcat  8040
gacgttattt atgagatggg tttttatgat tagagtcccg caattataca tttaatacgc  8100
gatagaaaac aaaatatagc gcgcaaacta ggataaatta tcgcgcgcgg tgtcatctat  8160
```

-continued

```
gttactagat cgggaattgg cgagctcgaa ttaattcagt acattaaaaa cgtccgcaat  8220
gtgttattaa gttgtctaag cgtcaatttg tttacaccac aatatatcct gcca        8274

SEQ ID NO: 164         moltype = DNA  length = 8280
FEATURE                Location/Qualifiers
misc_feature           1..8280
                       note = Synthetic construct, pAG4990
source                 1..8280
                       mol_type = other DNA
                       organism = synthetic construct
SEQUENCE: 164
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctccaggag tttggtggcg gactggtgca gccaggtggc  1800
agcctcaggc tgagctgcgc tgctagcggt agaaccggca gcagctatgc tatgggatgg  1860
tttagacagg ctccaggcaa ggagcgtgaa tttgttgctg ccattagctg gagcggaggt  1920
agcaccgatt atgctgacag cgtgaagggc aggtttacca ttagcagaga taatgccaag  1980
aacaccatgt acctccagat gaatagcctg aagccagagg ataccgctgt ttattactgc  2040
gccgtggacc gtaatctctt taagctgagg gttgctgtgc aggaatacac caacctcggc  2100
cagggaaccc aggttaccgt gagcagcaag gacgagctgt aacctaggtc cccgaatttc  2160
cccgatcgtt caaacatttg gcaataaagt ttcttaagat tgaatcctgt tgccggtctt  2220
gcgatgatta tcatataatt tctgttgaat tacgttaagc atgtaataat taacatgtaa  2280
tgcatgacgt tatttatgag atgggttttt atgattagag tcccgcaatt atacatttaa  2340
tacgcgatag aaaacaaaat atagcgcgca aactaggata aattatcgcg cgcggtgtca  2400
tctatgttac tagatcggga attgttaatt aagtctaact cgagttactg gtacgtatac  2460
agggttcctt gcgtgaagaa gggtggcctg cggttcacca ttaacggtca cgactacttc  2520
cagctagtac tggtgaccaa cgtcgcggcg gcagggtcaa tcaagtccat ggaggttatg  2580
ggttccaaca cagcggattg gatgccgatg gcacgtaact ggggcgccca atggcactca  2640
ctggcctacc tcaccggtca aggtctatcc tttagggtca ccaacacaga tgaccaaacg  2700
ctcgtcttca ccaacgtcgt gccaccagga tggaagtttg gccagacatt tgcaagcaag  2760
ctgcagttca agtgagagga gaagcctgaa ttgataccgg agcgtttctt ttgggagtaa  2820
catctctggt tgcctagcaa acatatgatt gtatataagt ttcgttgtgc gtttattctt  2880
tcggtgtgta aaataacata catgctttcc tgatattttc ttgtatatat gtacacacac  2940
acgacaaatc cttccatttc tattattatt gaacaattta attgcgaggg cgagtacttg  3000
tctgtttacc ttttttttt cagatggcat tttatagttt aacctttcat ggaccggcag  3060
tagttctaac catgaatgaa aagaaatcat agtccacacc acgcagggac attgtggtca  3120
ttttagacaa gacgatttga ttaatgtctt gtatgatatg gtcgacagtg aggactaaca  3180
aacatatggc atattttatt accggcgagt taaataaatt tatgtcacag taataaactg  3240
cctaataaat gcacgccaga aaatataatg ataaaaaaaa gaaaagatac ataagtccat  3300
tgcttctact tttttaaaaa ttaaatccaa cattttctat tttttggtat aaacttggaa  3360
gtactagttg gatatgcaaa atcatctaac ctccatatat ttcatcaatt tgtttacttt  3420
acatatggga gaggatagta tgtcaaagaa aatgacaaca agcttacaag tttcttattt  3480
taaaagttcc gctaacttat caagcatagt gtgccacgca aaactgacaa caaaccaaca  3540
aatttaagga gcgcctaact tatcatctat gacataccgc acaaaatgat aacatactag  3600
agaaacttta ttgcacaaaa ggaaatttat ccataaggca aaggaacatc ttaaggcttt  3660
ggatatacat ttaccaacaa gcattgtttg tattacccct aaagcgcaag acatgtcatc  3720
catgagtcat agtgtgtata tctcaacatt gcaaagctac ctttttttcta ttatactttt  3780
cgcattatag gctagatatt atctatacat gtcaacaaac tctatcccta cgtcatatct  3840
gaagattctt ttcttcacta tataagttgg cttccctgtc attgaactca catcaaccag  3900
cccaagtttc caataacatc ctcaaatagc tggatcctaa accatgaggg tgttgctcgt  3960
tgccctcgct ctcctggctc tcgctgcgag cgccacctcc caggttcagc tccaggagtt  4020
tggtggcgga ctggtgcagc caggtggcag cctcaggctg agctgcgctg ctagcggtag  4080
```

```
aaccggcagc agctatgcta tgggatggtt tagacaggct ccaggcaagg agcgtgaatt  4140
tgttgctgcc attagctgga gcggaggtag caccgattat gctgacagcg tgaagggcag  4200
gtttaccatt agcagagata atgccaagaa caccatgtac ctccagatga atagcctgaa  4260
gccagaggat accgctgttt attactgcgc cgtggaccgt aatctcttta agctgagggt  4320
tgctgtgcag gaatacacca acctcggcca gggaacccag gttaccgtga gcagcaagga  4380
cgagctgtaa cctaggtccc cgaatttccc cgatcgttca aacatttggc aataaagttt  4440
cttaagattg aatcctgttg ccggtcttgc gatgattatc atataatttc tgttgaatta  4500
cgttaagcat gtaataatta acatgtaatg catgacgtta tttatgagat gggtttttat  4560
gattagagtc ccgcaattat acatttaata cgcgatagaa aacaaaatat agcgcgcaaa  4620
ctaggataaa ttatcgcgcg cggtgtcatc tatgttacta gatcgggaat tggaattcct  4680
gcagtgcagc gtgacccggt cgtgcccctc tctagagata atgagcattg catgtctaag  4740
ttataaaaaa ttaccacata ttttttttgt cacacttgtt tgaagtgcag tttatctatc  4800
tttatacata tatttaaact ttactctacg aataatataa tctatagtac tacaataata  4860
tcagtgtttt agagaatcat ataaatgaac agttagacat ggtctaaagg acaattgagt  4920
attttgacaa caggactcta cagttttatc tttttagtgt gcatgtgttc tccttttttt  4980
ttgcaaatag cttcacctat ataatacttc atccatttta ttagtacatc catttagggt  5040
ttagggttaa tggtttttat agactaattt ttttagtaca tctattttat tctattttag  5100
cctctaaatt aagaaaacta aaactctatt ttagtttttt tatttaataa tttagatata  5160
aaatagaata aaataaagtg actaaaaatt aaacaaatac cctttaagaa attaaaaaaa  5220
ctaaggaaac atttttcttg tttcgagtag ataatgccag cctgttaaac gccgtcgacg  5280
agtctaacgg acaccaacca gcgaaccagc agcgtcgcgt cgggccaagc gaagcagacg  5340
gcacggcatc tctgtcgctg cctctggacc cctctcgaga gttccgctcc accgttggac  5400
ttgctccgct gtcggcatcc agaaattgcg tggcggagcg gcagacgtga gccggcacgg  5460
caggcggcct cctcctcctc tcacggcacg gcagctacgg gggattcctt tcccaccgct  5520
ccttcgcttt cccttcctcg cccgccgtaa taaatagaca ccccctccac accctctttc  5580
cccaacctcg tgttgttcgg agcgcacaca cacacaacca gatctccccc aaatccaccc  5640
gtcggcacct ccgcttcaag gtacgccgct cgtcctcccc cccccccct ctctaccttc  5700
tctagatcgg cgttccggtc catggttagg gcccggtagt tctacttctg ttcatgtttg  5760
tgttagatcc gtgtttgtgt tagatccgtg ctgctagcgt tcgtacacgg atgcgacctg  5820
tacgtcagac acgttctgat tgctaacttg ccagtgtttc tctttgggga atcctgggat  5880
ggctctagcc gttccgcaga cgggatcgat ttcatgattt tttttgtttc gttgcatagg  5940
gtttggtttg cccttttcct ttatttcaat atatgccgtg cacttgtttg tcgggtcatc  6000
ttttcatgct tttttttgtc ttggttgtga tgatgtggtc tggttgggcg gtcgttctag  6060
atcggagtag aattctgttt caaactacct ggtggattta ttaattttgg atctgtatgt  6120
gtgtgccata catattcata gttacgaatt gaagatgatg gatggaaata tcgatctagg  6180
ataggtatac atgttgatgc gggttttact gatgcatata cagagatgct ttttgttcgc  6240
ttggttgtga tgatgtggtg tggttgggcg gtcgttcatt cgttctagat cggagtagaa  6300
tactgtttca aactacctgg tgtatttatt aattttggaa ctgtatgtgt gtgtcataca  6360
tcttcatagt tacgagttta agatggatgg aaatatcgat ctaggatagg tatacatgtt  6420
gatgtgggtt ttactgatgc atatacatga tggcatatgc agcatctatt catatgctct  6480
aaccttgagt acctatctat tataataaac aagtatgttt tataattatt ttgatcttga  6540
tatacttgga tgatggcata tgcagcagct atatgtggat ttttttagcc ctgccttcat  6600
acgctattta tttgcttggt actgtttctt ttgtcgatgc tcaccctgtt gtttggtgtt  6660
acttctgcag atccagatct aaaccatgca gaaactcatt aactcagtgc aaaactatgc  6720
ctggggcagc aaaacggcgt tgactgaact ttatggtatg gaaaatccgt ccagccagcc  6780
gatggccgag ctgtggatgg gcgcacatcc gaaaagcagt tcacgagtgc agaatgccgc  6840
cggagatatc gtttcactgc gtgatgtgat tgagagtgat aaatcgactc tgctcggaga  6900
ggccgttgcc aaacgctttg gcgaactgcc tttcctgttc aaagtattat gcgcagcaca  6960
gccactctcc attcaggttc atccaaacaa acacaattct gaaatcggtt ttgccaaaga  7020
aaatgccgca ggtatcccga tggatgccgc cgagcgtaac tataaagatc ctaaccacaa  7080
gccggagctg gtttttgcgc tgacgccttt ccttgcgatg aacgcgtttc gtgaattttc  7140
cgagattgtc tccctactcc agccggtcgc aggtgcacat ccggcgattg ctcacttttt  7200
acaacagcct gatgccgaac gtttaagcga actgttcgcc agcctgttga atatgcaggg  7260
tgaagaaaaa tcccgcgcgc tggcgatttt aaaatcggcc ctcgatagcc agcagggtga  7320
accgtggcaa acgattcgtt taatttctga attttacccg gaagacagcg gtctgttctc  7380
cccgctattg ctgaatgtgg tgaaattgaa ccctggcgaa gcgatgttcc tgttcgctga  7440
aacaccgcac gcttacctgc aaggcgtggc gctggaagtg atggcaaact ccgataacgt  7500
gctgcgtgcg ggtctgacgc ctaaatacat tgatattccg gaactggttg ccaatgtgaa  7560
attcgaagcc aaaccggcta accagttgtt gacccagccg gtgaaacaag gtgcagaact  7620
ggacttcccg attccagtgg atgattttgc cttctcgctg catgacctta gtgataaaga  7680
aaccaccatt agccagcaga gtgccgccat tttgttctgc gtcgaaggcg atgcaacgtt  7740
gtggaaaggt tctcagcagt tacagcttaa accgggtgaa tcagcgttta ttgccgccaa  7800
cgaatcaccg gtgactgtca aaggccacgg ccgtttagcg cgtgtttaca acaagctgta  7860
agagcttact gaaaaaatta acatctcttg ctaagctggg agctctagat ccccgaattt  7920
ccccgatcgt tcaaacattt ggcaataaag tttcttaaga ttgaatcctg ttgccggtct  7980
tgcgatgatt atcatataat ttctgttgaa ttacgttaag catgtaataa ttaacatgta  8040
atgcatgacg ttatttatga gatgggtttt tatgattaga gtcccgcaat tatacattta  8100
atacgcgata gaaaacaaaa tatagcgcgc aaactaggat aaattatcgc gcgcggtgtc  8160
atctatgtta ctagatcggg aattggcgag ctcgaattaa ttcagtacat taaaaacgtc  8220
cgcaatgtgt tattaagttg tctaagcgtc aatttgttta caccacaata tatcctgcca  8280
```

```
SEQ ID NO: 165          moltype = DNA  length = 6029
FEATURE                 Location/Qualifiers
misc_feature            1..6029
                        note = Synthetic construct, pAG4991
source                  1..6029
                        mol_type = other DNA
                        organism = synthetic construct
SEQUENCE: 165
```

-continued

```
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctccaggct tcgggcggcg ggctcgtcca ggcgggcggc  1800
tcgctcaggc tctcgtgcgc ggcgtcgggg cggactttca acagctacgc ttggggctgg  1860
ttcaggcagg cgccgggcaa ggagcgcggc ttcgtggcca ggatctcctt cagcggcggc  1920
cacacctact actccgacag cgtcaagggc cgcttcacga tctccaggga caacgccaag  1980
aacagcgtgt acctccagat gaactccctg aagcccgagg acacggccgt ctactactgc  2040
gcggcggacc cgacgcccta cggcctcagg aacgagcgga actaccatta ctgggggcag  2100
ggcacgcagg tcactgtctc ttcgaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt ggaattcctg cagtgcagcg tgacccggtc gtgcccctct  2460
ctagagataa tgagcattgc atgtctaagt tataaaaaat taccacatat ttttttgtc  2520
acacttgttt gaagtgcagt ttatctatct ttatacatat atttaaactt tactctacga  2580
ataatataat ctatagtact acaataatat cagtgtttta gagaatcata taaatgaaca  2640
gttagacatg gtctaaagga caattgagta ttttgacaac aggactctac agttttatct  2700
ttttagtgtg catgtgttct cctttttttt tgcaaatagc ttcacctata taatacttca  2760
tccattttat tagtacatcc atttagggtt tagggttaat ggtttttata gactaatttt  2820
tttagtacat ctattttatt ctatttttagc ctctaaatta agaaaactaa aactctattt  2880
tagttttttt atttaataat ttagatataa aatagaataa aataaagtga ctaaaaatta  2940
aacaaatacc ctttaagaaa ttaaaaaaac taaggaaaca tttttcttgt ttcgagtaga  3000
taatgccagc ctgttaaacg ccgtcgacga gtctaacgga caccaaccag cgaaccagca  3060
gcgtcgcgtc gggccaagcg aagcagacgg cacggcatct ctgtcgctgc ctctggaccc  3120
ctctcgagag ttccgctcca ccgttggact tgctccgctg tcggcatcca gaaattgcgt  3180
ggcggagcgg cagacgtgag ccggcacggc aggcggcctc ctcctcctct cacggcacgg  3240
cagctacggg ggattccttt cccaccgctc cttcgctttc ccttcctcgc ccgccgtaat  3300
aaatagacac cccctccaca ccctctttcc ccaacctcgt gttgttcgga gcgcacacac  3360
acacaaccag atctccccca aatccacccg tcggcacctc cgcttcaagg tacgccgctc  3420
gtcctccccc cccccccctc tctaccttct ctagatcggc gttccggtcc atggttaggg  3480
cccggtagtt ctacttctgt tcatgtttgt gttagatccg tgtttgtgtt agatccgtgc  3540
tgctagcgtt cgtacacgga tgcgacctgt acgtcagaca cgttctgatt gctaacttgc  3600
cagtgtttct ctttggggaa tcctgggatg gctctagccg ttccgcagac gggatcgatt  3660
tcatgatttt ttttgtttcg ttgcataggg tttggtttgc ccttttcctt tatttcaata  3720
tatgccgtgc acttgtttgt cgggtcatct tttcatgctt ttttttgtct tggttgtgat  3780
gatgtggtct ggttgggcgg tcgttctaga tcggagtaga attctgtttc aaactacctg  3840
gtggatttat taattttgga tctgtatgtg tgtgccatac atattcatag ttacgaattg  3900
aagatgatgg atggaaatat cgatctagga taggtataca tgttgatgcg ggttttactg  3960
atgcatatac agagatgctt tttgttcgct tggttgtgat gatgtggtgt ggttgggcgg  4020
tcgttcattc gttctagatc ggagtagaat actgtttcaa actacctggt gtatttatta  4080
attttggaac tgtatgtgtg tgtcatacat cttcatagtt acgagtttaa gatggatgga  4140
aatatcgatc taggataggt atacatgttg atgtgggttt tactgatgca tatacatgat  4200
ggcatatgca gcatctattc atatgctcta accttgagta cctatctatt ataataaaca  4260
agtatgtttt ataattattt tgatcttgat atacttggat gatggcatat gcagcagcta  4320
tatgtggatt tttttagccc tgccttcata cgctatttat ttgcttggta ctgtttcttt  4380
tgtcgatgct caccctgttg tttggtgtta cttctgcaga tccagatcta aaccatgcag  4440
aaactcatta actcagtgca aaactatgcc tggggcagca aaacggcgtt gactgaactt  4500
tatggtatgg aaaatccgtc cagccagccg atggccgagc tgtggatggg cgcacatccg  4560
aaaagcagtt cacgagtgca gaatgccgcc ggagatatcg tttcactgcg tgatgtgatt  4620
gagagtgata aatcgactct gctcggagag gccgttgcca aacgctttgg cgaactgcct  4680
ttcctgttca aagtattatg cgcagcacag ccactctcca ttcaggttca tccaaacaaa  4740
```

```
cacaattctg aaatcggttt tgccaaagaa aatgccgcag gtatcccgat ggatgccgcc  4800
gagcgtaact ataaagatcc taaccacaag ccggagctgg tttttgcgct gacgcctttc  4860
cttgcgatga acgcgtttcg tgaattttcc gagattgtct ccctactcca gccggtcgca  4920
ggtgcacatc cggcgattgc tcacttttta caacagcctg atgccgaacg tttaagcgaa  4980
ctgttcgcca gcctgttgaa tatgcagggt gaagaaaaat cccgcgcgct ggcgatttta  5040
aaatcggccc tcgatagcca gcagggtgaa ccgtggcaaa cgattcgttt aatttctgaa  5100
ttttacccgg aagacagcgg tctgttctcc ccgctattgc tgaatgtggt gaaattgaac  5160
cctggcgaag cgatgttcct gttcgctgaa acaccgcacg cttacctgca aggcgtggcg  5220
ctggaagtga tggcaaactc cgataacgtg ctgcgtgcgg gtctgacgcc taaatacatt  5280
gatattccgg aactggttgc caatgtgaaa ttcgaagcca aaccggctaa ccagttgttg  5340
acccagccgg tgaaacaagg tgcagaactg gacttcccga ttccagtgga tgattttgcc  5400
ttctcgctgc atgaccttag tgataaagaa accaccatta gccagcagag tgccgccatt  5460
ttgttctgcg tcgaaggcga tgcaacgttg tggaaaggtt ctcagcagtt acagcttaaa  5520
ccgggtgaat cagcgtttat tgccgccaac gaatcaccgg tgactgtcaa aggccacggc  5580
cgtttagcgc gtgtttacaa caagctgtaa gagcttactg aaaaaattaa catctcttgc  5640
taagctggga gctctagatc cccgaatttc cccgatcgtt caaacatttg gcaataaagt  5700
ttcttaagat tgaatcctgt tgccggtctt gcgatgatta tcatataatt tctgttgaat  5760
tacgttaagc atgtaataat taacatgtaa tgcatgacgt tatttatgag atgggttttt  5820
atgattagag tcccgcaatt atacatttaa tacgcgatag aaaacaaaat atagcgcgca  5880
aactaggata aattatcgcg cgcggtgtca tctatgttac tagatcggga attggcgagc  5940
tcgaattaat tcagtacatt aaaaacgtcc gcaatgtgtt attaagttgt ctaagcgtca  6000
atttgtttac accacaatat atcctgcca                                6029

SEQ ID NO: 166          moltype = DNA  length = 8274
FEATURE                 Location/Qualifiers
misc_feature            1..8274
                        note = Synthetic construct, pAG4992
source                  1..8274
                        mol_type = other DNA
                        organism = synthetic construct
SEQUENCE: 166
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggttca gctccaggct tcgggcggcg ggctcgtcca ggcgggcggc  1800
tcgctcaggc tctcgtgcgc ggcgtcgggg cggactttca acagctacgc ttggggctgg  1860
ttcaggcagg cgccgggcaa ggagcgcggc ttcgtggcca ggatctcctt cagcggcggc  1920
cacacctact actccgacag cgtcaagggc cgcttcacga tctccaggga caacgccaag  1980
aacagcgtgt acctccagat gaactccctg aagcccgagg acacggccgt ctactactgc  2040
gcggcggacc cgacgcccta cggcctcagg aacgagcgga actaccatta ctgggggcag  2100
ggcacgcagg tcactgtctc ttcgaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt gttaattaag tctaactcga gttactggta cgtatacagg  2460
gttccttgcg tgaagaaggg tggcctgcgg ttcaccatta acggtcacga ctacttccag  2520
ctagtactgg tgaccaacgt cgcggcggca gggtcaatca agtccatgga ggttatgggt  2580
tccaacacag cggattggat gccgatggca cgtaactggg gcgcccaatg gcactcactg  2640
gcctacctca ccggtcaagg tctatccttt agggtcacca acacagatga ccaaacgctc  2700
gtcttcacca acgtcgtgcc accaggatgg aagtttggcc agacatttgc aagcaagctg  2760
cagttcaagt gagaggagaa gcctgaattg ataccggagc gtttcttttg ggagtaacat  2820
ctctggttgc ctagcaaaca tatgattgta tataagtttc gttgtgcgtt tattctttcg  2880
```

-continued

```
gtgtgtaaaa taacatacat gctttcctga tattttcttg tatatatgta cacacacacg  2940
acaaatcctt ccatttctat tattattgaa caatttaatt gcgagggcga gtacttgtct  3000
gtttaccttt ttttttcag atggcatttt atagtttaac ctttcatgga ccggcagtag  3060
ttctaaccat gaatgaaaag aaatcatagt ccacaccacg cagggacatt gtggtcattt  3120
tagacaagac gatttgatta atgtcttgta tgatatggtc gacagtgagg actaacaaac  3180
atatggcata ttttattacc ggcgagttaa ataaatttat gtcacagtaa taaactgcct  3240
aataaatgca cgccagaaaa tataatgata aaaaaaagaa aagatacata agtccattgc  3300
ttctactttt ttaaaaatta aatccaacat tttctatttt ttggtataaa cttggaagta  3360
ctagttggat atgcaaaatc atctaacctc catatatttc atcaatttgt ttactttaca  3420
tatgggagag gatagtatgt caaagaaaat gacaacaagc ttacaagttt cttattttaa  3480
aagttccgct aacttatcaa gcatagtgtg ccacgcaaaa ctgacaacaa accaacaaat  3540
ttaaggagcg cctaacttat catctatgac ataccgcaca aaatgataac atactagaga  3600
aactttattg cacaaaagga aatttatcca taaggcaaag gaacatctta aggctttgga  3660
tatacattta ccaacaagca ttgtttgtat taccccctaaa gcgcaagaca tgtcatccat  3720
gagtcatagt gtgtatatct caacattgca aagctacctt ttttctatta tacttttcgc  3780
attataggct agatattatc tatacatgtc aacaaactct atccctacgt catatctgaa  3840
gattcttttc ttcactatat aagttggctt ccctgtcatt gaactcacat caaccagccc  3900
aagtttccaa taacatcctc aaatagctgg atcctaaacc atgagggtgt tgctcgttgc  3960
cctcgctctc ctggctctcg ctgcgagcgc cacctcccag gttcagctcc aggcttcggg  4020
cggcgggctc gtccaggcgg gcggctcgct caggctctcg tgcgcggcgt cggggcggac  4080
tttcaacagc tacgcttggg gctggttcag gcaggcgccg ggcaaggagc gcggcttcgt  4140
ggccaggatc tccttcagcg gcggccacac ctactactcc gacagcgtca agggccgctt  4200
cacgatctcc agggacaacg ccaagaacag cgtgtacctc cagatgaact ccctgaagcc  4260
cgaggacacg gccgtctact actgcgcggc ggacccgacg ccctacggcc tcaggaacga  4320
gcggaactac cattactggg ggcagggcac gcaggtcact gtctcttcga aggacgagct  4380
gtaacctagg tccccgaatt tccccgatcg ttcaaacatt tggcaataaa gtttcttaag  4440
attgaatcct gttgccggtc ttgcgatgat tatcatataa tttctgttga attacgttaa  4500
gcatgtaata attaacatgt aatgcatgac gttatttatg agatgggttt ttatgattag  4560
agtcccgcaa ttatacattt aatacgcgat agaaaacaaa atatagcgcg caaactagga  4620
taaattatcg cgcgcggtgt catctatgtt actagatcgg gaattggaat tcctgcagtg  4680
cagcgtgacc cggtcgtgcc cctctctaga gataatgagc attgcatgtc taagttataa  4740
aaaattacca catatttttt ttgtcacact tgtttgaagt gcagtttatc tatctttata  4800
catatattta aactttactc tacgaataat ataatctata gtactacaat aatatcagtg  4860
ttttagagaa tcatataaat gaacagttag acatggtcta aaggacaatt gagtattttg  4920
acaacaggac tctacagttt tatcttttta gtgtgcatgt gttctccttt ttttttgcaa  4980
atagcttcac ctatataata cttcatccat tttattagta catccattta gggtttaggg  5040
ttaatggttt ttatagacta attttttag tacatctatt ttattctatt ttagcctcta  5100
aattaagaaa actaaaactc tattttagtt tttttattta ataatttaga tataaaatag  5160
aataaaataa agtgactaaa aattaaacaa ataccttta agaaattaaa aaaactaagg  5220
aaacattttt cttgtttcga gtagataatg ccagcctgtt aaacgccgtc gacgagtcta  5280
acggacacca accagcgaac cagcagcgtc gcgtcgggcc aagcgaagca gacggcacgg  5340
catctctgtc gctgcctctg gacccctctc gagagttccg ctccaccgtt ggacttgctc  5400
cgctgtcggc atccagaaat tgcgtggcgg agcggcagac gtgagccggc acggcaggcg  5460
gcctcctcct cctctcacgg cacggcagct acgggggatt cctttcccac cgctccttcg  5520
ctttcccttc ctcgcccgcc gtaataaata gacacccct ccacaccctc tttccccaac  5580
ctcgtgttgt tcggagcgca cacacacaca accagatctc ccccaaatcc acccgtcggc  5640
acctccgctt caaggtacgc cgctcgtcct cccccccccc ccctctctac cttctctaga  5700
tcggcgttcc ggtccatggt tagggcccgg tagttctact tctgttcatg tttgtgttag  5760
atccgtgttt gtgttagatc cgtgctgcta gcgttcgtac acggatgcga cctgtacgtc  5820
agacacgttc tgattgctaa cttgccagtg tttctctttg gggaatcctg ggatggctct  5880
agccgttccg cagacgggat cgatttcatg attttttttg tttcgttgca tagggtttgg  5940
tttgcccttt tcctttattt caatatatgc cgtgcacttg tttgtcgggt catcttttca  6000
tgcttttttt tgtcttggtt gtgatgatgt ggtctggttg ggcggtcgtt ctagatcgga  6060
gtagaattct gtttcaaact acctggtgga tttattaatt ttggatctgt atgtgtgtgc  6120
catacatatt catagttacg aattgaagat gatggatgga aatatcgatc taggataggt  6180
atacatgttg atgcgggttt tactgatgca tatacagaga tgcttttttgt tcgcttggtt  6240
gtgatgatgt ggtgtggttg ggcggtcgtt cattcgttct agatcggagt agaatactgt  6300
ttcaaactac ctggtgtatt tattaatttt ggaactgtat gtgtgtgtca tacatcttca  6360
tagttacgag tttaagatgg atggaaatat cgatctagga taggtataca tgttgatgtg  6420
ggttttactg atgcatatac atgatggcat atgcagcatc tattcatatg ctctaacctt  6480
gagtacctat ctattataat aaacaagtat gttttataat tattttgatc ttgatatact  6540
tggatgatgg catatgcagc agctatatgt ggattttttt agccctgcct tcatacgcta  6600
tttatttgct tggtactgtt tcttttgtcg atgctcaccc tgttgtttgg tgttacttct  6660
gcagatccag atctaaacca tgcagaaact cattaactca gtgcaaaact atgcctgggg  6720
cagcaaaacg gcgttgactg aactttatgg tatggaaaat ccgtccagcc agccgatggc  6780
cgagctgtgg atgggcgcac atccgaaaag cagttcacga gtgcagaatg ccgccggaga  6840
tatcgtttca ctgcgtgatg tgattgagag tgataaatcg actctgctcg gagaggccgt  6900
tgccaaacgc tttggcgaac tgcctttcct gttcaaagta ttatgcgcag cacagccact  6960
ctccattcag gttcatccaa acaaacacaa ttctgaaatc ggttttgcca aagaaaatgc  7020
cgcaggtatc ccgatggatg ccgccgagcg taactataaa gatcctaacc acaagccgga  7080
gctggttttt gcgctgacgc ctttccttgc gatgaacgcg tttcgtgaat tttccgagat  7140
tgtctcccta ctccagccgg tcgcaggtgc acatccggcg attgctcact tttacaaca  7200
gcctgatgcc gaacgtttaa gcgaactgtt cgccagcctg ttgaatatgc agggtgaaga  7260
aaaatcccgc gcgctggcga ttttaaaatc ggccctcgat agccagcagg gtgaaccgtg  7320
gcaaacgatt cgtttaattt ctgaatttta cccggaagac agcggtctgt tctccccgct  7380
attgctgaat gtggtgaaat tgaaccctgg cgaagcgatg ttcctgttcg ctgaaacacc  7440
gcacgcttac ctgcaaggcg tggcgctgga agtgatggca aactccgata acgtgctgcg  7500
tgcgggtctg acgcctaaat acattgatat tccggaactg gttgccaatg tgaaattcga  7560
agccaaaccg gctaaccagt tgttgaccca gccggtgaaa caaggtgcag aactggactt  7620
```

```
cccgattcca gtggatgatt ttgccttctc gctgcatgac cttagtgata aagaaaccac  7680
cattagccag cagagtgccg ccattttgtt ctgcgtcgaa ggcgatgcaa cgttgtggaa  7740
aggttctcag cagttacagc ttaaaccggg tgaatcagcg tttattgccg ccaacgaatc  7800
accggtgact gtcaaaggcc acggccgttt agcgcgtgtt tacaacaagc tgtaagagct  7860
tactgaaaaa attaacatct cttgctaagc tgggagctct agatccccga atttccccga  7920
tcgttcaaac atttggcaat aaagtttctt aagattgaat cctgttgccg gtcttgcgat  7980
gattatcata taatttctgt tgaattacgt taagcatgta ataattaaca tgtaatgcat  8040
gacgttattt atgagatggg tttttatgat tagagtcccg caattataca tttaatacgc  8100
gatagaaaac aaaatatagc gcgcaaacta ggataaatta tcgcgcgcgg tgtcatctat  8160
gttactagat cgggaattgg cgagctcgaa ttaattcagt acattaaaaa cgtccgcaat  8220
gtgttattaa gttgtctaag cgtcaatttg tttacaccac aatatatcct gcca        8274

SEQ ID NO: 167          moltype = DNA  length = 6029
FEATURE                 Location/Qualifiers
misc_feature            1..6029
                        note = Synthetic construct, pAG4993
source                  1..6029
                        mol_type = other DNA
                        organism = synthetic construct
SEQUENCE: 167
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggtgca gctccaggag tccggcggcg gcctcgtgca gccgggcggc  1800
tccctccgcc tgagctgcgc cgcgtccggc aacatcttca gcatcaacac gatgggctgg  1860
tacaggcagg cccccggcaa gcagcgggag ctcgtggcct ccatcaccac gggcggcacc  1920
acgaactacg aggacagcgt caagggccgc ttcaccatct ccagggacaa cgccaagaag  1980
acggtgtacc tccagatgaa ccgcctgaag ccggaggaca cggcggtcta ctactgcaac  2040
caccgcaggt cctacagcgg cagggactac cccgtgtacg gcatggacta ctggggcaag  2100
ggcaccctcg tgaccgtgtc ctccaaggac gagctgtgac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt ggaattcctg cagtgcagcg tgacccggtc gtgcccctct  2460
ctagagataa tgagcattgc atgtctaagt tataaaaaat taccacatat ttttttttgtc  2520
acacttgttt gaagtgcagt ttatctatct ttatacatat atttaaactt tactctacga  2580
ataatataat ctatagtact acaataatat cagtgtttta gagaatcata taaatgaaca  2640
gttagacatg gtctaaagga caattgagta ttttgacaac aggactctac agttttatct  2700
ttttagtgtg catgtgttct ccttttttttt tgcaaatagc ttcacctata taatacttca  2760
tccattttat tagtacatcc atttagggtt tagggttaat ggtttttata gactaatttt  2820
tttagtacat ctattttatt ctattttagc ctctaaatta agaaaactaa aactctattt  2880
tagttttttt atttaataat ttagatataa aatagaataa aataaagtga ctaaaaatta  2940
aacaaatacc ctttaagaaa ttaaaaaaac taaggaaaca tttttcttgt ttcgagtaga  3000
taatgccagc ctgttaaacg ccgtcgacga gtctaacgga caccaaccag cgaaccagca  3060
gcgtcgcgtc gggccaagcg aagcagacgg cacggcatct ctgtcgctgc ctctggaccc  3120
ctctcgagag ttccgctcca ccgttggact tgctccgctg tcggcatcca gaaattgcgt  3180
ggcggagcgg cagacgtgag ccggcacggc aggcggcctc ctcctcctct cacggcacgg  3240
cagctacggg ggattccttt cccaccgctc cttcgctttc ccttcctcgc ccgccgtaat  3300
aaatagacac cccctccaca ccctctttcc ccaacctcgt gttgttcgga gcgcacacac  3360
acacaaccag atctcccccca aatccacccg tcggcacctc cgcttcaagg tacgccgctc  3420
gtcctccccc cccccccctc tctaccttct ctagatcggc gttccggtcc atggttaggg  3480
cccggtagtt ctacttctgt tcatgtttgt gttagatccg tgtttgtgtt agatccgtgc  3540
```

-continued

```
tgctagcgtt cgtacacgga tgcgacctgt acgtcagaca cgttctgatt gctaacttgc  3600
cagtgtttct ctttggggaa tcctgggatg gctctagccg ttccgcagac gggatcgatt  3660
tcatgatttt ttttgtttcg ttgcataggg tttggtttgc ccttttcctt tatttcaata  3720
tatgccgtgc acttgtttgt cgggtcatct tttcatgctt ttttttgtct tggttgtgat  3780
gatgtggtct ggttgggcgg tcgttctaga tcggagtaga attctgtttc aaactacctg  3840
gtggatttat taattttgga tctgtatgtg tgtgccatac atattcatag ttacgaattg  3900
aagatgatgg atggaaatat cgatctagga taggtataca tgttgatgcg ggttttactg  3960
atgcatatac agagatgctt tttgttcgct tggttgtgat gatgtggtgt ggttgggcgg  4020
tcgttcattc gttctagatc ggagtagaat actgtttcaa actacctggt gtatttatta  4080
attttggaac tgtatgtgtg tgtcatacat cttcatagtt acgagtttaa gatggatgga  4140
aatatcgatc taggataggt atacatgttg atgtgggttt tactgatgca tatacatgat  4200
ggcatatgca gcatctattc atatgctcta accttgagta cctatctatt ataataaaca  4260
agtatgtttt ataattattt tgatcttgat atacttggat gatggcatat gcagcagcta  4320
tatgtggatt tttttagccc tgccttcata cgctatttat ttgcttggta ctgtttcttt  4380
tgtcgatgct caccctgttg tttggtgtta cttctgcaga tccagatcta aaccatgcag  4440
aaactcatta actcagtgca aaactatgcc tggggcagca aaacggcgtt gactgaactt  4500
tatggtatgg aaaatccgtc cagccagccg atggccgagc tgtggatggg cgcacatccg  4560
aaaagcagtt cacgagtgca gaatgccgcc ggagatatcg tttcactgcg tgatgtgatt  4620
gagagtgata aatcgactct gctcggagag gccgttgcca aacgctttgg cgaactgcct  4680
ttcctgttca aagtattatg cgcagcacag ccactctcca ttcaggttca tccaaacaaa  4740
cacaattctg aaatcggttt tgccaaagaa aatgccgcag gtatcccgat ggatgccgcc  4800
gagcgtaact ataaagatcc taaccacaag ccggagctgg tttttgcgct gacgcctttc  4860
cttgcgatga acgcgtttcg tgaattttcc gagattgtct ccctactcca gccggtcgca  4920
ggtgcacatc cggcgattgc tcacttttta caacagcctg atgccgaacg tttaagcgaa  4980
ctgttcgcca gcctgttgaa tatgcagggt gaagaaaaat cccgcgcgct ggcgatttta  5040
aaatcggccc tcgatagcca gcagggtgaa ccgtggcaaa cgattcgttt aatttctgaa  5100
ttttacccgg aagacagcgg tctgttctcc ccgctattgc tgaatgtggt gaaattgaac  5160
cctggcgaag cgatgttcct gttcgctgaa acaccgcacg cttacctgca aggcgtggcg  5220
ctggaagtga tggcaaactc cgataacgtg ctgcgtgcgg gtctgacgcc taaatacatt  5280
gatattccgg aactggttgc caatgtgaaa ttcgaagcca aaccggctaa ccagttgttg  5340
acccagccgg tgaaacaagg tgcagaactg gacttcccga ttccagtgga tgattttgcc  5400
ttctcgctgc atgaccttag tgataaagaa accaccatta gccagcagag tgccgccatt  5460
ttgttctgcg tcgaaggcga tgcaacgttg tggaaaggtt ctcagcagtt acagcttaaa  5520
ccgggtgaat cagcgtttat tgccgccaac gaatcaccgg tgactgtcaa aggccacggc  5580
cgtttagcgc gtgtttacaa caagctgtaa gagcttactg aaaaaattaa catctcttgc  5640
taagctggga gctctagatc cccgaatttc cccgatcgtt caaacatttg gcaataaagt  5700
ttcttaagat tgaatcctgt tgccggtctt gcgatgatta tcatataatt tctgttgaat  5760
tacgttaagc atgtaataat taacatgtaa tgcatgacgt tatttatgag atgggttttt  5820
atgattagag tcccgcaatt atacatttaa tacgcgatag aaaacaaaat atagcgcgca  5880
aactaggata aattatcgcg cgcggtgtca tctatgttac tagatcggga attggcgagc  5940
tcgaattaat tcagtacatt aaaaacgtcc gcaatgtgtt attaagttgt ctaagcgtca  6000
atttgtttac accacaatat atcctgcca                                    6029
```

```
SEQ ID NO: 168          moltype = DNA  length = 6032
FEATURE                 Location/Qualifiers
misc_feature            1..6032
                        note = Synthetic construct, pAG4994
source                  1..6032
                        mol_type = other DNA
                        organism = synthetic construct
SEQUENCE: 168
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
```

-continued

```
accggatcct aaaccatgag ggtgttgctc gttgccctcg ctctcctggc tctcgctgcg  1740
agcgccacct cccaggtgca gctccaggag ttcggcggcg gcctcgtgca gccgggcggc  1800
tccctccgcc tgagctgcgc cgcgtccggc aggacgggct ccagctacgc gatgggctgg  1860
ttcaggcagg cgcccggcaa ggagagggag ttcgtggcgg ccatctcgtg gagcggcggc  1920
agcaccgact acgctgactc cgtcaagggc cgcttcacca tcagcaggga caacgcgaag  1980
aacacgatgt acctccagat gaactccctg aagccggagg acaccgccgt gtactactgc  2040
gcggtcgacc gcaacctctt caagctgagg gtggccgtcc aggagtacac caacctcggc  2100
cagggcaccc aggtgaccgt gtcctccaag gacgagctgt gacctaggtc cccgaatttc  2160
cccgatcgtt caaacatttg gcaataaagt ttcttaagat tgaatcctgt tgccggtctt  2220
gcgatgatta tcatataatt tctgttgaat tacgttaagc atgtaataat taacatgtaa  2280
tgcatgacgt tatttatgag atgggttttt atgattagag tcccgcaatt atacatttaa  2340
tacgcgatag aaaacaaaat atagcgcgca aactaggata aattatcgcg cgcggtgtca  2400
tctatgttac tagatcggga attggaattc ctgcagtgca gcgtgacccg gtcgtgcccc  2460
tctctagaga taatgagcat tgcatgtcta agttataaaa aattaccaca tattttttt  2520
gtcacacttg tttgaagtgc agtttatcta tctttataca tatatttaaa ctttactcta  2580
cgaataatat aatctatagt actacaataa tatcagtgtt ttagagaatc atataaatga  2640
acagttagac atggtctaaa ggacaattga gtattttgac aacaggactc tacagtttta  2700
tctttttagt gtgcatgtgt tctccttttt ttttgcaaat agcttcacct atataatact  2760
tcatccattt tattagtaca tccatttagg gtttagggtt aatggttttt atagactaat  2820
tttttagta catctatttt attctatttt agcctctaaa ttaagaaaac taaaactcta  2880
ttttagtttt tttatttaat aatttagata taaaatagaa taaaataaag tgactaaaaa  2940
ttaaacaaat accctttaag aaattaaaaa aactaaggaa acatttttct tgtttcgagt  3000
agataatgcc agcctgttaa acgccgtcga cgagtctaac ggacaccaac cagcgaacca  3060
gcagcgtcgc gtcgggccaa gcgaagcaga cggcacggca tctctgtcgc tgcctctgga  3120
cccctctcga gagttccgct ccaccgttgg acttgctccg ctgtcggcat ccagaaattg  3180
cgtggcggag cggcagacgt gagccggcac ggcaggcggc ctcctcctcc tctcacggca  3240
cggcagctac gggggattcc tttcccaccg ctccttcgct ttcccttcct cgcccgccgt  3300
aataaataga cacccctcc acaccctctt tccccaacct cgtgttgttc ggagcgcaca  3360
cacacacaac cagatctccc ccaaatccac ccgtcggcac ctccgcttca aggtacgccg  3420
ctcgtcctcc cccccccccc ctctctacct tctctagatc ggcgttccgg tccatggtta  3480
gggcccggta gttctacttc tgttcatgtt tgtgttagat ccgtgtttgt gttagatccg  3540
tgctgctagc gttcgtacac ggatgcgacc tgtacgtcag acacgttctg attgctaact  3600
tgccagtgtt tctctttggg gaatcctggg atggctctag ccgttccgca gacgggatcg  3660
atttcatgat ttttttgtt tcgttgcata gggtttggtt tgcccttttc ctttatttca  3720
atatatgccg tgcacttgtt tgtcgggtca tcttttcatg cttttttttg tcttggttgt  3780
gatgatgtgg tctggttggg cggtcgttct agatcggagt agaattctgt ttcaaactac  3840
ctggtggatt tattaatttt ggatctgtat gtgtgtgcca tacatattca tagttacgaa  3900
ttgaagatga tggatggaaa tatcgatcta ggataggtat acatgttgat gcgggtttta  3960
ctgatgcata tacagagatg ctttttgttc gcttggttgt gatgatgtgg tgtggttggg  4020
cggtcgttca ttcgttctag atcggagtag aatactgttt caaactacct ggtgtattta  4080
ttaattttgg aactgtatgt gtgtgtcata catcttcata gttacgagtt taagatggat  4140
ggaaatatcg atctaggata ggtatacatg ttgatgtggg ttttactgat gcatatacat  4200
gatggcatat gcagcatcta ttcatatgct ctaaccttga gtacctatct attataataa  4260
acaagtatgt tttataatta ttttgatctt gatatacttg gatgatggca tatgcagcag  4320
ctatatgtgg attttttag ccctgccttc atacgctatt tatttgcttg gtactgtttc  4380
ttttgtcgat gctcaccctg ttgtttggtg ttacttctgc agatccagat ctaaaccatg  4440
cagaaactca ttaactcagt gcaaaactat gcctggggca gcaaaacggc gttgactgaa  4500
ctttatggta tggaaaatcc gtccagccag ccgatggccg agctgtggat gggcgcacat  4560
ccgaaaagca gttcacgagt gcagaatgcc gccggagata tcgtttcact gcgtgatgtg  4620
attgagagtg ataaatcgac tctgctcgga gaggccgttg ccaaacgctt tggcgaactg  4680
cctttcctgt tcaaagtatt atgcgcagca cagccactct ccattcaggt tcatccaaac  4740
aaacacaatt ctgaaatcgg ttttgccaaa gaaaatgccg caggtatccc gatggatgcc  4800
gccgagcgta actataaaga tcctaaccac aagccggagc tggtttttgc gctgacgcct  4860
ttccttgcga tgaacgcgtt tcgtgaattt tccgagattg tctccctact ccagccggtc  4920
gcaggtgcac atccggcgat tgctcacttt ttacaacagc ctgatgccga acgtttaagc  4980
gaactgttcg ccagcctgtt gaatatgcag ggtgaagaaa aatcccgcgc gctggcgatt  5040
ttaaaatcgg ccctcgatag ccagcagggt gaaccgtggc aaacgattcg tttaatttct  5100
gaattttacc cggaagacag cggtctgttc tccccgctat tgctgaatgt ggtgaaattg  5160
aaccctggcg aagcgatgtt cctgttcgct gaaacaccgc acgcttacct gcaaggcgtg  5220
gcgctggaag tgatggcaaa ctccgataac gtgctgcgtg cgggtctgac gcctaaatac  5280
attgatattc cggaactggt tgccaatgtg aaattcgaag ccaaaccggc taaccagttg  5340
ttgacccagc cggtgaaaca aggtgcagaa ctggacttcc cgattccagt ggatgatttt  5400
gccttctcgc tgcatgacct tagtgataaa gaaaccacca ttagccagca gagtgccgcc  5460
attttgttct gcgtcgaagg cgatgcaacg ttgtggaaag gttctcagca gttacagctt  5520
aaaccgggtg aatcagcgtt tattgccgcc aacgaatcac cggtgactgt caaaggccac  5580
ggccgtttag cgcgtgttta caacaagctg taagagctta ctgaaaaaat taacatctct  5640
tgctaagctg ggagctctag atccccgaat ttccccgatc gttcaaacat ttggcaataa  5700
agtttcttaa gattgaatcc tgttgccggt cttgcgatga ttatcatata atttctgttg  5760
aattacgtta agcatgtaat aattaacatg taatgcatga cgttatttat gagatgggtt  5820
tttatgatta gagtcccgca attatacatt taatacgcga tagaaaacaa aatatagcgc  5880
gcaaactagg ataaattatc gcgcgcggtg tcatctatgt tactagatcg ggaattggcg  5940
agctcgaatt aattcagtac attaaaaacg tccgcaatgt gttattaagt tgtctaagcg  6000
tcaatttgtt tacaccacaa tatatcctgc ca                                6032
```

```
SEQ ID NO: 169          moltype = DNA  length = 6029
FEATURE                 Location/Qualifiers
misc_feature            1..6029
                        note = Synthetic construct, pAG4995
source                  1..6029
```

mol_type = other DNA
organism = synthetic construct
SEQUENCE: 169
```
gtttacccgc caatatatcc tgtcaaacac tgatagttta aactgaaggc gggaaacgac 60
aacctgatca tgagcggaga attaagggag tcacgttatg acccccgccg atgacgcggg 120
acaagccgtt ttacgtttgg aactgacaga accgcaacgt tgaaggagcc actcagccta 180
agcggccgca ttggacttaa ttaagtgagg ccggccaagc gtcgatttaa atgtaccaca 240
tggcgcgcca actatcatgc gatcgcttca tgtctaactc gagttactgg tacgtaccaa 300
atccatggaa tcaaggtacc aaagtaatca tattatttta tgtgtgaatc ttctttactt 360
tttcatttga ttatgattat gaaggtatga ccttcataac cttcgtccga aatccattat 420
atccaaagga aaataatgct tcgaaggacg aaggattttg atatttaaca ttttatgttg 480
ccttgttctt aattcatagc atttgagaac aagtccccaa caccaatctt tatctttact 540
atattaaagc accagttcaa cgatcgtctc gtgtcaatat tattaaaaaa ctcctacatt 600
tctttataat caacccgcac tcttataatc tcttctctta ctactataat aagagagttt 660
atgtacaaaa taaggtgaaa ttatgtataa gtgttctgga ccttggttgt tggctcatat 720
tcacacaacc taatcaatag aaaacatatg ttttattaaa acaaaattta tcatatatat 780
atatatatat atatatatat atatatatat atataatata aaccgtagca atgcacaggc 840
atatgactag tggcaactta ataccatgtg tgtattaaga tgaataagag gtatccaaat 900
aaataacttg ttcgcttacg tctggatcga aaggggttgg aaacgattaa atctcttcct 960
agtcaaaatt aaatagaagg agatttaatc gatttctccc aatccccttc gatccaggtg 1020
caaccgaata agtccttaaa tgttgaggaa cacgaaacaa ccatgcattg gcatgtaaag 1080
ctccaagaat tcgttgtatc cttaacaact cacagaacat caaccaaaat tgcacgtcaa 1140
gggtattggg taagaaacaa tcaaacaaat cctctctgtg tgcaaagaaa cacggtgagt 1200
catgccgaga tcatactcat ctgatataca tgcttacagc tcacaagaca ttacaaacaa 1260
ctcatattgc attacaaaga tcgtttcatg aaaaataaaa taggccggaa caggacaaaa 1320
atccttgacg tgtaaagtaa atttacaaca aaaaaaaagc catatgtcaa gctaaatcta 1380
attcgtttta cgtagatcaa caacctgtag aaggcaacaa aactgagcca cgcagaagta 1440
cagaatgatt ccagatgaac catcgacgtg ctacgtaaag agagtgacga gtcatataca 1500
tttggcaaga aaccatgaag ctgcctacag ccgtctcggt ggcataagaa cacaagaaat 1560
tgtgttaatt aatcaaagct ataaataacg ctcgcatgcc tgtgcacttc tccatcacca 1620
ccactgggtc ttcagaccat tagctttatc tactccagag cgcagaagaa cccgatcgac 1680
accggatcct aaaccatgag ggtgttgctc gttgccctcg ctctcctggc tctcgctgcg 1740
agcgccacct cccaggtgca gctccaggcc tccggcggcg gcctcgtgca ggcgggcggc 1800
tccctccgcc tgagctgcgc cgcgtccggc aggaccttca acagctacgc ttggggctgg 1860
ttcaggcagg cgccgggcaa ggagcgcggc ttcgtggcca ggatctcctt cagcggcggc 1920
cacacctact actccgacag cgtcaagggc cgcttcacga tcagcaggga caacgccaag 1980
aactccgtgt acctccagat gaacagcctg aagcccgagg acacggccgt ctactactgc 2040
gcggcggacc cgaccccata cggcctccgc aacgagagga actaccacta ctggggccag 2100
ggcacccagg tgaccgtgtc ctccaaggac gagctgtgac ctaggtcccc gaatttcccc 2160
gatcgttcaa acatttggca ataaagtttc ttaagattga atcctgttgc cggtcttgcg 2220
atgattatca tataatttct gttgaattac gttaagcatg taataattaa catgtaatgc 2280
atgacgttat ttatgagatg ggtttttatg attagagtcc cgcaattata catttaatac 2340
gcgatagaaa acaaaatata gcgcgcaaac taggataaat tatcgcgcgc ggtgtcatct 2400
atgttactag atcgggaatt ggaattcctg cagtgcagcg tgacccggtc gtgcccctct 2460
ctagagataa tgagcattgc atgtctaagt tataaaaaat taccacatat ttttttttgtc 2520
acacttgttt gaagtgcagt ttatctatct ttatacatat atttaaactt tactctacga 2580
ataatataat ctatagtact acaataatat cagtgtttta gagaatcata taaatgaaca 2640
gttagacatg gtctaaagga caattgagta ttttgacaac aggactctac agttttatct 2700
ttttagtgtg catgtgttct cctttttttt tgcaaatagc ttcacctata taatacttca 2760
tccattttat tagtacatcc atttagggtt tagggttaat ggtttttata gactaatttt 2820
tttagtacat ctattttatt ctattttagc ctctaaatta agaaaactaa aactctattt 2880
tagttttttt atttaataat ttagatataa aatagaataa aataaagtga ctaaaaatta 2940
aacaaatacc ctttaagaaa ttaaaaaaac taaggaaaca tttttcttgt ttcgagtaga 3000
taatgccagc ctgttaaacg ccgtcgacga gtctaacgga caccaaccag cgaaccagca 3060
gcgtcgcgtc gggccaagcg aagcagacgg cacggcatct ctgtcgctgc ctctggaccc 3120
ctctcgagag ttccgctcca ccgttggact tgctccgctg tcggcatcca gaaattgcgt 3180
ggcggagcgg cagacgtgag ccggcacggc aggcggcctc ctcctcctct cacggcacgg 3240
cagctacggg ggattccttt cccaccgctc cttcgctttc ccttcctcgc ccgccgtaat 3300
aaatagacac cccctccaca ccctctttcc ccaacctcgt gttgttcgga gcgcacacac 3360
acacaaccag atctccccca aatccacccg tcggcacctc cgcttcaagg tacgccgctc 3420
gtcctccccc ccccccccctc tctaccttct ctagatcggc gttccggtcc atggttaggg 3480
cccggtagtt ctacttctgt tcatgtttgt gttagatccg tgtttgtgtt agatccgtgc 3540
tgctagcgtt cgtacacgga tgcgacctgt acgtcagaca cgttctgatt gctaacttgc 3600
cagtgtttct ctttggggaa tcctgggatg gctctagccg ttccgcagac gggatcgatt 3660
tcatgatttt ttttgtttcg ttgcataggg tttggtttgc ccttttcctt tatttcaata 3720
tatgccgtgc acttgtttgt cgggtcatct tttcatgctt ttttttgtct tggttgtgat 3780
gatgtggtct ggttgggcgg tcgttctaga tcggagtaga attctgtttc aaactacctg 3840
gtggatttat taattttgga tctgtatgtg tgtgccatac atattcatag ttacgaattg 3900
aagatgatgg atggaaatat cgatctagga taggtataca tgttgatgcg ggttttactg 3960
atgcatatac agagatgctt tttgttcgct tggttgtgat gatgtggtgt ggttgggcgg 4020
tcgttcattc gttctagatc ggagtagaat actgtttcaa actacctggt gtatttatta 4080
attttggaac tgtatgtgtg tgtcatacat cttcatagtt acgagtttaa gatggatgga 4140
aatatcgatc taggataggt atacatgttg atgtgggttt tactgatgca tatacatgat 4200
ggcatatgca gcatctattc atatgctcta accttgagta cctatctatt ataataaaca 4260
agtatgtttt ataattattt tgatcttgat atacttggat gatggcatat gcagcagcta 4320
tatgtggatt tttttagccc tgccttcata cgctatttat ttgcttggta ctgtttcttt 4380
tgtcgatgct caccctgttg tttggtgtta cttctgcaga tccagatcta aaccatgcag 4440
aaactcatta actcagtgca aaactatgcc tggggcagca aaacggcgtt gactgaactt 4500
tatggtatgg aaaatccgtc cagccagccg atggccgagc tgtggatggg cgcacatccg 4560
```

```
aaaagcagtt cacgagtgca gaatgccgcc ggagatatcg tttcactgcg tgatgtgatt  4620
gagagtgata aatcgactct gctcggagag gccgttgcca aacgctttgg cgaactgcct  4680
ttcctgttca aagtattatg cgcagcacag ccactctcca ttcaggttca tccaaacaaa  4740
cacaattctg aaatcggttt tgccaaagaa aatgccgcag gtatcccgat ggatgccgcc  4800
gagcgtaact ataaagatcc taaccacaag ccggagctgg tttttgcgct gacgcctttc  4860
cttgcgatga acgcgtttcg tgaattttcc gagattgtct ccctactcca gccggtcgca  4920
ggtgcacatc cggcgattgc tcactttttta caacagcctg atgccgaacg tttaagcgaa  4980
ctgttcgcca gcctgttgaa tatgcagggt gaagaaaaat cccgcgcgct ggcgatttta  5040
aaatcggccc tcgatagcca gcagggtgaa ccgtggcaaa cgattcgttt aatttctgaa  5100
ttttacccgg aagacagcgg tctgttctcc ccgctattgc tgaatgtggt gaaattgaac  5160
cctggcgaag cgatgttcct gttcgctgaa acaccgcacg cttacctgca aggcgtggcg  5220
ctggaagtga tggcaaactc cgataacgtg ctgcgtgcgg gtctgacgcc taaatacatt  5280
gatattccgg aactggttgc caatgtgaaa ttcgaagcca aaccggctaa ccagttgttg  5340
acccagccgg tgaaacaagg tgcagaactg gacttccccga ttccagtgga tgattttgcc  5400
ttctcgctgc atgaccttag tgataaagaa accaccatta gccagcagag tgccgccatt  5460
ttgttctgcg tcgaaggcga tgcaacgttg tggaaaggtt ctcagcagtt acagcttaaa  5520
ccgggtgaat cagcgtttat tgccgccaac gaatcaccgg tgactgtcaa aggccacggc  5580
cgtttagcgc gtgtttacaa caagctgtaa gagcttactg aaaaaattaa catctcttgc  5640
taagctggga gctctagatc cccgaatttc cccgatcgtt caaacatttg gcaataaagt  5700
ttcttaagat tgaatcctgt tgccggtctt gcgatgatta tcatataatt tctgttgaat  5760
tacgttaagc atgtaataat taacatgtaa tgcatgacgt tatttatgag atgggttttt  5820
atgattagag tcccgcaatt atacatttaa tacgcgatag aaaacaaaat atagcgcgca  5880
aactaggata aattatcgcg cgcggtgtca tctatgttac tagatcggga attggcgagc  5940
tcgaattaat tcagtacatt aaaaacgtcc gcaatgtgtt attaagttgt ctaagcgtca  6000
atttgtttac accacaatat atcctgcca                                    6029

SEQ ID NO: 170          moltype = DNA  length = 8274
FEATURE                 Location/Qualifiers
misc_feature            1..8274
                        note = Synthetic construct, pAG4996
source                  1..8274
                        mol_type = other DNA
                        organism = synthetic construct
SEQUENCE: 170
gtttacccgc caatatatcc tgtcaaacac tgatagttta aactgaaggc gggaaacgac  60
aacctgatca tgagcggaga attaagggag tcacgttatg accccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggtgca gctccaggag tccggcggcg gcctcgtgca gccgggcggc  1800
tccctccgcc tgagctgcgc cgcgtccggc aacatcttca gcatcaacac gatgggctgg  1860
tacaggcagg cccccggcaa gcagcgggag ctcgtggcct ccatcaccac gggcggcacc  1920
acgaactacg aggacagcgt caagggccgc ttcaccatct ccagggacaa cgccaagaag  1980
acggtgtacc tccagatgaa ccgcctgaag ccggaggaca cggcggtcta ctactgcaac  2040
caccgcaggt cctacagcgg cagggactac cccgtgtacg gcatggacta ctggggcaag  2100
ggcaccctcg tgaccgtgtc ctccaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt gttaattaag tctaactcga gttactggta cgtatacagg  2460
gttccttgcg tgaagaaggg tggcctgcgg ttcaccatta acggtcacga ctacttccag  2520
ctagtactgg tgaccaacgt cgcggcggca gggtcaatca agtccatgga ggttatgggt  2580
tccaacacag cggattggat gccgatggca cgtaactggg gcgcccaatg gcactcactg  2640
gcctacctca ccggtcaagg tctatccttt agggtcacca acacagatga ccaaacgctc  2700
```

-continued

```
gtcttcacca acgtcgtgcc accaggatgg aagtttggcc agacatttgc aagcaagctg  2760
cagttcaagt gagaggagaa gcctgaattg ataccggagc gtttcttttg ggagtaacat  2820
ctctggttgc ctagcaaaca tatgattgta tataagtttc gttgtgcgtt tattctttcg  2880
gtgtgtaaaa taacatacat gctttcctga tattttcttg tatatatgta cacacacacg  2940
acaaatcctt ccatttctat tattattgaa caatttaatt gcgagggcga gtacttgtct  3000
gtttaccttt ttttttcag atggcatttt atagtttaac ctttcatgga ccggcagtag  3060
ttctaaccat gaatgaaaag aaatcatagt ccacaccacg cagggacatt gtggtcattt  3120
tagacaagac gatttgatta atgtcttgta tgatatggtc gacagtgagg actaacaaac  3180
atatggcata ttttattacc ggcgagttaa ataaatttat gtcacagtaa taaactgcct  3240
aataaatgca cgccagaaaa tataatgata aaaaaaagaa aagatacata agtccattgc  3300
ttctactttt ttaaaaatta aatccaacat tttctatttt ttggtataaa cttggaagta  3360
ctagttggat atgcaaaatc atctaacctc catatatttc atcaatttgt ttactttaca  3420
tatgggagag gatagtatgt caaagaaaat gacaacaagc ttacaagttt cttattttaa  3480
aagttccgct aacttatcaa gcatagtgtg ccacgcaaaa ctgacaacaa accaacaaat  3540
ttaaggagcg cctaacttat catctatgac ataccgcaca aaatgataac atactagaga  3600
aactttattg cacaaaagga aatttatcca taaggcaaag gaacatctta aggctttgga  3660
tatacattta ccaacaagca ttgtttgtat taccccctaaa gcgcaagaca tgtcatccat  3720
gagtcatagt gtgtatatct caacattgca aagctacctt ttttctatta tacttttcgc  3780
attataggct agatattatc tatacatgtc aacaaactct atccctacgt catatctgaa  3840
gattcttttc ttcactatat aagttggctt ccctgtcatt gaactcacat caaccagccc  3900
aagtttccaa taacatcctc aaatagctgg atcctaaacc atgagggtgt tgctcgttgc  3960
cctcgctctc ctggctctcg ctgcgagcgc cacctcccag gttcagctgc aggaaagcgg  4020
tggcggactg gtgcagccag gtggcagcct caggctgagc tgcgctgcta gcggcaatat  4080
ttttagcatt aacacaatgg gttggtatag acaggctcct ggcaagcagc gtgagctcgt  4140
tgccagcatt accacgggtg gtacaaccaa ttatgaagat agcgtgaagg gtcgttttac  4200
cattagcagg gacaatgcta agaagaccgt ttacctccag atgaacaggc tgaagccaga  4260
agataccgcc gtgtattact gcaaccacag gagaagctat agcggaagag attatcctgt  4320
ttacggtatg gactactggg gcaagggaac cctggttacc gtgagcagca aggacgagct  4380
gtaacctagg tccccgaatt tccccgatcg ttcaaacatt tggcaataaa gtttcttaag  4440
attgaatcct gttgccggtc ttgcgatgat tatcatataa tttctgttga attacgttaa  4500
gcatgtaata attaacatgt aatgcatgac gttatttatg agatgggttt ttatgattag  4560
agtcccgcaa ttatacattt aatacgcgat agaaaacaaa atatagcgcg caaactagga  4620
taaattatcg cgcgcggtgt catctatgtt actagatcgg gaattggaat tcctgcagtg  4680
cagcgtgacc cggtcgtgcc cctctctaga gataatgagc attgcatgtc taagttataa  4740
aaaattacca catatttttt ttgtcacact tgtttgaagt gcagtttatc tatctttata  4800
catatattta aactttactc tacgaataat ataatctata gtactacaat aatatcagtg  4860
ttttagagaa tcatataaat gaacagttag acatggtcta aaggacaatt gagtattttg  4920
acaacaggac tctacagttt tatcttttta gtgtgcatgt gttctccttt tttttgcaa  4980
atagcttcac ctatataata cttcatccat ttttattagta catccattta gggtttaggg  5040
ttaatggttt ttatagacta attttttag tacatctatt ttattctatt ttagcctcta  5100
aattaagaaa actaaaactc tattttagtt tttttattta ataatttaga tataaaatag  5160
aataaaataa agtgactaaa aattaaacaa ataccctta agaaattaaa aaaactaagg  5220
aaacattttt cttgtttcga gtagataatg ccagcctgtt aaacgccgtc gacgagtcta  5280
acggacacca accagcgaac cagcagcgtc gcgtcgggcc aagcgaagca gacggcacgg  5340
catctctgtc gctgcctctg gacccctctc gagagttccg ctccaccgtt ggacttgctc  5400
cgctgtcggc atccagaaat tgcgtggcgg agcggcagac gtgagccggc acggcaggcg  5460
gcctcctcct cctctcacgg cacggcagct acgggggatt cctttcccac cgctccttcg  5520
ctttcccttc ctcgcccgcc gtaataaata gacacccccct ccacaccctc tttccccaac  5580
ctcgtgttgt tcggagcgca cacacacaca accagatctc ccccaaatcc acccgtcggc  5640
acctccgctt caaggtacgc cgctcgtcct cccccccccc ccctctctac cttctctaga  5700
tcggcgttcc ggtccatggt tagggcccgg tagttctact tctgttcatg tttgtgttag  5760
atccgtgttt gtgttagatc cgtgctgcta gcgttcgtac acggatgcga cctgtacgtc  5820
agacacgttc tgattgctaa cttgccagtg tttctctttg gggaatcctg ggatggctct  5880
agccgttccg cagacgggat cgatttcatg atttttttttg tttcgttgca tagggtttgg  5940
tttgcccttt tcctttattt caatatatgc cgtgcacttg tttgtcgggt catcttttca  6000
tgcttttttt tgtcttggtt gtgatgatgt ggtctggttg ggcggtcgtt ctagatcgga  6060
gtagaattct gtttcaaact acctggtgga tttattaatt ttggatctgt atgtgtgtgc  6120
catacatatt catagttacg aattgaagat gatggatgga aatatcgatc taggataggt  6180
atacatgttg atgcgggttt tactgatgca tatacagaga tgctttttgt tcgcttggtt  6240
gtgatgatgt ggtgtggttg ggcggtcgtt cattcgttct agatcggagt agaatactgt  6300
ttcaaactac ctggtgtatt tattaatttt ggaactgtat gtgtgtgtca tacatcttca  6360
tagttacgag tttaagatgg atggaaatat cgatctagga taggtataca tgttgatgtg  6420
ggttttactg atgcatatac atgatggcat atgcagcatc tattcatatg ctctaacctt  6480
gagtacctat ctattataat aaacaagtat gttttataat tattttgatc ttgatatact  6540
tggatgatgg catatgcagc agctatatgt ggattttttt agccctgcct tcatacgcta  6600
tttatttgct tggtactgtt tcttttgtcg atgctcaccc tgttgtttgg tgttacttct  6660
gcagatccag atctaaacca tgcagaaact cattaactca gtgcaaaact atgcctgggg  6720
cagcaaaacg gcgttgactg aactttatgg tatggaaaat ccgtccagcc agccgatggc  6780
cgagctgtgg atgggcgcac atccgaaaag cagttcacga gtgcagaatg ccgccggaga  6840
tatcgtttca ctgcgtgatg tgattgagag tgataaatcg actctgctcg gagaggccgt  6900
tgccaaacgc tttggcgaac tgcctttcct gttcaaagta ttatgcgcag cacagccact  6960
ctccattcag gttcatccaa acaaacacaa ttctgaaatc ggttttgcca aagaaaatgc  7020
cgcaggtatc ccgatggatg ccgccgagcg taactataaa gatcctaacc acaagccgga  7080
gctggttttt gcgctgacgc ctttccttgc gatgaacgcg tttcgtgaat tttccgagat  7140
tgtctcccta ctccagccgg tcgcaggtgc acatccggcg attgctcact tttacaaca  7200
gcctgatgcc gaacgtttaa gcgaactgtt cgccagcctg ttgaatatgc agggtgaaga  7260
aaaatcccgc gcgctggcga ttttaaaatc ggccctcgat agccagcagg gtgaaccgtg  7320
gcaaacgatt cgtttaattt ctgaatttta cccggaagac agcggtctgt tctccccgct  7380
attgctgaat gtggtgaaat tgaaccctgg cgaagcgatg ttcctgttcg ctgaaacacc  7440
```

```
gcacgcttac ctgcaaggcg tggcgctgga agtgatggca aactccgata acgtgctgcg  7500
tgcgggtctg acgcctaaat acattgatat tccggaactg gttgccaatg tgaaattcga  7560
agccaaaccg gctaaccagt tgttgaccca gccggtgaaa caaggtgcag aactggactt  7620
cccgattcca gtggatgatt ttgccttctc gctgcatgac cttagtgata aagaaaccac  7680
cattagccag cagagtgccg ccattttgtt ctgcgtcgaa ggcgatgcaa cgttgtggaa  7740
aggttctcag cagttacagc ttaaaccggg tgaatcagcg tttattgccg ccaacgaatc  7800
accggtgact gtcaaaggcc acggccgttt agcgcgtgtt tacaacaagc tgtaagagct  7860
tactgaaaaa attaacatct cttgctaagc tgggagctct agatccccga atttccccga  7920
tcgttcaaac atttggcaat aaagtttctt aagattgaat cctgttgccg gtcttgcgat  7980
gattatcata taatttctgt tgaattacgt taagcatgta ataattaaca tgtaatgcat  8040
gacgttattt atgagatggg tttttatgat tagagtcccg caattataca tttaatacgc  8100
gatagaaaac aaaatatagc gcgcaaacta ggataaatta tcgcgcgcgg tgtcatctat  8160
gttactagat cgggaattgg cgagctcgaa ttaattcagt acattaaaaa cgtccgcaat  8220
gtgttattaa gttgtctaag cgtcaatttg tttacaccac aatatatcct gcca        8274

SEQ ID NO: 171          moltype = DNA  length = 8280
FEATURE                 Location/Qualifiers
misc_feature            1..8280
                        note = Synthetic construct, pAG4997
source                  1..8280
                        mol_type = other DNA
                        organism = synthetic construct
SEQUENCE: 171
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggtgca gctccaggag ttcggcggcg gcctcgtgca gccgggcggc  1800
tccctccgcc tgagctgcgc cgcgtccggc aggacgggct ccagctacgc gatgggctgg  1860
ttcaggcagg cgcccggcaa ggagagggag ttcgtggcgg ccatctcgtg gagcggcggc  1920
agcaccgact acgctgactc cgtcaagggc cgcttcacca tcagcaggga caacgcgaag  1980
aacacgatgt acctccagat gaactccctg aagccggagg acaccgccgt gtactactgc  2040
gcggtcgacc gcaacctctt caagctgagg gtggccgtcc aggagtacac caacctcggc  2100
cagggcaccc aggtgaccgt gtcctccaag gacgagctgt aacctaggtc cccgaatttc  2160
cccgatcgtt caaacatttg gcaataaagt ttcttaagat tgaatcctgt tgccggtctt  2220
gcgatgatta tcatataatt tctgttgaat tacgttaagc atgtaataat taacatgtaa  2280
tgcatgacgt tatttatgag atgggttttt atgattagag tcccgcaatt atacatttaa  2340
tacgcgatag aaaacaaaat atagcgcgca aactaggata aattatcgcg cgcggtgtca  2400
tctatgttac tagatcggga attgttaatt aagtctaact cgagttactg gtacgtatac  2460
agggttcctt gcgtgaagaa gggtggcctg cggttcacca ttaacggtca cgactacttc  2520
cagctagtac tggtgaccaa cgtcgcggcg gcagggtcaa tcaagtccat ggaggttatg  2580
ggttccaaca cagcggattg gatgccgatg gcacgtaact ggggcgccca atggcactca  2640
ctggcctacc tcaccggtca aggtctatcc tttagggtca ccaacacaga tgaccaaacg  2700
ctcgtcttca ccaacgtcgt gccaccagga tggaagtttg gccagacatt tgcaagcaag  2760
ctgcagttca agtgagagga gaagcctgaa ttgataccgg agcgtttctt ttgggagtaa  2820
catctctggt tgcctagcaa acatatgatt gtatataagt ttcgttgtgc gtttattctt  2880
tcggtgtgta aaataacata catgctttcc tgatattttc ttgtatatat gtacacacac  2940
acgacaaatc cttccatttc tattattatt gaacaattta attgcgaggg cgagtacttg  3000
tctgtttacc tttttttttt cagatggcat tttatagttt aacctttcat ggaccggcag  3060
tagttctaac catgaatgaa aagaaatcat agtccacacc acgcagggac attgtggtca  3120
ttttagacaa gacgatttga ttaatgtctt gtatgatatg gtcgacagtg aggactaaca  3180
aacatatggc atattttatt accggcgagt taaataaatt tatgtcacag taataaactg  3240
cctaataaat gcacgccaga aaatataatg ataaaaaaaa gaaaagatac ataagtccat  3300
tgcttctact tttttaaaaa ttaaatccaa cattttctat tttttggtat aaacttggaa  3360
```

-continued

```
gtactagttg gatatgcaaa atcatctaac ctccatatat ttcatcaatt tgtttacttt  3420
acatatggga gaggatagta tgtcaaagaa aatgacaaca agcttacaag tttcttattt  3480
taaaagttcc gctaacttat caagcatagt gtgccacgca aaactgacaa caaaccaaca  3540
aatttaagga gcgcctaact tatcatctat gacataccgc acaaaatgat aacatactag  3600
agaaacttta ttgcacaaaa ggaaatttat ccataaggca aaggaacatc ttaaggcttt  3660
ggatatacat ttaccaacaa gcattgtttg tattacccct aaagcgcaag acatgtcatc  3720
catgagtcat agtgtgtata tctcaacatt gcaaagctac ctttttttcta ttatactttt  3780
cgcattatag gctagatatt atctatacat gtcaacaaac tctatcccta cgtcatatct  3840
gaagattctt ttcttcacta tataagttgg cttccctgtc attgaactca catcaaccag  3900
cccaagtttc caataacatc ctcaaatagc tggatcctaa accatgaggg tgttgctcgt  3960
tgccctcgct ctcctggctc tcgctgcgag cgccacctcc caggttcagc tccaggagtt  4020
tggtggcgga ctggtgcagc caggtggcag cctcaggctg agctgcgctg ctagcggtag  4080
aaccggcagc agctatgcta tgggatggtt tagacaggct ccaggcaagg agcgtgaatt  4140
tgttgctgcc attagctgga gcggaggtag caccgattat gctgacagcg tgaagggcag  4200
gtttaccatt agcagagata atgccaagaa caccatgtac ctccagatga atagcctgaa  4260
gccagaggat accgctgttt attactgcgc cgtggaccgt aatctcttta agctgagggt  4320
tgctgtgcag gaatacacca acctcggcca gggaacccag gttaccgtga gcagcaagga  4380
cgagctgtaa cctaggtccc cgaatttccc cgatcgttca aacatttggc aataaagttt  4440
cttaagattg aatcctgttg ccggtcttgc gatgattatc atataatttc tgttgaatta  4500
cgttaagcat gtaataatta acatgtaatg catgacgtta tttatgagat gggtttttat  4560
gattagagtc ccgcaattat acatttaata cgcgatagaa aacaaaatat agcgcgcaaa  4620
ctaggataaa ttatcgcgcg cggtgtcatc tatgttacta gatcgggaat tggaattcct  4680
gcagtgcagc gtgacccggt cgtgcccctc tctagagata atgagcattg catgtctaag  4740
ttataaaaaa ttaccacata tttttttgt cacacttgtt tgaagtgcag tttatctatc  4800
tttatacata tatttaaact ttactctacg aataatataa tctatagtac tacaataata  4860
tcagtgtttt agagaatcat ataaatgaac agttagacat ggtctaaagg acaattgagt  4920
attttgacaa caggactcta cagttttatc tttttagtgt gcatgtgttc tccttttttt  4980
ttgcaaatag cttcacctat ataatacttc atccatttta ttagtacatc catttagggt  5040
ttagggttaa tggtttttat agactaattt ttttagtaca tctattttat tctattttag  5100
cctctaaatt aagaaaacta aaactctatt ttagtttttt tatttaataa tttagatata  5160
aaatagaata aaataaagtg actaaaaatt aaacaaatac cctttaagaa attaaaaaaa  5220
ctaaggaaac atttttcttg tttcgagtag ataatgccag cctgttaaac gccgtcgacg  5280
agtctaacgg acaccaacca gcgaaccagc agcgtcgcgt cgggccaagc gaagcagacg  5340
gcacggcatc tctgtcgctg cctctggacc cctctcgaga gttccgctcc accgttggac  5400
ttgctccgct gtcggcatcc agaaattgcg tggcggagcg gcagacgtga gccggcacgg  5460
caggcggcct cctcctcctc tcacggcacg gcagctacgg gggattcctt tcccaccgct  5520
ccttcgcttt cccttcctcg cccgccgtaa taaatagaca cccccctccac accctctttc  5580
cccaacctcg tgttgttcgg agcgcacaca cacacaacca gatctccccc aaatccaccc  5640
gtcggcacct ccgcttcaag gtacgccgct cgtcctcccc cccccccct ctctaccttc  5700
tctagatcgg cgttccggtc catggttagg gcccggtagt tctacttctg ttcatgtttg  5760
tgttagatcc gtgtttgtgt tagatccgtg ctgctagcgt tcgtacacgg atgcgacctg  5820
tacgtcagac acgttctgat tgctaacttg ccagtgtttc tctttgggga atcctgggat  5880
ggctctagcc gttccgcaga cgggatcgat ttcatgattt tttttgtttc gttgcatagg  5940
gtttggtttg cccttttcct ttatttcaat atatgccgtg cacttgtttg tcgggtcatc  6000
ttttcatgct tttttttgtc ttggttgtga tgatgtggtc tggttgggcg gtcgttctag  6060
atcggagtag aattctgttt caaactacct ggtggattta ttaattttgg atctgtatgt  6120
gtgtgccata catattcata gttacgaatt gaagatgatg gatggaaata tcgatctagg  6180
ataggtatac atgttgatgc gggttttact gatgcatata cagagatgct ttttgttcgc  6240
ttggttgtga tgatgtggtg tggttgggcg gtcgttcatt cgttctagat cggagtagaa  6300
tactgtttca aactacctgg tgtatttatt aattttggaa ctgtatgtgt gtgtcataca  6360
tcttcatagt tacgagttta agatggatgg aaatatcgat ctaggatagg tatacatgtt  6420
gatgtgggtt ttactgatgc atatacatga tggcatatgc agcatctatt catatgctct  6480
aaccttgagt acctatctat tataataaac aagtatgttt tataattatt ttgatcttga  6540
tatacttgga tgatggcata tgcagcagct atatgtggat ttttttagcc ctgccttcat  6600
acgctattta tttgcttggt actgtttctt ttgtcgatgc tcaccctgtt gtttggtgtt  6660
acttctgcag atccagatct aaaccatgca gaaactcatt aactcagtgc aaaactatgc  6720
ctggggcagc aaaacggcgt tgactgaact ttatggtatg gaaaatccgt ccagccagcc  6780
gatggccgag ctgtggatgg gcgcacatcc gaaaagcagt tcacgagtgc agaatgccgc  6840
cggagatatc gtttcactgc gtgatgtgat tgagagtgat aaatcgactc tgctcggaga  6900
ggccgttgcc aaacgctttg gcgaactgcc tttcctgttc aaagtattat gcgcagcaca  6960
gccactctcc attcaggttc atccaaacaa acacaattct gaaatcggtt ttgccaaaga  7020
aaatgccgca ggtatcccga tggatgccgc cgagcgtaac tataaagatc ctaaccacaa  7080
gccggagctg gtttttgcgc tgacgccttt ccttgcgatg aacgcgtttc gtgaattttc  7140
cgagattgtc tccctactcc agccggtcgc aggtgcacat ccggcgattg ctcacttttt  7200
acaacagcct gatgccgaac gtttaagcga actgttcgcc agcctgttga atatgcaggg  7260
tgaagaaaaa tcccgcgcgc tggcgatttt aaaatcggcc ctcgatagcc agcagggtga  7320
accgtggcaa acgattcgtt taatttctga attttacccg gaagacagcg gtctgttctc  7380
cccgctattg ctgaatgtgg tgaaattgaa ccctggcgaa gcgatgttcc tgttcgctga  7440
aacaccgcac gcttacctgc aaggcgtggc gctggaagtg atggcaaact ccgataacgt  7500
gctgcgtgcg ggtctgacgc ctaaatacat tgatattccg gaactggttg ccaatgtgaa  7560
attcgaagcc aaaccggcta accagttgtt gacccagccg gtgaaacaag gtgcagaact  7620
ggacttcccg attccagtgg atgattttgc cttctcgctg catgacctta gtgataaaga  7680
aaccaccatt agccagcaga gtgccgccat tttgttctgc gtcgaaggcg atgcaacgtt  7740
gtggaaaggt tctcagcagt tacagcttaa accgggtgaa tcagcgttta ttgccgccaa  7800
cgaatcaccg gtgactgtca aaggccacgg ccgtttagcg cgtgtttaca acaagctgta  7860
agagcttact gaaaaaatta acatctcttg ctaagctggg agctctagat ccccgaattt  7920
ccccgatcgt tcaaacattt ggcaataaag tttcttaaga ttgaatcctg ttgccggtct  7980
tgcgatgatt atcatataat ttctgttgaa ttacgttaag catgtaataa ttaacatgta  8040
atgcatgacg ttatttatga gatgggtttt tatgattaga gtcccgcaat tatacattta  8100
```

-continued

```
atacgcgata gaaaacaaaa tatagcgcgc aaactaggat aaattatcgc gcgcggtgtc  8160
atctatgtta ctagatcggg aattggcgag ctcgaattaa ttcagtacat taaaaacgtc  8220
cgcaatgtgt tattaagttg tctaagcgtc aatttgttta caccacaata tatcctgcca  8280

SEQ ID NO: 172          moltype = DNA  length = 8274
FEATURE                 Location/Qualifiers
misc_feature            1..8274
                        note = Synthetic construct, pAG4998
source                  1..8274
                        mol_type = other DNA
                        organism = synthetic construct
SEQUENCE: 172
gtttacccgc caatatatcc tgtcaaacac tgatagttta aactgaaggc gggaaacgac  60
aacctgatca tgagcggaga attaagggag tcacgttatg acccccgccg atgacgcggg  120
acaagccgtt ttacgtttgg aactgacaga accgcaacgt tgaaggagcc actcagccta  180
agcggccgca ttggacttaa ttaagtgagg ccggccaagc gtcgatttaa atgtaccaca  240
tggcgcgcca actatcatgc gatcgcttca tgtctaactc gagttactgg tacgtaccaa  300
atccatggaa tcaaggtacc aaagtaatca tattatttta tgtgtgaatc ttctttactt  360
tttcatttga ttatgattat gaaggtatga ccttcataac cttcgtccga aatccattat  420
atccaaagga aaataatgct tcgaaggacg aaggattttg atatttaaca ttttatgttg  480
ccttgttctt aattcatagc atttgagaac aagtccccaa caccaatctt tatctttact  540
atattaaagc accagttcaa cgatcgtctc gtgtcaatat tattaaaaaa ctcctacatt  600
tctttataat caacccgcac tcttataatc tcttctctta ctactataat aagagagttt  660
atgtacaaaa taaggtgaaa ttatgtataa gtgttctgga ccttggttgt tggctcatat  720
tcacacaacc taatcaatag aaaacatatg ttttattaaa acaaaattta tcatatatat  780
atatatatat atatatatat atatatatat atataatata aaccgtagca atgcacaggc  840
atatgactag tggcaactta ataccatgtg tgtattaaga tgaataagag gtatccaaat  900
aaataacttg ttcgcttacg tctggatcga aaggggttgg aaacgattaa atctcttcct  960
agtcaaaatt aaatagaagg agatttaatc gatttctccc aatccccttc gatccaggtg  1020
caaccgaata agtccttaaa tgttgaggaa cacgaaacaa ccatgcattg gcatgtaaag  1080
ctccaagaat tcgttgtatc cttaacaact cacagaacat caaccaaaat tgcacgtcaa  1140
gggtattggg taagaaacaa tcaaacaaat cctctctgtg tgcaaagaaa cacggtgagt  1200
catgccgaga tcatactcat ctgatataca tgcttacagc tcacaagaca ttacaaacaa  1260
ctcatattgc attacaaaga tcgtttcatg aaaaataaaa taggccggaa caggacaaaa  1320
atccttgacg tgtaaagtaa atttacaaca aaaaaaaagc catatgtcaa gctaaatcta  1380
attcgtttta cgtagatcaa caacctgtag aaggcaacaa aactgagcca cgcagaagta  1440
cagaatgatt ccagatgaac catcgacgtg ctacgtaaag agagtgacga gtcatataca  1500
tttggcaaga aaccatgaag ctgcctacag ccgtctcggt ggcataagaa cacaagaaat  1560
tgtgttaatt aatcaaagct ataaataacg ctcgcatgcc tgtgcacttc tccatcacca  1620
ccactgggtc ttcagaccat tagctttatc tactccagag cgcagaagaa cccgatcgac  1680
accggatcct aaaccatgag ggtgttgctc gttgccctcg ctctcctggc tctcgctgcg  1740
agcgccacct cccaggtgca gctccaggcc tccggcggcg gcctcgtgca ggcgggcggc  1800
tccctccgcc tgagctgcgc cgcgtccggc aggaccttca acagctacgc ttggggctgg  1860
ttcaggcagg cgccgggcaa ggagcgcggc ttcgtggcca ggatctcctt cagcggcggc  1920
cacacctact actccgacag cgtcaagggc cgcttcacga tcagcaggga caacgccaag  1980
aactccgtgt acctccagat gaacagcctg aagcccgagg acacggccgt ctactactgc  2040
gcggcggacc cgaccccata cggcctccgc aacgagagga actaccacta ctggggccag  2100
ggcacccagg tgaccgtgtc ctccaaggac gagctgtaac ctaggtcccc gaatttcccc  2160
gatcgttcaa acatttggca ataaagtttc ttaagattga atcctgttgc cggtcttgcg  2220
atgattatca tataatttct gttgaattac gttaagcatg taataattaa catgtaatgc  2280
atgacgttat ttatgagatg ggtttttatg attagagtcc cgcaattata catttaatac  2340
gcgatagaaa acaaaatata gcgcgcaaac taggataaat tatcgcgcgc ggtgtcatct  2400
atgttactag atcgggaatt gttaattaag tctaactcga gttactggta cgtatacagg  2460
gttccttgcg tgaagaaggg tggcctgcgg ttcaccatta acggtcacga ctacttccag  2520
ctagtactgg tgaccaacgt cgcggcggca gggtcaatca agtccatgga ggttatgggt  2580
tccaacacag cggattggat gccgatggca cgtaactggg gcgcccaatg gcactcactg  2640
gcctacctca ccggtcaagg tctatccttt agggtcacca acacagatga ccaaacgctc  2700
gtcttcacca acgtcgtgcc accaggatgg aagtttggcc agacatttgc aagcaagctg  2760
cagttcaagt gagaggagaa gcctgaattg ataccggagc gtttcttttg ggagtaacat  2820
ctctggttgc ctagcaaaca tatgattgta tataagtttc gttgtgcgtt tattctttcg  2880
gtgtgtaaaa taacatacat gctttcctga tattttcttg tatatatgta cacacacacg  2940
acaaatcctt ccatttctat tattattgaa caatttaatt gcgagggcga gtacttgtct  3000
gtttaccttt tttttttcag atggcatttt atagtttaac ctttcatgga ccggcagtag  3060
ttctaaccat gaatgaaaag aaatcatagt ccacaccacg cagggacatt gtggtcattt  3120
tagacaagac gatttgatta atgtcttgta tgatatggtc gacagtgagg actaacaaac  3180
atatggcata ttttattacc ggcgagttaa ataaatttat gtcacagtaa taaactgcct  3240
aataaatgca cgccagaaaa tataatgata aaaaaaagaa aagatacata agtccattgc  3300
ttctactttt ttaaaaatta aatccaacat tttctatttt ttggtataaa cttggaagta  3360
ctagttggat atgcaaaatc atctaacctc catatatttc atcaatttgt ttactttaca  3420
tatgggagag gatagtatgt caaagaaaat gacaacaagc ttacaagttt cttattttaa  3480
aagttccgct aacttatcaa gcatagtgtg ccacgcaaaa ctgacaacaa accaacaaat  3540
ttaaggagcg cctaacttat catctatgac ataccgcaca aaatgataac atactagaga  3600
aactttattg cacaaaagga aatttatcca taaggcaaag gaacatctta aggctttgga  3660
tatacattta ccaacaagca ttgtttgtat taccccctaaa gcgcaagaca tgtcatccat  3720
gagtcatagt gtgtatatct caacattgca aagctacctt ttttctatta tacttttcgc  3780
attataggct agatattatc tatacatgtc aacaaactct atccctacgt catatctgaa  3840
gattcttttc ttcactatat aagttggctt ccctgtcatt gaactcacat caaccagccc  3900
aagtttccaa taacatcctc aaatagctgg atcctaaacc atgagggtgt tgctcgttgc  3960
cctcgctctc ctggctctcg ctgcgagcgc cacctcccag gttcagctcc aggcttcggg  4020
```

-continued

```
cggcgggctc gtccaggcgg gcggctcgct caggctctcg tgcgcggcgt cggggcggac  4080
tttcaacagc tacgcttggg gctggttcag gcaggcgccg ggcaaggagc gcggcttcgt  4140
ggccaggatc tccttcagcg gcggccacac ctactactcc gacagcgtca agggccgctt  4200
cacgatctcc agggacaacg ccaagaacag cgtgtacctc cagatgaact ccctgaagcc  4260
cgaggacacg gccgtctact actgcgcggc ggacccgacg ccctacggcc tcaggaacga  4320
gcggaactac cattactggg ggcagggcac gcaggtcact gtctcttcga aggacgagct  4380
gtaacctagg tccccgaatt tccccgatcg ttcaaacatt tggcaataaa gtttcttaag  4440
attgaatcct gttgccggtc ttgcgatgat tatcatataa tttctgttga attacgttaa  4500
gcatgtaata attaacatgt aatgcatgac gttatttatg agatgggttt ttatgattag  4560
agtcccgcaa ttatacattt aatacgcgat agaaaacaaa atatagcgcg caaactagga  4620
taaattatcg cgcgcggtgt catctatgtt actagatcgg gaattggaat tcctgcagtg  4680
cagcgtgacc cggtcgtgcc cctctctaga gataatgagc attgcatgtc taagttataa  4740
aaaattacca catatttttt ttgtcacact tgtttgaagt gcagtttatc tatctttata  4800
catatattta aactttactc tacgaataat ataatctata gtactacaat aatatcagtg  4860
ttttagagaa tcatataaat gaacagttag acatggtcta aaggacaatt gagtattttg  4920
acaacaggac tctacagttt tatcttttta gtgtgcatgt gttctccttt ttttttgcaa  4980
atagcttcac ctatataata cttcatccat tttattagta catccattta gggtttaggg  5040
ttaatggttt ttatagacta atttttttag tacatctatt ttattctatt ttagcctcta  5100
aattaagaaa actaaaactc tattttagtt tttttattta ataatttaga tataaaatag  5160
aataaaataa agtgactaaa aattaaacaa ataccccttta agaaattaaa aaaactaagg  5220
aaacattttt cttgtttcga gtagataatg ccagcctgtt aaacgccgtc gacgagtcta  5280
acggacacca accagcgaac cagcagcgtc gcgtcgggcc aagcgaagca gacggcacgg  5340
catctctgtc gctgcctctg gacccctctc gagagttccg ctccaccgtt ggacttgctc  5400
cgctgtcggc atccagaaat tgcgtggcgg agcggcagac gtgagccggc acggcaggcg  5460
gcctcctcct cctctcacgg cacggcagct acgggggatt cctttcccac cgctccttcg  5520
ctttcccttc ctcgcccgcc gtaataaata gacacccct ccacaccctc tttccccaac  5580
ctcgtgttgt tcggagcgca cacacacaca accagatctc ccccaaatcc acccgtcggc  5640
acctccgctt caaggtacgc cgctcgtcct cccccccccc ccctctctac cttctctaga  5700
tcggcgttcc ggtccatggt tagggcccgg tagttctact tctgttcatg tttgtgttag  5760
atccgtgttt gtgttagatc cgtgctgcta gcgttcgtac acggatgcga cctgtacgtc  5820
agacacgttc tgattgctaa cttgccagtg tttctctttg gggaatcctg ggatggctct  5880
agccgttccg cagacgggat cgatttcatg attttttttg tttcgttgca tagggtttgg  5940
tttgcccttt tcctttattt caatatatgc cgtgcacttg tttgtcgggt catcttttca  6000
tgcttttttt tgtcttggtt gtgatgatgt ggtctggttg ggcggtcgtt ctagatcgga  6060
gtagaattct gtttcaaact acctggtgga tttattaatt ttggatctgt atgtgtgtgc  6120
catacatatt catagttacg aattgaagat gatggatgga aatatcgatc taggataggt  6180
atacatgttg atgcgggttt tactgatgca tatacagaga tgcttttttgt tcgcttggtt  6240
gtgatgatgt ggtgtggttg ggcggtcgtt cattcgttct agatcggagt agaatactgt  6300
ttcaaactac ctggtgtatt tattaatttt ggaactgtat gtgtgtgtca tacatcttca  6360
tagttacgag tttaagatgg atggaaatat cgatctagga taggtataca tgttgatgtg  6420
ggttttactg atgcatatac atgatggcat atgcagcatc tattcatatg ctctaacctt  6480
gagtacctat ctattataat aaacaagtat gttttataat tattttgatc ttgatatact  6540
tggatgatgg catatgcagc agctatatgt ggattttttt agccctgcct tcatacgcta  6600
tttatttgct tggtactgtt tcttttgtcg atgctcaccc tgttgtttgg tgttacttct  6660
gcagatccag atctaaacca tgcagaaact cattaactca gtgcaaaact atgcctgggg  6720
cagcaaaacg gcgttgactg aactttatgg tatggaaaat ccgtccagcc agccgatggc  6780
cgagctgtgg atgggcgcac atccgaaaag cagttcacga gtgcagaatg ccgccggaga  6840
tatcgtttca ctgcgtgatg tgattgagag tgataaatcg actctgctcg gagaggccgt  6900
tgccaaacgc tttggcgaac tgcctttcct gttcaaagta ttatgcgcag cacagccact  6960
ctccattcag gttcatccaa acaaacacaa ttctgaaatc ggttttgcca aagaaaatgc  7020
cgcaggtatc ccgatggatg ccgccgagcg taactataaa gatcctaacc acaagccgga  7080
gctggttttt gcgctgacgc ctttccttgc gatgaacgcg tttcgtgaat tttccgagat  7140
tgtctcccta ctccagccgg tcgcaggtgc acatccggcg attgctcact ttttacaaca  7200
gcctgatgcc gaacgtttaa gcgaactgtt cgccagcctg ttgaatatgc agggtgaaga  7260
aaaatcccgc gcgctggcga ttttaaaatc ggccctcgat agccagcagg gtgaaccgtg  7320
gcaaacgatt cgtttaattt ctgaatttta cccggaagac agcggtctgt tctccccgct  7380
attgctgaat gtggtgaaat tgaaccctgg cgaagcgatg ttcctgttcg ctgaaacacc  7440
gcacgcttac ctgcaaggcg tggcgctgga agtgatggca aactccgata acgtgctgcg  7500
tgcgggtctg acgcctaaat acattgatat tccggaactg gttgccaatg tgaaattcga  7560
agccaaaccg gctaaccagt tgttgaccca gccggtgaaa caaggtgcag aactggactt  7620
cccgattcca gtggatgatt ttgccttctc gctgcatgac cttagtgata aagaaaccac  7680
cattagccag cagagtgccg ccattttgtt ctgcgtcgaa ggcgatgcaa cgttgtggaa  7740
aggttctcag cagttacagc ttaaaccggg tgaatcagcg tttattgccg ccaacgaatc  7800
accggtgact gtcaaaggcc acggccgttt agcgcgtgtt tacaacaagc tgtaagagct  7860
tactgaaaaa attaacatct cttgctaagc tgggagctct agatccccga atttccccga  7920
tcgttcaaac atttggcaat aaagtttctt aagattgaat cctgttgccg gtcttgcgat  7980
gattatcata taatttctgt tgaattacgt taagcatgta ataattaaca tgtaatgcat  8040
gacgttattt atgagatggg tttttatgat tagagtcccg caattataca tttaatacgc  8100
gatagaaaac aaaatatagc gcgcaaacta ggataaatta tcgcgcgcgg tgtcatctat  8160
gttactagat cgggaattgg cgagctcgaa ttaattcagt acattaaaaa cgtccgcaat  8220
gtgttattaa gttgtctaag cgtcaatttg tttacaccac aatatatcct gcca        8274
```

```
SEQ ID NO: 173          moltype = DNA  length = 372
FEATURE                 Location/Qualifiers
misc_feature            1..372
                        note = Synthetic construct, chIL101A11A coding seq
source                  1..372
                        mol_type = other DNA
                        organism = synthetic construct
```

```
SEQUENCE: 173
caggttcagc tgcaggaaag cggtggcgga ctggtgcagc caggtggcag cctcaggctg  60
agctgcgctg ctagcggcaa tatttttagc attaacacaa tgggttggta tagacaggct  120
cctggcaagc agcgtgagct cgttgccagc attaccacgg gtggtacaac caattatgaa  180
gatagcgtga agggtcgttt taccattagc agggacaatg ctaagaagac cgtttacctc  240
cagatgaaca ggctgaagcc agaagatacc gccgtgtatt actgcaacca caggagaagc  300
tatagcggaa gagattatcc tgtttacggt atggactact ggggcaaggg aaccctggtt  360
accgtgagca gc                                                     372

SEQ ID NO: 174         moltype = DNA  length = 372
FEATURE                Location/Qualifiers
misc_feature           1..372
                       note = Synthetic construct, chIL101A11B coding seq
source                 1..372
                       mol_type = other DNA
                       organism = synthetic construct
SEQUENCE: 174
caggtgcagc tccaggagtc cggcggcggc ctcgtgcagc cgggcggctc cctccgcctg  60
agctgcgccg cgtccggcaa catcttcagc atcaacacga tgggctggta caggcaggcc  120
cccggcaagc agcgggagct cgtggcctcc atcaccacgg gcggcaccac gaactacgag  180
gacagcgtca agggccgctt caccatctcc agggacaacg ccaagaagac ggtgtacctc  240
cagatgaacc gcctgaagcc ggaggacacg gcggtctact actgcaacca ccgcaggtcc  300
tacagcggca gggactaccc cgtgtacggc atggactact ggggcaaggg caccctcgtg  360
accgtgtcct cc                                                     372

SEQ ID NO: 175         moltype = DNA  length = 375
FEATURE                Location/Qualifiers
misc_feature           1..375
                       note = Synthetic construct, chIL101F11A coding seq
source                 1..375
                       mol_type = other DNA
                       organism = synthetic construct
SEQUENCE: 175
caggttcagc tccaggagtt tggtggcgga ctggtgcagc caggtggcag cctcaggctg  60
agctgcgctg ctagcggtag aaccggcagc agctatgcta tgggatggtt tagacaggct  120
ccaggcaagg agcgtgaatt tgttgctgcc attagctgga gcggaggtag caccgattat  180
gctgacagcg tgaagggcag gtttaccatt agcagagata atgccaagaa caccatgtac  240
ctccagatga atagcctgaa gccagaggat accgctgttt attactgcgc cgtggaccgt  300
aatctcttta agctgagggt tgctgtgcag gaatacacca acctcggcca gggaacccag  360
gttaccgtga gcagc                                                  375

SEQ ID NO: 176         moltype = DNA  length = 375
FEATURE                Location/Qualifiers
misc_feature           1..375
                       note = Synthetic construct, chIL101F11B coding seq
source                 1..375
                       mol_type = other DNA
                       organism = synthetic construct
SEQUENCE: 176
caggtgcagc tccaggagtt cggcggcggc ctcgtgcagc cgggcggctc cctccgcctg  60
agctgcgccg cgtccggcag gacgggctcc agctacgcga tgggctggtt caggcaggcg  120
cccggcaagg agagggagtt cgtggcggcc atctcgtgga gcggcggcag caccgactac  180
gctgactccg tcaagggccg cttcaccatc agcagggaca acgcgaagaa cacgatgtac  240
ctccagatga actccctgaa gccggaggac accgccgtgt actactgcgc ggtcgaccgc  300
aacctcttca agctgagggt ggccgtccag gagtacacca acctcggcca gggcacccag  360
gtgaccgtgt cctcc                                                  375

SEQ ID NO: 177         moltype = DNA  length = 372
FEATURE                Location/Qualifiers
misc_feature           1..372
                       note = Synthetic construct, chIL101H1A coding seq
source                 1..372
                       mol_type = other DNA
                       organism = synthetic construct
SEQUENCE: 177
caggttcagc tccaggcttc gggcggcggg ctcgtccagg cgggcggctc gctcaggctc  60
tcgtgcgcgg cgtcggggcg gactttcaac agctacgctt ggggctggtt caggcaggcg  120
ccgggcaagg agcgcggctt cgtggccagg atctccttca gcggcggcca cacctactac  180
tccgacagcg tcaagggccg cttcacgatc tccagggaca acgccaagaa cagcgtgtac  240
ctccagatga actccctgaa gcccgaggac acggccgtct actactgcgc ggcggacccg  300
acgccctacg gcctcaggaa cgagcggaac taccattact gggggcaggg cacgcaggtc  360
actgtctctt cg                                                     372

SEQ ID NO: 178         moltype = DNA  length = 372
FEATURE                Location/Qualifiers
misc_feature           1..372
                       note = Synthetic construct, chIL101H1B coding seq
source                 1..372
                       mol_type = other DNA
```

```
                        organism = synthetic construct
SEQUENCE: 178
caggtgcagc tccaggcctc cggcggcggc ctcgtgcagg cgggcggctc cctccgcctg  60
agctgcgccg cgtccggcag gaccttcaac agctacgctt ggggctggtt caggcaggcg  120
ccgggcaagg agcgcggctt cgtggccagg atctccttca gcggcggcca cacctactac  180
tccgacagcg tcaagggccg cttcacgatc agcagggaca acgccaagaa ctccgtgtac  240
ctccagatga acagcctgaa gcccgaggac acggccgtct actactgcgc ggcggacccg  300
accccatacg gcctccgcaa cgagaggaac taccactact ggggccaggg cacccaggtg  360
accgtgtcct cc                                                     372

SEQ ID NO: 179          moltype = AA  length = 147
FEATURE                 Location/Qualifiers
REGION                  1..147
                        note = Synthetic construct, xGZein27ss:chIL10sdAb1H1:KDEL
source                  1..147
                        mol_type = protein
                        organism = synthetic construct
SEQUENCE: 179
MRVLLVALAL LALAASATSQ VQLQASGGGL VQAGGSLRLS CAASGRTFNS YAWGWFRQAP  60
GKERGFVARI SFSGGHTYYS DSVKGRFTIS RDNAKNSVYL QMNSLKPEDT AVYYCAADPT  120
PYGLRNERNY HYWGQGTQVT VSSKDEL                                      147

SEQ ID NO: 180          moltype = AA  length = 8
FEATURE                 Location/Qualifiers
REGION                  1..8
                        note = Synthetic construct, counter selection peptide 1
source                  1..8
                        mol_type = protein
                        organism = synthetic construct
SEQUENCE: 180
DDELNIQL                                                          8

SEQ ID NO: 181          moltype = AA  length = 8
FEATURE                 Location/Qualifiers
REGION                  1..8
                        note = Synthetic construct, counter selection peptide 2
source                  1..8
                        mol_type = protein
                        organism = synthetic construct
SEQUENCE: 181
VLPRAMQT                                                          8

SEQ ID NO: 182          moltype = AA  length = 8
FEATURE                 Location/Qualifiers
REGION                  1..8
                        note = Synthetic construct, counter selection peptide 3
source                  1..8
                        mol_type = protein
                        organism = synthetic construct
SEQUENCE: 182
EKMDENGI                                                          8

SEQ ID NO: 183          moltype = AA  length = 8
FEATURE                 Location/Qualifiers
REGION                  1..8
                        note = Synthetic construct, counter selection peptide 4
source                  1..8
                        mol_type = protein
                        organism = synthetic construct
SEQUENCE: 183
EPTCLHFS                                                          8

SEQ ID NO: 184          moltype = AA  length = 7
FEATURE                 Location/Qualifiers
REGION                  1..7
                        note = Synthetic construct, counter selection peptide 5
source                  1..7
                        mol_type = protein
                        organism = synthetic construct
SEQUENCE: 184
DQMGDLL                                                           7

SEQ ID NO: 185          moltype = AA  length = 7
FEATURE                 Location/Qualifiers
REGION                  1..7
                        note = Synthetic construct, counter selection peptide 6
source                  1..7
                        mol_type = protein
                        organism = synthetic construct
```

```
SEQUENCE: 185
DQLHSLL                                                   7

SEQ ID NO: 186          moltype = AA  length = 8
FEATURE                 Location/Qualifiers
REGION                  1..8
                        note = Synthetic construct, counter selection peptide 7
source                  1..8
                        mol_type = protein
                        organism = synthetic construct
SEQUENCE: 186
VMPKAESD                                                  8

SEQ ID NO: 187          moltype = AA  length = 8
FEATURE                 Location/Qualifiers
REGION                  1..8
                        note = Synthetic construct, counter selection peptide 8
source                  1..8
                        mol_type = protein
                        organism = synthetic construct
SEQUENCE: 187
VMPQAENH                                                  8

SEQ ID NO: 188          moltype = AA  length = 8
FEATURE                 Location/Qualifiers
REGION                  1..8
                        note = Synthetic construct, counter selection peptide
source                  1..8
                        mol_type = protein
                        organism = synthetic construct
SEQUENCE: 188
SKLQERGV                                                  8

SEQ ID NO: 189          moltype = AA  length = 8
FEATURE                 Location/Qualifiers
REGION                  1..8
                        note = Synthetic construct, counter selection peptide 10
source                  1..8
                        mol_type = protein
                        organism = synthetic construct
SEQUENCE: 189
SELQERGV                                                  8

SEQ ID NO: 190          moltype = AA  length = 8
FEATURE                 Location/Qualifiers
REGION                  1..8
                        note = Synthetic construct, counter selection peptide 11
source                  1..8
                        mol_type = protein
                        organism = synthetic construct
SEQUENCE: 190
ENSCIHFP                                                  8

SEQ ID NO: 191          moltype = AA  length = 8
FEATURE                 Location/Qualifiers
REGION                  1..8
                        note = Synthetic construct, counter selection peptide 12
source                  1..8
                        mol_type = protein
                        organism = synthetic construct
SEQUENCE: 191
DSSCIHLP                                                  8

SEQ ID NO: 192          moltype = AA  length = 7
FEATURE                 Location/Qualifiers
REGION                  1..7
                        note = Synthetic construct, counter selection peptide 13
source                  1..7
                        mol_type = protein
                        organism = synthetic construct
SEQUENCE: 192
DQLNSML                                                   7

SEQ ID NO: 193          moltype = AA  length = 8
FEATURE                 Location/Qualifiers
REGION                  1..8
                        note = Synthetic construct, counter selection peptide 14
source                  1..8
                        mol_type = protein
```

-continued

```
                        organism = synthetic construct
SEQUENCE: 193
NMLQERGV                                                                    8

SEQ ID NO: 194          moltype = AA  length = 8
FEATURE                 Location/Qualifiers
REGION                  1..8
                        note = Synthetic construct, counter selection peptide 15
source                  1..8
                        mol_type = protein
                        organism = synthetic construct
SEQUENCE: 194
DSSCTHFP                                                                    8

SEQ ID NO: 195          moltype = AA  length = 7
FEATURE                 Location/Qualifiers
REGION                  1..7
                        note = Synthetic construct; counter selection peptide 16
source                  1..7
                        mol_type = protein
                        organism = synthetic construct
SEQUENCE: 195
DDLEIGL                                                                     7

SEQ ID NO: 196          moltype = AA  length = 12
FEATURE                 Location/Qualifiers
REGION                  1..12
                        note = Synthetic construct, counter selection peptide 17
source                  1..12
                        mol_type = protein
                        organism = synthetic construct
SEQUENCE: 196
VLPTAIADMT EE                                                               12

SEQ ID NO: 197          moltype = AA  length = 8
FEATURE                 Location/Qualifiers
REGION                  1..8
                        note = Synthetic construct, counter selection peptide 18
source                  1..8
                        mol_type = protein
                        organism = synthetic construct
SEQUENCE: 197
TQMEGKGP                                                                    8

SEQ ID NO: 198          moltype = AA  length = 7
FEATURE                 Location/Qualifiers
REGION                  1..7
                        note = Synthetic construct, counter selection peptide 19
source                  1..7
                        mol_type = protein
                        organism = synthetic construct
SEQUENCE: 198
NQCCRFV                                                                     7

SEQ ID NO: 199          moltype = AA  length = 6
FEATURE                 Location/Qualifiers
REGION                  1..6
                        note = Synthetic construct, IEGRMD linker
source                  1..6
                        mol_type = protein
                        organism = synthetic construct
SEQUENCE: 199
IEGRMD                                                                      6

SEQ ID NO: 200          moltype = DNA  length = 20
FEATURE                 Location/Qualifiers
misc_feature            1..20
                        note = Synthetic construct, forward primer 3661
source                  1..20
                        mol_type = other DNA
                        organism = synthetic construct
SEQUENCE: 200
cgtgcccaag ttcagttaca                                                       20

SEQ ID NO: 201          moltype = DNA  length = 22
FEATURE                 Location/Qualifiers
misc_feature            1..22
                        note = Synthetic construct, [00171], reverse primer 3662
source                  1..22
```

```
                        mol_type = other DNA
                        organism = synthetic construct
SEQUENCE: 201
ttgcaacaag ttctctttgc tt                                             22

SEQ ID NO: 202          moltype = DNA  length = 372
FEATURE                 Location/Qualifiers
misc_feature            1..372
                        note = Synthetic cosntruct, Nb1A11
source                  1..372
                        mol_type = other DNA
                        organism = synthetic construct
SEQUENCE: 202
caagttcagt tacaggaaag cgggggaggt ttagttcagc ctgggggttc attgaggttg  60
agttgtgcag caagtggaaa tattttttct attaatacta tgggatggta tagacaagct  120
ccaggaaagc aaagagaact tgttgcaagt attactactg gaggaactac aaattacgaa  180
gatagtgtta aaggaagatt cactatttca agagataatg ctaagaaaac agtttatctt  240
cagatgaata gattgaagcc agaagataca gcagtttact actgtaatca tagaagatca  300
tactctggta gagattatcc tgtttatggt atggattatt ggggaaaagg gacattagtt  360
acagttagca gc                                                        372

SEQ ID NO: 203          moltype = DNA  length = 676
FEATURE                 Location/Qualifiers
misc_feature            1..676
                        note = Synthetic construct, Nb1A11:AtUBQ10i
source                  1..676
                        mol_type = other DNA
                        organism = synthetic construct
SEQUENCE: 203
caagttcagt tacaggaaag cgggggaggt ttagttcagc ctgggggttc attgaggttg  60
agttgtgcag caagtggaaa tattttttct attaatacta tgggatggta tagacaagct  120
ccaggtaaat ttctgtgttc cttattctct caaaatcttc gattttgttt tcgttcgatc  180
ccaatttcgt atatgttctt tggtttagat tctgttaatc ttagatcgaa gacgattttc  240
tgggtttgat cgttagatat catcttaatt ctcgattagg gtttcataga tatcatccga  300
tttgttcaaa taatttgagt tttgtcgaat aattactctt cgatttgtga tttctatcta  360
gatctggtgt tagtttctag tttgtgcgat cgaatttgtc gattaatctg agtttttctg  420
attaacagga aagcaaagag aacttgttgc aagtattact actggaggaa ctacaaatta  480
cgaagatagt gttaaaggaa gattcactat ttcaagagat aatgctaaga aaacagttta  540
tcttcagatg aatagattga agccagaaga tacagcagtt tactactgta atcatagaag  600
atcatactct ggtagagatt atcctgttta tggtatggat tattggggaa aagggacatt  660
agttacagtt agcagc                                                    676

SEQ ID NO: 204          moltype = DNA  length = 1466
FEATURE                 Location/Qualifiers
misc_feature            1..1466
                        note = Synthetic construct, prNbUbi1
source                  1..1466
                        mol_type = other DNA
                        organism = synthetic construct
SEQUENCE: 204
catgaaagtc cacatcatca gctcgtccca aacatcacta ctagacccaa ctcgttcaat  60
cttctcgact acaacaaatg aaatccgctc atcaaggtgt ctgaggctga tctcaataaa  120
tggagggact aattgtatgg atcgaaatct gccccaaaat atttagggta aggtacattg  180
aagaaagagt catcgaggtc gatcaggaaa cgatcgagat gttaacaatg gtcgatgtcg  240
agcaccgcat gtagagttgt aacacctagt ttttagaata ggataataca aagaatattc  300
tattggatat cctttacact tatattatta gagtttgtta ggaaaatgac ccacataaat  360
aggaaaaaag acaatgaatg gagacaggtg acatttatct gatgagaaca gacttttgat  420
agaagatatt ttctctctca ctaagataca aacactacat tttcatcaag attcttgttc  480
atatcattgt acacttttct atcaaatctg aaataattta aatattctag gatttgtctg  540
tcactcatca ttgtcagacg ggataatcat gtactcatcc ttttttggca aaccactttt  600
tctatttact taaatgccat ttattgatat ctattgctag tcattcctcc accgttgctc  660
atactttttt gcaatagtat gcatgttgat atcaatccac caccaaatct tctaacatta  720
atcatatttt cacaacttac atttataaat attattatta actaagttta actcactatt  780
atataaactc aattgtttta ctcgaaagtt acactattat attgagaatt acgtttccaa  840
actttttaag catttattgt gtaaccataa gagactttga ttttttaaaa attatttaga  900
ttttattaat gagaatggca caacattatg gtcaactatg tatttcatca ttaactaaat  960
agttagcact ttgattcttt cacatgaatt atgaatttat gatgggctca aattaaaatt  1020
aaattattca caaaaactta tttttatatt ctacgacacc cacttttcta gctttttccc  1080
gaaggggcgt gagagtgtca cacacgctcc aaatttccca accaaacaag gaaagggcag  1140
agaaagatag ctttagcgtg ttgttttggt gcactacacg tcattaggac acgtgtcatg  1200
atataatagg ccaatcccac gaggcggttt cgtcttgagt cggccatagt gtccataaat  1260
gagggctctc cgtcggtttc cccatcattc atcagattta tcttctatac ttcatcgcct  1320
tcatatttct ctctcaaggt ttgagaattt cttcaatttc tcgctttagc agttcttttt  1380
tattgaatca acgatttcgg catctaaagt cctaattttg aagttcattg ctttaattgt  1440
ttgttgttga ttttatatta ttacag                                         1466

SEQ ID NO: 205          moltype = DNA  length = 90
FEATURE                 Location/Qualifiers
misc_feature            1..90
```

```
                          note = Synthetic construct, ssPR1a
source                    1..90
                          mol_type = other DNA
                          organism = synthetic construct
SEQUENCE: 205
atgggatttg ttctcttttc acaattgcct tcatttcttc ttgtctctac acttctctta  60
ttcctagtaa tatcccactc ttgccgtgcc                                   90

SEQ ID NO: 206            moltype = DNA  length = 102
FEATURE                   Location/Qualifiers
misc_feature              1..102
                          note = Synthetic construct, myc:6xHis:KDEL
source                    1..102
                          mol_type = other DNA
                          organism = synthetic construct
SEQUENCE: 206
acttctggac caggaggaca aggagctgaa caaaagttga tttctgaaga ggatcttgga  60
gctcatcatc atcatcatca tggagcttct aaggatgaac tt                     102

SEQ ID NO: 207            moltype = AA  length = 149
FEATURE                   Location/Qualifiers
REGION                    1..149
                          note = MISC_FEATURE - Llama Il-10
source                    1..149
                          mol_type = protein
                          organism = Llama glama
SEQUENCE: 207
ENSCAHFPAS LPHMLRELRA AFGRVKTFFQ MKDQLDNMLL TRSLLEDFKG YLGCQALSEM  60
IQFYLEEVMP QAENHGPDIK EHVNSLGEKL KTLRLRLRRC HRFLPCENKS KAVEQVRGVF  120
SKLQEKGVYK AMSEFDIFIN YIEAYMTMK                                    149

SEQ ID NO: 208            moltype = AA  length = 154
FEATURE                   Location/Qualifiers
REGION                    1..154
                          note = Synthetic construct, 40-IL-bR2-1H5 (FIG.4)
source                    1..154
                          mol_type = protein
                          organism = synthetic construct
SEQUENCE: 208
QVQLQESGGG LVQAGGSLRL SCAASGRTFN SYAWGWFRQA PGKERGFVAR ISFSGGHTYY  60
SDSVKGRFTI SRDNAKNSVY LQMNSLKPED TAVYYCAADP TPYGLRNERN YHYWGQGTQV  120
TVSSTSGPGG QGAEQKLISE EDLGAHHHHH HGAS                               154

SEQ ID NO: 209            moltype = AA  length = 7
FEATURE                   Location/Qualifiers
REGION                    1..7
                          note = Synthetic construct, 68-IL-bR2-1D9_ AA 28 - 34
source                    1..7
                          mol_type = protein
                          organism = synthetic construct
SEQUENCE: 209
RLSINVM                                                            7

SEQ ID NO: 210            moltype = AA  length = 4
FEATURE                   Location/Qualifiers
REGION                    1..4
                          note = Synthetic construct, 68-IL-bR2-1D9_AA 54-57
source                    1..4
                          mol_type = protein
                          organism = synthetic construct
SEQUENCE: 210
NSRS                                                               4

SEQ ID NO: 211            moltype = AA  length = 5
FEATURE                   Location/Qualifiers
REGION                    1..5
                          note = Synthetic construct, 03-IL-bR2-1C1_AA 30-34
source                    1..5
                          mol_type = protein
                          organism = synthetic construct
SEQUENCE: 211
SINTM                                                              5

SEQ ID NO: 212            moltype = AA  length = 7
FEATURE                   Location/Qualifiers
REGION                    1..7
                          note = Synthetic construct, 03-IL-bR2-1C1 AA 97-103
source                    1..7
                          mol_type = protein
```

```
                        organism = synthetic construct
SEQUENCE: 212
NHRRSYS                                                                      7

SEQ ID NO: 213          moltype = AA  length = 9
FEATURE                 Location/Qualifiers
REGION                  1..9
                        note = Synthetic construct, 03-IL-bR2-1C1_AA105-112
source                  1..9
                        mol_type = protein
                        organism = synthetic construct
SEQUENCE: 213
RDYPVYGMD                                                                    9

SEQ ID NO: 214          moltype = AA  length = 5
FEATURE                 Location/Qualifiers
REGION                  1..5
                        note = Synthetic construct, 35-IL-bR2-1C5_AA 30-34
source                  1..5
                        mol_type = protein
                        organism = synthetic construct
SEQUENCE: 214
GINVM                                                                        5

SEQ ID NO: 215          moltype = AA  length = 5
FEATURE                 Location/Qualifiers
REGION                  1..5
                        note = Synthetic construct, 35-IL-bR2-1C5_AA 50 -54
source                  1..5
                        mol_type = protein
                        organism = synthetic construct
SEQUENCE: 215
TVTTG                                                                        5

SEQ ID NO: 216          moltype = AA  length = 8
FEATURE                 Location/Qualifiers
REGION                  1..8
                        note = Synthetic construct, 48-IL-bR2-1H6_AA 27-34
source                  1..8
                        mol_type = protein
                        organism = synthetic construct
SEQUENCE: 216
SISSIDGM                                                                     8

SEQ ID NO: 217          moltype = AA  length = 5
FEATURE                 Location/Qualifiers
REGION                  1..5
                        note = Synthetic construct, 48-IL-bR2-1H6_AA 75-79
source                  1..5
                        mol_type = protein
                        organism = synthetic construct
SEQUENCE: 217
DQTTL                                                                        5

SEQ ID NO: 218          moltype = AA  length = 9
FEATURE                 Location/Qualifiers
REGION                  1..9
                        note = Synthetic construct, 48-IL-bR2-1H6_AA 105 - 112
source                  1..9
                        mol_type = protein
                        organism = synthetic construct
SEQUENCE: 218
VPDWYYGMD                                                                    9

SEQ ID NO: 219          moltype = AA  length = 4
FEATURE                 Location/Qualifiers
REGION                  1..4
                        note = Synthetic construct, 01-IL-bR2-2A8_AA 76-79
source                  1..4
                        mol_type = protein
                        organism = synthetic construct
SEQUENCE: 219
QTTL                                                                         4

SEQ ID NO: 220          moltype = AA  length = 7
FEATURE                 Location/Qualifiers
REGION                  1..7
                        note = Synthetic construct, 85-IL-bR2-1E11_AA 102-108
source                  1..7
```

```
                       mol_type = protein
                       organism = synthetic construct
SEQUENCE: 220
ASLSIYR                                                     7

SEQ ID NO: 221         moltype = AA  length = 9
FEATURE                Location/Qualifiers
REGION                 1..9
                       note = Synthetic construct, 44-IL-bR2-1D6_AA 26 - 34
source                 1..9
                       mol_type = protein
                       organism = synthetic construct
SEQUENCE: 221
ESISSINTM                                                   9

SEQ ID NO: 222         moltype = AA  length = 4
FEATURE                Location/Qualifiers
REGION                 1..4
                       note = Synthetic construct, 44-IL-bR2-1D6_AA 99-102
source                 1..4
                       mol_type = protein
                       organism = synthetic construct
SEQUENCE: 222
GVPT                                                        4

SEQ ID NO: 223         moltype = AA  length = 11
FEATURE                Location/Qualifiers
REGION                 1..11
                       note = Synthetic construct, 44-IL-bR2-1D6_AA 104-113
source                 1..11
                       mol_type = protein
                       organism = synthetic construct
SEQUENCE: 223
DDDAMPISWR F                                                11

SEQ ID NO: 224         moltype = AA  length = 5
FEATURE                Location/Qualifiers
REGION                 1..5
                       note = Synthetic construct, 27-IL-bR2-1C4_AA 27 - 31
source                 1..5
                       mol_type = protein
                       organism = synthetic construct
SEQUENCE: 224
FSLEN                                                       5

SEQ ID NO: 225         moltype = AA  length = 5
FEATURE                Location/Qualifiers
REGION                 1..5
                       note = Synthetic construct, 27-IL-bR2-1C4_AA 46 - 50
source                 1..5
                       mol_type = protein
                       organism = synthetic construct
SEQUENCE: 225
EGLSC                                                       5

SEQ ID NO: 226         moltype = AA  length = 9
FEATURE                Location/Qualifiers
REGION                 1..9
                       note = Synthetic construct, 27-IL-bR2-1C4_AA 53-61
source                 1..9
                       mol_type = protein
                       organism = synthetic construct
SEQUENCE: 226
STDDSIFSV                                                   9

SEQ ID NO: 227         moltype = AA  length = 8
FEATURE                Location/Qualifiers
REGION                 1..8
                       note = Synthetic construct, 27-IL-bR2-1C4_AA 98-105
source                 1..8
                       mol_type = protein
                       organism = synthetic construct
SEQUENCE: 227
TSRGLGSC                                                    8

SEQ ID NO: 228         moltype = AA  length = 6
FEATURE                Location/Qualifiers
REGION                 1..6
                       note = Synthetic construct, 32-IL-bR2-1H4_AA 52 - 57
```

```
source                  1..6
                        mol_type = protein
                        organism = synthetic construct
SEQUENCE: 228
TNADRI                                                                      6

SEQ ID NO: 229          moltype = AA  length = 5
FEATURE                 Location/Qualifiers
REGION                  1..5
                        note = Synthetic construct, 32-IL-bR2-1H4_AA 98 - 102
source                  1..5
                        mol_type = protein
                        organism = synthetic construct
SEQUENCE: 229
TNFYS                                                                       5

SEQ ID NO: 230          moltype = AA  length = 5
FEATURE                 Location/Qualifiers
REGION                  1..5
                        note = Synthetic construct, 86-IL-bR2-1F11_AA 100-104
source                  1..5
                        mol_type = protein
                        organism = synthetic construct
SEQUENCE: 230
RNLFK                                                                       5

SEQ ID NO: 231          moltype = AA  length = 5
FEATURE                 Location/Qualifiers
REGION                  1..5
                        note = Synthetic construct, 86-IL-bR2-1F11_AA 107-110
source                  1..5
                        mol_type = protein
                        organism = synthetic construct
SEQUENCE: 231
VAVQE                                                                       5

SEQ ID NO: 232          moltype = AA  length = 4
FEATURE                 Location/Qualifiers
REGION                  1..4
                        note = Synthetic construct, 20-IL-bR2-1D3_AA 44 - 47
source                  1..4
                        mol_type = protein
                        organism = synthetic construct
SEQUENCE: 232
GLEW                                                                        4

SEQ ID NO: 233          moltype = AA  length = 4
FEATURE                 Location/Qualifiers
REGION                  1..4
                        note = Synthetic construct, 20-IL-bR2-1D3_AA 52-55
source                  1..4
                        mol_type = protein
                        organism = synthetic construct
SEQUENCE: 233
TWNV                                                                        4

SEQ ID NO: 234          moltype = AA  length = 8
FEATURE                 Location/Qualifiers
REGION                  1..8
                        note = Synthetic construct, 20-IL-bR2-1D3_AA 100-107
source                  1..8
                        mol_type = protein
                        organism = synthetic construct
SEQUENCE: 234
GIAPRRYY                                                                    8

SEQ ID NO: 235          moltype = AA  length = 9
FEATURE                 Location/Qualifiers
REGION                  1..9
                        note = Synthetic construct, 49-IL-bR2-1A7_AA 27 - 35
source                  1..9
                        mol_type = protein
                        organism = synthetic construct
SEQUENCE: 235
NIYDINTMA                                                                   9

SEQ ID NO: 236          moltype = AA  length = 13
FEATURE                 Location/Qualifiers
REGION                  1..13
```

-continued

```
                        note = Synthetic construct, 49-IL-bR2-1A7_AA 97-109
source                  1..13
                        mol_type = protein
                        organism = synthetic construct
SEQUENCE: 236
NVKTGRGRNL YSD                                                  13

SEQ ID NO: 237          moltype = AA  length = 8
FEATURE                 Location/Qualifiers
REGION                  1..8
                        note = Synthetic construct, 24-IL-bR2-1H3_AA 27 - 34
source                  1..8
                        mol_type = protein
                        organism = synthetic construct
SEQUENCE: 237
SISSIDTM                                                        8

SEQ ID NO: 238          moltype = AA  length = 4
FEATURE                 Location/Qualifiers
REGION                  1..4
                        note = Synthetic construct, 24-IL-bR2-1H3_AA 98-101
source                  1..4
                        mol_type = protein
                        organism = synthetic construct
SEQUENCE: 238
VVVS                                                            4

SEQ ID NO: 239          moltype = AA  length = 6
FEATURE                 Location/Qualifiers
REGION                  1..6
                        note = Synthetic construct, 24-IL-bR2-1H3_AA 103 - 108
source                  1..6
                        mol_type = protein
                        organism = synthetic construct
SEQUENCE: 239
TLIAGS                                                          6

SEQ ID NO: 240          moltype = AA  length = 10
FEATURE                 Location/Qualifiers
REGION                  1..10
                        note = Synthetic construct, 58-IL-bR2-1B8-_AA 26-35
source                  1..10
                        mol_type = protein
                        organism = synthetic construct
SEQUENCE: 240
ESIDTFDIID                                                      10

SEQ ID NO: 241          moltype = AA  length = 18
FEATURE                 Location/Qualifiers
REGION                  1..18
                        note = Synthetic construct, 58-IL-bR2-1B8_AA 46 - 61
source                  1..18
                        mol_type = protein
                        organism = synthetic construct
SEQUENCE: 241
DQRELVAQML PVGATTYA                                             18

SEQ ID NO: 242          moltype = AA  length = 11
FEATURE                 Location/Qualifiers
REGION                  1..11
                        note = Synthetic construct, 58-IL-bR2-1B8_AA 97-107
source                  1..11
                        mol_type = protein
                        organism = synthetic construct
SEQUENCE: 242
HSINRDHNIW C                                                    11

SEQ ID NO: 243          moltype = AA  length = 6
FEATURE                 Location/Qualifiers
REGION                  1..6
                        note = Synthetic construct, 10-IL-bR2-1B2_AA 27 - 32
source                  1..6
                        mol_type = protein
                        organism = synthetic construct
SEQUENCE: 243
VIPDAS                                                          6

SEQ ID NO: 244          moltype = AA  length = 7
FEATURE                 Location/Qualifiers
```

-continued

```
REGION               1..7
                     note = Synthetic construct, 10-IL-bR2-1B2_AA 52-59
source               1..7
                     mol_type = protein
                     organism = synthetic construct
SEQUENCE: 244
VGPTNIL                                                                     7

SEQ ID NO: 245       moltype = AA  length = 6
FEATURE              Location/Qualifiers
REGION               1..6
                     note = Synthetic construct, 10-IL-bR2-1B2_AA75-80
source               1..6
                     mol_type = protein
                     organism = synthetic construct
SEQUENCE: 245
GGDTIS                                                                      6

SEQ ID NO: 246       moltype = AA  length = 8
FEATURE              Location/Qualifiers
REGION               1..8
                     note = Synthetic construct, 10-IL-bR2-1B2_AA 97-104
source               1..8
                     mol_type = protein
                     organism = synthetic construct
SEQUENCE: 246
NLLQSGTN                                                                    8

SEQ ID NO: 247       moltype = AA  length = 5
FEATURE              Location/Qualifiers
REGION               1..5
                     note = Synthetic construct, 12-IL-bR2-1D2_AA 30-34
source               1..5
                     mol_type = protein
                     organism = synthetic construct
SEQUENCE: 247
SRNTM                                                                       5

SEQ ID NO: 248       moltype = AA  length = 4
FEATURE              Location/Qualifiers
REGION               1..4
                     note = Synthetic construct, 12-IL-bR2-1D2_AA 55-58
source               1..4
                     mol_type = protein
                     organism = synthetic construct
SEQUENCE: 248
DITN                                                                        4

SEQ ID NO: 249       moltype = AA  length = 5
FEATURE              Location/Qualifiers
REGION               1..5
                     note = Synthetic construct, 76-IL-bR2-1D10_AA 99-103
source               1..5
                     mol_type = protein
                     organism = synthetic construct
SEQUENCE: 249
IRGVN                                                                       5
```

What is claimed is:

1. An anti-IL-10 single domain antibody comprising an amino acid sequence of SEQ ID NO: 135, wherein the anti-IL-10 single domain antibody binds a polypeptide comprising an amino acid sequence of SEQ ID NO: 80 with an $EC_{50}$ of 30 nM or less, as measured by ELISA.

2. The anti-IL-10 single domain antibody of claim 1, wherein the antibody is stable at a temperature in a range from 70° C. to 90° C.

3. The anti-IL-10 single domain antibody of claim 1, wherein the antibody is digestible in pepsin.

4. The anti-IL-10 single domain antibody of claim 1, wherein the anti-IL-10 single domain antibody is encoded by a synthetic polynucleotide comprising a sequence with at least 90% identity to the sequence of SEQ ID NO: 175 or 176.

5. An animal feed comprising the anti-IL-10 single domain antibody of claim 1.

6. The animal feed of claim 5, wherein the anti-IL-10 single domain antibody is active upon expression in a plant and exposure to a temperature in the range from 25° C. to 130° C.

7. The animal feed of claim 5 further comprising a feed supplement.

8. The animal feed of claim 7, wherein the feed supplement is plant material.

9. The animal feed of claim 8, wherein the plant material is a non-transgenic plant or a transgenic plant.

10. The animal feed of claim 8, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.

11. The animal feed of claim 7, wherein the feed supplement includes one or more exogenous enzymes.

12. The animal feed of claim 11, wherein the one or more exogenous enzymes includes a hydrolytic enzyme selected from the group consisting of: xylanase, endoglucanase, cellulase, protease, phytase, amylase and mannanase.

13. The animal feed of claim 7, wherein the feed supplement includes at least one component selected from the group consisting of: soluble solids, fat and vermiculite, limestone, plain salt, DL-methionine, L-lysine, L-threonine, monensin, vitamin premix, dicalcium phosphate, selenium premix, choline chloride, sodium chloride, and mineral premix.

14. A method of treating or preventing a gastrointestinal infection in an animal comprising administering to the animal the anti-IL-10 single domain antibody of claim 1 or an animal feed comprising the anti-IL-10 single domain antibody.

15. The method of claim 14, wherein the step of administering is performed by feeding or injecting.

16. The method of claim 14, wherein the gastrointestinal infection is caused by a gastrointestinal pathogen selected from the group consisting of: a bacteria, yeast, fungi, archae, virus, and protozoa.

17. The method of claim 16, wherein the gastrointestinal pathogen belongs to the genus *Eimeria*.

18. The method of claim 16, wherein the gastrointestinal pathogen is selected from the group consisting of: *Eimeria tenella, Eimeria acervulina*, and *Eimeria maxima*.

19. The method of claim 14, wherein treating stimulates the immune system and enhances growth of the animal.

20. The method of claim 18, wherein the animal is selected from the group consisting of: a chicken, a turkey, or a duck.

* * * * *